US007816326B2

(12) United States Patent
Velazquez et al.

(10) Patent No.: US 7,816,326 B2
(45) Date of Patent: *Oct. 19, 2010

(54) SULFUR COMPOUNDS AS INHIBITORS OF HEPATITIS C VIRUS NS3 SERINE PROTEASE

(75) Inventors: Francisco Velazquez, Clinton, NJ (US); Stephane L. Bogen, Somerset, NJ (US); Ashok Arasappan, Bridgewater, NJ (US); Srikanth Venkatraman, Woodbridge, NJ (US); F. George Njoroge, Warren, NJ (US); Neng-Yang Shih, Warren, NJ (US)

(73) Assignee: Schering Corporation, Kenilworth, NJ (US)

( * ) Notice: Subject to any disclaimer, the term of this patent is extended or adjusted under 35 U.S.C. 154(b) by 564 days.

This patent is subject to a terminal disclaimer.

(21) Appl. No.: 11/733,479

(22) Filed: Apr. 10, 2007

(65) Prior Publication Data

US 2007/0197448 A1 Aug. 23, 2007

Related U.S. Application Data

(63) Continuation-in-part of application No. 11/064,673, filed on Feb. 24, 2005.

(60) Provisional application No. 60/548,670, filed on Feb. 27, 2004.

(51) Int. Cl.
*A61K 38/05* (2006.01)
(52) U.S. Cl. .......................................... 514/18; 530/331
(58) Field of Classification Search ...................... None
See application file for complete search history.

(56) References Cited

U.S. PATENT DOCUMENTS

| 5,712,145 | A | 1/1998 | Houghton et al. | |
|---|---|---|---|---|
| 6,608,027 | B1 | 8/2003 | Tsantrizos et al. | |
| 6,911,428 | B2 * | 6/2005 | Zhu et al. | 514/9 |
| 7,012,066 | B2 * | 3/2006 | Saksena et al. | 514/18 |
| 7,244,721 | B2 * | 7/2007 | Saksena et al. | 514/210.21 |
| 2007/0197448 | A1 | 8/2007 | Velazquez et al. | |

FOREIGN PATENT DOCUMENTS

| WO | WO 98/14181 | A1 | 4/1998 |
|---|---|---|---|
| WO | WO 98/17679 | A1 | 4/1998 |
| WO | WO 98/22496 | A2 | 5/1998 |
| WO | WO 99/07734 | A2 | 2/1999 |
| WO | WO 00/09543 | A2 | 2/2000 |
| WO | WO 00/09558 | A1 | 2/2000 |
| WO | WO 01/74768 | A2 | 10/2001 |
| WO | WO 01/77113 | A2 | 10/2001 |
| WO | WO 01/81325 | A2 | 11/2001 |
| WO | WO 02/08187 | A1 | 1/2002 |
| WO | WO 02/08244 | A2 | 1/2002 |
| WO | WO 02/08251 | A2 | 1/2002 |
| WO | WO 02/08256 | A2 | 1/2002 |
| WO | WO 02/48172 | A2 | 6/2002 |
| WO | WO 2005/087731 | A | 9/2005 |
| WO | WO 2006/130628 | A | 12/2006 |

OTHER PUBLICATIONS

PCT International Search Report dated Mar. 25, 2009 for corresponding PCT Application No. PCT/US2008/004549.
Berenguer et al., "Hepatitis B and C Viruses: Molecular Identification and Targeted Antiviral Therapies", Proceedings of the Association of American Physicians, 110(2):98-112 (1998).
Dimasi et al., "Characterization of Engineered Hepatitis C Virus NS3 Protease Inhibitors Affinity Selected from Human Pancreatic Secretory Trypsin Inhibitor and Minibody Repertoires", Journal of Virology, 71(10):7461-7469 (1997).
Elzouki et al., "Serine Protease Inhibitors in Patients with Chronic Viral Hepatitis", Journal of Hepatology, 27:42-48 (1997).
Failla et al., "Redesigning the Substrate Specificity of the Hepatitis C Virus NS3 Protease", Folding & Design, 1(1):35-42 (1996).
Han et al., "α-Ketoamides, α-Ketoesters and α-Diketones as HCV NS3 Protease Inhibitors", Bioorganic & Medicinal Chemistry Letters, 10:711-713 (2000).
Hoofnagle et al., "The Treatment of Chronic Viral Hepatitis", The New England Journal of Medicine, 336(5):347-356 (1997).
Ingallinella et al., "Potent Peptide Inhibitors of Human Hepatitis C Virus NS3 Protease are Obtained by Optimizing the Cleavage Products", Biochemistry, 37:8906-8914 (1998).
Kolykhalov et al., "Specificity of the Hepatitis C Virus NS3 Serine Protease: Effects of Substitutions at the 3/4A, 4A/4B, 4B/5A, and 5A/5B Cleavage Sites on Polyprotein Processing", Journal of Virology, 68(11):7525-7533 (1994).
Komoda et al., "Substrate Requirements of Hepatitis C Virus Serine Proteinase for Intermolecular Polypeptide Cleavage in *Escherichia Coli*", Journal of Virology, 68(11):7351-7357 (1994).
Landro et al., "Mechanistic Role of an NS4A Peptide Cofactor with the Truncated NS3 Protease of Hepatitis C Virus: Elucidation of the NS4A Stimulatory Effect via Kinetic Analysis and Inhibitor Mapping", Biochemistry, 36:9340-9348 (1997).
Llinas-Brunet et al., "Peptide-Based inhibitors of the Hepatitis C Virus Serine Protease", Bioorganic & Medicinal Chemistry Letters 8:1713-1718 (1998).
Marchetti et al., "Synthesis of Two Novel Cyclic Biphenyl Ether Analogs of an Inhibitor of HCV NS3 Protease", Synlett S1:1000-1002 (1999).
Martin et al., "Design of Selective Eglin Inhibitors of HCV NS3 Proteinase", Biochemistry, 37:11459-11468 (1998).
Martin et al., "Affinity Selection of a Camelized $V_H$ Domain Antibody Inhibitor of Hepatitis C Virus NS3 Protease", Protein Engineering, 10(5):607-614 (1997).

(Continued)

*Primary Examiner*—Cecilia Tsang
*Assistant Examiner*—Roy Teller
(74) *Attorney, Agent, or Firm*—Palaiyur Kalyanaraman; Serena Farquharson-Torres

(57) ABSTRACT

The present invention discloses novel compounds which have HCV protease inhibitory activity as well as methods for preparing such compounds. In another embodiment, the invention discloses pharmaceutical compositions comprising such compounds as well as methods of using them to treat disorders associated with the HCV protease.

18 Claims, No Drawings

OTHER PUBLICATIONS

Pizzi et al., "Molecular Model of the Specificity Pocket of the Hepatitis C Virus Protease: Implications for Substrate Recognition", Proceedings of the National Academy Sciences of the USA, 91:888-892 (1994).

BioWorld Today, 9(217):1-5 (1998).
International Search Report for corresponding PCT Application No. PCT/US01/22678 dated Jun. 7, 2002.

* cited by examiner

SULFUR COMPOUNDS AS INHIBITORS OF HEPATITIS C VIRUS NS3 SERINE PROTEASE

REFERENCE TO RELATED APPLICATIONS

This application is a Continuation-in-Part of U.S. patent application Ser. No. 11/064,673, filed Feb. 24, 2005 (which published as US2007/004,2968 on Feb. 22, 2007), which claims priority to U.S. provisional application Ser. No. 60/548,670 filed Feb. 27, 2004.

FIELD OF THE INVENTION

The present invention relates to novel hepatitis C virus ("HCV") protease inhibitors, pharmaceutical compositions containing one or more such inhibitors, methods of preparing such inhibitors and methods of using such inhibitors to treat hepatitis C and related disorders. This invention additionally discloses novel compounds as inhibitors of the HCV NS3/NS4a serine protease.

BACKGROUND OF THE INVENTION

Hepatitis C virus (HCV) is a (+)-sense single-stranded RNA virus that has been implicated as the major causative agent in non-A, non-B hepatitis (NANBH), particularly in blood-associated NANBH (BB-NANBH) (see, International Patent Application Publication No. WO 89/04669 and European Patent Application Publication No. EP 381 216). NANBH is to be distinguished from other types of viral-induced liver disease, such as hepatitis A virus (HAV), hepatitis B virus (HBV), delta hepatitis virus (HDV), cytomegalovirus (CMV) and Epstein-Barr virus (EBV), as well as from other forms of liver disease such as alcoholism and primary biliar cirrhosis.

Recently, an HCV protease necessary for polypeptide processing and viral replication has been identified, cloned and expressed. (See, e.g., U.S. Pat. No. 5,712,145). This approximately 3000 amino acid polyprotein contains, from the amino terminus to the carboxy terminus, a nucleocapsid protein (C), envelope proteins (E1 and E2) and several non-structural proteins (NS1, 2, 3, 4a, 5a and 5b). NS3 is an approximately 68 kda protein, encoded by approximately 1893 nucleotides of the HCV genome, and has two distinct domains: (a) a serine protease domain consisting of approximately 200 of the N-terminal amino acids; and (b) an RNA-dependent ATPase domain at the C-terminus of the protein. The NS3 protease is considered a member of the chymotrypsin family because of similarities in protein sequence, overall three-dimensional structure and mechanism of catalysis. Other chymotrypsin-like enzymes are elastase, factor Xa, thrombin, trypsin, plasmin, urokinase, tPA and PSA. The HCV NS3 serine protease is responsible for proteolysis of the polypeptide (polyprotein) at the NS3/NS4a, NS4a/NS4b, NS4b/NS5a and NS5a/NS5b junctions and is thus responsible for generating four viral proteins during viral replication. This has made the HCV NS3 serine protease an attractive target for antiviral chemotherapy. The inventive compounds can inhibit such protease. They also can modulate the processing of hepatitis C virus (HCV) polypeptide.

It has been determined that the NS4a protein, an approximately 6 kda polypeptide, is a co-factor for the serine protease activity of NS3. Autocleavage of the NS3/NS4a junction by the NS3/NS4a serine protease occurs intramolecularly (i.e., cis) while the other cleavage sites are processed intermolecularly (i.e., trans).

Analysis of the natural cleavage sites for HCV protease revealed the presence of cysteine at P1 and serine at P1' and that these residues are strictly conserved in the NS4a/NS4b, NS4b/NS5a and NS5a/NS5b junctions. The NS3/NS4a junction contains a threonine at P1 and a serine at P1'. The Cys→Thr substitution at NS3/NS4a is postulated to account for the requirement of cis rather than trans processing at this junction. See, e.g., Pizzi et al. (1994) *Proc. Natl. Acad. Sci (USA)* 91:888-892, Failla et al. (1996) *Folding & Design* 1:3542. The NS3/NS4a cleavage site is also more tolerant of mutagenesis than the other sites. See, e.g., Kollykhalov et al. (1994) *J. Virol.* 68:7525-7533. It has also been found that acidic residues in the region upstream of the cleavage site are required for efficient cleavage. See, e.g., Komoda et al. (1994) *J. Virol.* 68:7351-7357.

Inhibitors of HCV protease that have been reported include antioxidants (see, International Patent Application Publication No. WO 98/14181), certain peptides and peptide analogs (see, International Patent Application Publication No. WO 98/17679, Landro et al. (1997) *Biochem.* 36:9340-9348, Ingallinella et al. (1998) *Biochem.* 37:8906-8914, Llinàs-Brunet et al. (1998) *Bioorg. Med. Chem. Lett.* 8:1713-1718), inhibitors based on the 70-amino acid polypeptide eglin c (Martin et al. (1998) *Biochem.* 37:11459-11468, inhibitors affinity selected from human pancreatic secretory trypsin inhibitor (hPSTI-C3) and minibody repertoires (MBip) (Dimasi et al. (1997) *J. Virol.* 71:7461-7469), $cV_HE2$ (a "camelized" variable domain antibody fragment) (Martin et al. (1997) *Protein Eng.* 10:607-614), and α1-antichymotrypsin (ACT) (Elzouki et al.) (1997) *J. Hepat.* 27:42-28). A ribozyme designed to selectively destroy hepatitis C virus RNA has recently been disclosed (see, *BioWorld Today* 9(217): 4 (Nov. 10, 1998)).

Reference is also made to the PCT Publications, No. WO 98/17679, published Apr. 30, 1998 (Vertex Pharmaceuticals Incorporated); WO 98/22496, published May 28, 1998 (F. Hoffmann-La Roche AG); and WO 99/07734, published Feb. 18, 1999 (Boehringer Ingelheim Canada Ltd.).

HCV has been implicated in cirrhosis of the liver and in induction of hepatocellular carcinoma. The prognosis for patients suffering from HCV infection is currently poor. HCV infection is more difficult to treat than other forms of hepatitis due to the lack of immunity or remission associated with HCV infection. Current data indicates a less than 50% survival rate at four years post cirrhosis diagnosis. Patients diagnosed with localized resectable hepatocellular carcinoma have a five-year survival rate of 10-30%, whereas those with localized unresectable hepatocellular carcinoma have a five-year survival rate of less than 1%.

Reference is made to WO 00/59929 (U.S. Pat. No. 6,608,027, Assignee: Boehringer Ingelheim (Canada) Ltd.; Published Oct. 12, 2000) which discloses peptide derivatives of the formula:

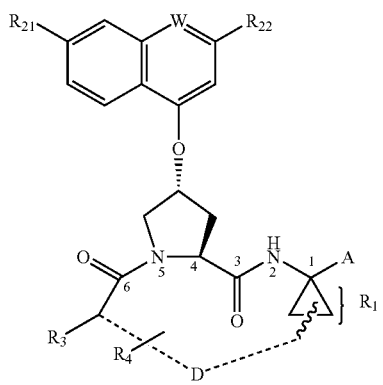

Reference is made to A. Marchetti et al, *Synlett*, S1, 1000-1002 (1999) describing the synthesis of bicylic analogs of an inhibitor of HCV NS3 protease. A compound disclosed therein has the formula,

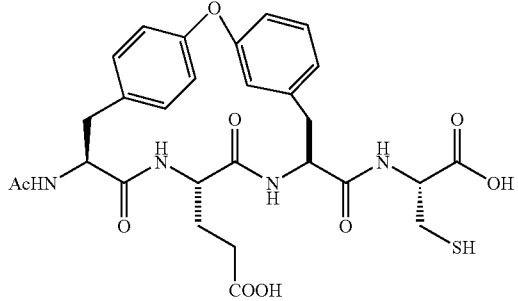

Reference is also made to W. Han et al, *Bioorganic & Medicinal Chem. Lett*, (2000) 10, 711-713, which describes the preparation of certain α-ketoamides, α-ketoesters and α-diketones containing allyl and ethyl functionalities.

Reference is also made to WO 00/09558 (Assignee: Boehringer Ingelheim Limited; Published Feb. 24, 2000) which discloses peptide derivatives of the formula:

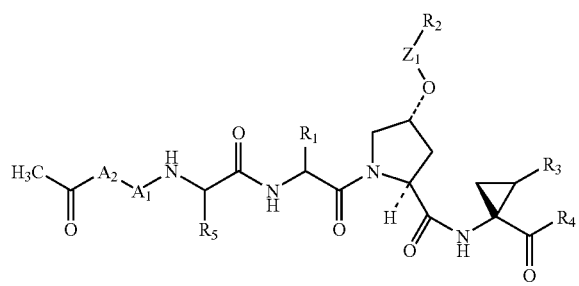

where the various elements are defined therein. An illustrative compound of that series is:

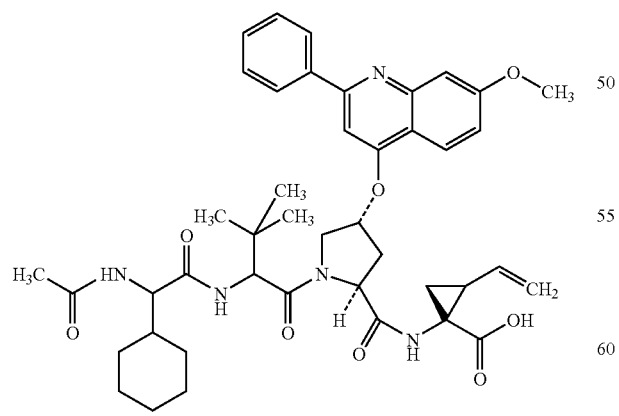

Reference is also made to WO 00/09543 (Assignee: Boehringer Ingelheim Limited; Published Feb. 24, 2000) which discloses peptide derivatives of the formula:

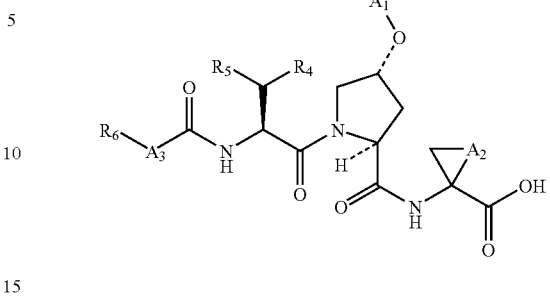

where the various elements are defined therein. An illustrative compound of that series is:

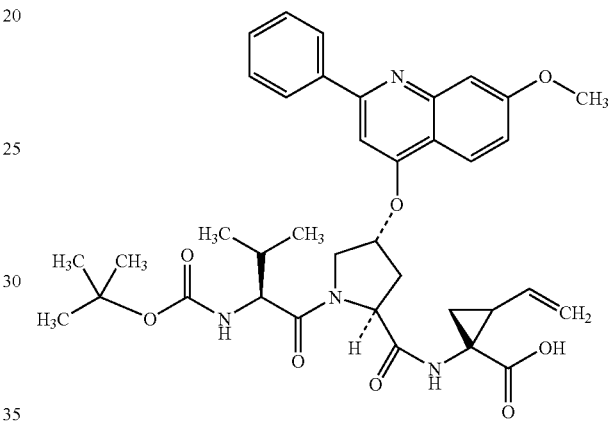

Reference is also made to U.S. Pat. No. 6,608,027 (Boehringer Ingelheim, Canada) which discloses NS3 protease inhibitors of the type:

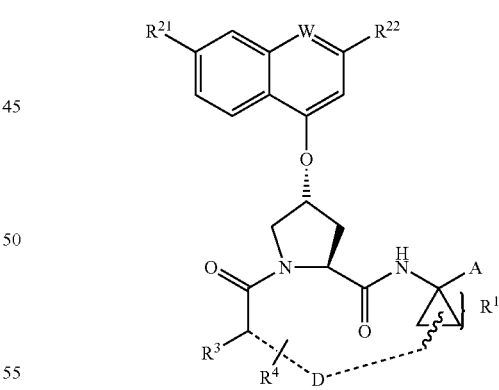

wherein the various moieties are defined therein.

Current therapies for hepatitis C include interferon-α (INF$_\alpha$) and combination therapy with ribavirin and interferon. See, e.g., Beremguer et al., (1998) *Proc. Assoc. Am. Physicians* 110(2)98-112. These therapies suffer from a low sustained response rate and frequent side effects. See, e.g., Hoofnagle et al. (1997) *N. Engl. J. Med.* 336:347. Currently, no vaccine is available for HCV infection.

Reference is further made to WO 01/74768 (Assignee) Vertex Pharmaceuticals Inc) published Oct. 11, 2001, which discloses certain compounds of the following general formula (R is defined therein) as NS3-serine protease inhibitors of Hepatitis C virus:

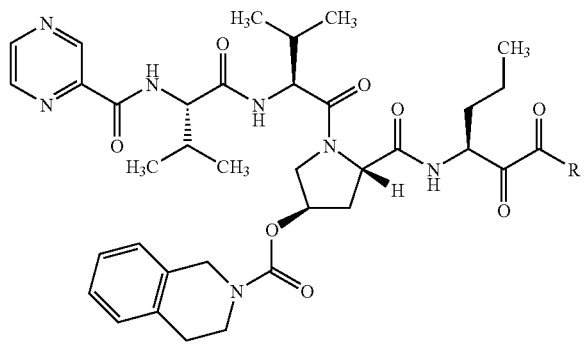

A specific compound disclosed in the afore-mentioned WO 01/74768 has the following formula:

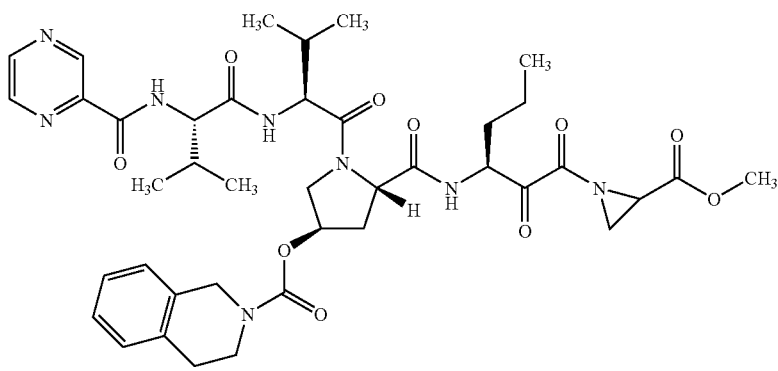

PCT Publications WO 01/77113; WO 01/081325; WO 02/08198; WO 02/08256; WO 02/08187; WO 02/08244; WO 02/48172; WO 02/08251; and pending U.S. patent application Ser. No. 10/052,386, filed Jan. 18, 2002, disclose various types of peptides and/or other compounds as NS-3 serine protease inhibitors of hepatitis C virus. The disclosures of those applications are incorporated herein by reference thereto.

There is a need for new treatments and therapies for HCV infection. There is a need for compounds useful in the treatment or prevention or amelioration of one or more symptoms of hepatitis C.

There is a need for methods of treatment or prevention or amelioration of one or more symptoms of hepatitis C.

There is a need for methods for modulating the activity of serine proteases, particularly the HCV NS3/NS4a serine protease, using the compounds provided herein.

There is a need for methods of modulating the processing of the HCV polypeptide using the compounds provided herein.

SUMMARY OF THE INVENTION

U.S. patent application Ser. No. 11/064,673, filed Feb. 24, 2005 (which published as US2007/0042968 on Feb. 22, 2007), the entire disclosure of which, is incorporated herein, by reference.

In its many embodiments, the present invention provides novel compounds as inhibitors of the HCV protease, pharmaceutical compositions containing one or more of the compounds, methods of preparing pharmaceutical formulations comprising one or more of such compounds, methods of treatment or prevention of HCV or amelioration of one or more of the symptoms of hepatitis C using one or more of such compounds or one or more of such formulations, and methods of modulating the interaction of an HCV polypeptide with HCV protease using one or more of such compounds or one or more of such formulations. The present invention discloses compounds, as well as pharmaceutically acceptable salts, solvates or esters of said compounds, said compound being selected from the compounds of structures listed below:

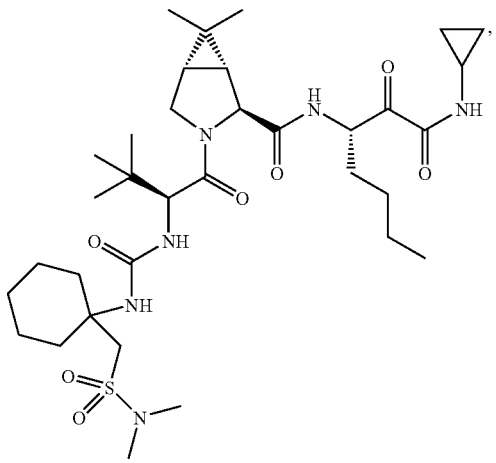

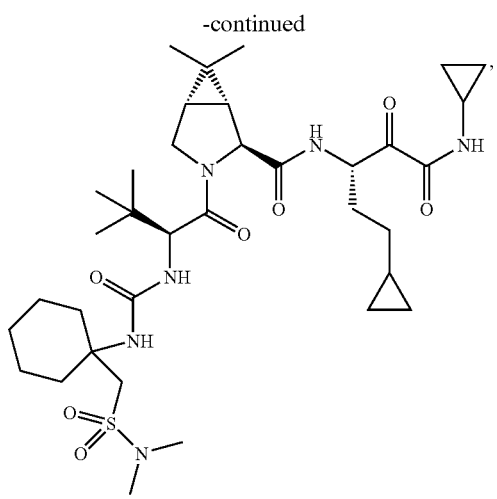
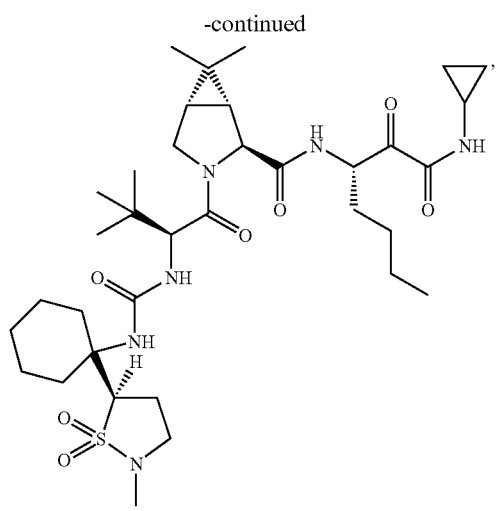
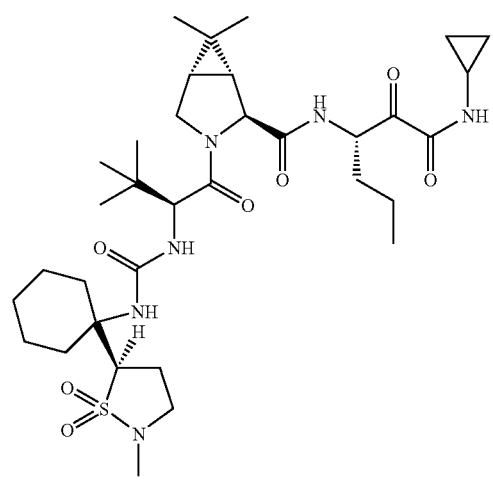
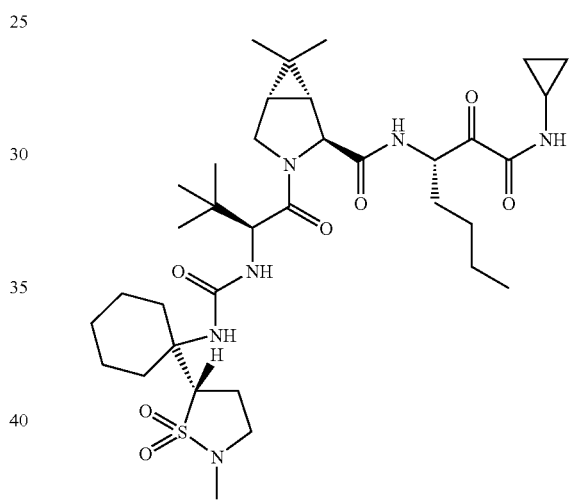
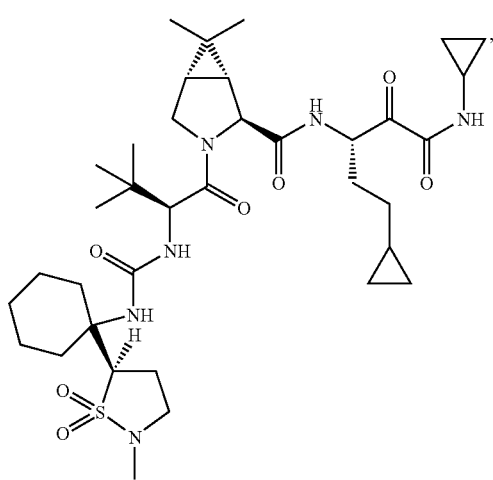
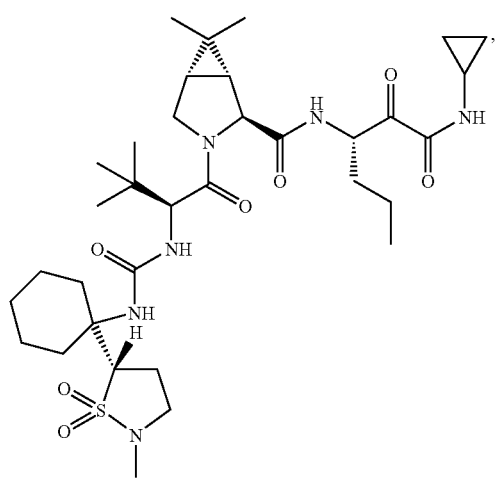

-continued
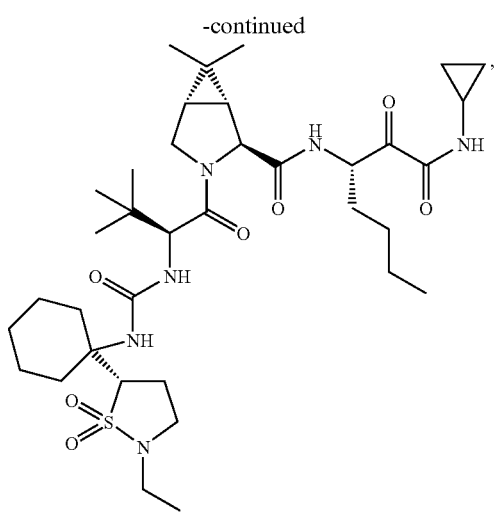
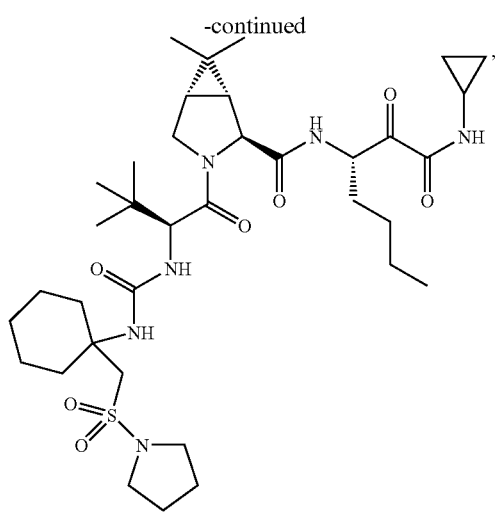
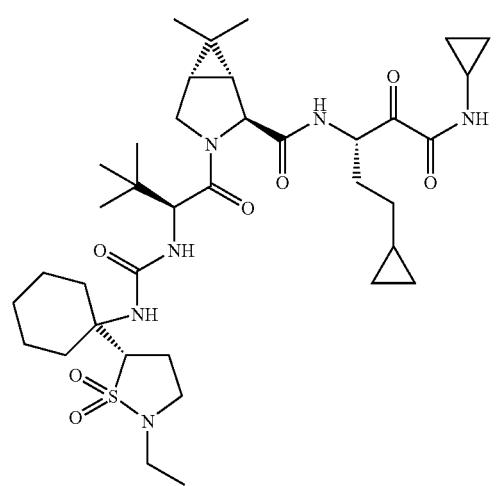
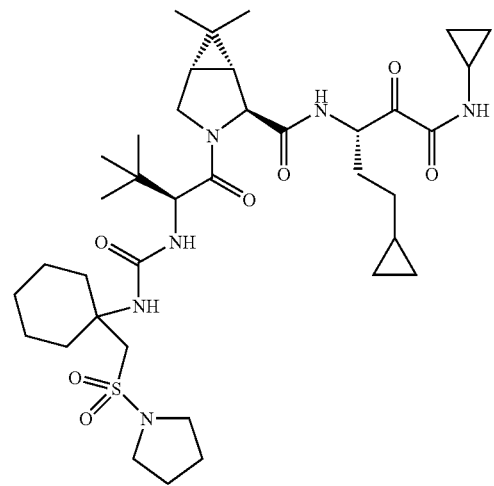
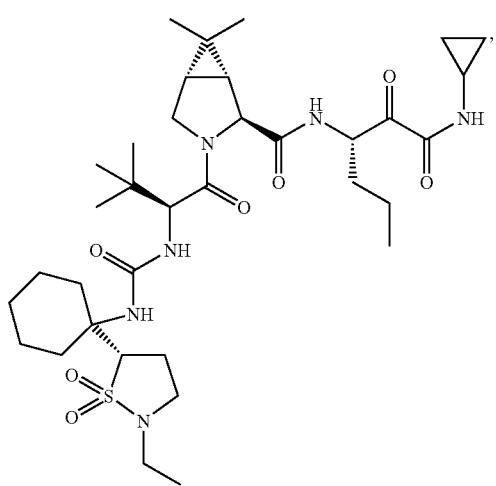
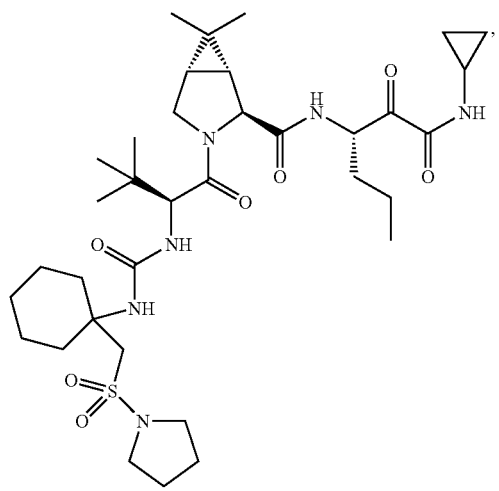

-continued
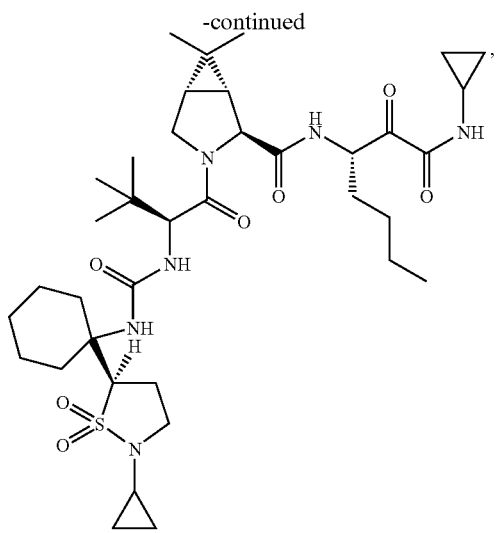
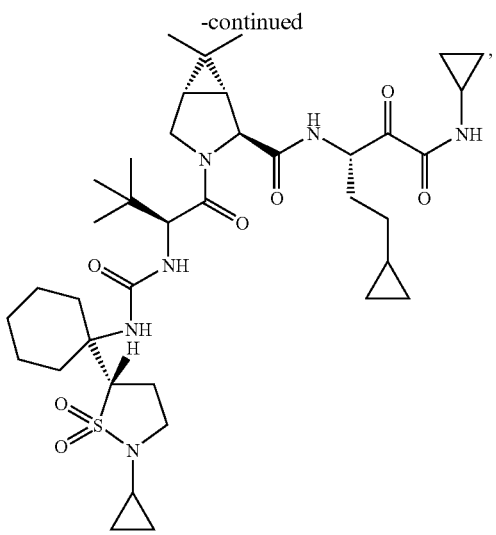
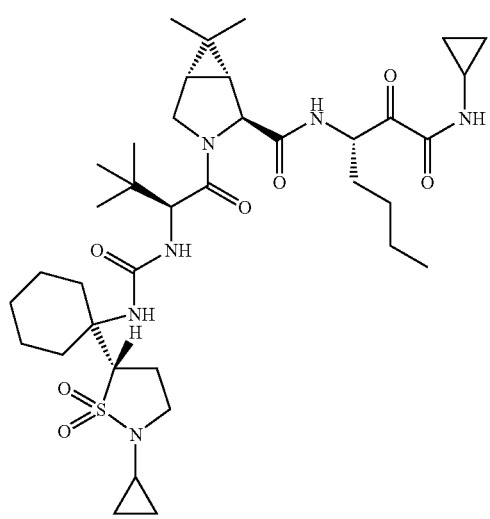
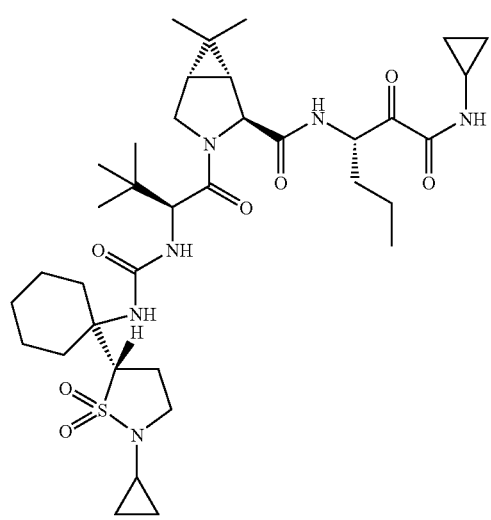
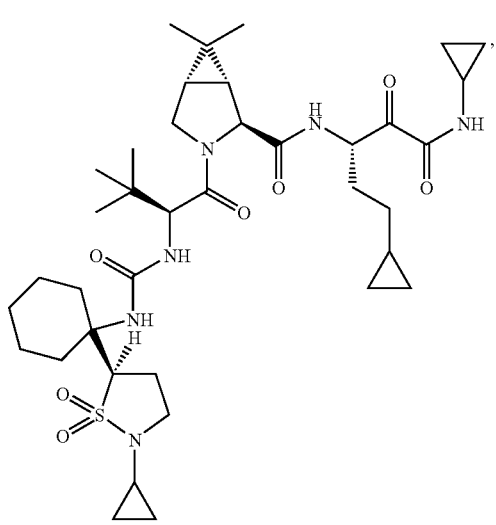
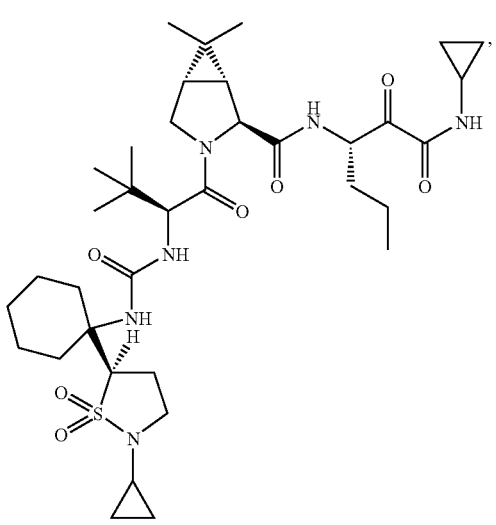

-continued
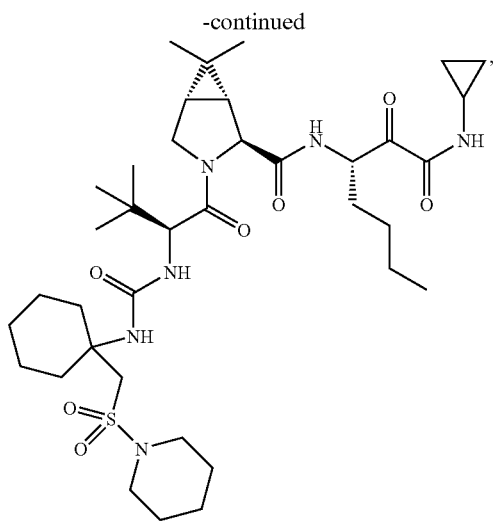
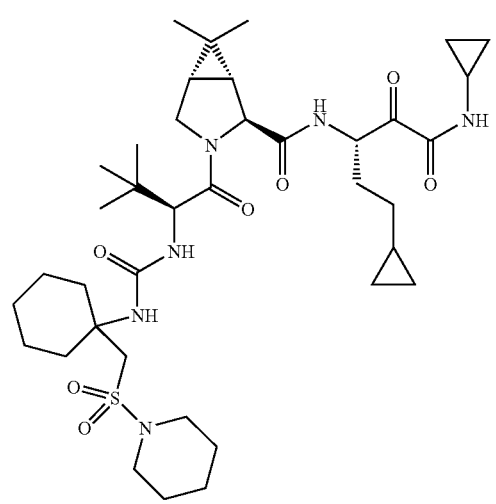
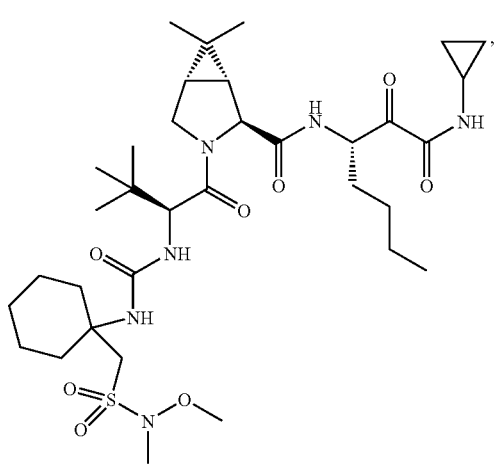
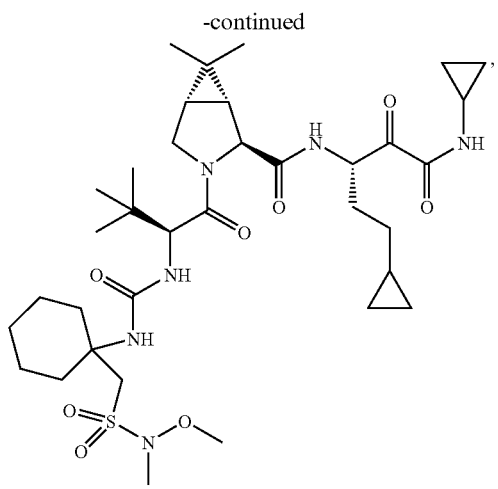
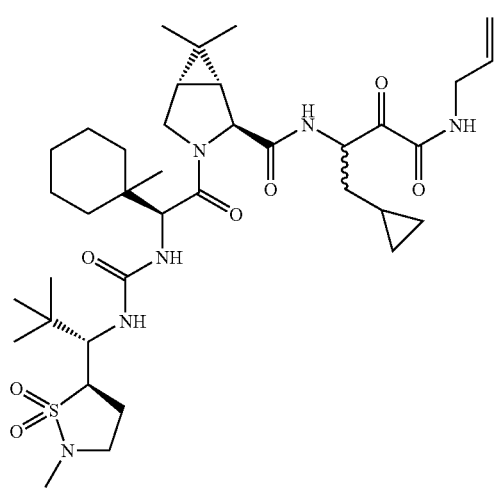
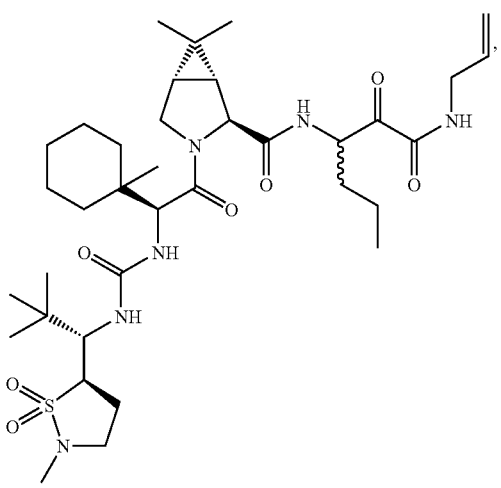

-continued
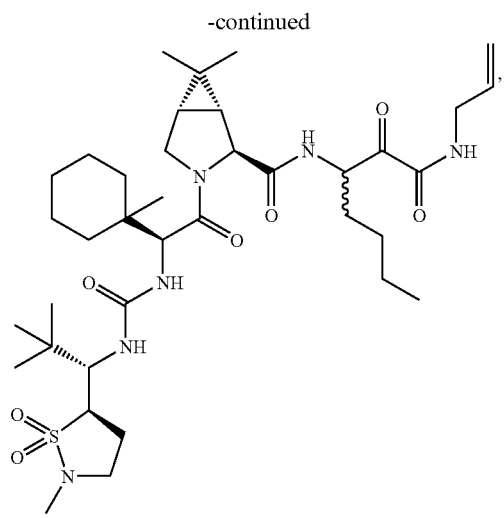
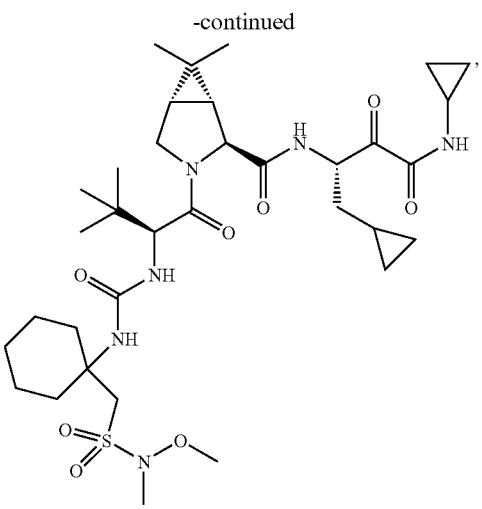
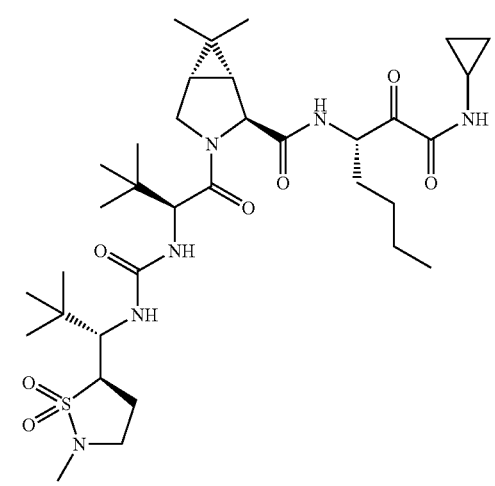
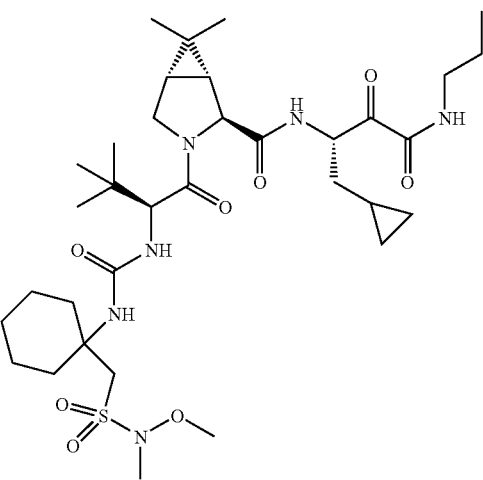
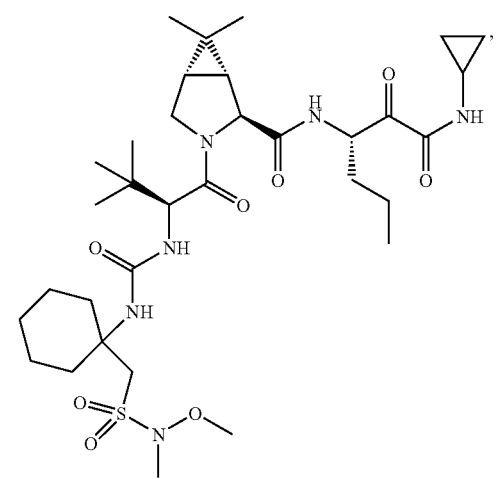
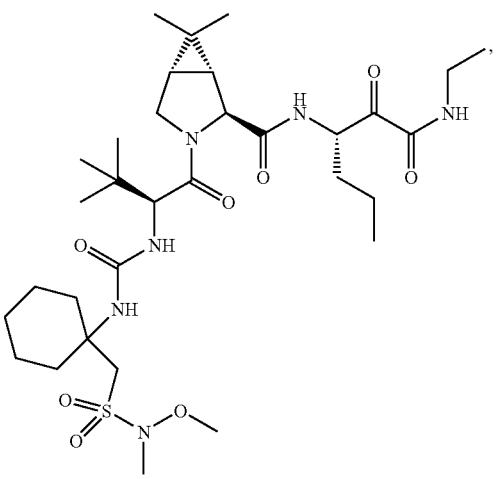

-continued
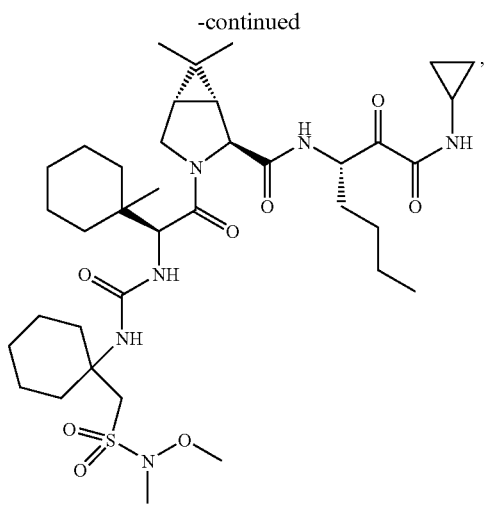
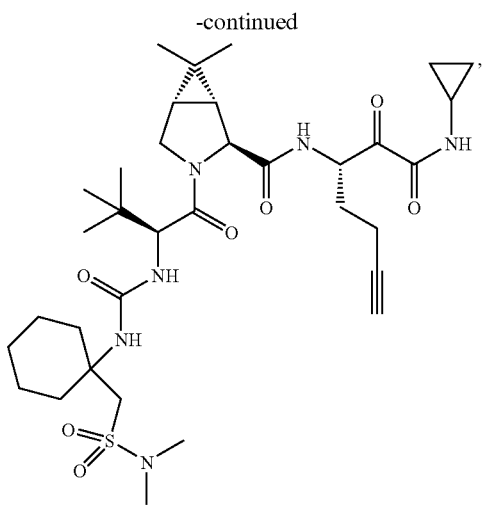
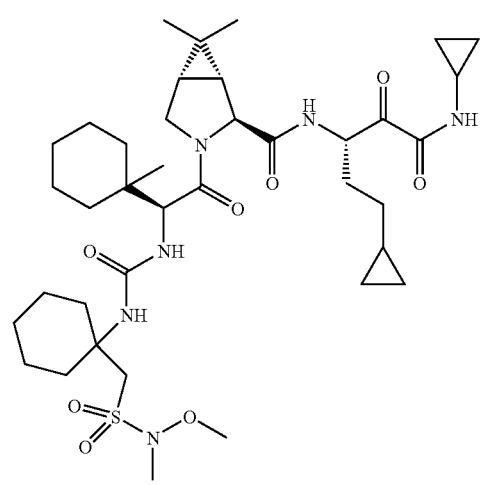
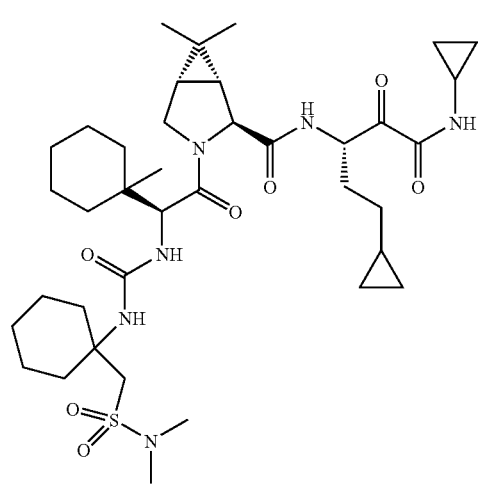
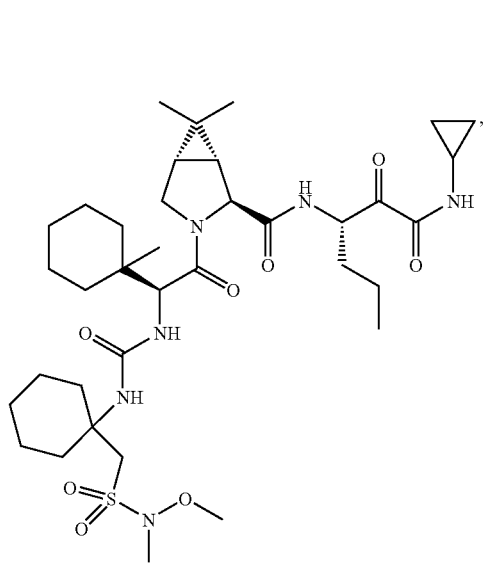
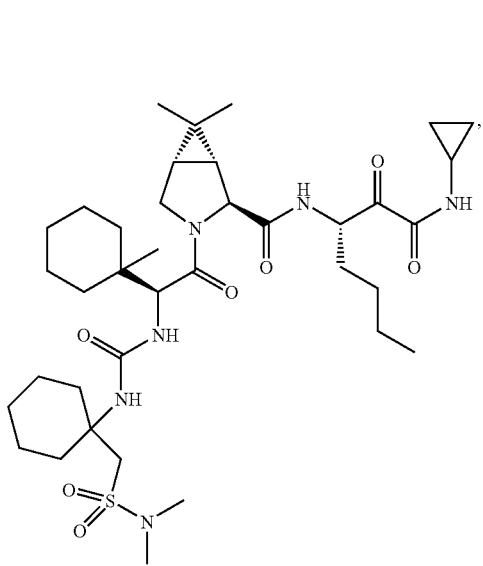

19
-continued
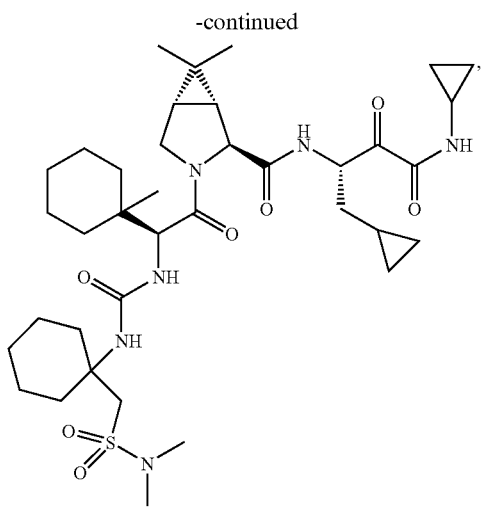
20
-continued
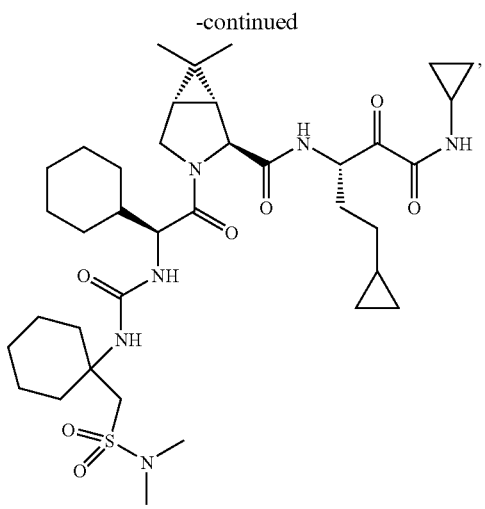
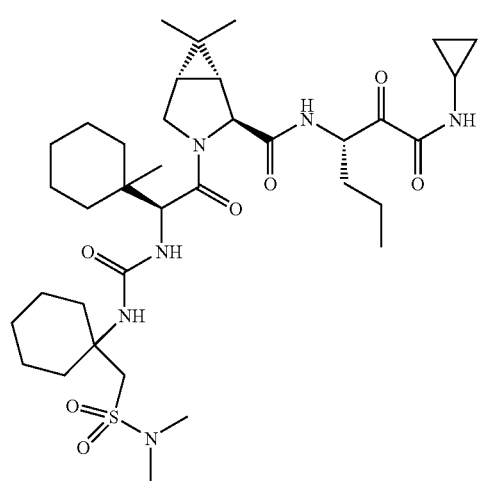
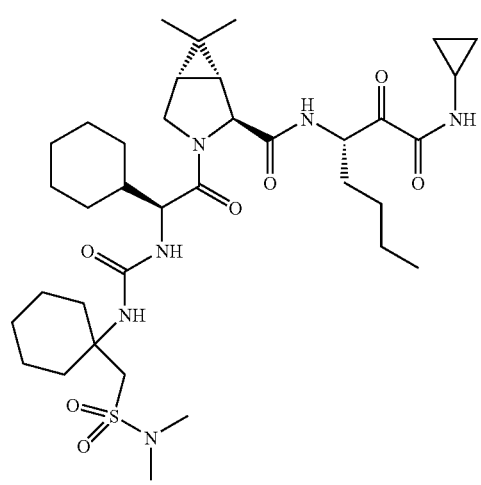
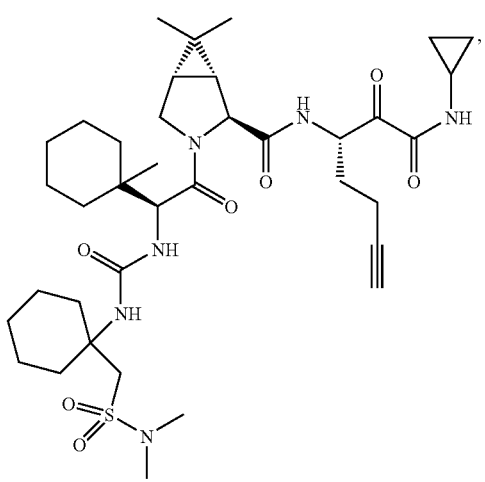
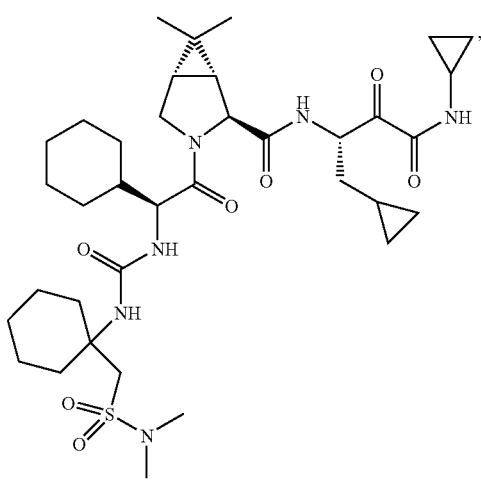

21
-continued
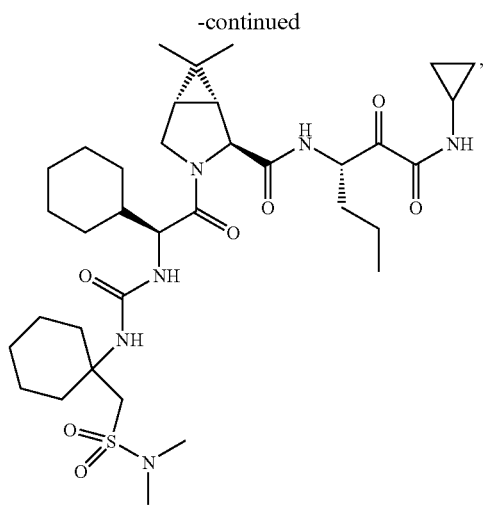
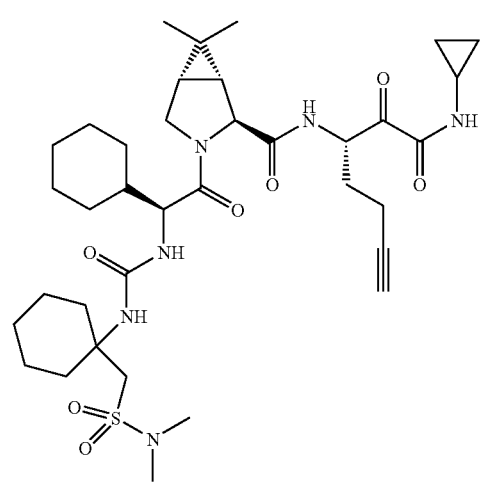
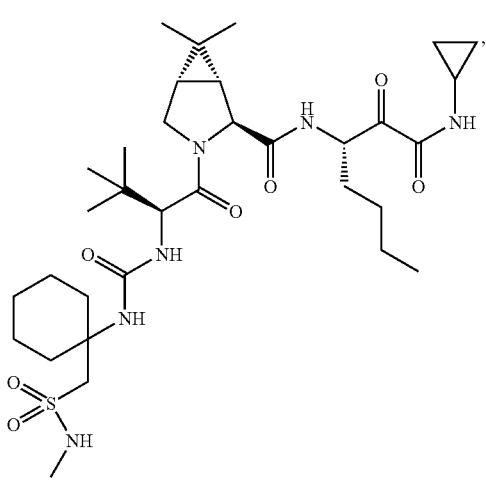
22
-continued
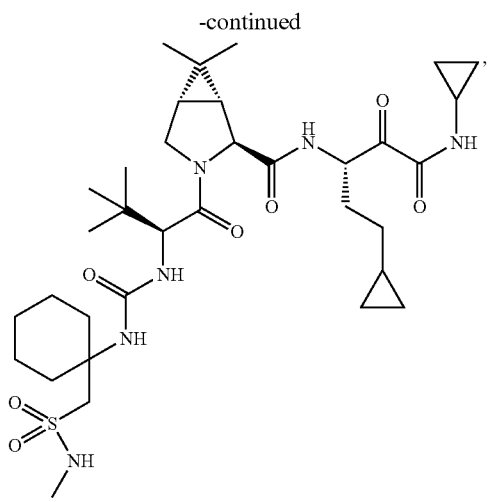
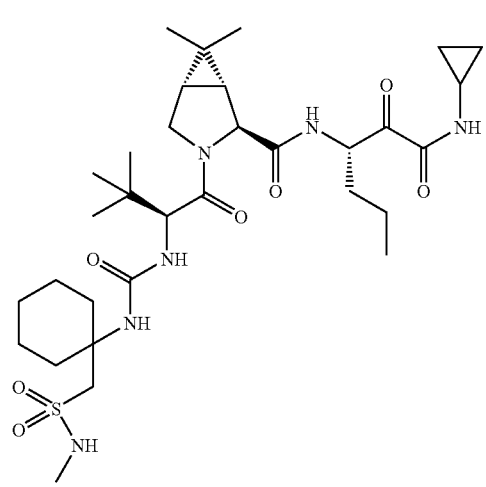
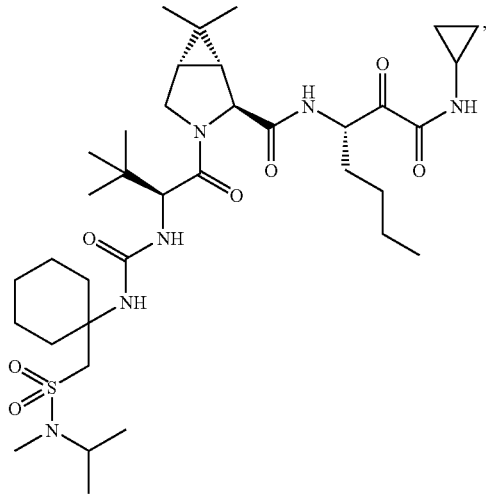

-continued
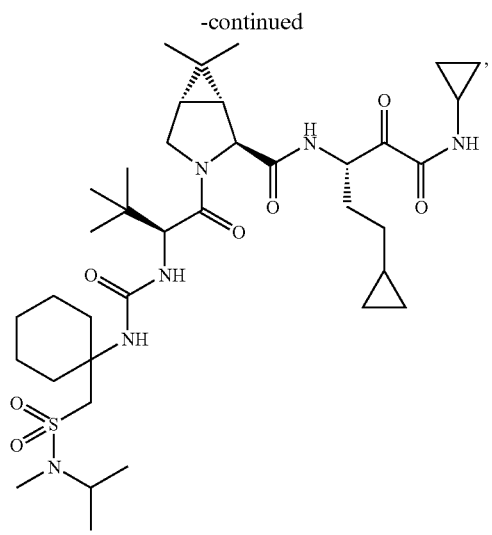
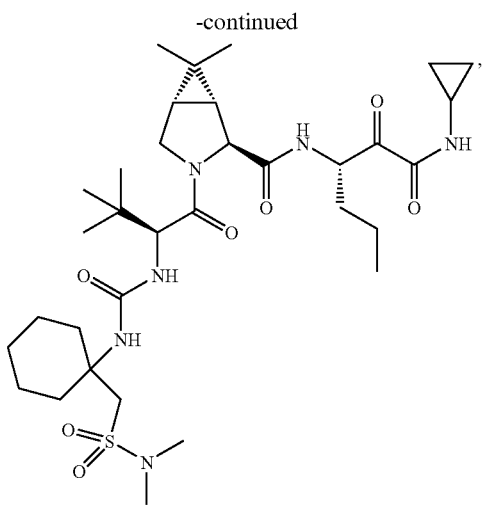
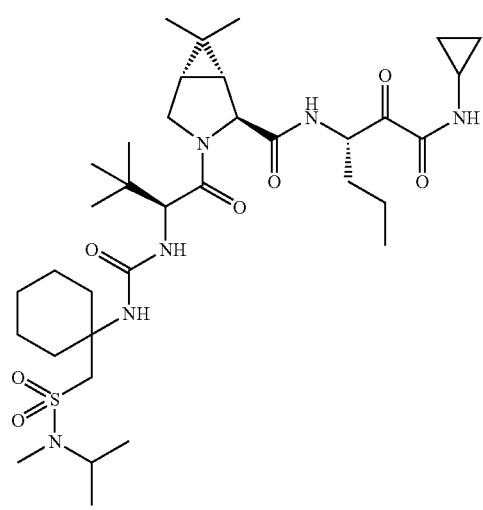
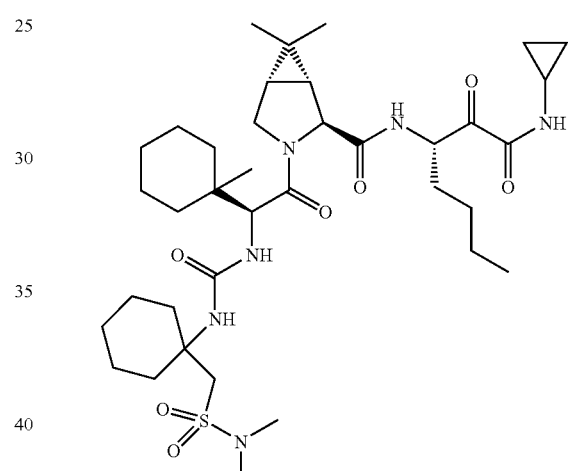
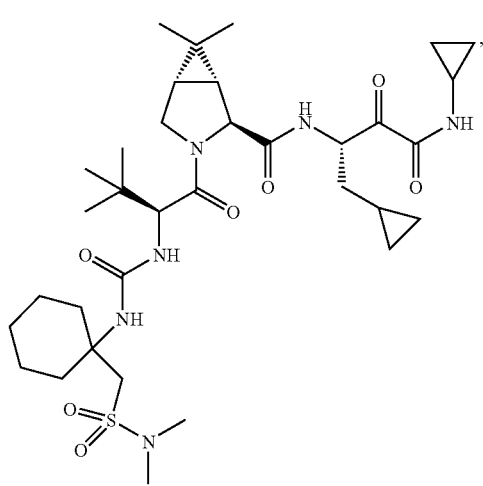
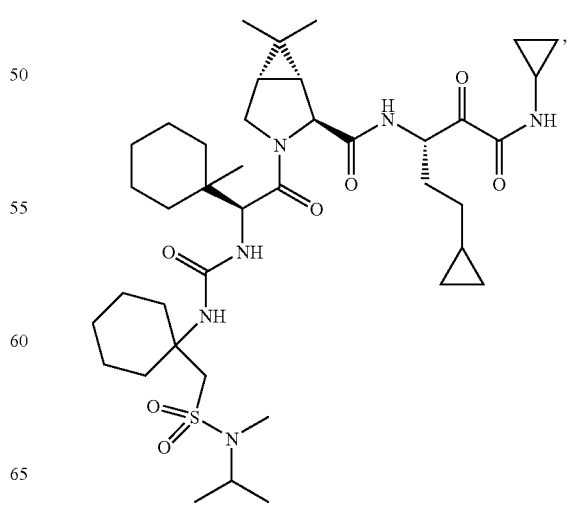

-continued
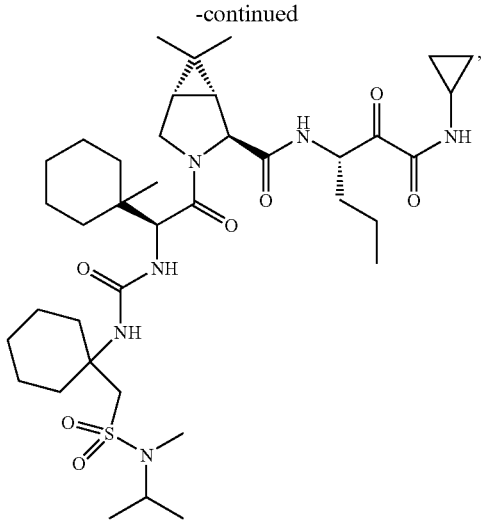
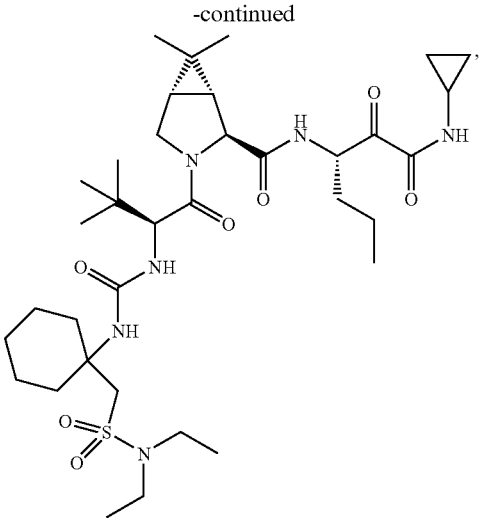
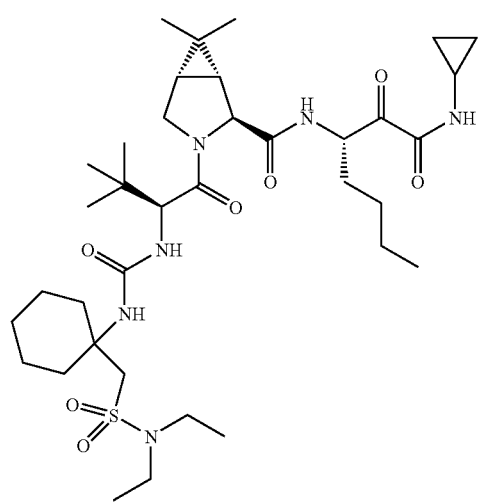
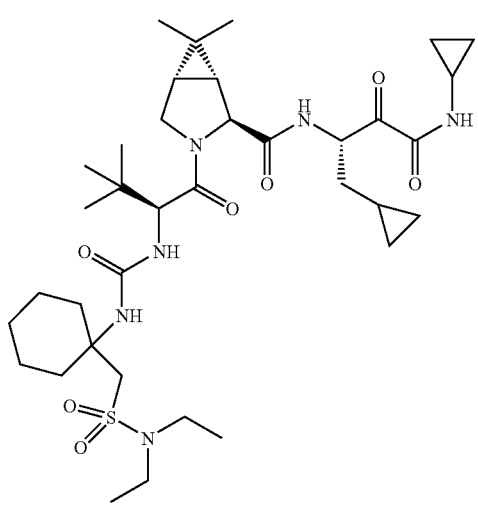
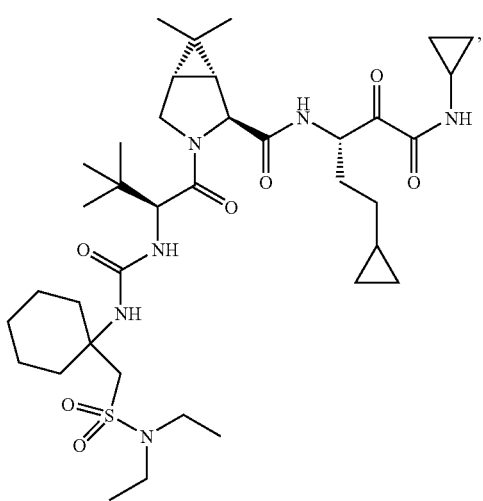
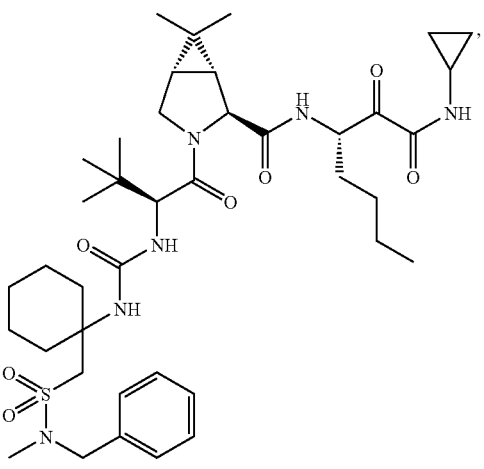

-continued
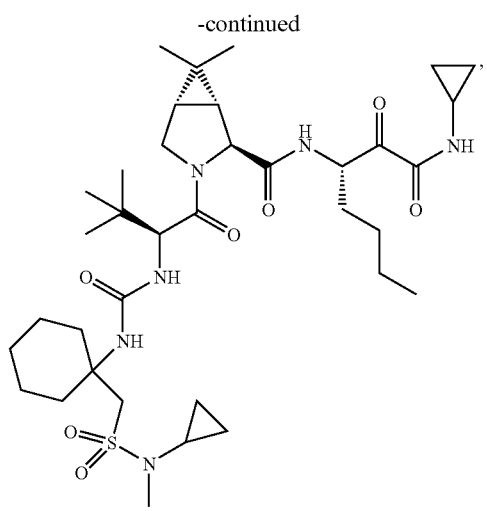
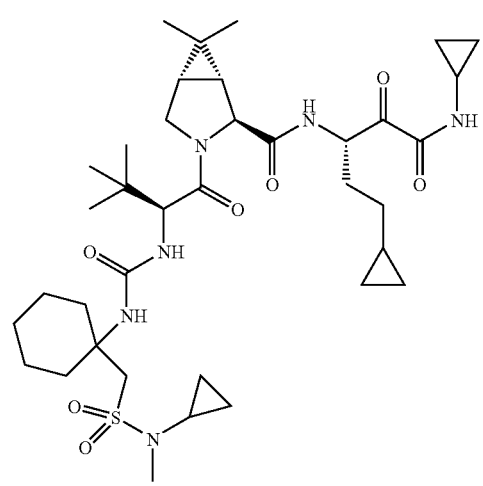
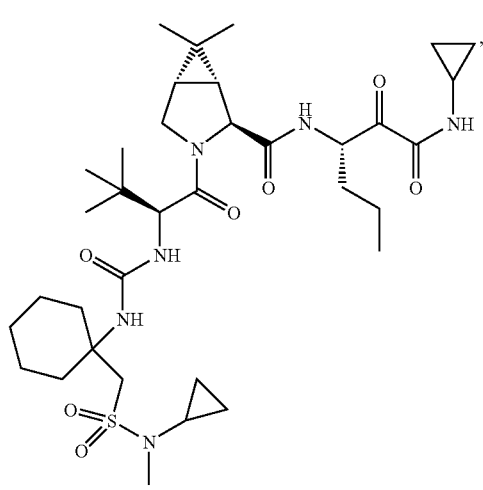
-continued
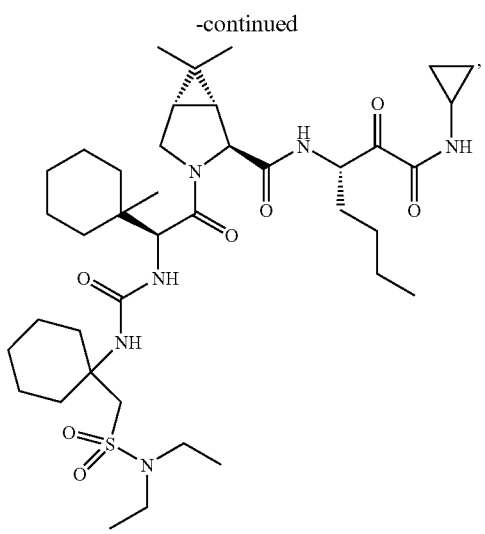
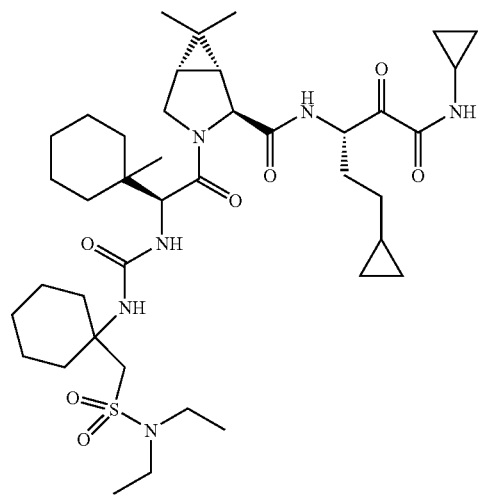
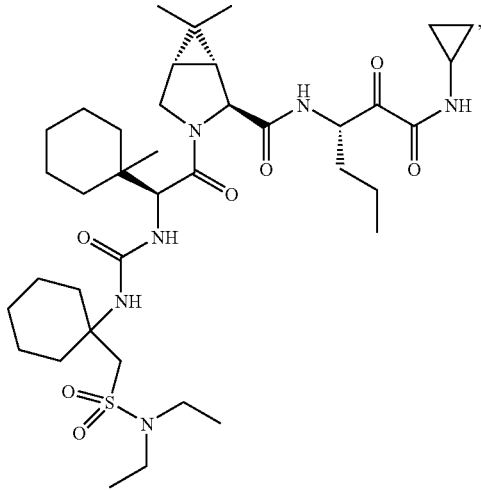

29
-continued
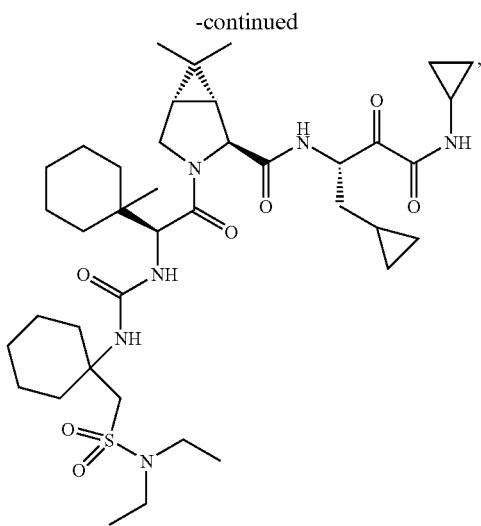
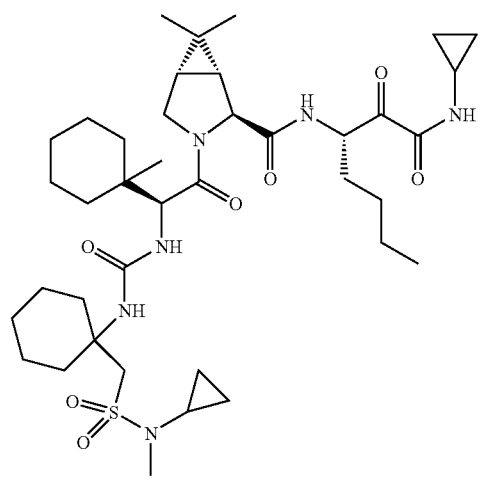
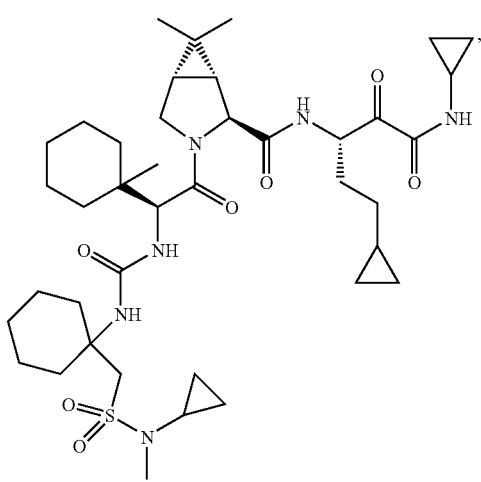
30
-continued
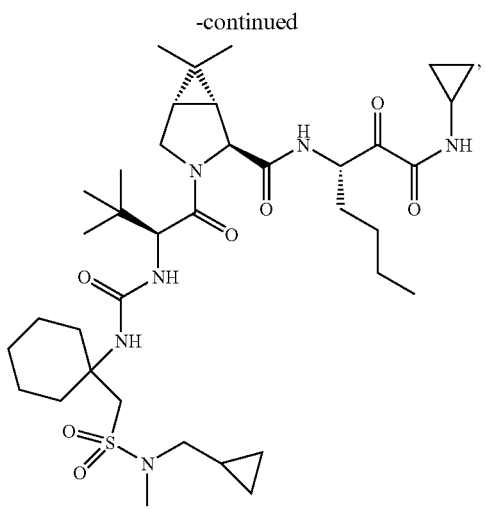
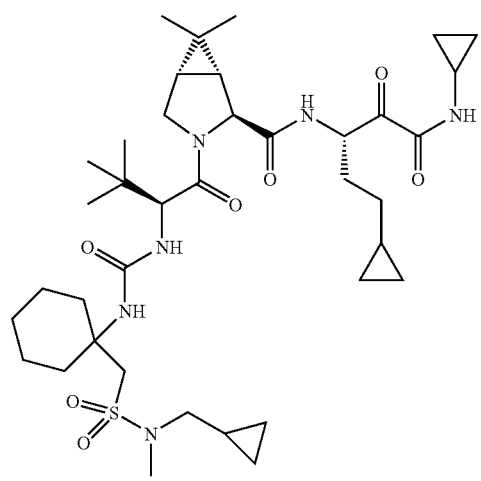
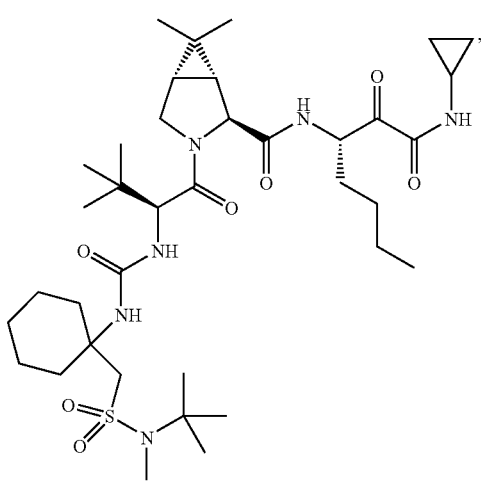

-continued
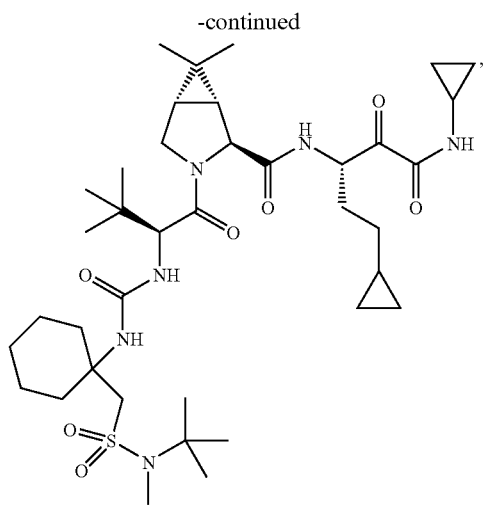
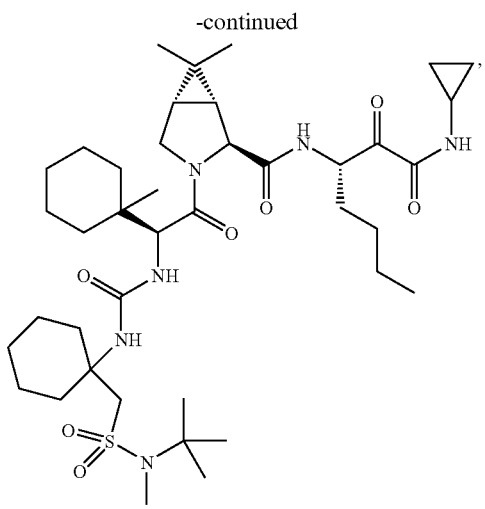
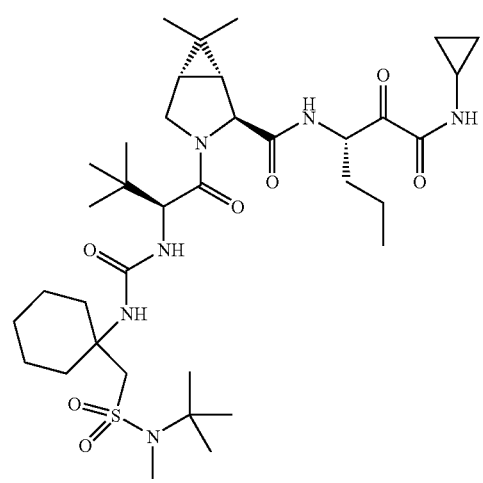
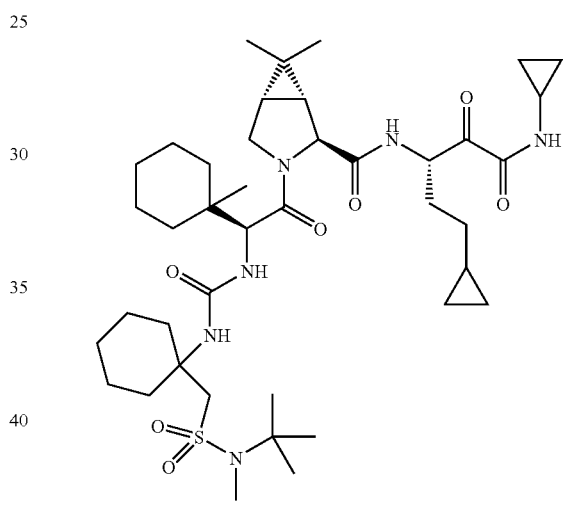
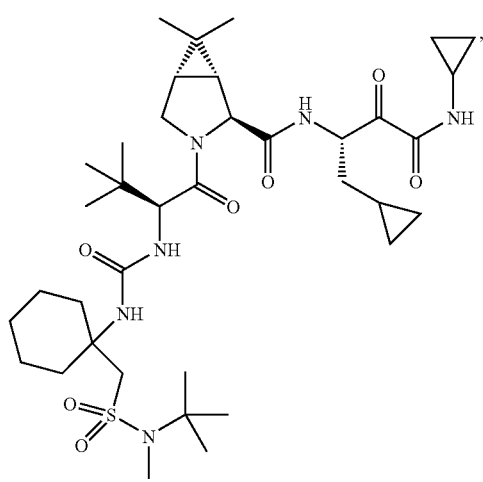
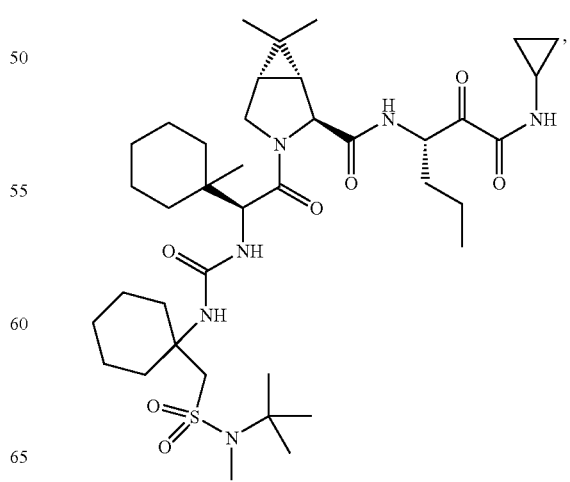

-continued
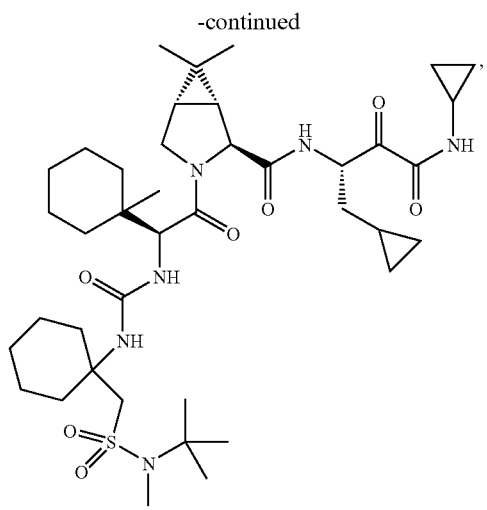
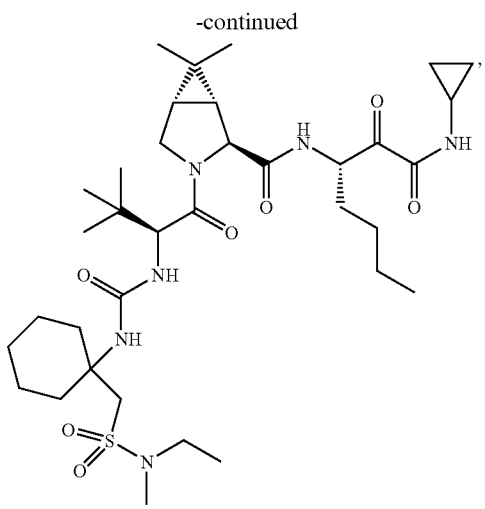
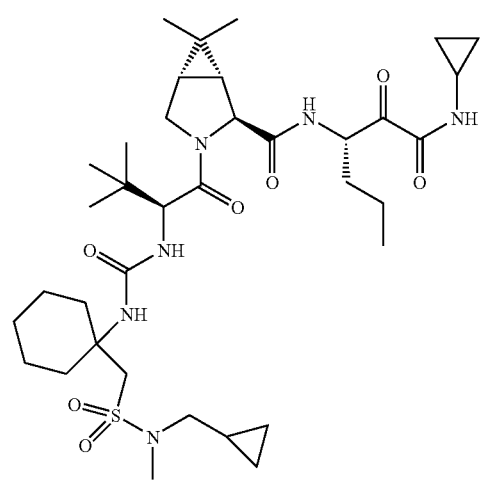
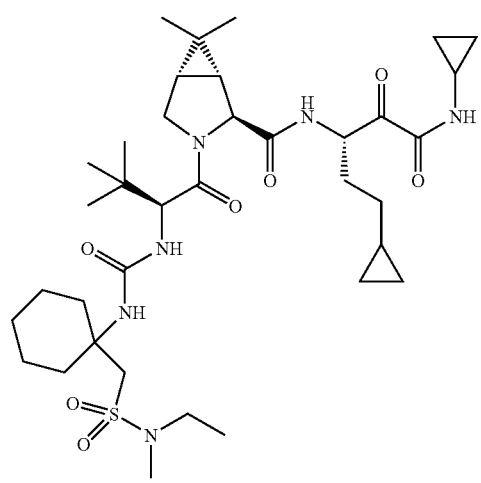
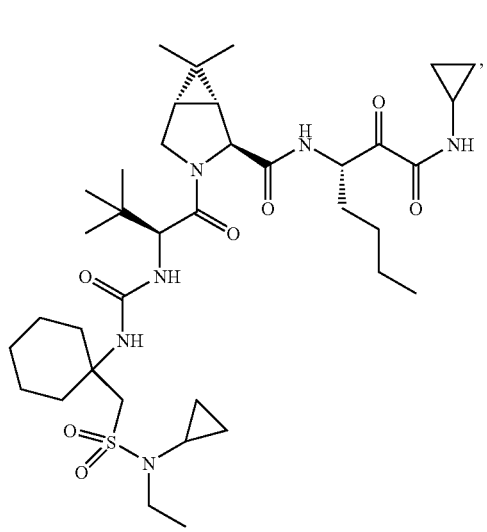
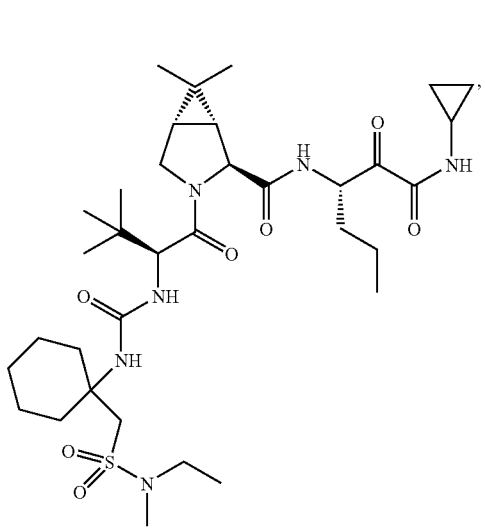

-continued
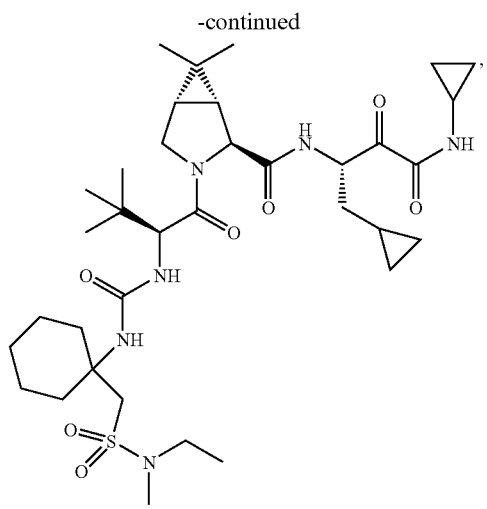
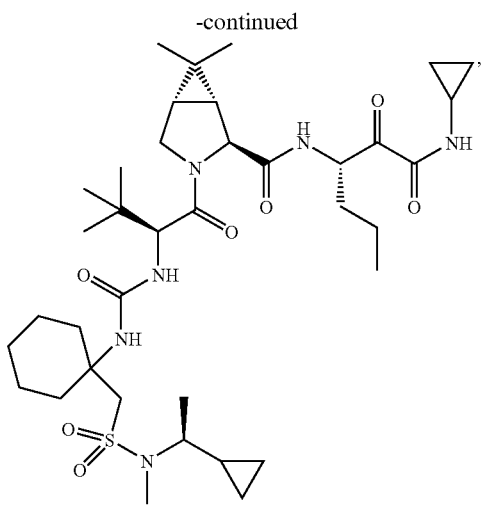
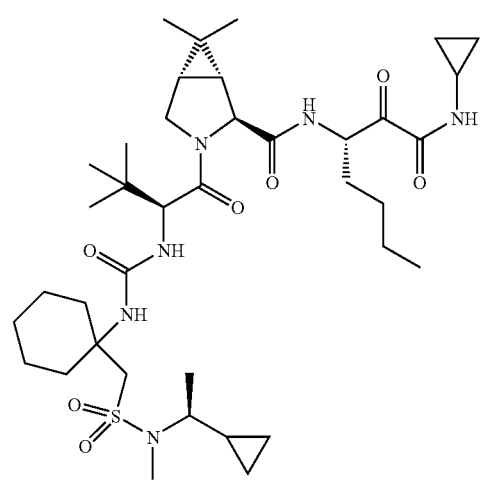
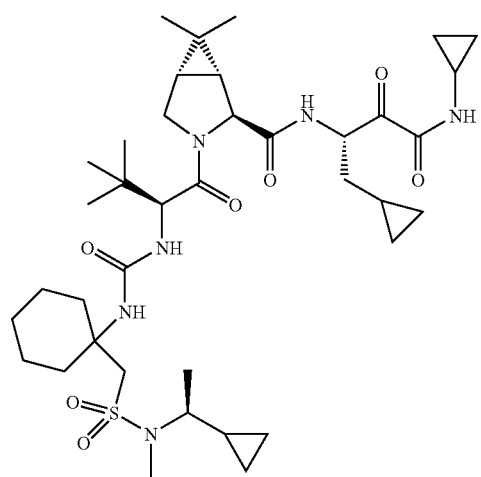
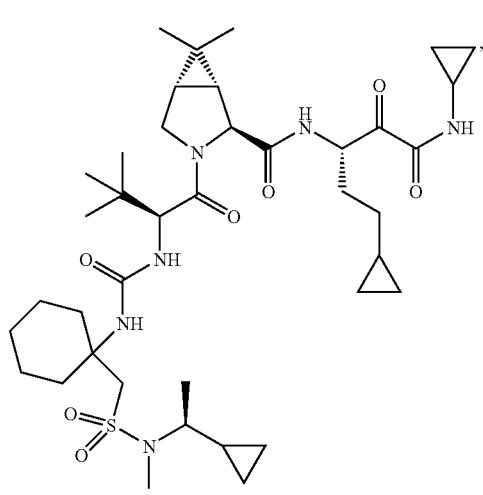
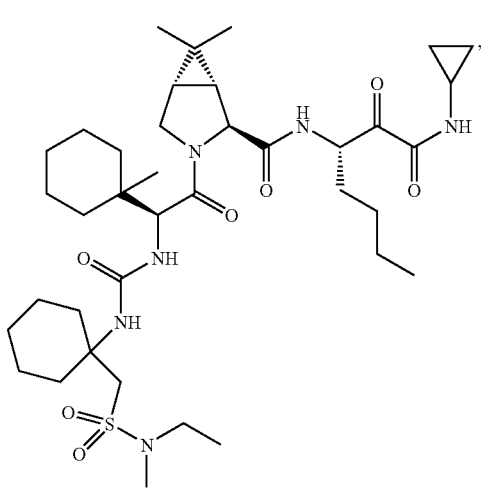

-continued
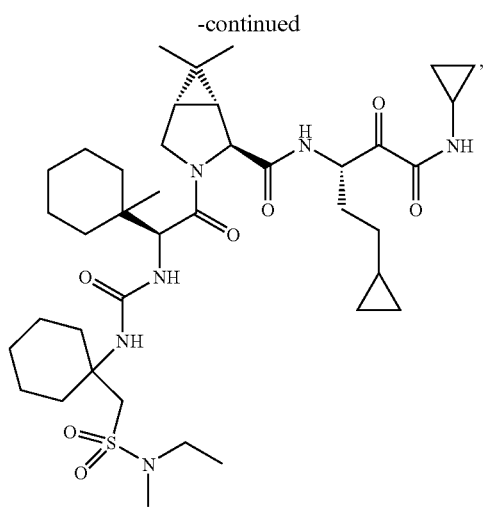
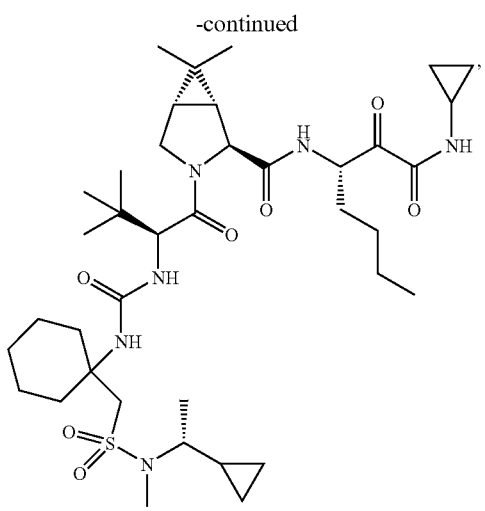
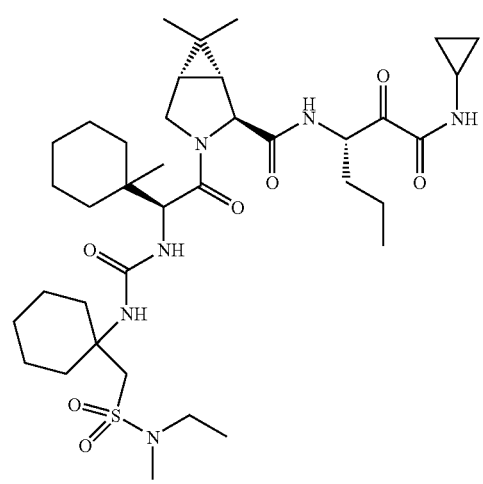
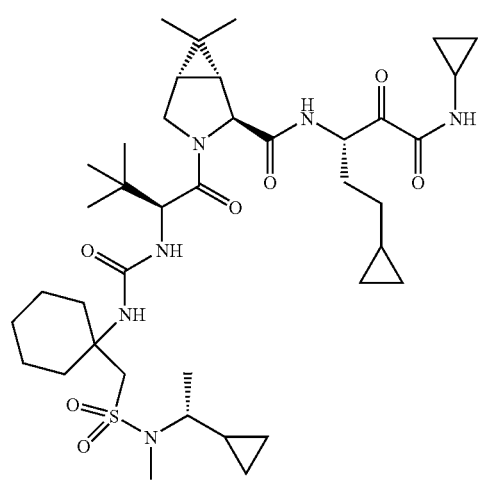
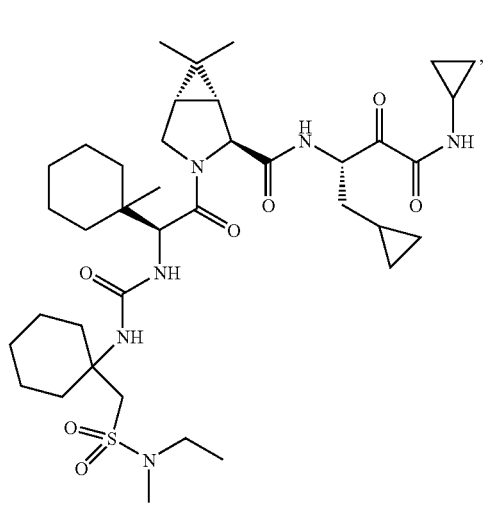
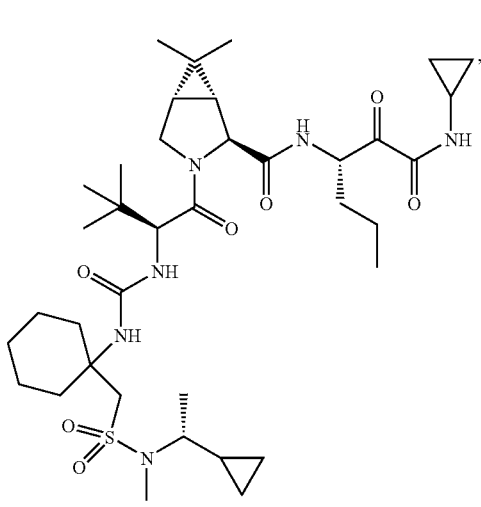

-continued
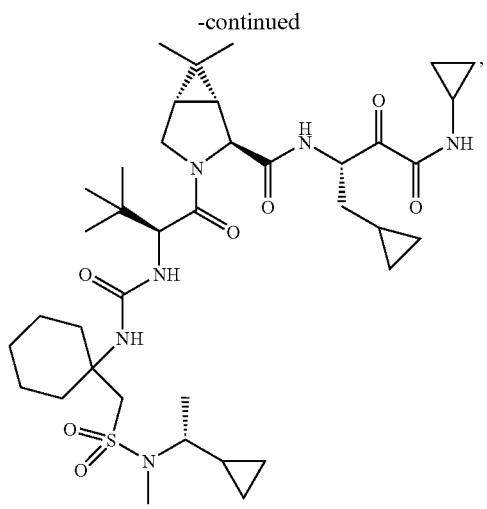
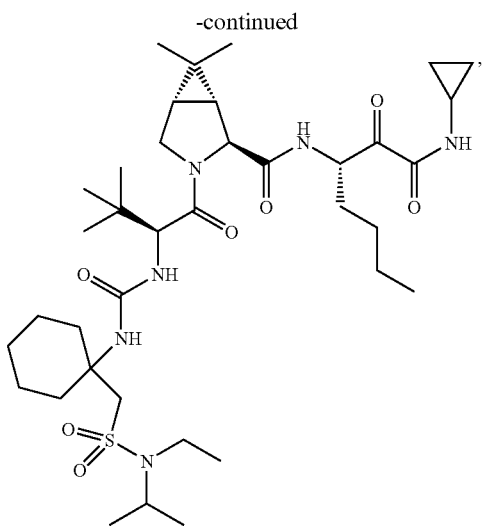
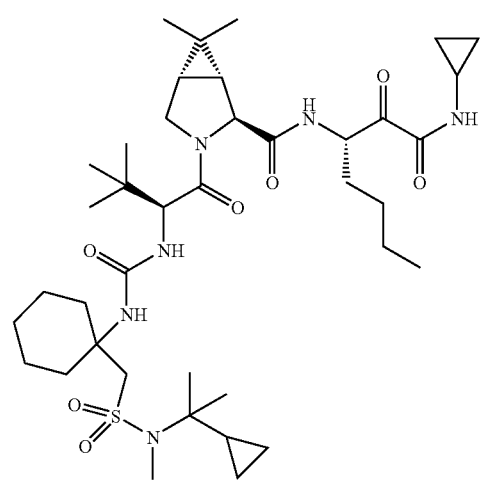
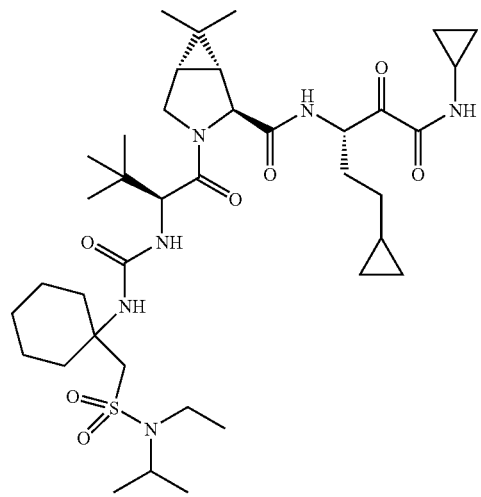
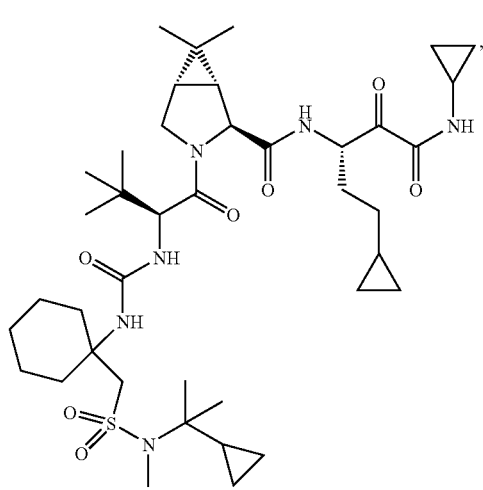
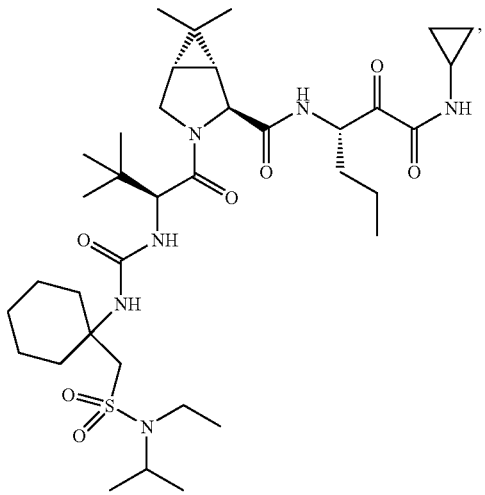

-continued
| 41 | 42 |
|---|---|
| 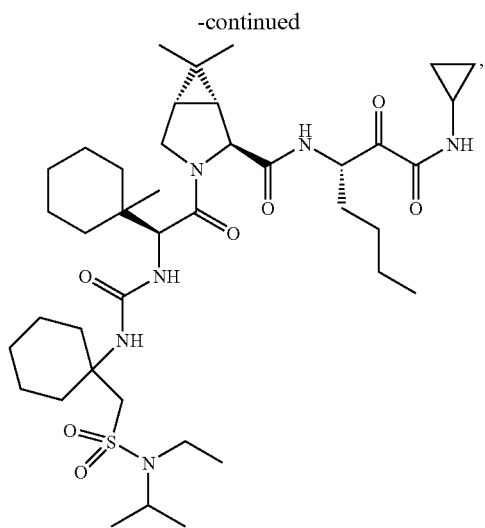 | 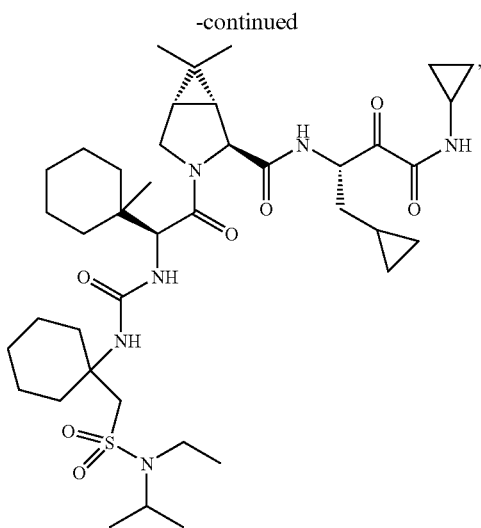 |
| 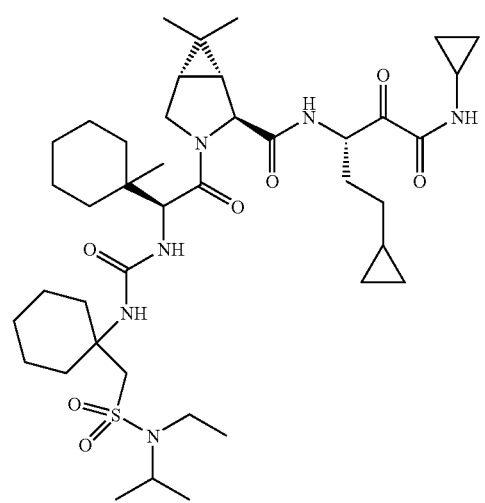 | 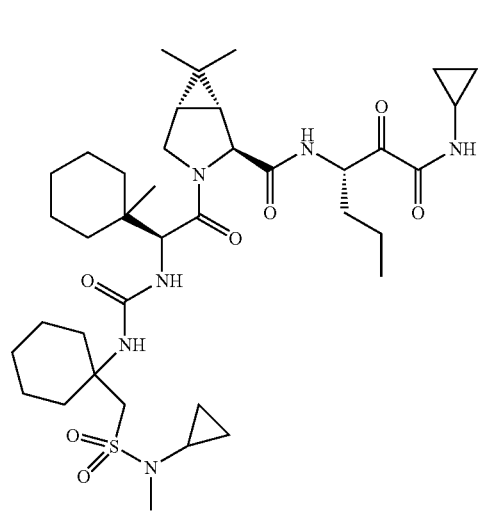 |
| 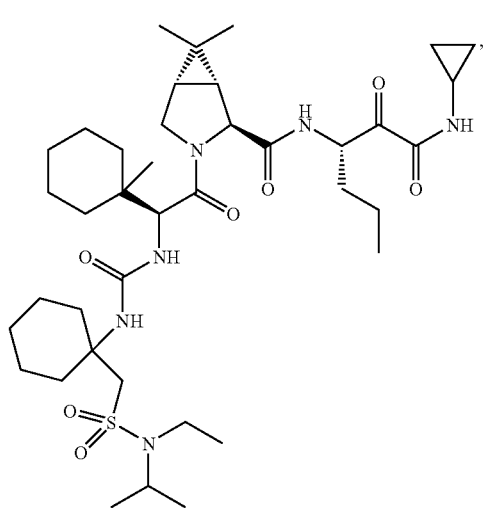 | 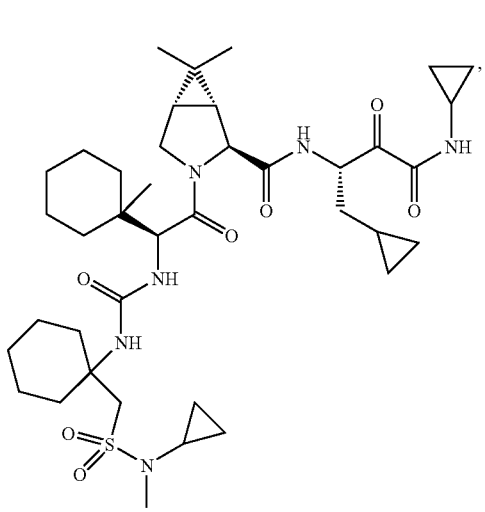 |

-continued
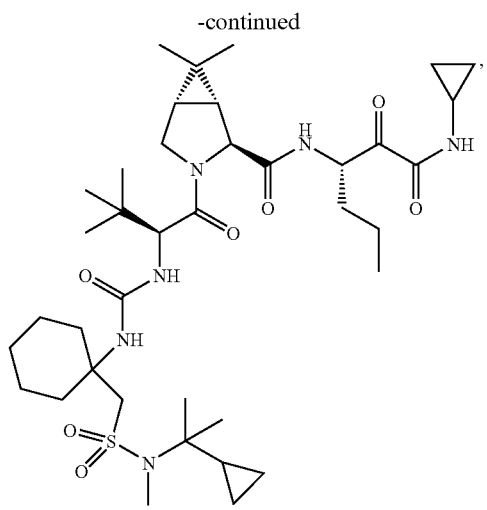
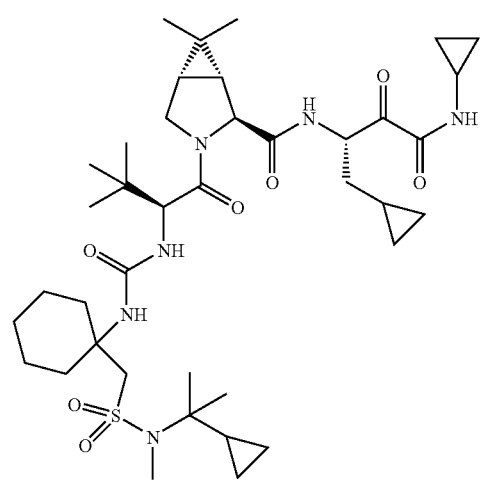
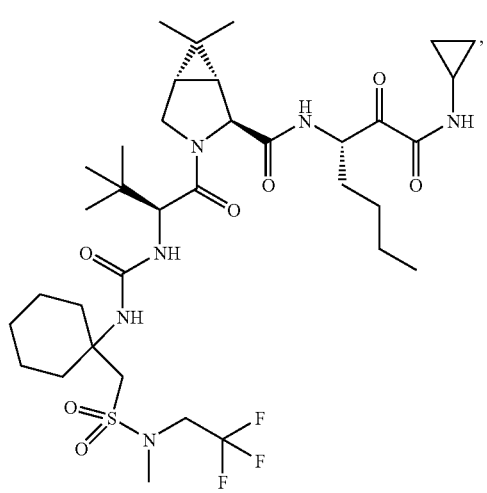
-continued
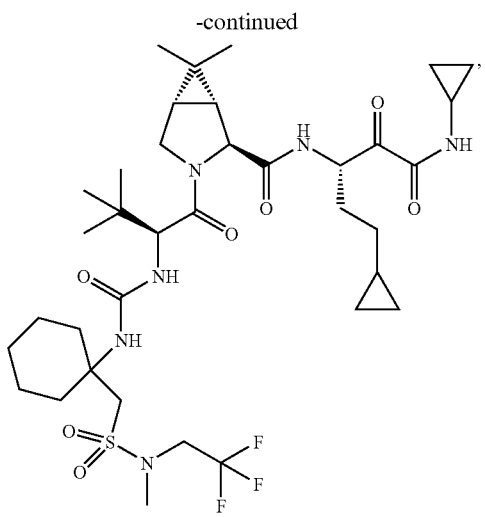
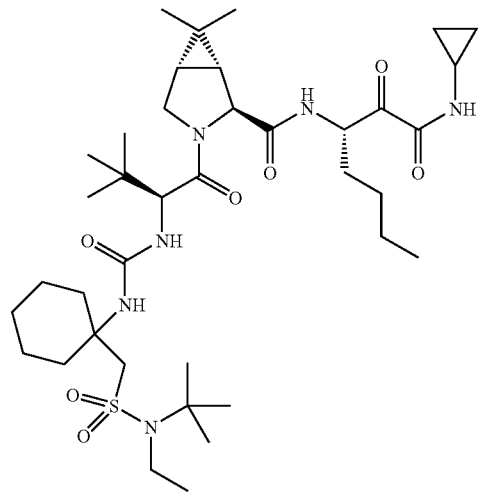
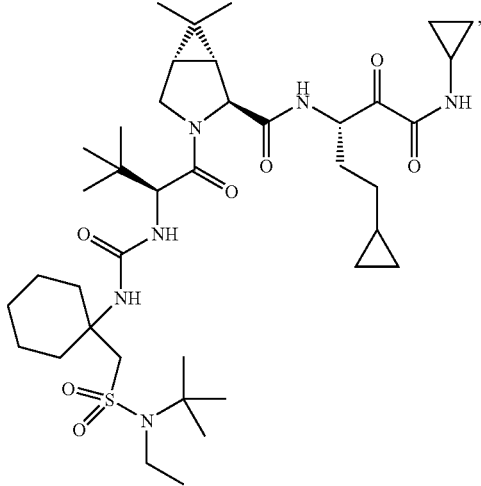

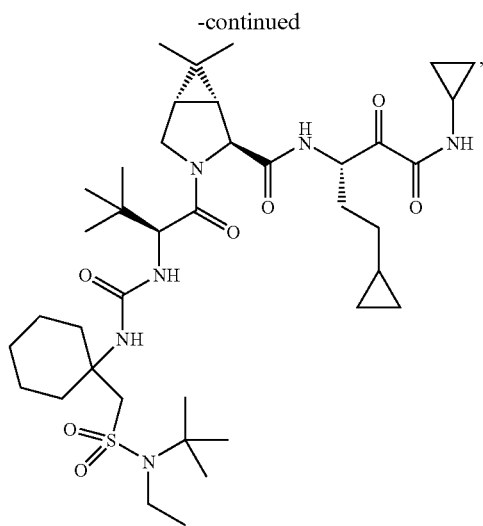
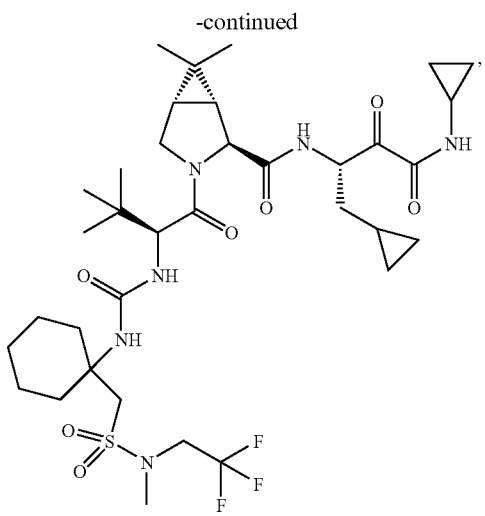
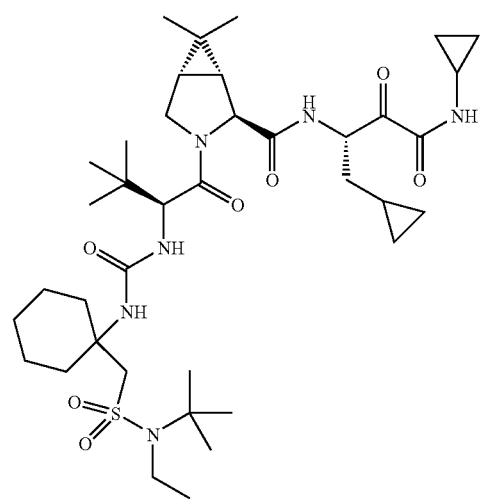
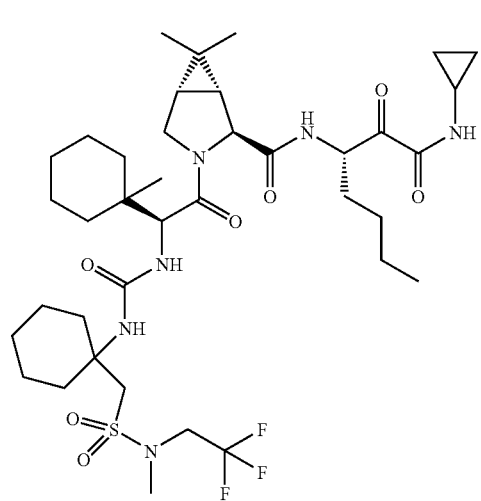
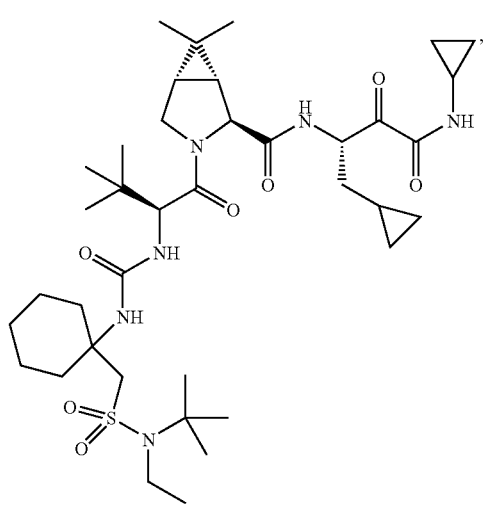
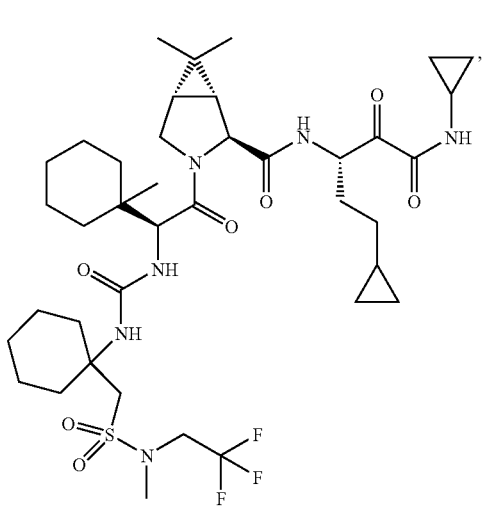

47
-continued
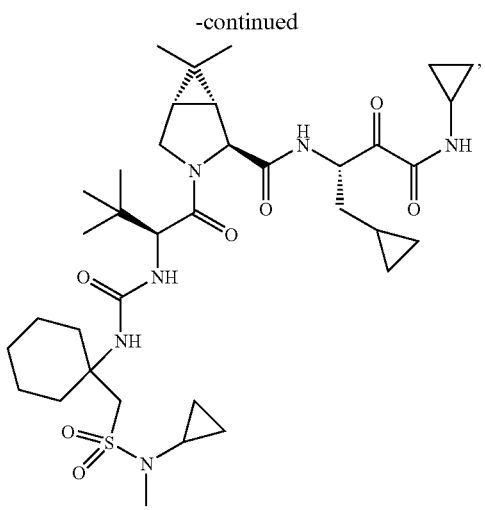
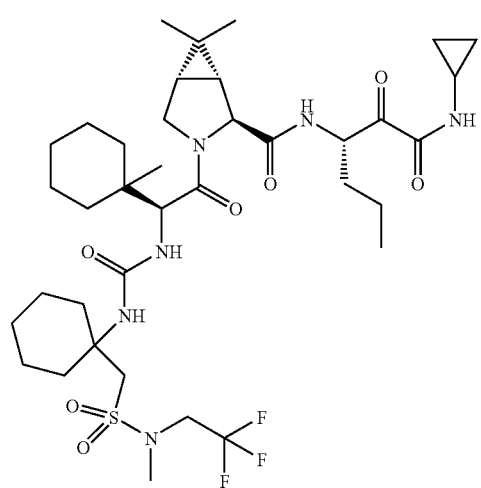
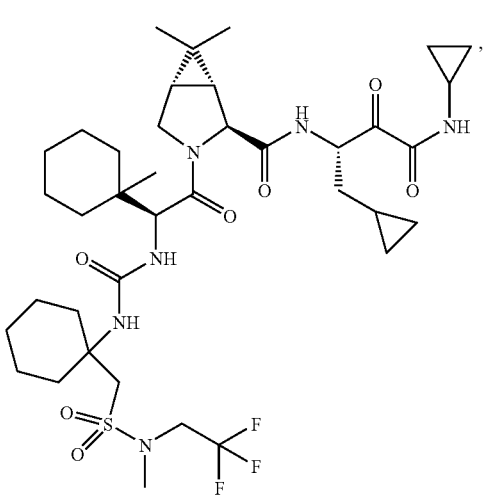
48
-continued
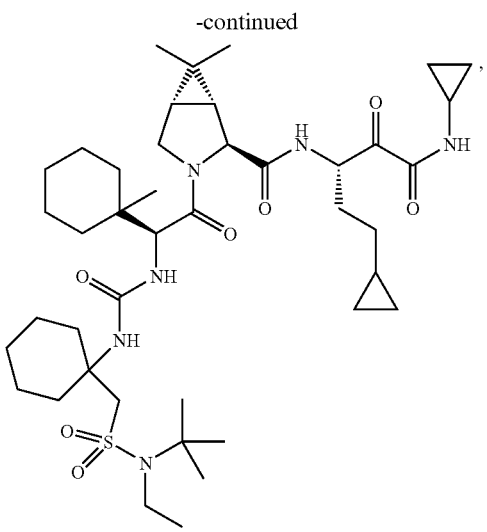
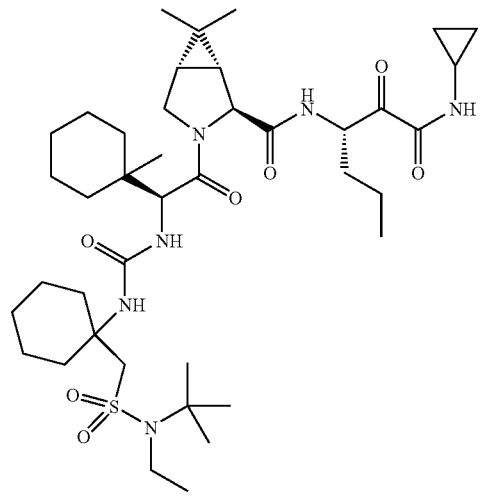
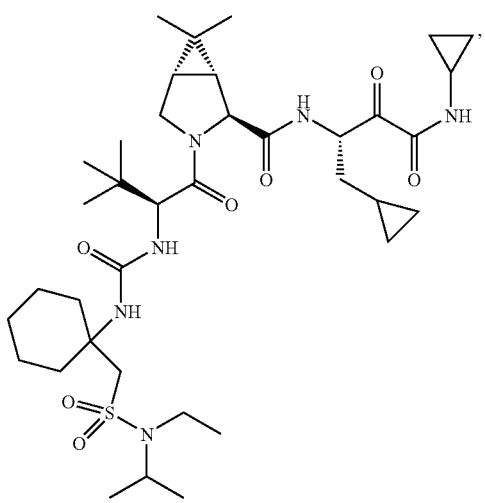

-continued
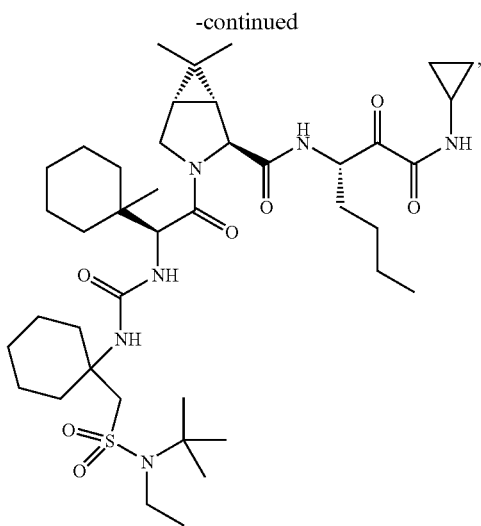
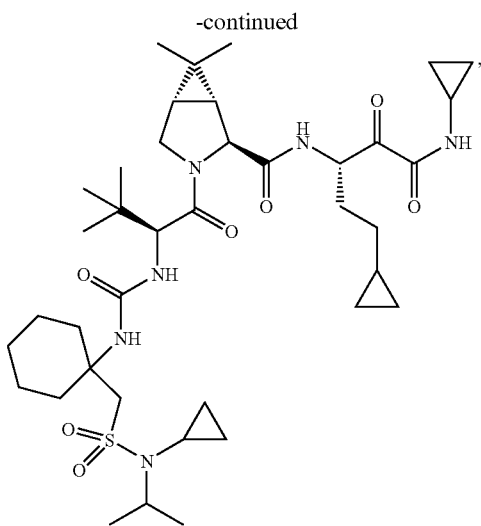
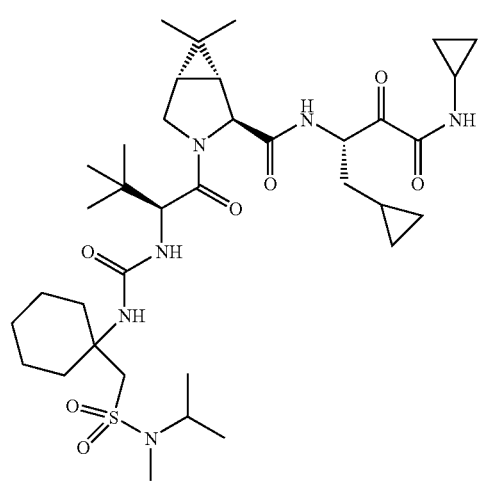
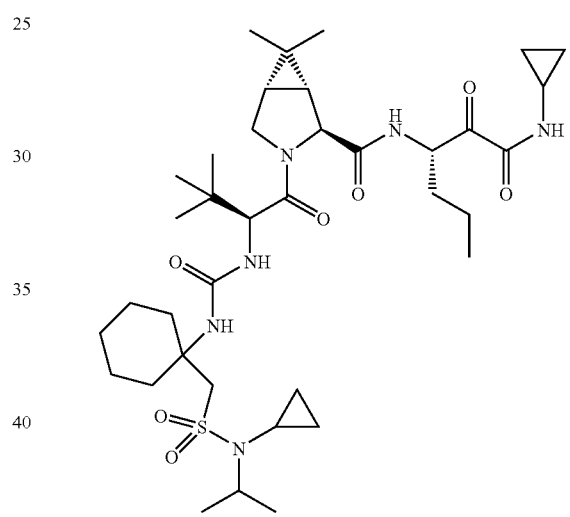
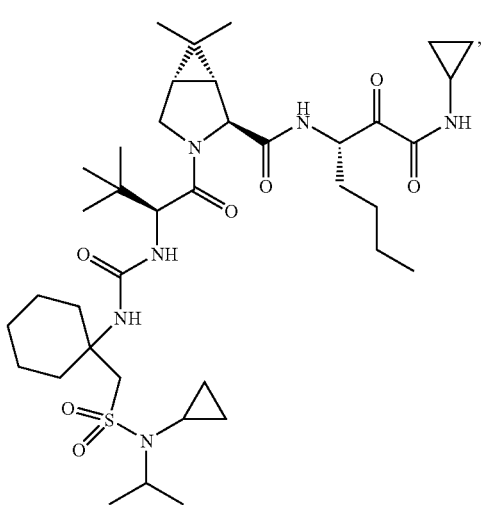
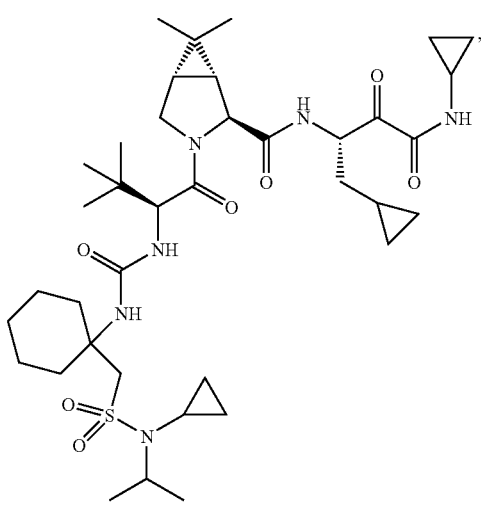

-continued
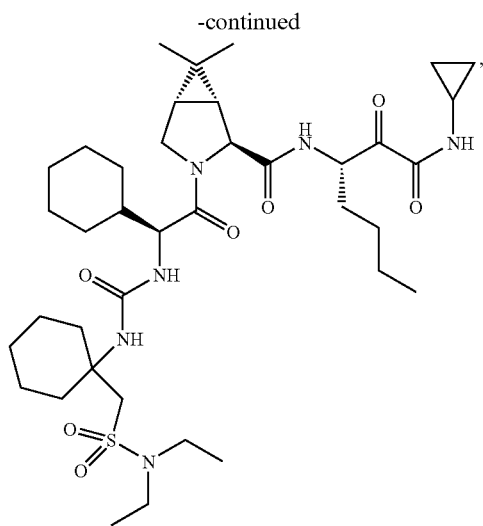
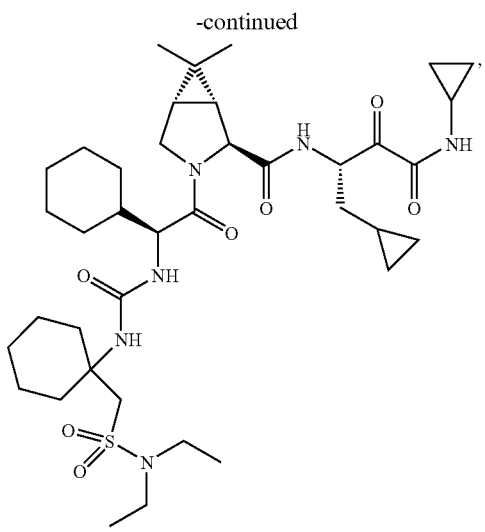
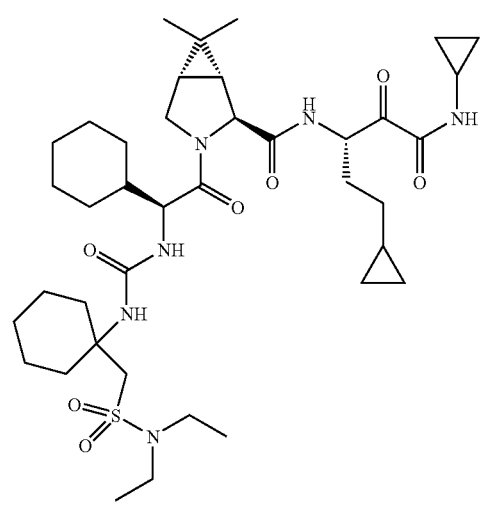
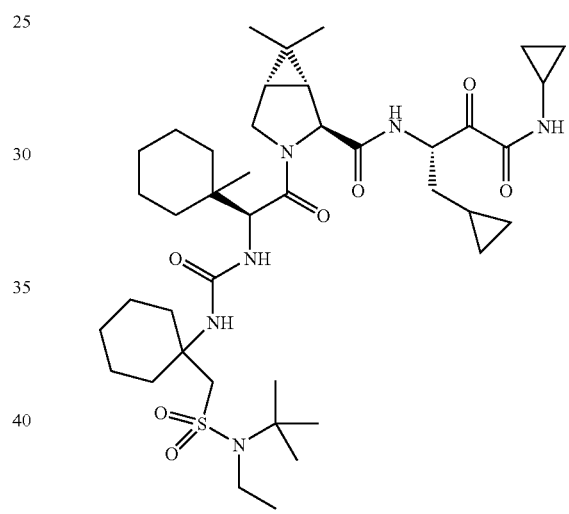
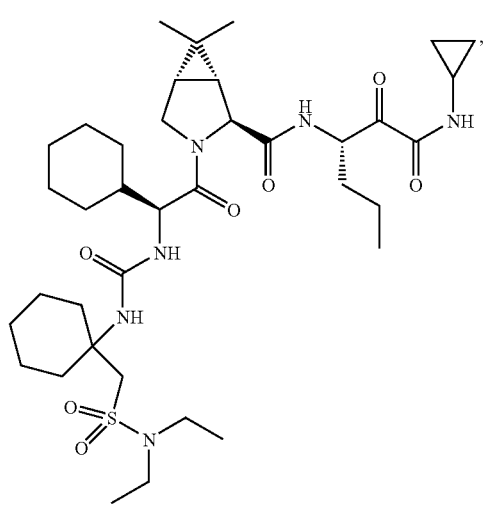
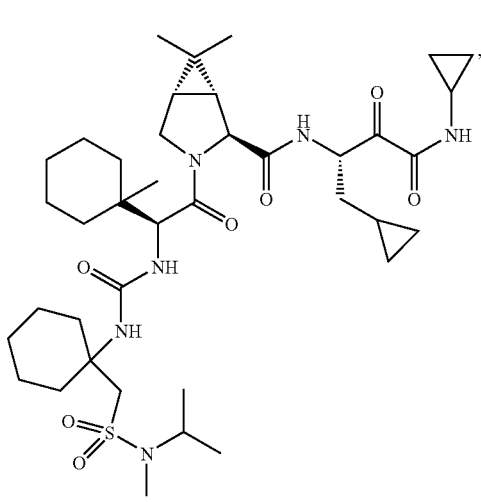

53
-continued
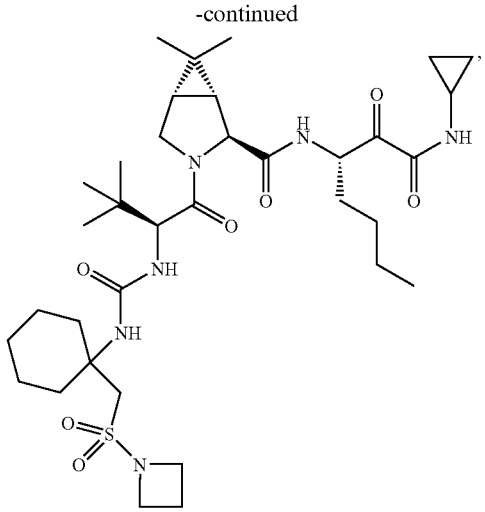
54
-continued
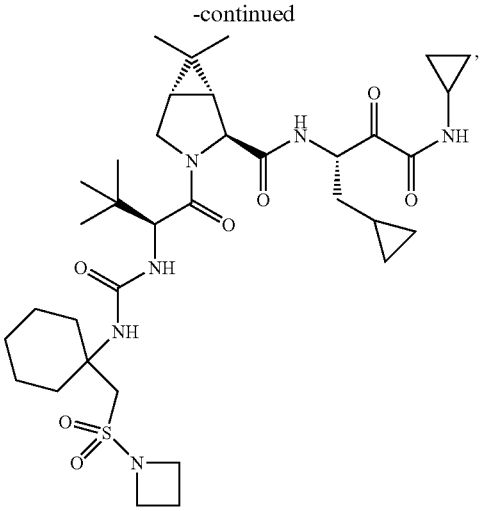

-continued
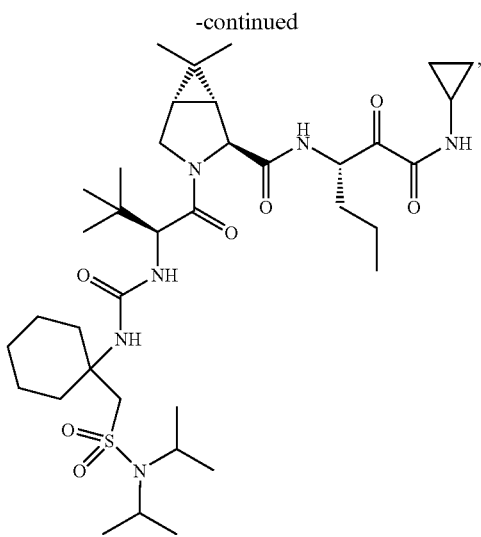
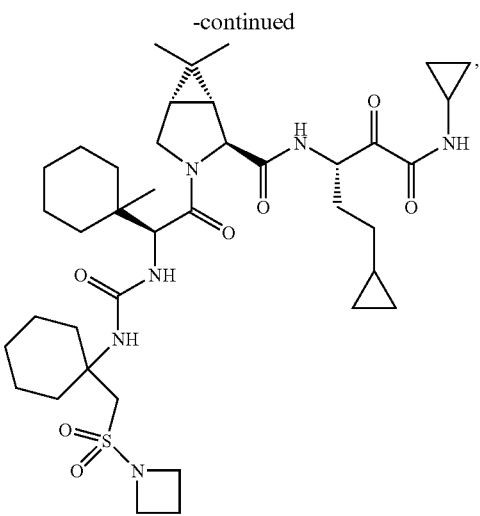
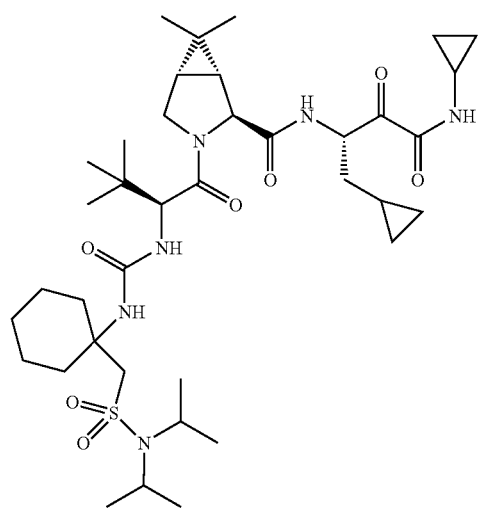
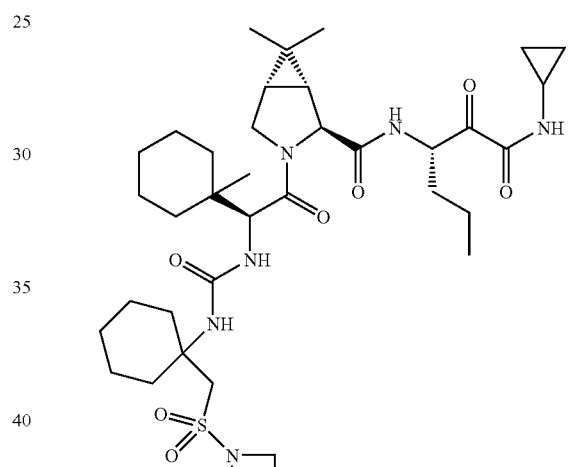
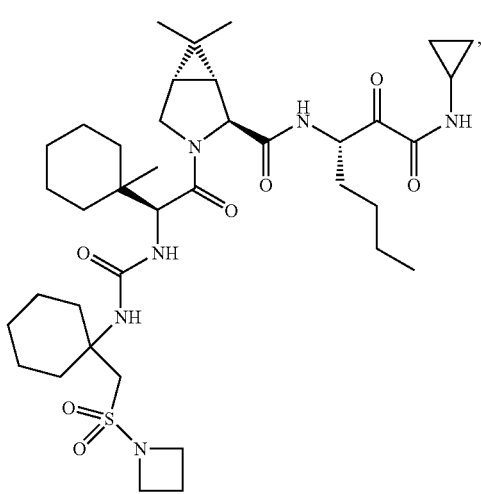
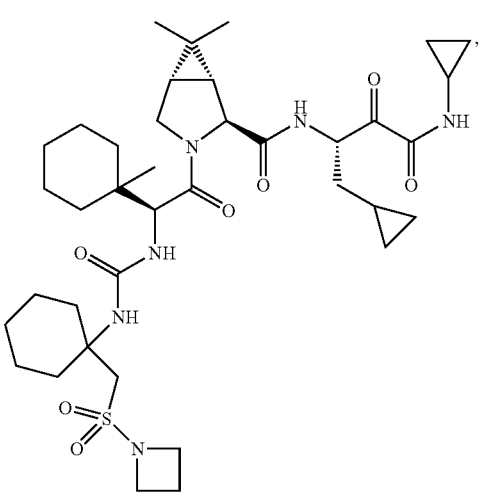

-continued
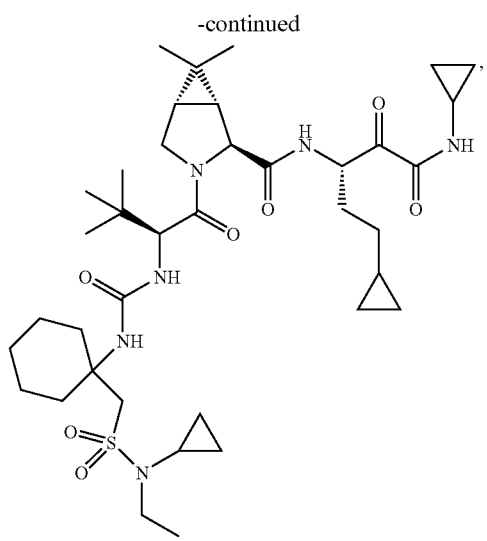
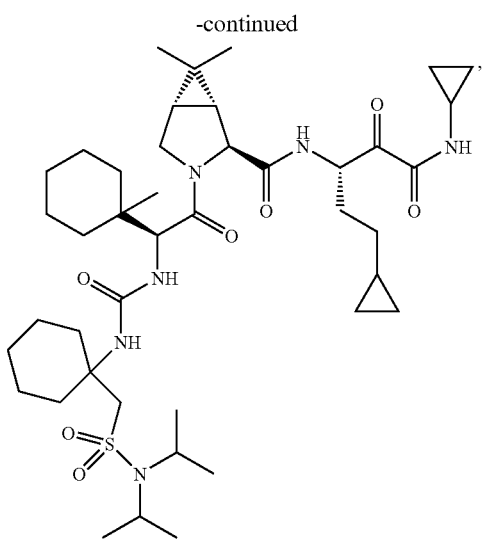
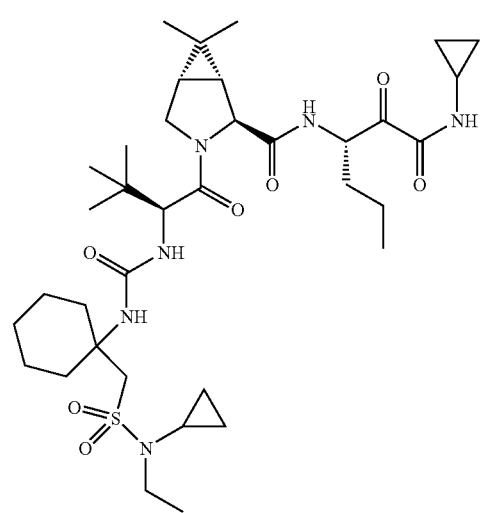
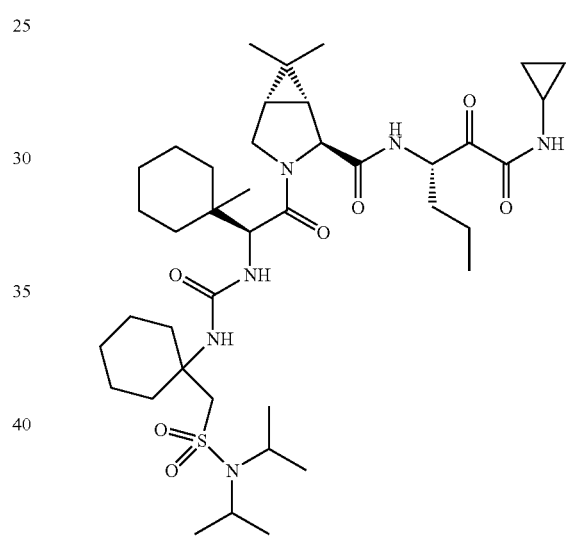
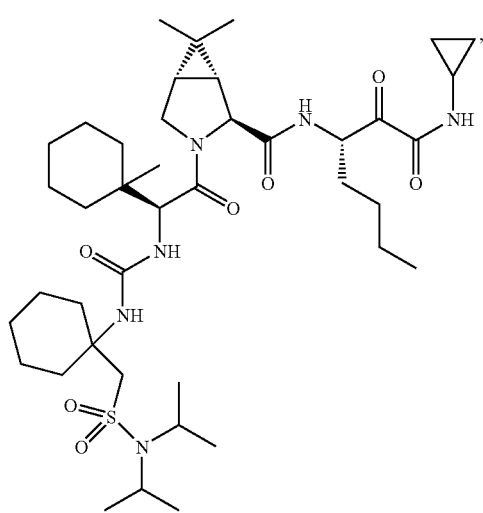
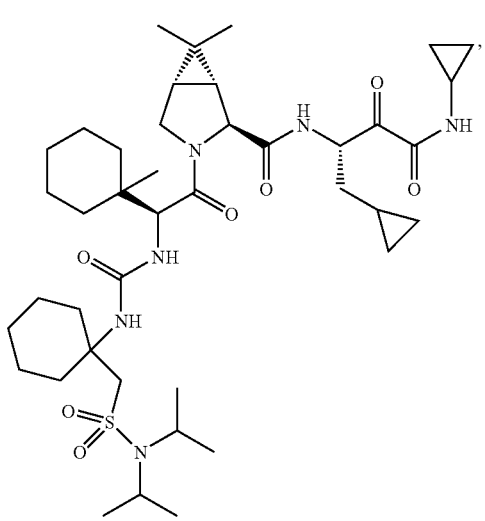

-continued
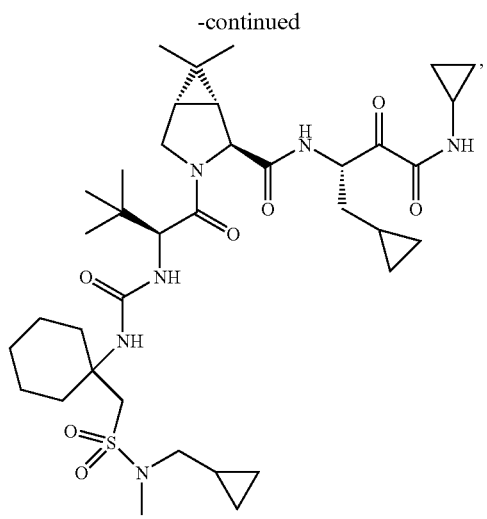
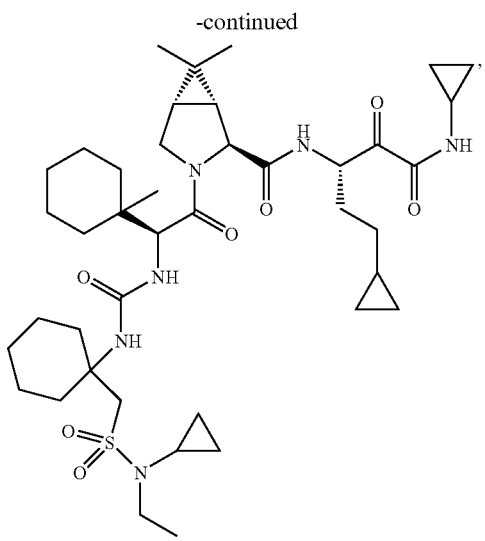
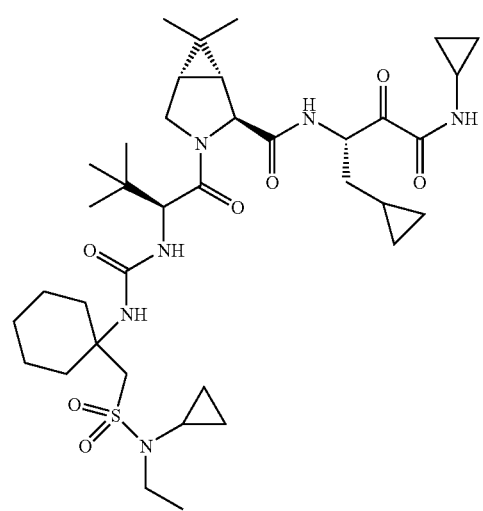
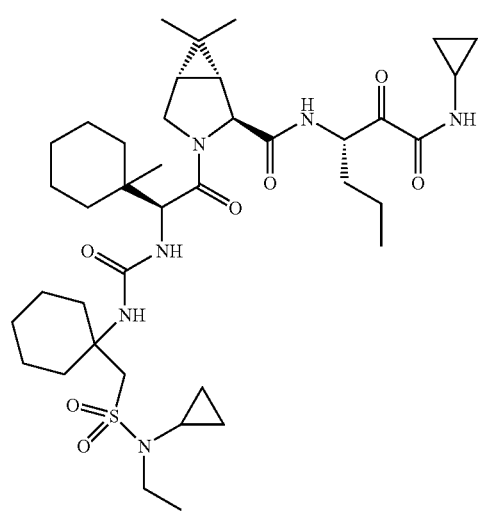
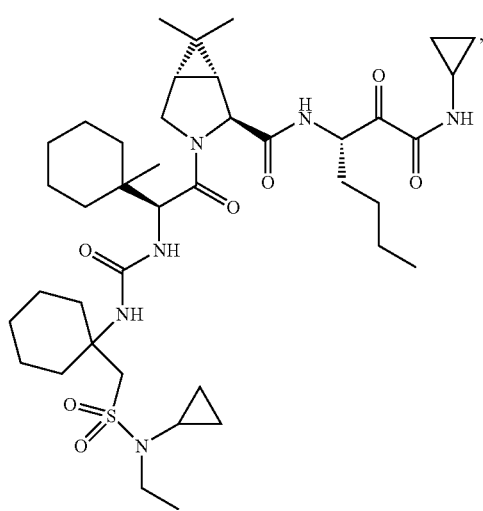
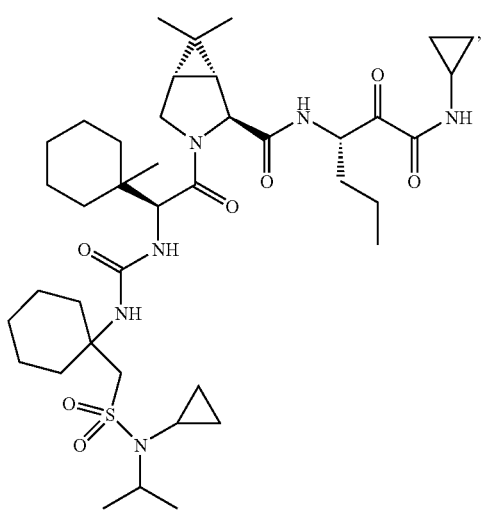

61
-continued
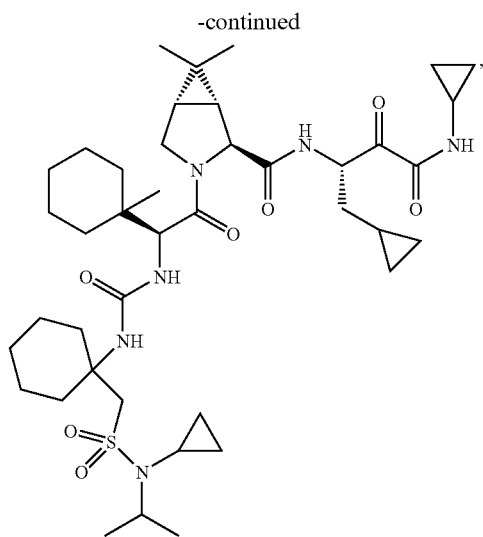
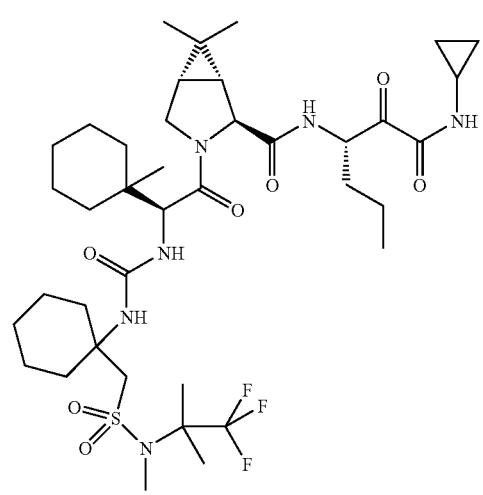
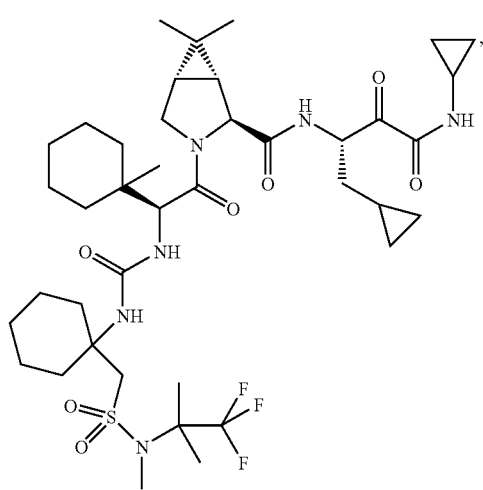
62
-continued
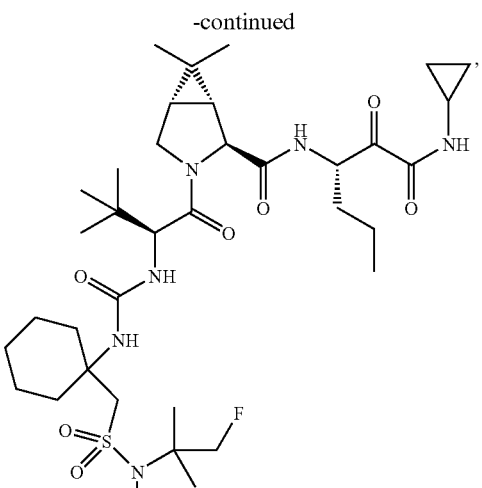
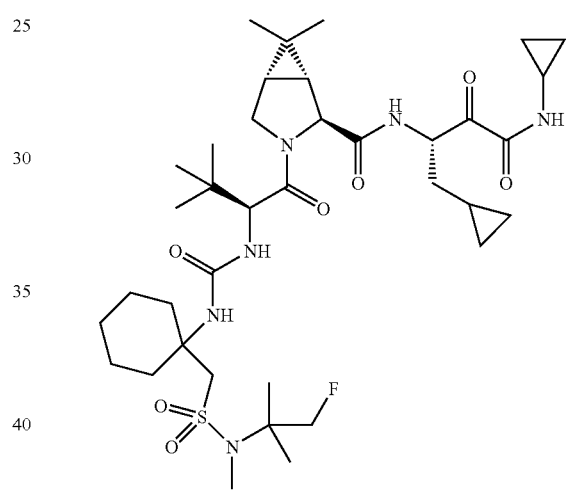
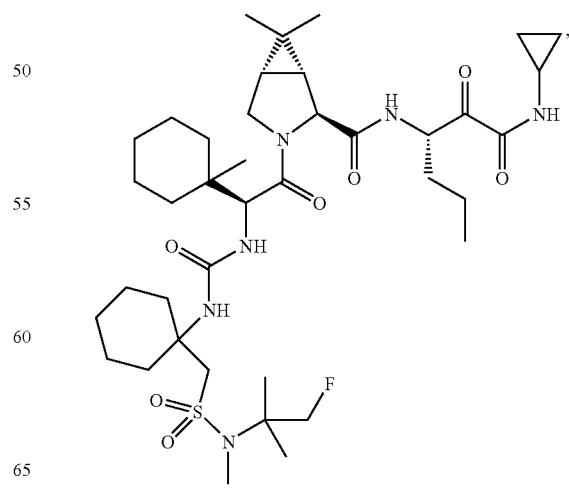

-continued
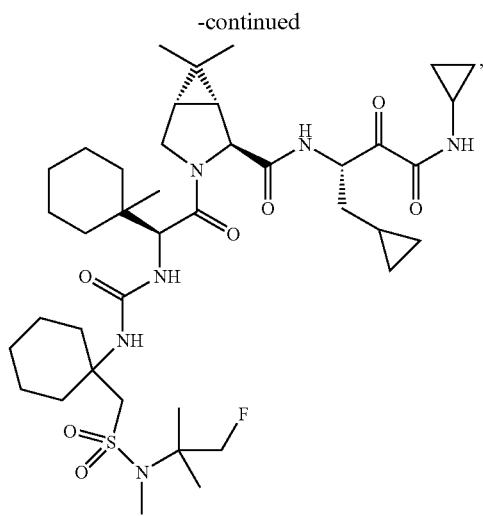
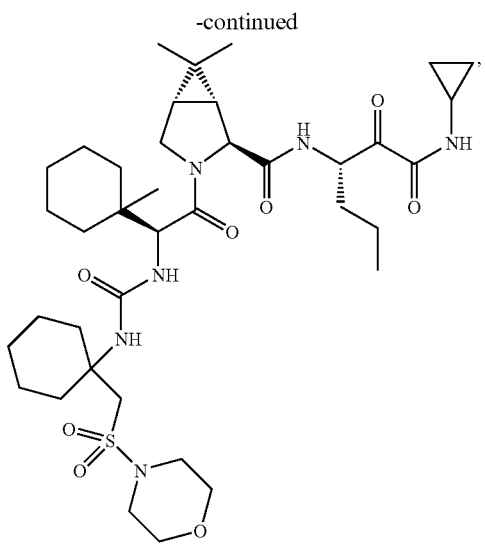
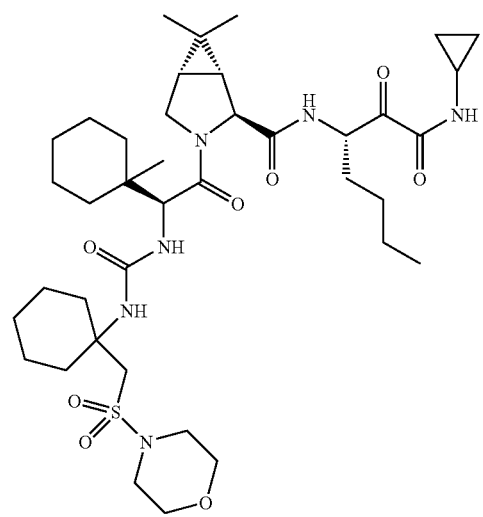
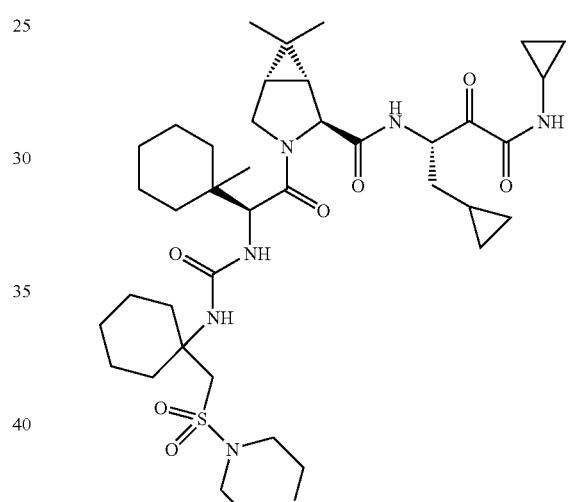
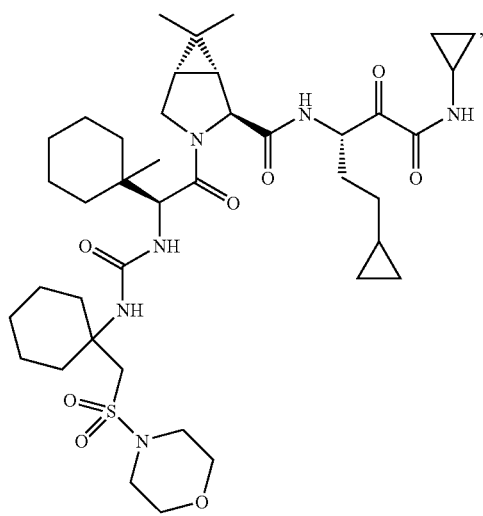
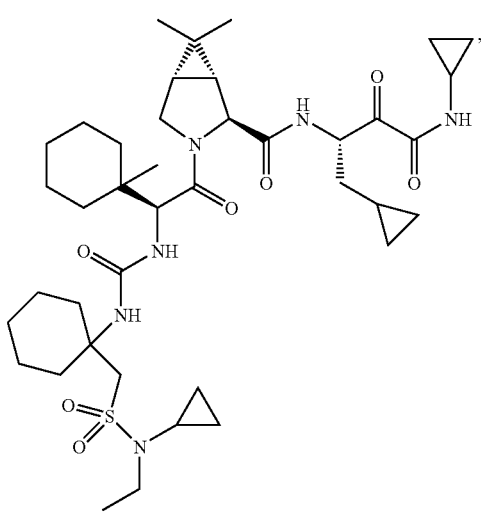

-continued
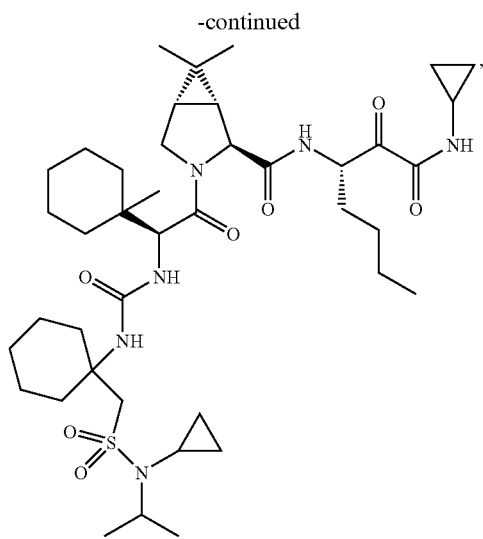
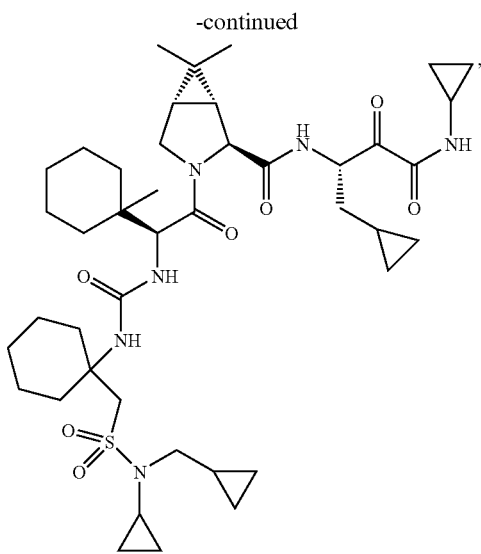
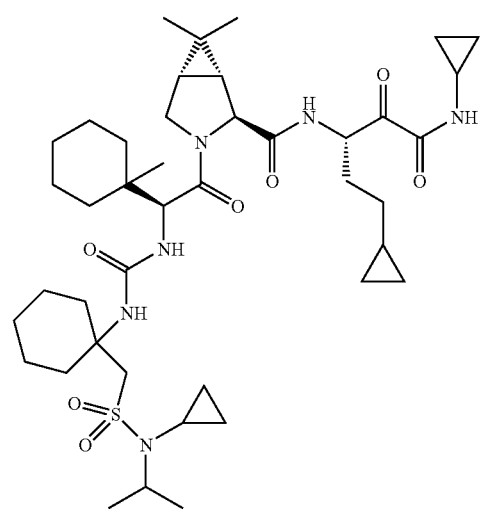
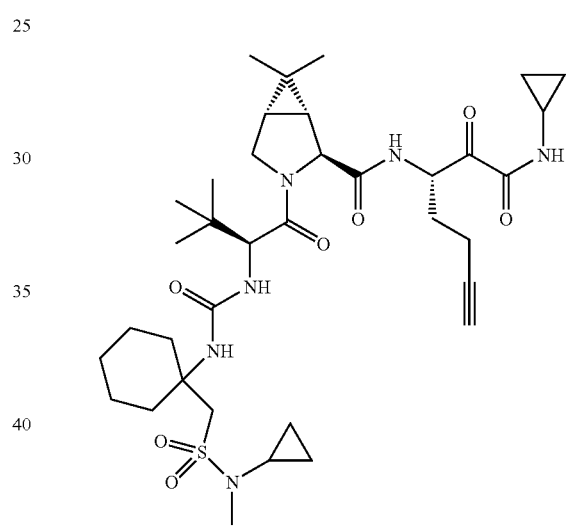
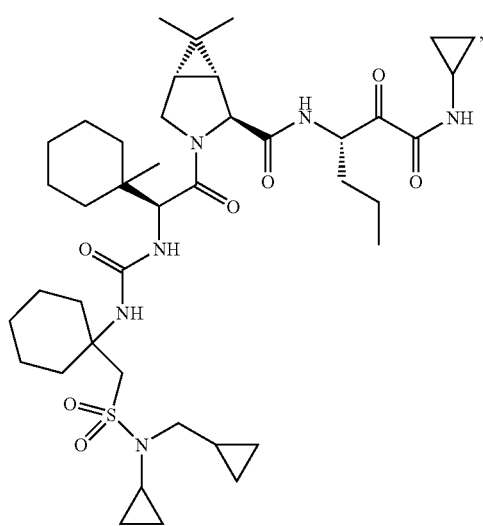
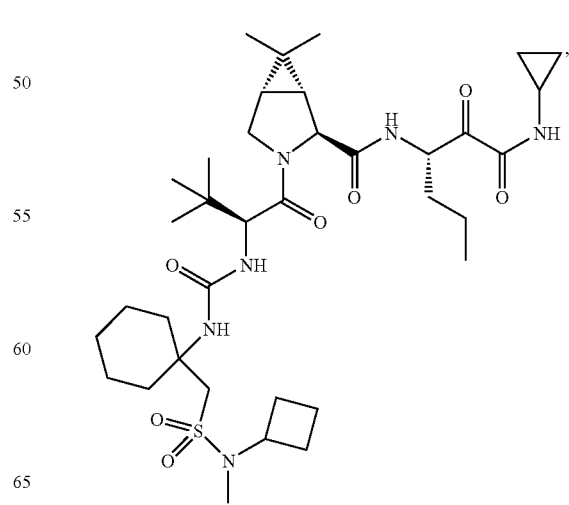

-continued
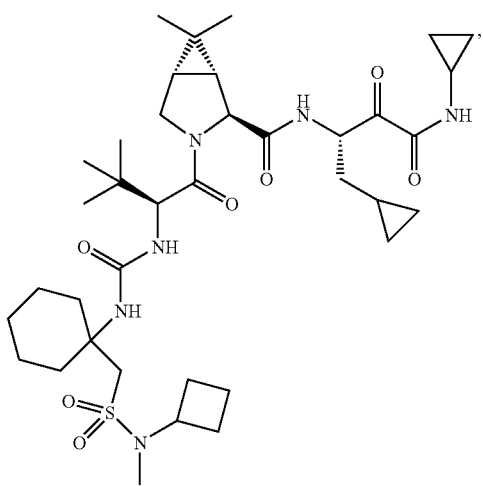
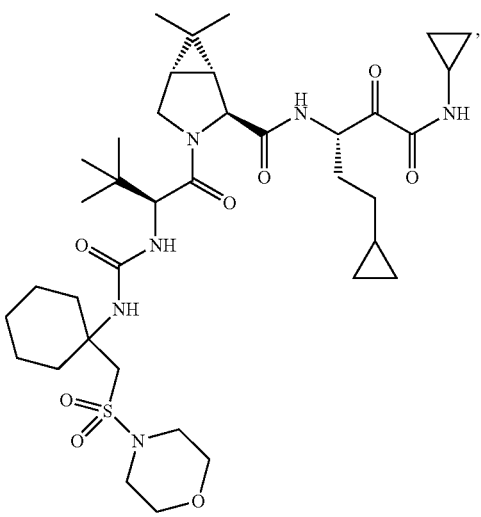
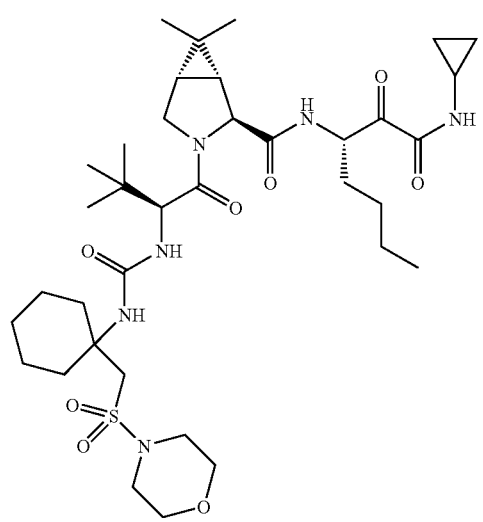
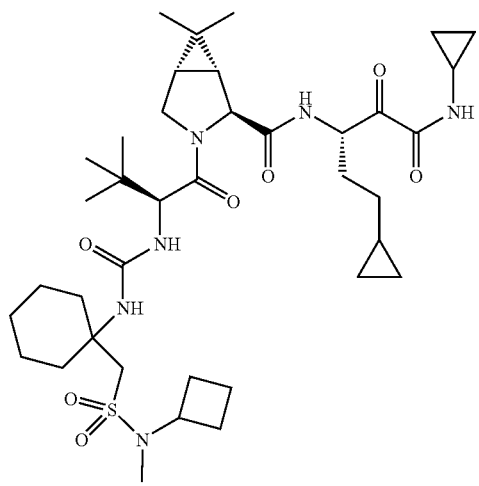
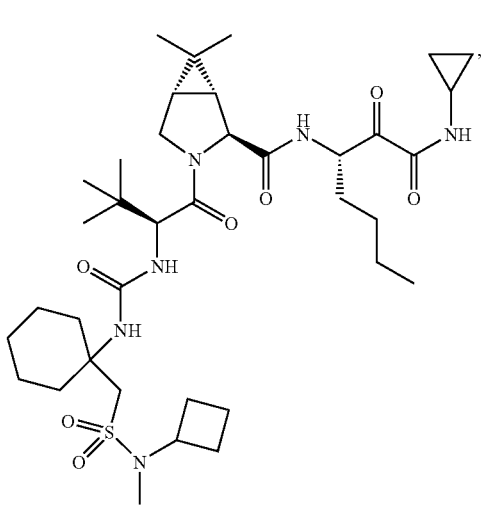
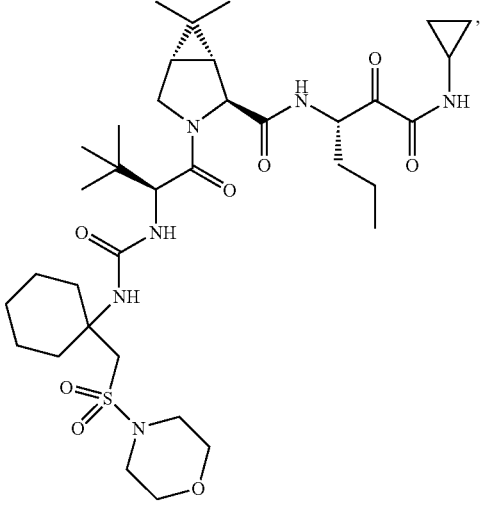

| 69 | 70 |
|---|---|
| -continued | -continued |
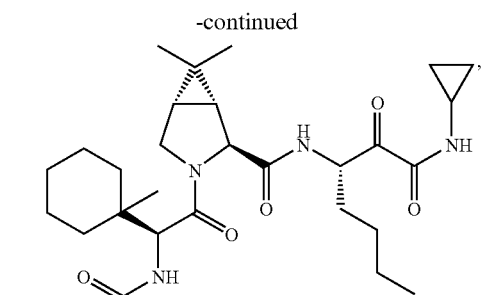
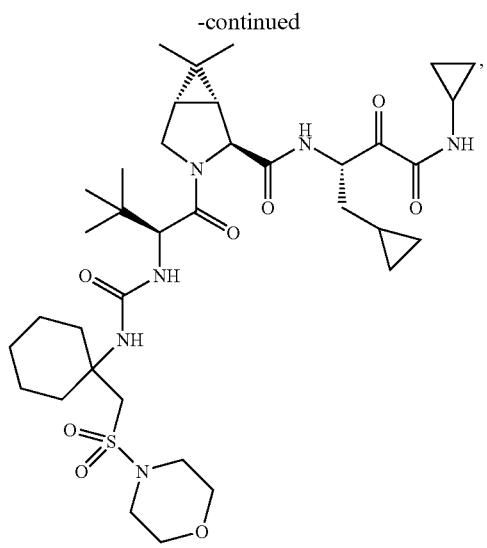
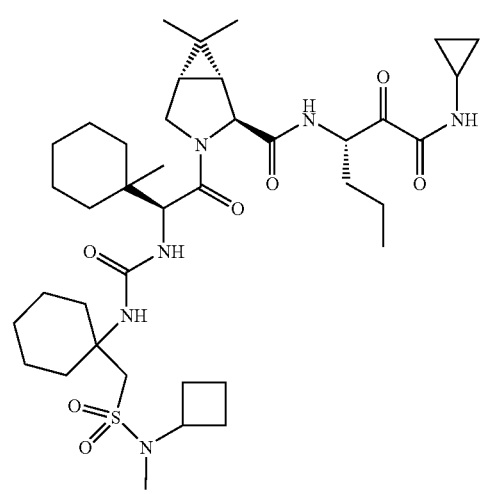
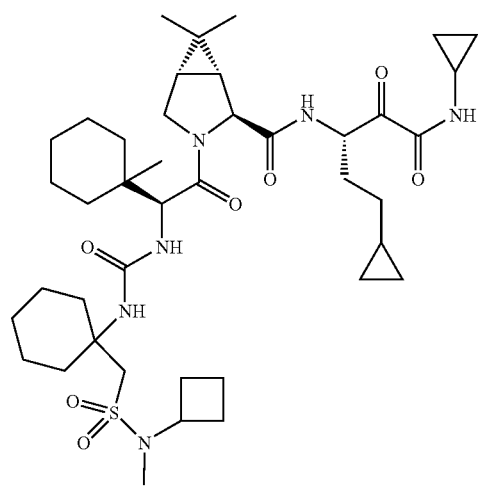
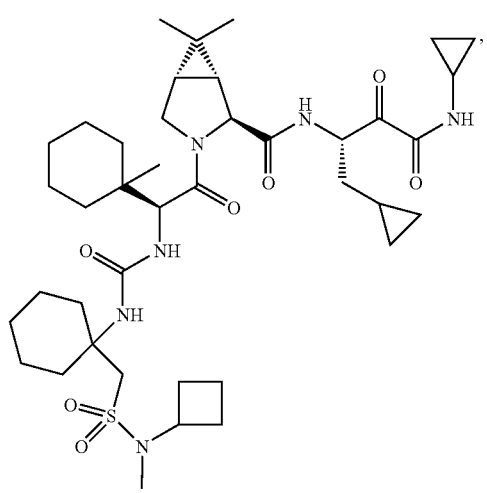
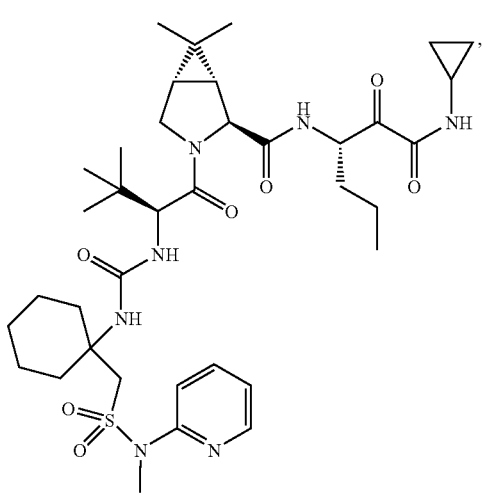

-continued
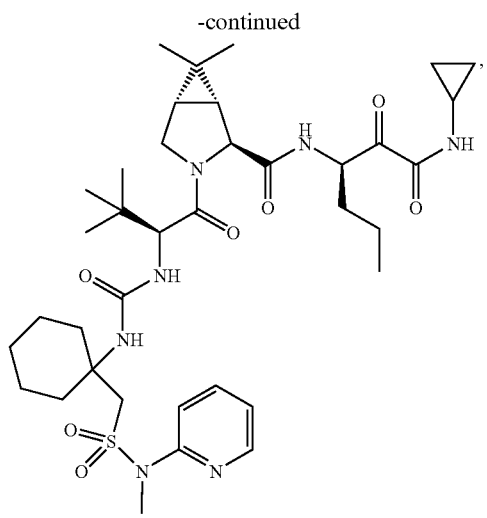
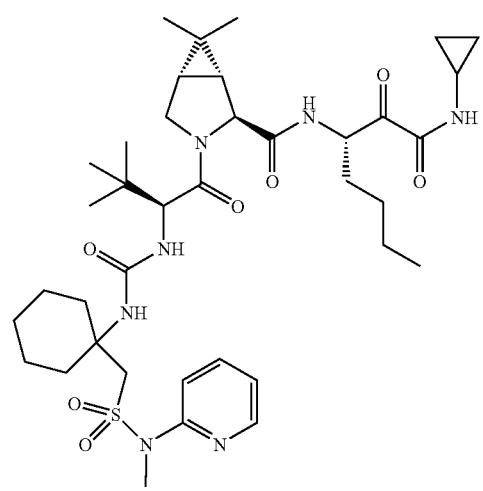
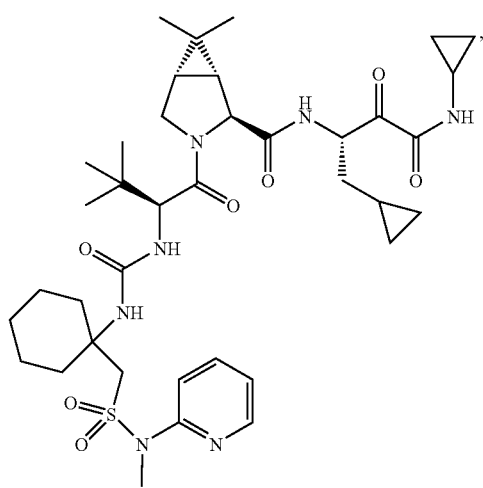
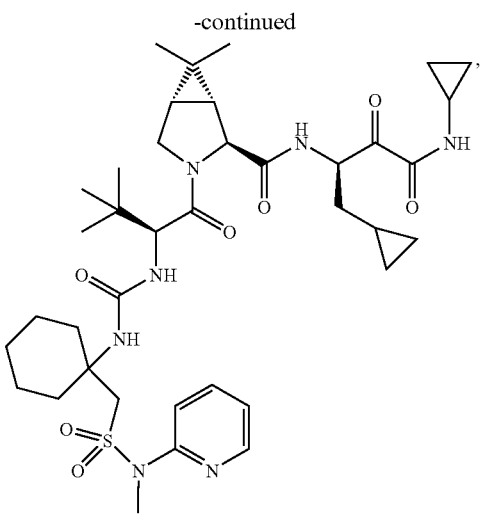
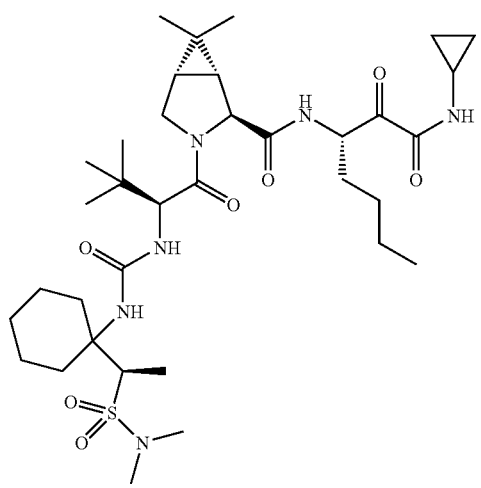
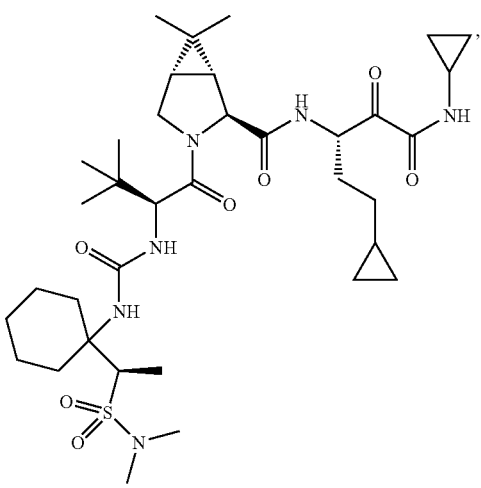

73
-continued
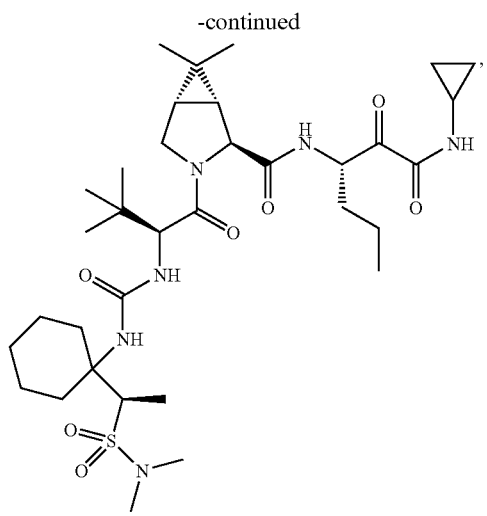
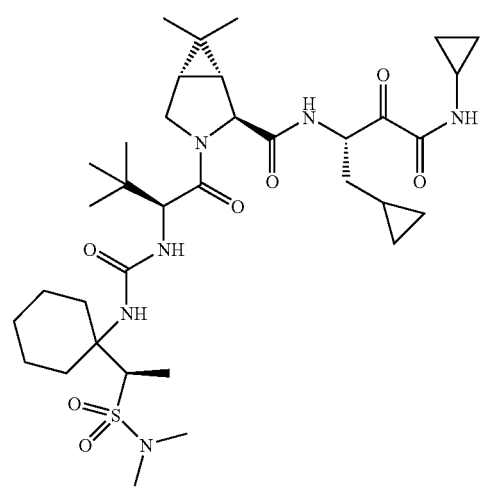
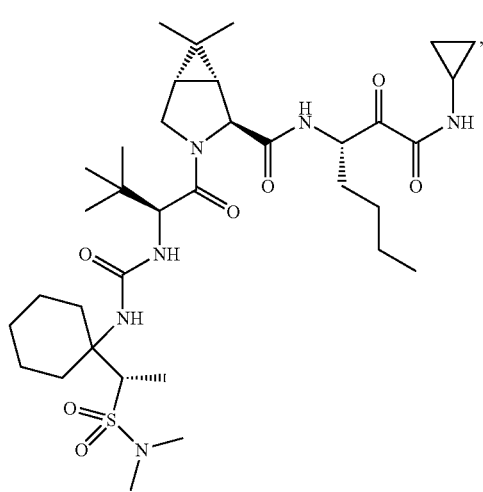
74
-continued
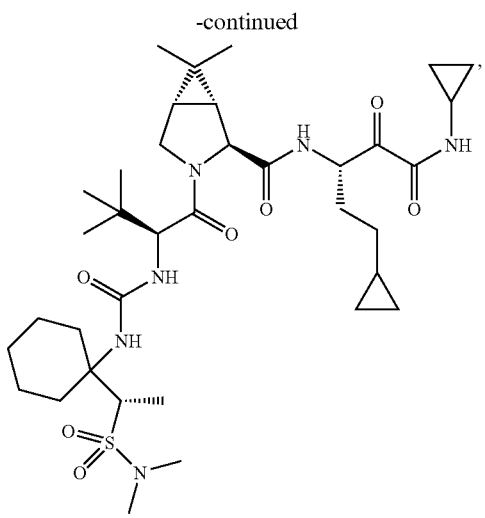
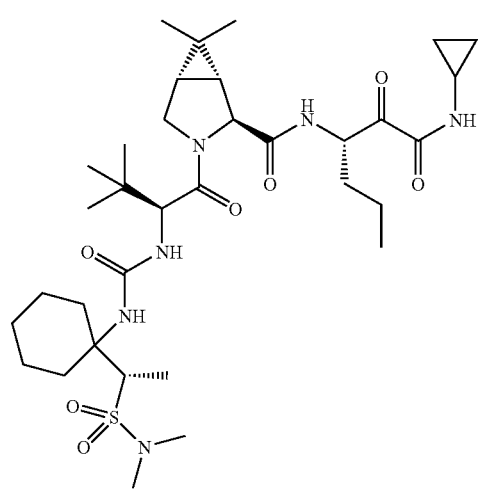
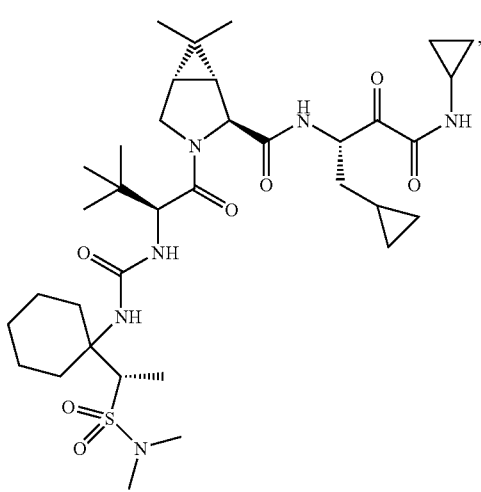

75
-continued
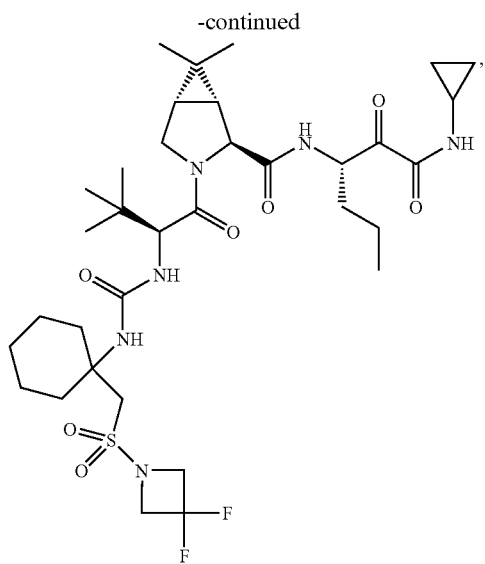
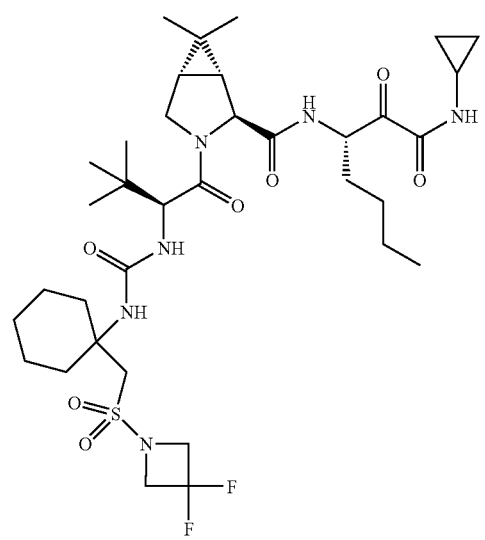
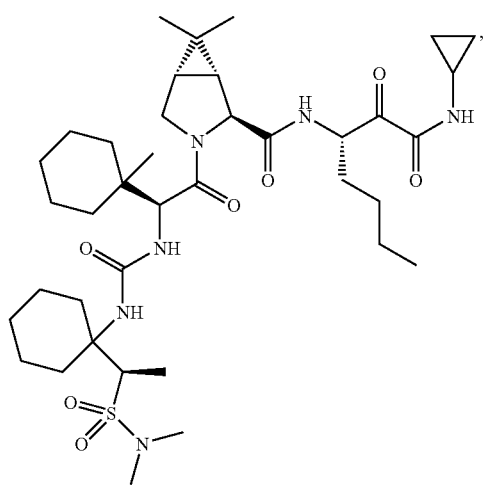
76
-continued
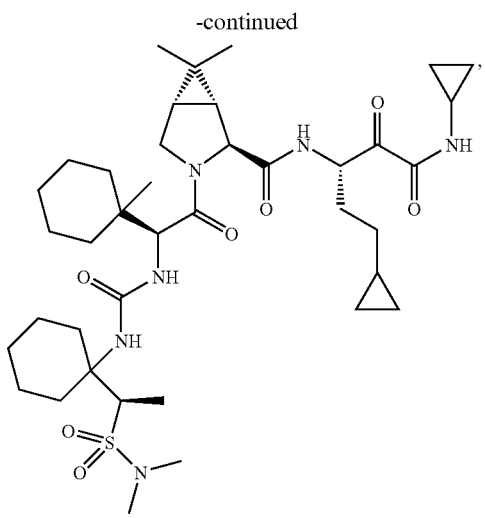
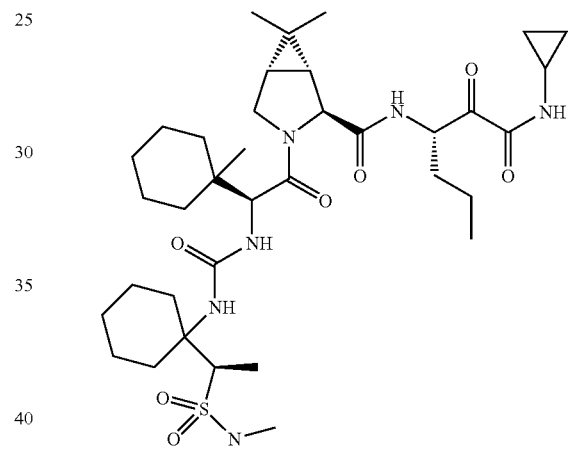
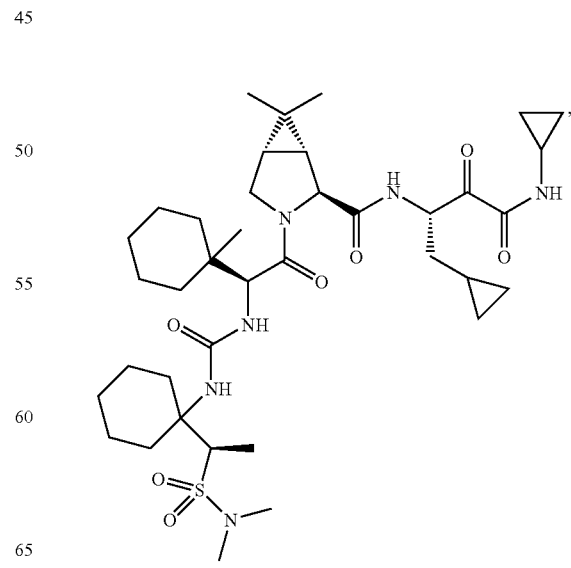

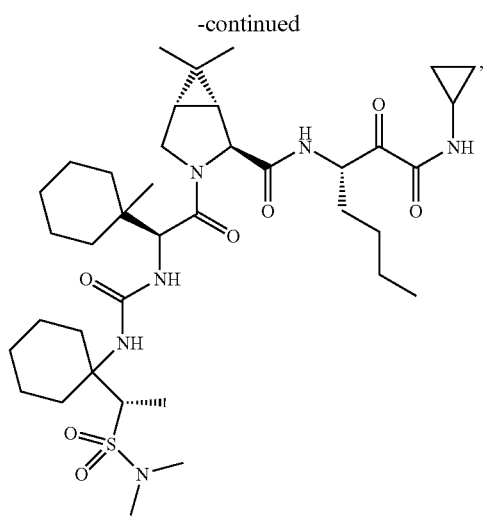
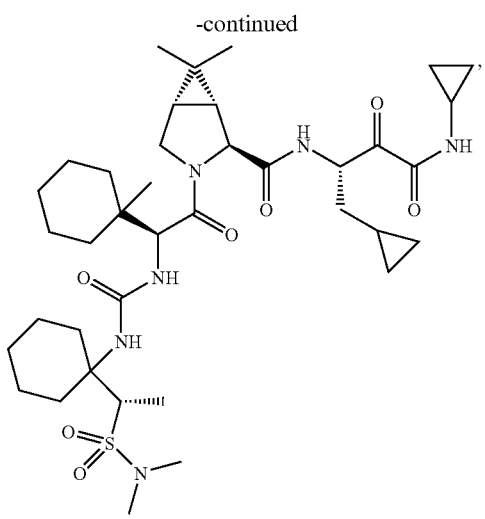
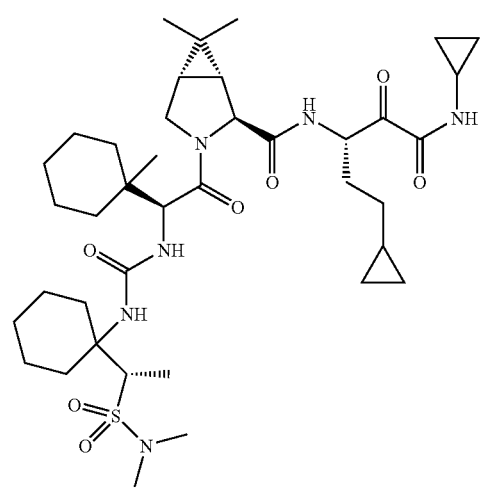
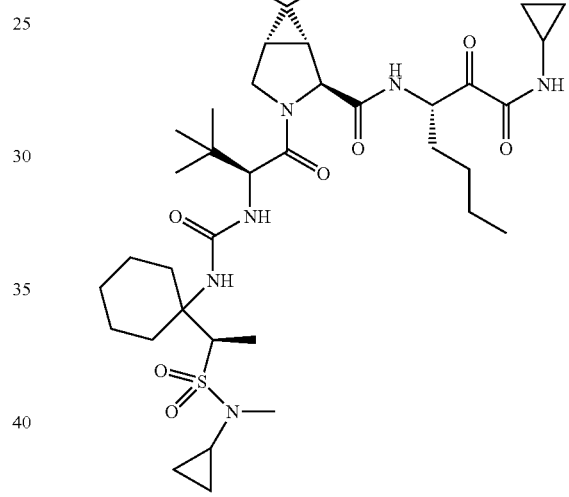
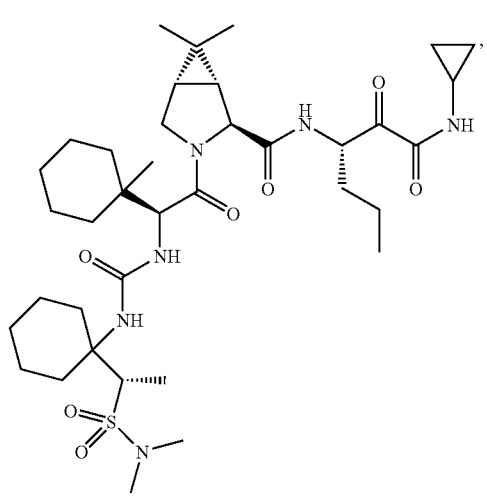
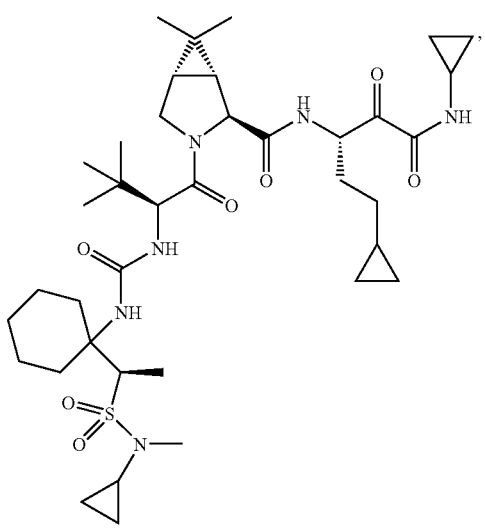

-continued
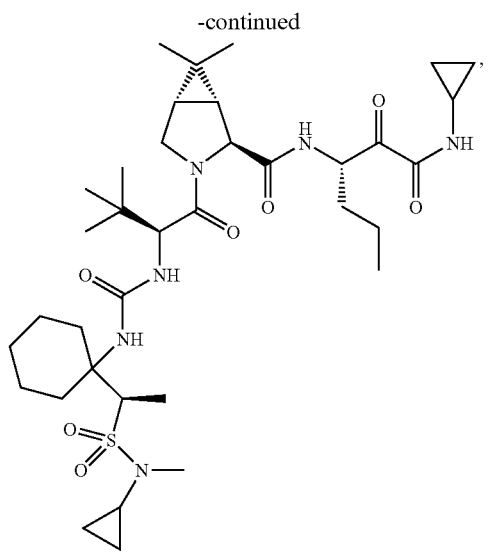
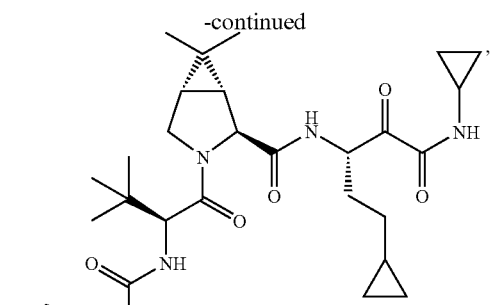
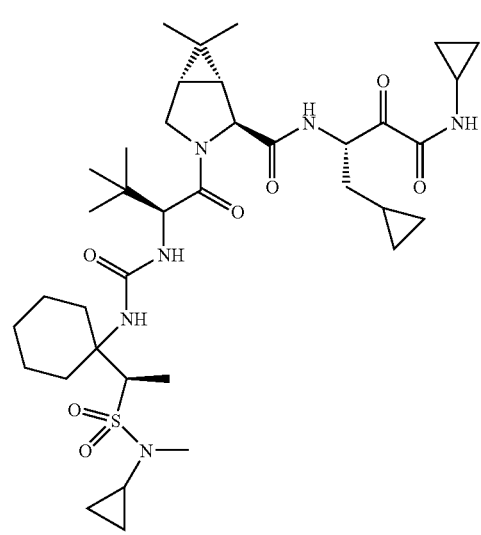
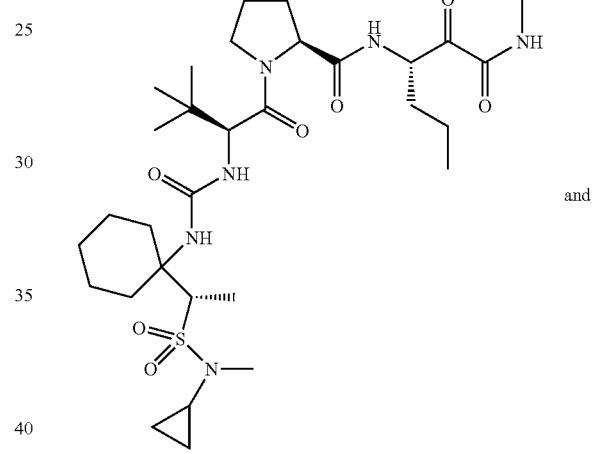
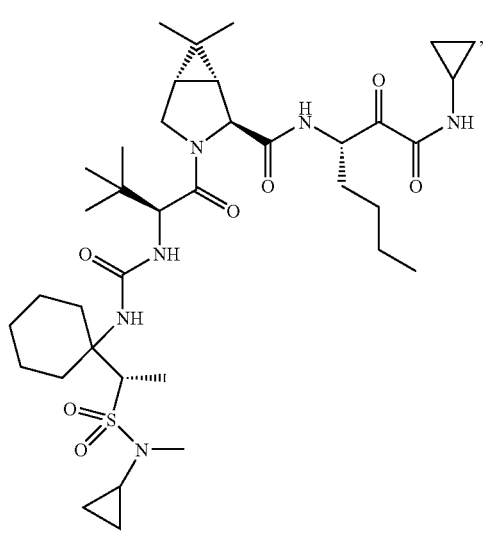
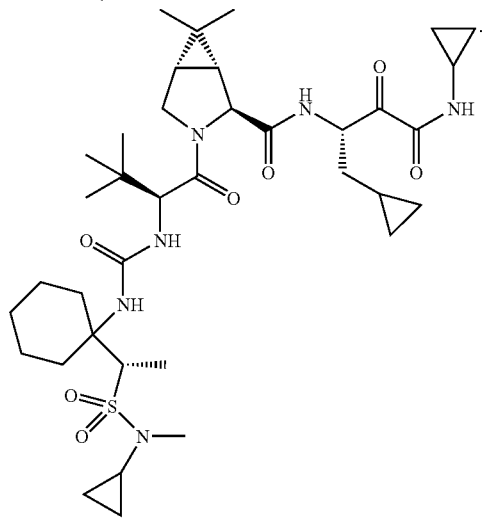
and
DETAILED DESCRIPTION
An embodiment of the invention discloses compounds listed above and shown later in Table 1 or a pharmaceutically acceptable salt or solvate or ester thereof.

As used above, and throughout this disclosure, the following terms, unless otherwise indicated, shall be understood to have the following meanings:

"Patient" includes both human and animals.

"Mammal" means humans and other mammalian animals.

The term "isolated" or "in isolated form" for a compound refers to the physical state of said compound after being isolated from a synthetic process or natural source or combination thereof. The term "purified" or "in purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any heteroatom with unsatisfied valences in the text, schemes, examples and Tables herein is assumed to have the hydrogen atom(s) to satisfy the valences.

The term "one or more" or "at least one", when indicating the number of substituents, compounds, combination agents and the like, refers to at least one, and up to the maximum number of chemically and physically permissible, substituents, compounds, combination agents and the like, that are present or added, depending on the context. Such techniques and knowledge are well known within the skills of the concerned artisan.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein, The term "prodrug", as employed herein, denotes a compound that is a drug precursor which, upon administration to a subject, undergoes chemical conversion by metabolic or chemical processes to yield a compound of Formula I or a salt and/or solvate thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting the HCV NS3/NS4a serine protease and thus producing the desired therapeutic, ameliorative, inhibitory or preventative effect.

The compounds of the present invention can form salts which are also within the scope of this invention. Reference to a compound of the present invention herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of the present invention contains both a basic moiety, such as, but not limited to a pyridine or imidazole, and an acidic moiety, such as, but not limited to a carboxylic acid, zwitterions ("inner salts") may be formed and are included within the term "salt(s)" as used herein Pharmaceutically acceptable (i.e., non-toxic, physiologically acceptable) salts are preferred, although other salts are also useful. Salts of the compounds of the present invention may be formed, for example, by reacting a compound of the present invention with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

Compounds of the present invention, and salts, solvates, esters and prodrugs thereof may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates, esters and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, positional isomers, racemates or prodrugs of the inventive compounds.

Polymorphic forms of the compounds of the present invention, and of the salts, solvates, esters and prodrugs thereof, are intended to be included in the present invention.

It is to be understood that the utility of the compounds of the present invention for the therapeutic applications discussed herein is applicable to each compound by itself or to the combination or combinations of one or more compounds as illustrated, for example, in the next immediate paragraph. The same understanding also applies to pharmaceutical composition(s) comprising such compound or compounds and method(s) of treatment involving such compound or compounds.

The compounds according to the invention can have pharmacological properties; in particular, the compounds of the invention can be inhibitors of HCV protease, each compound by itself or combined with one or more compounds selected from the compounds of the invention listed above. The compound(s) can be useful for treating diseases such as, for example, HCV, HIV, (AIDS, Acquired Immune Deficiency Syndrome), and related disorders, as well as for modulating the activity of hepatitis C virus (HCV) protease, preventing HCV, or ameliorating one or more symptoms of hepatitis C.

The compounds of the present invention may be used for the manufacture of a medicament to treat disorders associated with the HCV protease, for example, the method comprising bringing into intimate contact a compound of the present invention and a pharmaceutically acceptable carrier.

In another embodiment, this invention provides pharmaceutical compositions comprising the inventive compound or compounds as an active ingredient. The pharmaceutical compositions generally additionally comprise at least one pharmaceutically acceptable carrier diluent, excipient or carrier (collectively referred to herein as carrier materials). Because of their HCV inhibitory activity, such pharmaceutical compositions possess utility in treating hepatitis C and related disorders.

In yet another embodiment, the present invention discloses methods for preparing pharmaceutical compositions comprising the inventive compounds as an active ingredient. In the pharmaceutical compositions and methods of the present invention, the active ingredients will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture. Powders and tablets may be comprised of from about 5 to about 95 percent inventive composition.

Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like.

Sweetening and flavoring agents and preservatives may also be included where appropriate. Some of the terms noted above, namely disintegrants, diluents, lubricants, binders and the like, are discussed in more detail below.

Additionally, the compositions of the present invention may be formulated in sustained release form to provide the rate controlled release of any one or more of the components or active ingredients to optimize the therapeutic effects, i.e. HCV inhibitory activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and pacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as are conventional in the art for this purpose.

The compounds of the invention may also be administered orally, intravenously, intranasally or subcutaneously.

The compounds of the invention may also comprise preparations which are in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 1.0 milligram to about 1,000 milligrams, preferably from about 1.0 to about 950 milligrams, more preferably from about 1.0 to about 500 milligrams, and typically from about 1 to about 250 milligrams, according to the particular application. The actual dosage employed may be varied depending upon the patients age, sex, weight and severity of the condition being treated. Such techniques are well known to those skilled in the art.

Generally, the human oral dosage form containing the active ingredients can be administered 1 or 2 times per day. The amount and frequency of the administration will be regulated according to the judgment of the attending clinician. A generally recommended daily dosage regimen for oral administration may range from about 1.0 milligram to about 1,000 milligrams per day, in single or divided doses.

Some useful terms are described below:

Capsule—refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet—refers to a compressed or molded solid dosage form containing the active ingredients with suitable diluents. The tablet can be prepared by compression of mixtures or granulations obtained by wet granulation, dry granulation or by compaction.

Oral gel—refers to the active ingredients dispersed or solubilized in a hydrophillic semi-solid matrix.

Powder for constitution refers to powder blends containing the active ingredients and suitable diluents which can be suspended in water or juices.

Diluent—refers to substances that usually make up the major portion of the composition or dosage form. Suitable diluents include sugars such as lactose, sucrose, mannitol and sorbitol; starches derived from wheat, corn, rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

Disintegrant—refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

Binder—refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

Lubricant—refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

Glident—material that prevents caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

Coloring agents—excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

Bioavailability—refers to the rate and extent to which the active drug ingredient or therapeutic moiety is absorbed into the systemic circulation from an administered dosage form as compared to a standard or control.

Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

Another embodiment of the invention discloses the use of the inventive compounds or pharmaceutical compositions disclosed above for treatment of diseases such as, for example, hepatitis C and the like. The method comprises administering a therapeutically effective amount of the inventive compound or pharmaceutical composition to a patient having such a disease or diseases and in need of such a treatment.

In yet another embodiment, the compounds of the invention may be used for the treatment of HCV in humans in monotherapy mode or in a combination therapy (e.g., dual combination, triple combination etc.) mode such as, for example, in combination with antiviral and/or immunomodulatory agents. Examples of such antiviral and/or immunomodulatory agents include Ribavirin (from Schering-Plough Corporation, Madison, N.J.) and Levovirin™ (from ICN Pharmaceuticals, Costa Mesa, Calif.), VP 50406™ (from Viropharma, Incorporated, Exton, Pa.), ISIS 14803™ (from ISIS Pharmaceuticals, Carlsbad, Calif.), Heptazyme™ (from Ribozyme Pharmaceuticals, Boulder, Colo.), VX 497™ (from Vertex Pharmaceuticals, Cambridge, Mass.), Thymosin™ (from SciClone Pharmaceuticals, San Mateo, Calif.), Maxamine™ (Maxim Pharmaceuticals, San Diego, Calif.), mycophenolate mofetil (from Hoffman-LaRoche, Nutley, N.J.), interferon (such as, for example, interferon-alpha, PEG-interferon alpha conjugates) and the like. "PEG-interferon alpha conjugates" are interferon alpha molecules covalently attached to a PEG molecule. Illustrative PEG-interferon alpha conjugates include interferon alpha-2a (Roferon™, from Hoffman La-Roche, Nutley, N.J.) in the form of pegylated interferon alpha-2a (e.g., as sold under the trade name Pegasys™), interferon alpha-2b (Intron™, from Schering-Plough Corporation) in the form of pegylated interferon alpha-2b (e.g., as sold under the trade name PEG-Intron™), interferon alpha-2c (Berofor Alpha™, from Boehringer Ingelheim, Ingelheim, Germany) or consensus interferon as defined by determination of a consensus sequence of naturally occurring interferon alphas (Infergen™, from Amgen, Thousand Oaks, Calif.).

As stated earlier, the invention includes tautomers, rotamers, enantiomers and other stereoisomers of the inventive compounds also. Thus, as one skilled in the art appreciates, some of the inventive compounds may exist in suitable isomeric forms. Such variations are contemplated to be within the scope of the invention.

Another embodiment of the invention discloses a method of making the compounds disclosed herein. The compounds may be prepared by several techniques known in the art. Illustrative procedures are outlined in the following reaction schemes. The illustrations should not be construed to limit the scope of the invention which is defined in the appended claims. Alternative mechanistic pathways and analogous structures will be apparent to those skilled in the art.

It is to be understood that while the following illustrative schemes describe the preparation of a few representative inventive compounds, suitable substitution of any of both the natural and unnatural amino acids will result in the formation of the desired compounds based on such substitution. Such variations are contemplated to be within the scope of the invention.

For the procedures described below, the following abbreviations are used:

THF: Tetrahydrofuran

DMF: N,N-Dimethylformamide

EtOAc: Ethyl acetate

DCM: Dichloromethane

HATU: O-(7-azabenzotriazol-1-yl)-1,1,3,3-tetramethyluronium hexafluorophosphate

MeOH: Methanol

TLC: Thin Layer Chromatography pH: percent Hydrogen

Sat.: Saturated n-BuLi: n-butyl lithium

RT: Room Temperature

DPPA: Diphenyl phosphoryl azide

General Schemes for Preparation of Target Compounds

Compounds of the present invention were synthesized using the general schemes as described to make Preparative Examples 1200 and 1261 as described below.

Preparative Example 1200

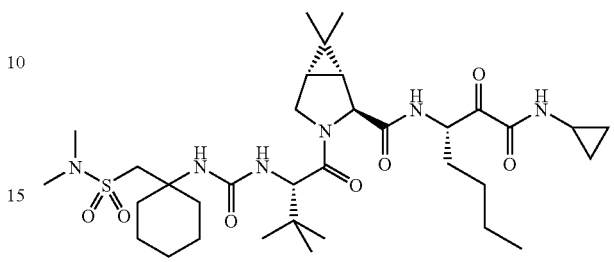

Step 1:

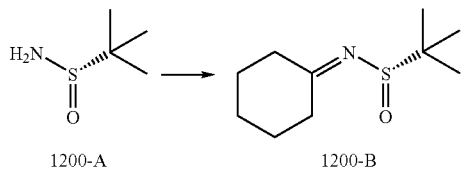

1200-A          1200-B

2-Methyl-propane-2-sulfinic acid cyclohexylideneamide (1200-B): Titanium tetraethoxide (2 eq, 3.56 mL, d 1.088) was added to a solution of cyclohexanone (1.2 eq, 1.0 g, 1.05 mL, d 0.947) in 20 mL of dry THF under nitrogen atmosphere. After 5 min, (S)-t-butanesulfinamide (1200-A, 1.028 g) in 10 mL of THF was added dropwise. The mixture was heated to 60° C. overnight. The reaction mixture was poured into an equal volume of aqueous saturated sodium bicarbonate solution with rapid stirring and immediately filtered through celite. The filter cake was washed with ethyl acetate (50 mL). The layers in the filtrate were separated and the aqueous layer was extracted with ethyl acetate (30 mL). The combined organic layers were dried over magnesium sulfate, filtered and concentrated. The residue was chromatographed on silica gel (gradient:ether/hexanes; 1:9 to 1.1) to afford the product 1200-B (1.3 g; 76%) as a colorless oil. The product was kept under inert atmosphere at −20° C.

Step 2:

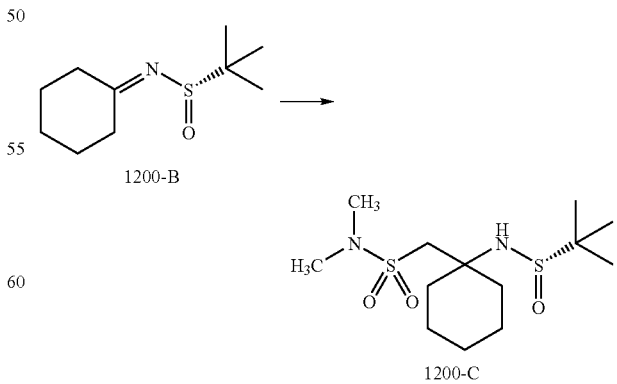

N,N-Dimethyl-C-[1-(2-methyl-propane-2-sulfinylamino)-cyclohexyl]-methanesulfonamide (1200-C): n-Butyllithium (1.3 eq, 8.07 mL of a 1.6M soln in hexanes) was added dropwise to a cooled (−78° C.) solution of N,N-dimethyl methanesulfonamide (1.35 eq, 1.65 g) in 100 mL of dry THF under anhydrous atmosphere. The mixture was stirred for 30 min at that temperature and then transferred via cannula to a solution of sulfinyl imine 1200-B (2.0 g) in 100 mL of dry THF at −78° C. After addition was completed, the reaction mixture was stirred for 1 h. The reaction was quenched at −78° C. by addition of 20 mL of aqueous saturated ammonium chloride solution. The mixture was allowed to reach room temp and then partitioned between dichloromethane (300 mL) and aqueous saturated sodium bicarbonate solution (300 mL). The aqueous layer was back extracted with dichloromethane (2×200 mL). The combined organic layers were dried over magnesium sulfate, filtered and concentrated. The residue was chromatographed on silica gel (gradient:dichloromethane/hexanes; 1:1 to 30% acetone in dichloromethane/hexanes; 1:1) to afford the product 1200-C (1.36 g; 42%) as a colorless oil.

Step 3:

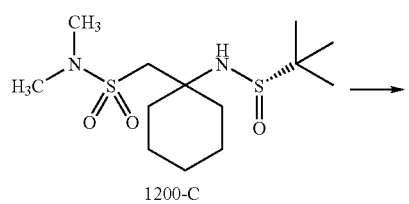

1200-C

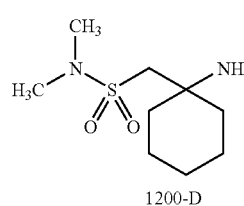

1200-D

C-(1-Amino-cyclohexyl)-N,N-dimethyl-methanesulfonamide hydrochloric salt (1200-D): The sulfinamide 1200-C (1.3 g) was dissolved in 40 mL of methanol and treated with 10 mL of 4M HCl solution in dioxane. The mixture was stirred for about 30 min until all the starting material had been consumed as determined by TLC (20% acetone in dichloromethane/hexanes, 1:1). The mixture was evaporated to dryness. Dichloromethane was added (15 mL) to make a cloudy solution. Upon addition of 100 mL of ether a white precipitated formed. The product 1200-D (1.02 g; 98%) was recovered by filtration using filter paper whatman #1.

Step 4:

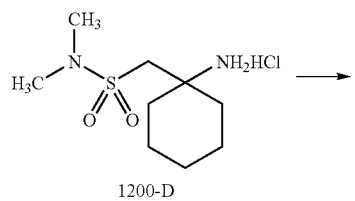

1200-D

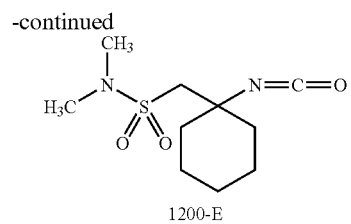

1200-E

C-(1-Isocyanato-cyclohexyl)-N,N-dimethyl-methanesulfonamide (1200-E): A solution of amine hydrochloride 1200-D (520 mg) in 40 mL of dichloromethane was treated with 20 mL of aqueous saturated sodium bicarbonate solution and stirred vigorously for 10 min at 0° C. Stirring was stopped and layers were allowed to separate. Phosgene (10 mL of 20% solution in toluene) was added to the organic layer (lower layer) in one portion. The mixture was vigorously stirred immediately after addition for 10 min at 0° C. and further stirred at room temp for 3 h. The mixture was diluted with 100 mL of dichloromethane and layers were separated. The organic layer was washed with 50 mL of cold aqueous saturated sodium bicarbonate solution and dried over magnesium sulfate. The organic layer was filtered and diluted with 15 mL of toluene. The resulting solution was concentrated under reduced pressure and the product 1200-E was maintained as a 0.2M solution.

Step 5:

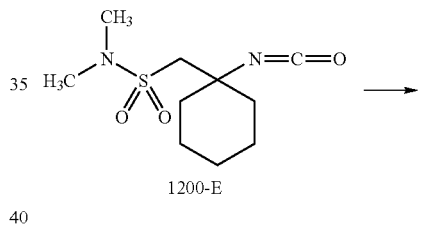

1200-E

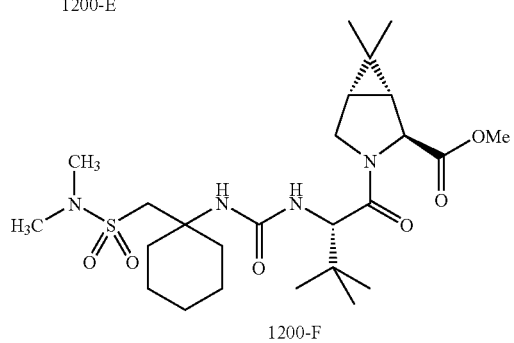

1200-F

3-{2-[3-(1-Dimethylsulfamoylmethyl-cyclohexyl)-ureido]-3,3-dimethyl-butyryl}-6,6-dimethyl-3-aza-bicyclo[3.1.0]hexane-2-carboxylic acid methyl ester (1200-F): A solution of previously described P2-P3 amine hydrochloride, 20.07 (U.S. patent application Ser. No. 11/064,673, Intermediate 20.07) (1.2 eq, 1.0 g) in 30 mL of dichloromethane was cooled to 0° C. and treated N-methylmorpholine (2.5 eq, 0.72 mL, d 0.920). After 5 min, a solution of isocyanate 1200-E (13.0 mL of 0.2M solution in toluene) was also added. The reaction mixture was stirred for further 3 h (temp from 0 to 25° C.). The mixture was treated with aqueous 1M HCl (50 mL) and the product was taken into ethyl acetate (300 mL). The organic layer was washed with brine (50 mL) and dried over magnesium sulfate. The mixture was filtered and con- Step 6:

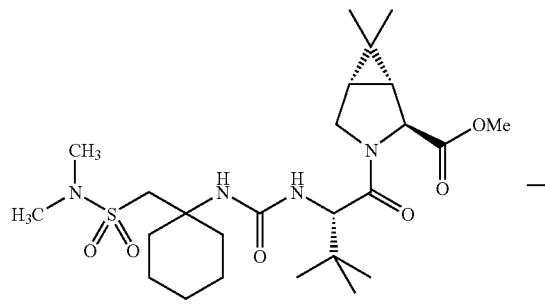

1200-F

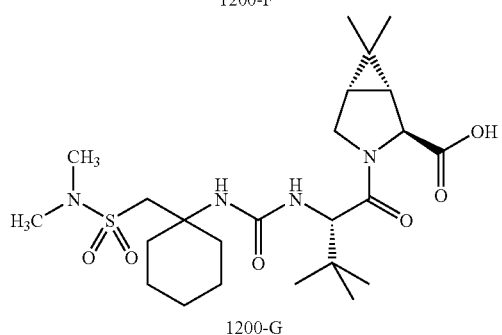

1200-G

3-{2-[3-(1-Dimethylsulfamoylmethyl-cyclohexyl)-ureido]-3,3-dimethyl-butyryl}-6,6-dimethyl-3-aza-bicyclo[3.1.0]hexane-2-carboxylic acid (1200-G): A solution of methylester 1200-F (840 mg) in 30 mL of a 2:1 mixture of THF/water was cooled to 0° C. and treated with lithium hydroxide monohydrate (2.5 eq, 166 mg). The mixture was stirred for 10 min and the cooling bath was removed. The reaction was stirred at room temp until all starting material had been consumed as determined by TLC (acetone/hexanes; 3:7). After 2 h, the mixture was treated with aqueous 1M HCl (aprox 50 mL) turning the mixture acidic (pH 2). The mixture was extracted with dichloromethane (3×50 mL). The combined organic layers were dried over magnesium sulfate, filtered and concentrated under reduced pressure to afford the product 1200-G (815 mg-98%) as a white solid.

Step 7:

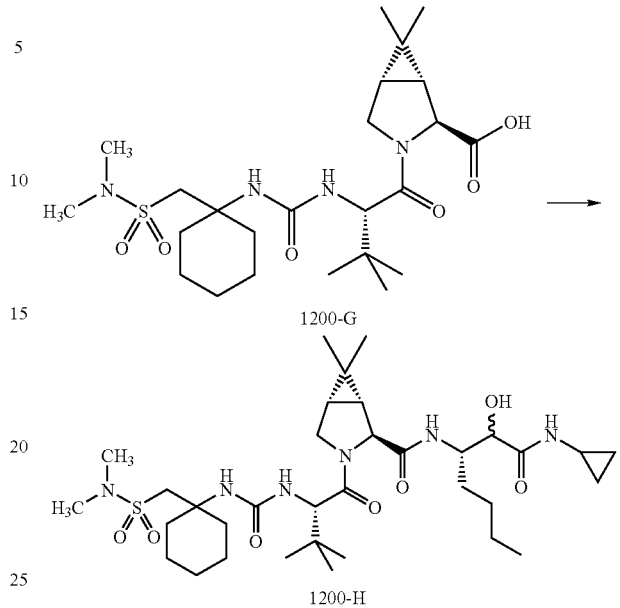

3-{2-[3-(1-Dimethylsulfamoylmethyl-cyclohexyl)-ureido]-3,3-dimethyl-butyryl}-6,6-dimethyl-3-aza-bicyclo[3.1.0]hexane-2-carboxylic acid [1-(cyclopropylcarbamoyl-hydroxy-methyl)-pentyl]-amide (1200-H): A solution of acid 1200-G (250 mg) in 5 mL of dry dichloromethane and 5 mL of dry DMF was stirred at 0° C. and treated with HATU (1.4 eq, 259 mg). The amine hydrochloride 837I (previously described in U.S. patent application Ser. No. 11/064,673, Example 837, Step H), (1.3 eq, 149 mg) was added followed by N-methylmorpholine (4 eq, 0.21 mL, d 0.920). The reaction mixture was stirred overnight (temp 0 to 25° C.). All the volatiles were removed in rotovap and the residue was dissolved in 80 mL of ethyl acetate. The organic layer was washed with water (15 mL), aqueous 1M HCl (15 mL), aqueous saturated sodium bicarbonate soln (15 mL), and brine (15 mL). The organic layer was dried over magnesium sulfate, filtered and concentrated in rotovap. The product 1200-H was used without further purification.

Step 8:

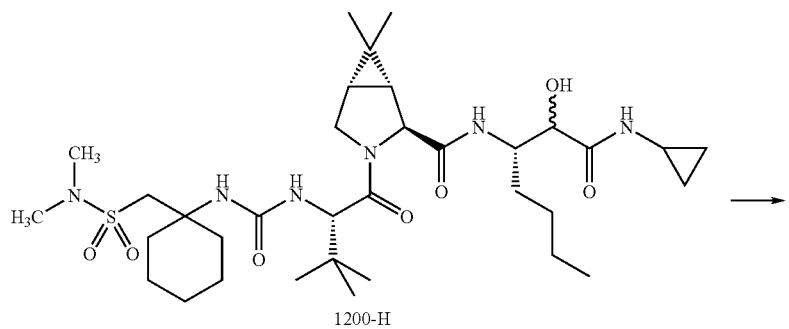

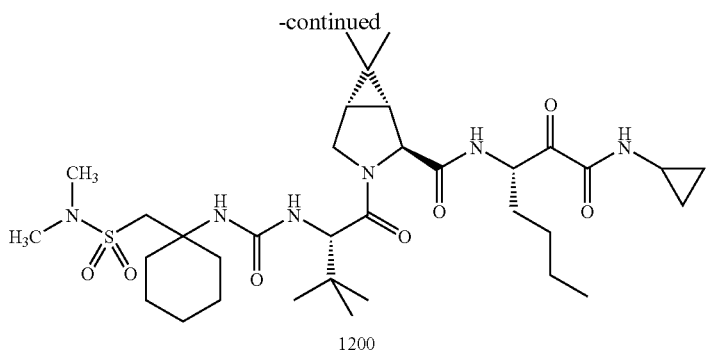

3-{2-[3-(1-Dimethylsulfamoylmethyl-cyclohexyl)-ureido]-3,3-dimethyl-butyryl}-6,6-dimethyl-3-aza-bicyclo[3.1.0]hexane-2-carboxylic acid(1-cyclopropylaminooxalyl-pentyl)-amide (1200): A solution of hydroxyamide 1200-H (0.485 mmol) in 5 mL of dichloromethane was treated with Dess-Martin periodinane (1.3 eq, 267 mg). The mixture was stirred for 30 min at room temp. The reaction was quenched by addition of aqueous sat sodium thiosulfate solution (10 mL). The mixture was stirred for 10 min followed by addition of aqueous sat sodium bicarbonate solution (20 mL). The mixture was stirred for further 10 min. The mixture was extracted with dichloromethane (3×20 mL). The combined organic layers were dried over magnesium sulfate, filtered and concentrated in rotovap. The residue was purified on silica gel (Biotage 25-S column; gradient: 10 to 50% acetone in hexanes) to afford the product 1200 (330 mg; 98%) as a white solid.

Preparative Example 1261

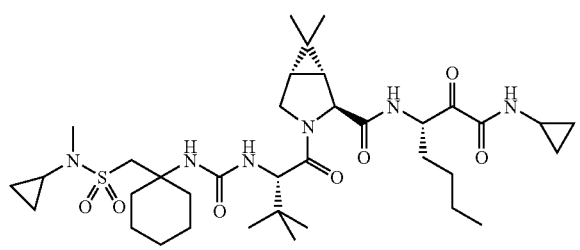

3-[2-(3-{1-[(Cyclopropyl-methyl-sulfamoyl)-methyl]-cyclohexyl}-ureido)-3,3-dimethyl-butyryl]-6,6-dimethyl-3-aza-bicyclo[3.1.0]hexane-2-carboxylic acid (1-cyclopropylaminooxalyl-pentyl)-amide (1261)

Step 1:

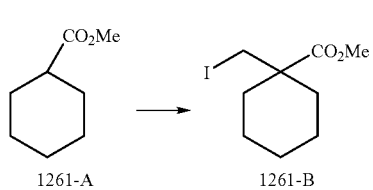

1-Iodomethyl-cyclohexanecarboxylic acid methyl ester (1261-B): To a −78° C. of Diisoprpyl amine (132 mmol, 18.65 mL) in THF (100 mL) was added n-BuLi (120 mmol, 75 mL). Cold bath was removed and put back after 30 minutes. Cyclohexane carboxylic acid methyl ester 1261-A (15.57 g, 109 mmol) was added dropwise in THF (50 mL). After 1 h, Diiodomethane (109 mmol, 8.78 mL) was added while keeping temperature below 10° C. After addition, reaction was warmed to RT and stirred overnight. After 18 h, reaction was quenched with NH$_4$Cl and extracted with EtOAc. Washed with brine, dried over MgSO$_4$, filtered and concentrated down to provide 35 g of product 1261-B.

Step 2:

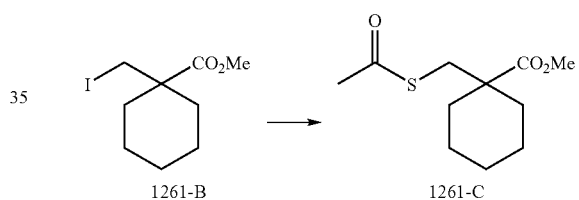

1-Acetylsulfanylmethyl-cyclohexanecarboxylic acid methyl ester (1261-C)

To a cold solution of crude 1261-B (109 mmol) in DMF (90 ml) was added Potassium thioacetate (1.2 equiv, 131 mmol, 15 g) maintaining temperature below 30° C. The reaction was stirred for 18 h then cooled to 10° C. and water (160 mL) was added. Reaction was extracted with EtOAc and washed with NaHCO$_3$ sat., then brine. The dark organic layer was dried over MgSO$_4$, filtered and concentrated down to a dark oil. Purification—HPFC (High Pressure Flash Chromatography) 75+M prepacked silica cartridge (1 to 5% EtOAc), UV collection. After concentration, 20.43 g of product 1261-C was obtained.

Step 3:

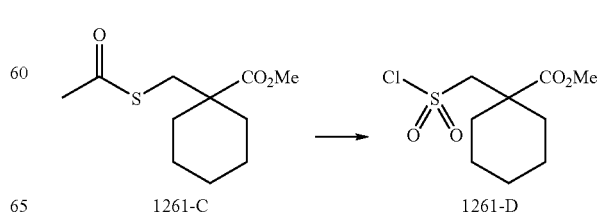

1-Chlorosulfonylmethyl-cyclohexanecarboxylic acid methyl ester (1261-D)

To a stirred solution of thioester 1261-C (53 mmol, 12.23 g) in acetic acid (55 mL) was added water (212 mmol, 3.8 g). Then, chlorine gas (11.3 g, balance in hood, 159 mmol) was bubbled lightly through for about 15-20 minutes. Balance indicated about 11.5 g when bubbling was stopped. Internal temp rose to 55° C. Reaction was cooled down. TLC indicated conversion to a slightly more polar spot. A very small amount of a second more polar spot is also visible. Diluted in DCM, washed with water (twice), then NaOH (0.5N) and brine. DCM layers were dried over MgSO$_4$, filtered and concentrated down to provide 12 g of 1261-D as a light yellow oil.

Step 4:

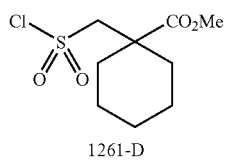

1261-D

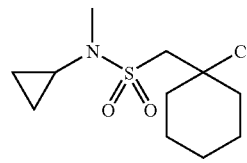

1261-E

1-[(Cyclopropyl-methyl-sulfamoyl)-methyl]-cyclohexanecarboxylic acid methyl ester (1261-E)

To a RT solution of DCM (10 mL) containing sulfonyl chloride 1261-D (4 mmol, 1 g) was added cyclopropyl amine (1.5 equiv, 6 mmol, 0.36 g) followed by Et$_3$N (2 mL). After 5 h, reaction was poured into EtOAc and washed with NaHCO$_3$, HCl 1.0N and brine. Organic layer was dried over MgSO$_4$, filtered and concentrated down to yield 1.28 g (99%) of cyclopropyl sulfonamide intermediate. To a 0° C. solution of sulfonamide (4 mmol) in DMF (10 mL) was added Cs$_2$CO$_3$ (1.5 equiv, 6 mmol, 2 g) followed by MeI (1.8 equiv, 7.2 mmol, 0.45 mL). Reaction was stirred over night. Diluted with EtOAc and washed with water (2×50 mL), NH$_4$Cl and brine. Organic layer was dried over MgSO$_4$, filtered and concentrated down to a light yellow oil, 1261-E (1.15 g).

Step 5:

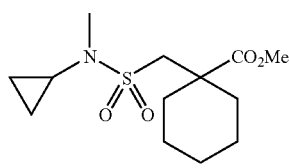

1261-E

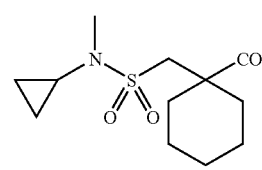

1261-F

1-[(Cyclopropyl-methyl-sulfamoyl)-methyl]-cyclohexanecarboxylic acid (1261-F)

To a RT solution of MeOH (30 mL) containing ester 1261-E (4 mmol, 1.1 g) was added aqueous KOH (17.6 mL, 61.7 mmol) and the reaction was brought to 55° C. for 18 hours. Volatile were removed under vacuum and residue was acidified to pH 4 with HCl 1.0N. Diluted with EtOAc and washed with water (2×20 mL) and brine. Organic layer was dried over MgSO$_4$, filtered and concentrated down to give acid 1261-F (1.09 g, 96%).

Step 6:

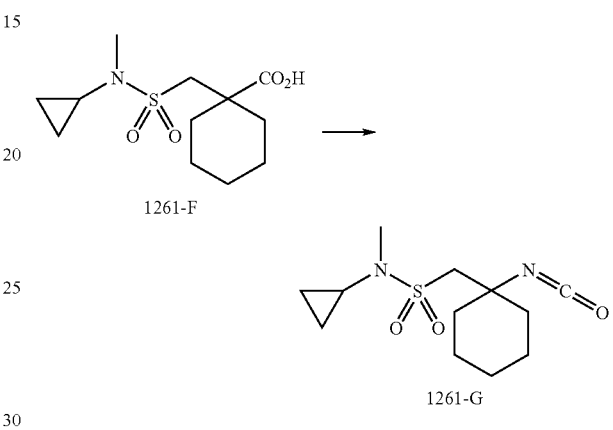

N-Cyclopropyl-C-(1-isocyanato-cyclohexyl)-N-methyl-methanesulfonamide (1261-G)

To a RT solution of toluene (15 mL) containing acid 1261-F (3.96 mmol, 1.0 g) was added DPPA (0.85 mL, 3.96 mmol) followed by Et$_3$N (0.56 mL, 3.96 mmol). The reaction was stirred at RT for 10 min then refluxed for 2 hours. Reaction was cooled down to RT and diluted with DCM (50 mL). Washed with NaHCO$_3$, brine and organic layer was dried over MgSO$_4$. The volatile were removed and the residue was diluted with DCM (15 mL) to give 1261-G as a 0.26M solution.

Step 7:

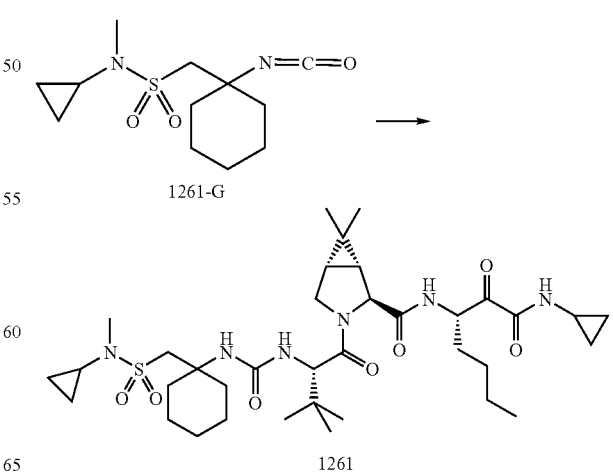

3-[2-(3-{1-[(Cyclopropyl-methyl-sulfamoyl)-methyl]-cyclohexyl}-ureido)-3,3-dimethyl-butyryl]-6,6-dimethyl-3-aza-bicyclo[3.1.0]hexane-2-carboxylic acid (1-cyclopropylaminooxalyl-pentyl)-amide (1261)

The required product 1261 was obtained from isocyanate 1261-G using procedures described above (similar to Prep Example 1200). All compounds (Preparative Examples) shown in Table 1 were prepared using essentially procedures described above (Prep Examples 1200 and 1261) using appropriate modifications.

Table 1 lists the inventive compounds and their HCV serine protease inhibitory activity ranges, as determined by the assay described later. The activity is shown as Ki* ranges (nanoMolar), which are:

(Ki* range: A<75 nM, B=75-250 nM; C>250 nM)

TABLE 1

| Preparative Example | Compound | Ki* Range |
|---|---|---|
| 1200 | 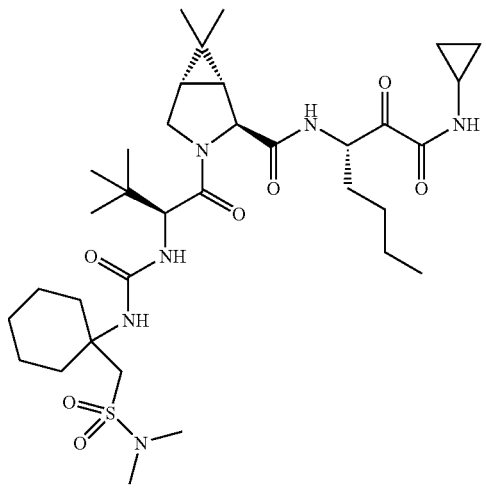 | A |
| 1201 | 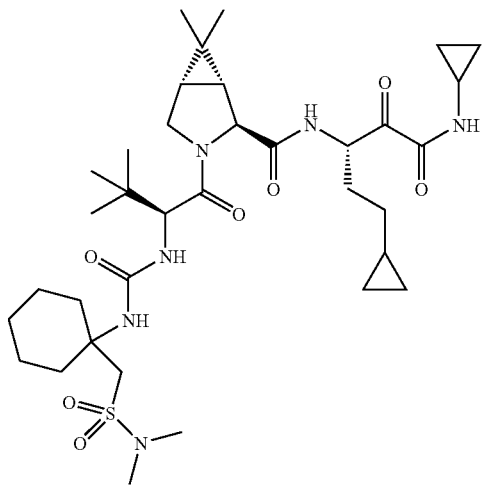 | A |

TABLE 1-continued

| Preparative Example | Compound | Ki* Range |
|---|---|---|
| 1202 | | A |
| 1203 | | A |
| 1204 | | A |

TABLE 1-continued

| Preparative Example | Compound | Ki* Range |
|---|---|---|
| 1205 | | A |
| 1206 | | A |
| 1207 | | A |

TABLE 1-continued

| Preparative Example | Compound | Ki* Range |
|---|---|---|
| 1208 | | A |
| 1209 | | A |
| 1210 | | A |

TABLE 1-continued
| Preparative Example | Compound | Ki* Range |
|---|---|---|
| 1211 | 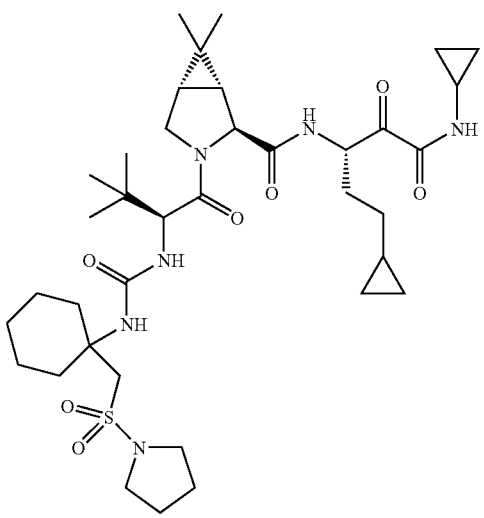 | A |
| 1212 | 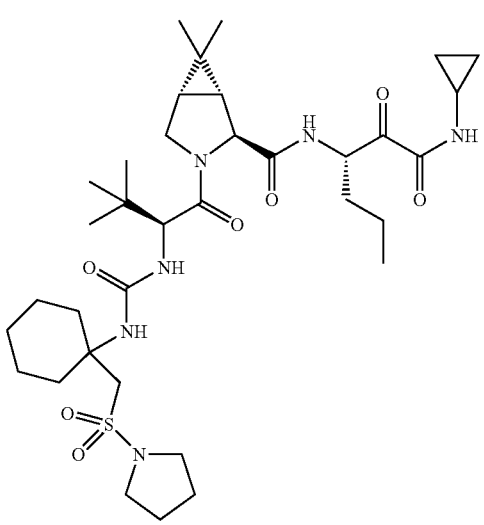 | A |
| 1213 | 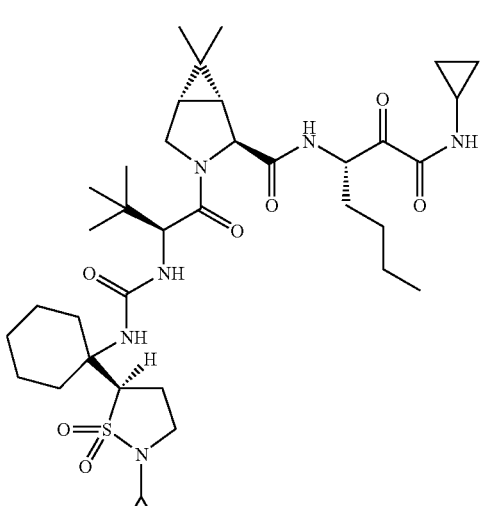 | A |

TABLE 1-continued

| Preparative Example | Compound | Ki* Range |
|---|---|---|
| 1214 | | A |
| 1215 | | A |
| 1216 | | A |

TABLE 1-continued

| Preparative Example | Compound | Ki* Range |
|---|---|---|
| 1217 | | A |
| 1218 | | A |
| 1219 | | A |

TABLE 1-continued

| Preparative Example | Compound | Ki* Range |
|---|---|---|
| 1220 | | A |
| 1221 | | A |
| 1222 | | A |

TABLE 1-continued

| Preparative Example | Compound | Ki* Range |
|---|---|---|
| 1223 | | C |
| 1224 | | B |
| 1225 | | C |

TABLE 1-continued

| Preparative Example | Compound | Ki* Range |
|---|---|---|
| 1226 | | C |
| 1227 | | A |
| 1228 | | A |

TABLE 1-continued

| Preparative Example | Compound | Ki* Range |
|---|---|---|
| 1229 | | A |
| 1230 | | A |
| 1231 | | A |

TABLE 1-continued
| Preparative Example | Compound | Ki* Range |
|---|---|---|
| 1232 | 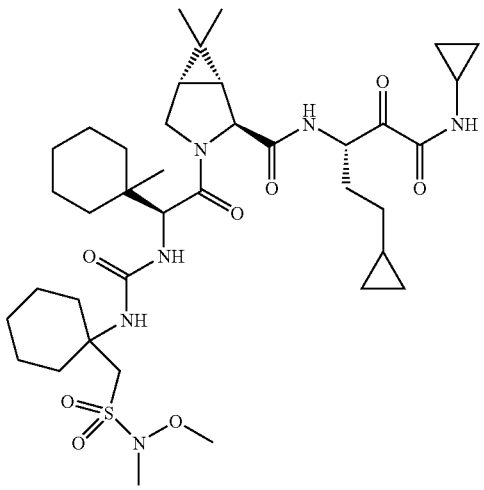 | A |
| 1233 | 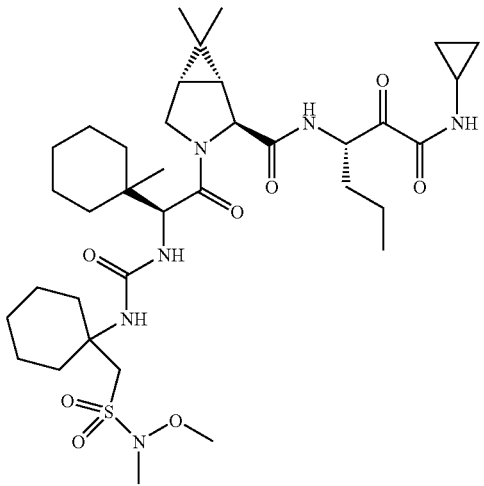 | A |
| 1234 | 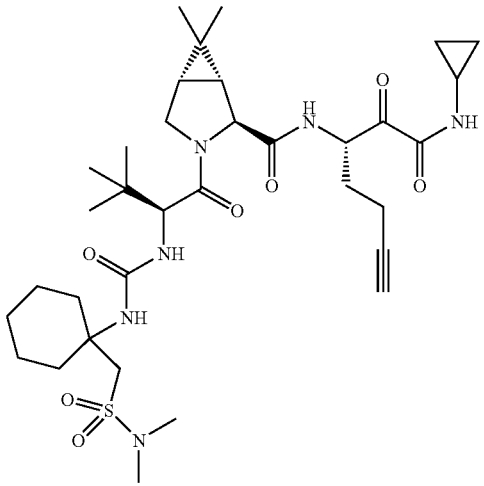 | A |

TABLE 1-continued

| Preparative Example | Compound | Ki* Range |
|---|---|---|
| 1235 | | A |
| 1236 | | A |
| 1237 | | A |

TABLE 1-continued

| Preparative Example | Compound | Ki* Range |
|---|---|---|
| 1238 | | A |
| 1239 | | A |
| 1240 | | A |

TABLE 1-continued

| Preparative Example | Compound | Ki* Range |
|---|---|---|
| 1241 | | A |
| 1242 | | A |
| 1243 | | A |

TABLE 1-continued

| Preparative Example | Compound | Ki* Range |
|---|---|---|
| 1244 | | A |
| 1245 | | A |
| 1246 | | A |

TABLE 1-continued

| Preparative Example | Compound | Ki* Range |
|---|---|---|
| 1247 | | A |
| 1248 | | A |
| 1249 | | A |

TABLE 1-continued

| Preparative Example | Compound | Ki* Range |
|---|---|---|
| 1250 | | A |
| 1251 | | A |
| 1252 | | A |

US 7,816,326 B2
TABLE 1-continued
| Preparative Example | Compound | Ki* Range |
|---|---|---|
| 1253 | 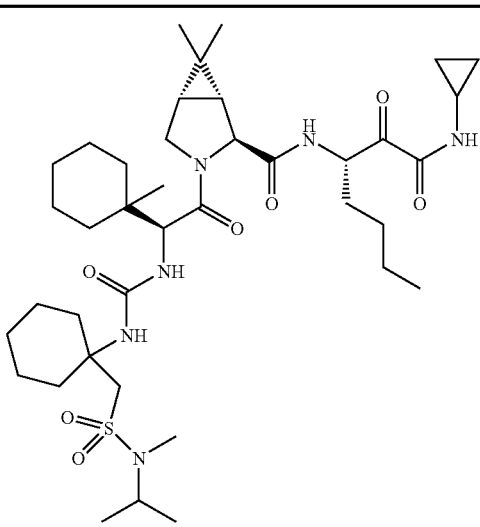 | A |
| 1254 | 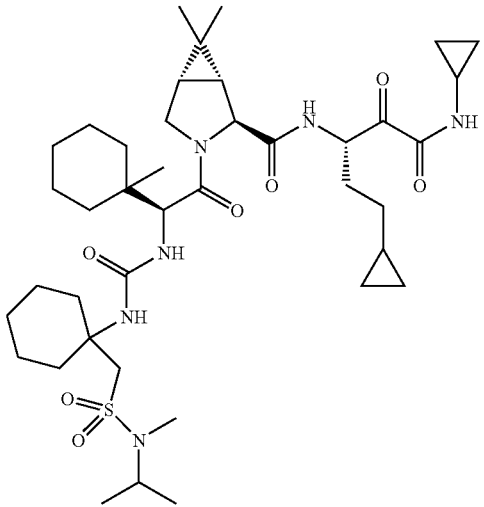 | A |
| 1255 | 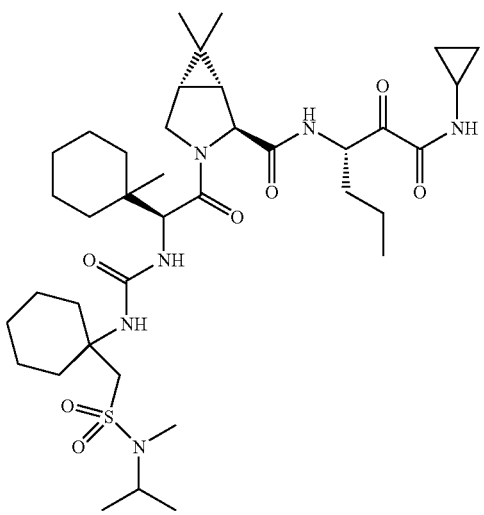 | A |

TABLE 1-continued

| Preparative Example | Compound | Ki* Range |
|---|---|---|
| 1256 | | A |
| 1257 | | A |
| 1258 | | A |

TABLE 1-continued

| Preparative Example | Compound | Ki* Range |
|---|---|---|
| 1259 | | A |
| 1260 | | A |
| 1261 | | A |

TABLE 1-continued

| Preparative Example | Compound | Ki* Range |
|---|---|---|
| 1262 | | A |
| 1263 | | A |
| 1264 | | A |

TABLE 1-continued

| Preparative Example | Compound | Ki* Range |
|---|---|---|
| 1265 | | A |
| 1266 | | A |
| 1267 | | A |

TABLE 1-continued

| Preparative Example | Compound | Ki* Range |
|---|---|---|
| 1268 | | A |
| 1269 | | A |
| 1270 | | A |

TABLE 1-continued
| Preparative Example | Compound | Ki* Range |
|---|---|---|
| 1271 | 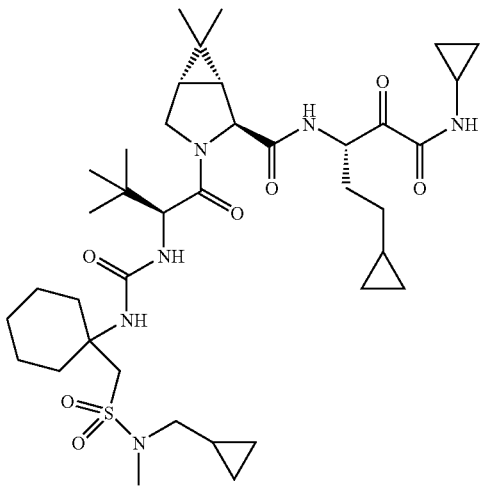 | A |
| 1272 | 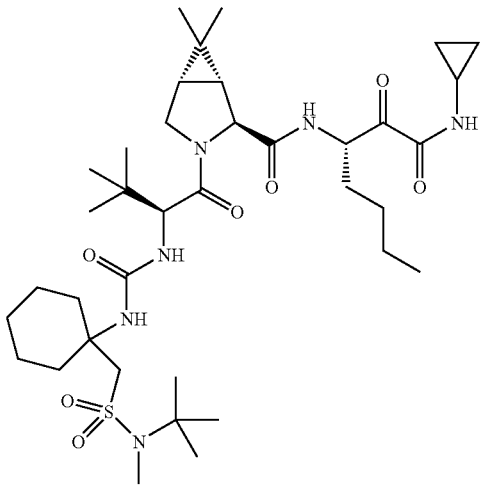 | A |
| 1273 | 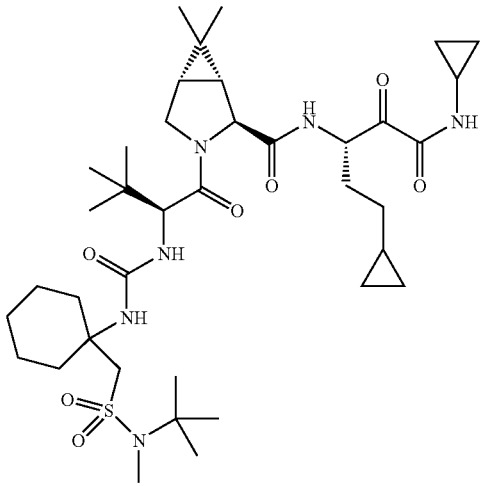 | A |

TABLE 1-continued

| Preparative Example | Compound | Ki* Range |
|---|---|---|
| 1274 | | A |
| 1275 | | A |
| 1276 | | A |

TABLE 1-continued
| Preparative Example | Compound | Ki* Range |
|---|---|---|
| 1277 | 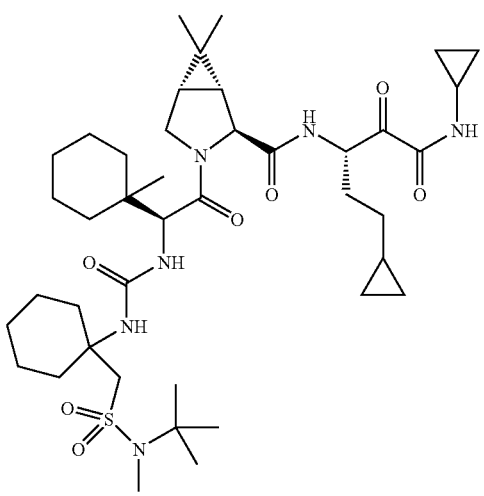 | A |
| 1278 | 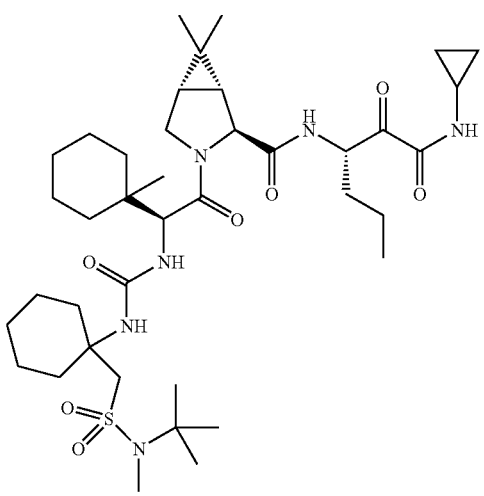 | A |
| 1279 | 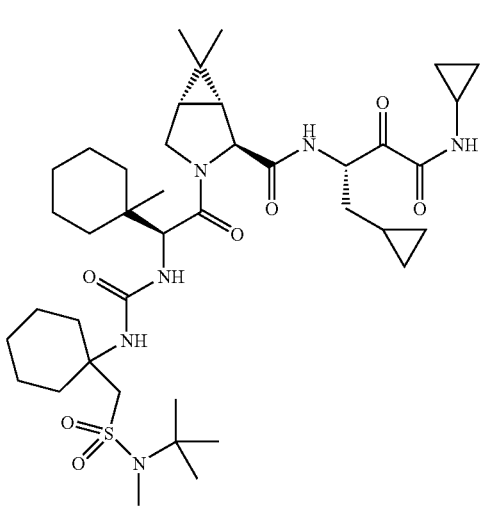 | A |

TABLE 1-continued

| Preparative Example | Compound | Ki* Range |
|---|---|---|
| 1280 | | A |
| 1281 | | A |
| 1282 | | A |

TABLE 1-continued
| Preparative Example | Compound | Ki* Range |
|---|---|---|
| 1283 | 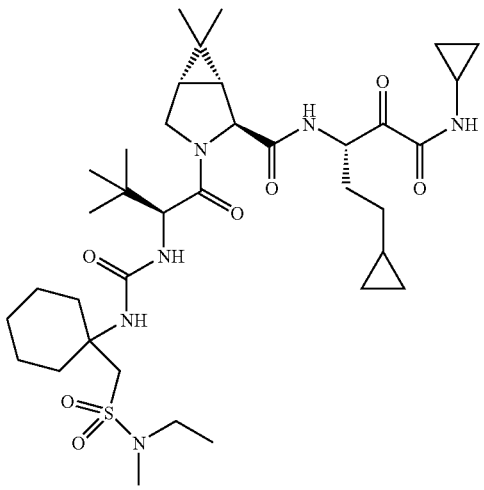 | A |
| 1284 | 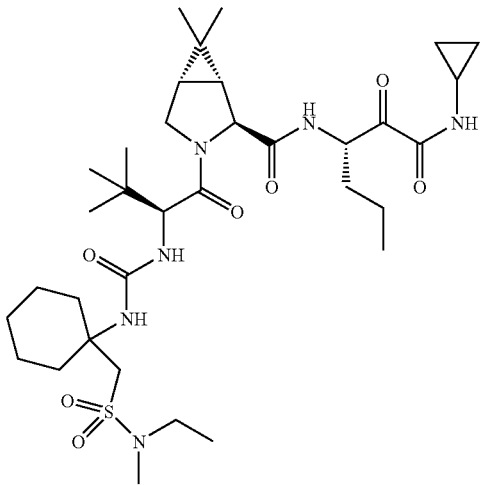 | A |
| 1285 | 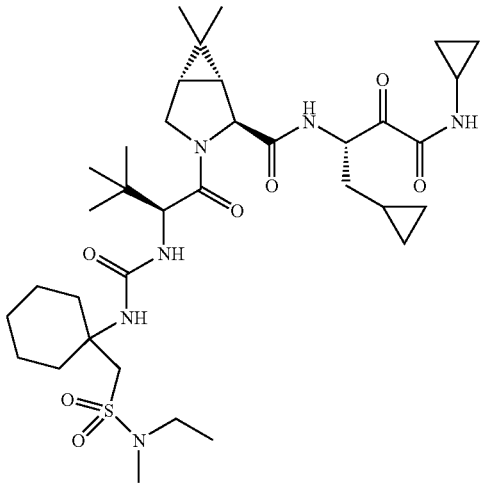 | A |

TABLE 1-continued

| Preparative Example | Compound | Ki* Range |
|---|---|---|
| 1286 | | A |
| 1287 | | A |
| 1288 | | A |

TABLE 1-continued

| Preparative Example | Compound | Ki* Range |
|---|---|---|
| 1289 | | A |
| 1290 | | A |
| 1291 | | A |

TABLE 1-continued

| Preparative Example | Compound | Ki* Range |
|---|---|---|
| 1292 | | A |
| 1293 | | A |
| 1294 | | A |

TABLE 1-continued

| Preparative Example | Compound | Ki* Range |
|---|---|---|
| 1295 | | A |
| 1296 | | A |
| 1297 | | A |

TABLE 1-continued

| Preparative Example | Compound | Ki* Range |
|---|---|---|
| 1298 | | A |
| 1299 | | A |
| 1300 | | A |

TABLE 1-continued

| Preparative Example | Compound | Ki* Range |
|---|---|---|
| 1301 | | A |
| 1302 | | A |
| 1303 | | A |

TABLE 1-continued
| Preparative Example | Compound | Ki* Range |
|---|---|---|
| 1304 | 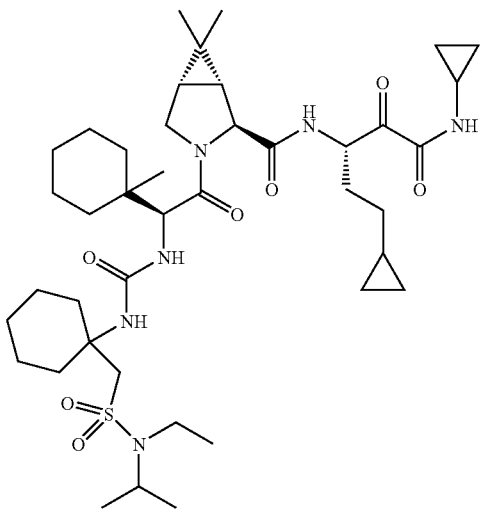 | A |
| 1305 | 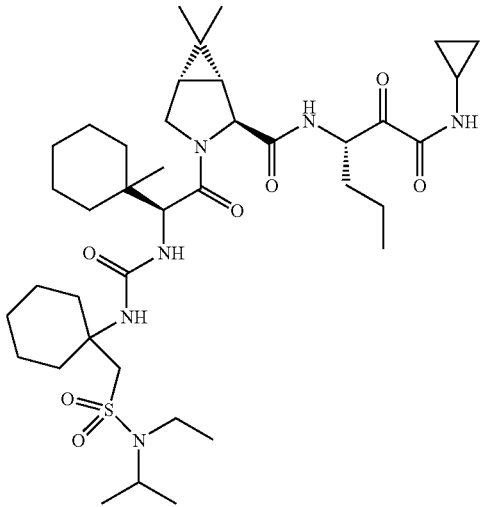 | A |
| 1306 | 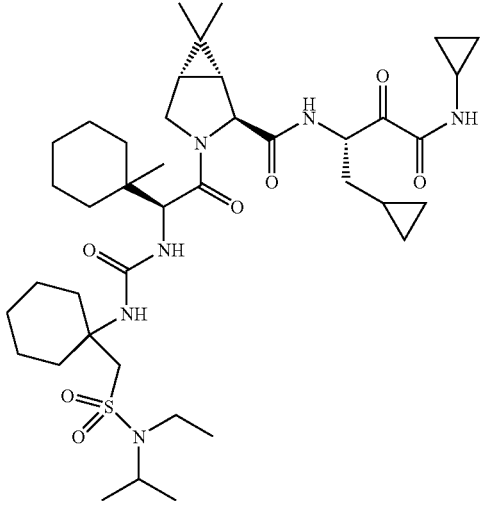 | A |

TABLE 1-continued

| Preparative Example | Compound | Ki* Range |
|---|---|---|
| 1307 | | A |
| 1308 | | A |
| 1309 | | A |

TABLE 1-continued

| Preparative Example | Compound | Ki* Range |
|---|---|---|
| 1310 | | A |
| 1311 | | A |
| 1312 | | A |

TABLE 1-continued

| Preparative Example | Compound | Ki* Range |
|---|---|---|
| 1313 | | A |
| 1314 | | A |
| 1315 | | A |

TABLE 1-continued

| Preparative Example | Compound | Ki* Range |
|---|---|---|
| 1316 | | A |
| 1317 | | A |
| 1318 | | A |

TABLE 1-continued

| Preparative Example | Compound | Ki* Range |
|---|---|---|
| 1319 | | A |
| 1320 | | A |
| 1321 | | A |

TABLE 1-continued

| Preparative Example | Compound | Ki* Range |
|---|---|---|
| 1322 | | A |
| 1323 | | A |
| 1324 | | A |

TABLE 1-continued

| Preparative Example | Compound | Ki* Range |
|---|---|---|
| 1325 | | A |
| 1326 | | A |
| 1327 | | A |

TABLE 1-continued

| Preparative Example | Compound | Ki* Range |
|---|---|---|
| 1328 | | A |
| 1329 | | A |
| 1330 | | A |

TABLE 1-continued

| Preparative Example | Compound | Ki* Range |
|---|---|---|
| 1331 | | A |
| 1332 | | A |
| 1333 | | A |

TABLE 1-continued

| Preparative Example | Compound | Ki* Range |
|---|---|---|
| 1334 | | A |
| 1335 | | A |
| 1336 | | A |

TABLE 1-continued

| Preparative Example | Compound | Ki* Range |
|---|---|---|
| 1337 | | A |
| 1338 | | A |
| 1339 | | A |

TABLE 1-continued

| Preparative Example | Compound | Ki* Range |
|---|---|---|
| 1340 | | A |
| 1341 | | A |
| 1342 | | A |

TABLE 1-continued

| Preparative Example | Compound | Ki* Range |
|---|---|---|
| 1343 | | A |
| 1344 | | A |
| 1345 | | A |

TABLE 1-continued

| Preparative Example | Compound | Ki* Range |
|---|---|---|
| 1346 | | A |
| 1347 | | A |
| 1348 | | A |

TABLE 1-continued

| Preparative Example | Compound | Ki* Range |
|---|---|---|
| 1349 | | A |
| 1350 | | A |
| 1351 | | A |

TABLE 1-continued

| Preparative Example | Compound | Ki* Range |
|---|---|---|
| 1352 | | A |
| 1353 | | A |
| 1354 | | A |

TABLE 1-continued

| Preparative Example | Compound | Ki* Range |
|---|---|---|
| 1355 | | A |
| 1356 | | A |
| 1357 | | A |

TABLE 1-continued

| Preparative Example | Compound | Ki* Range |
|---|---|---|
| 1358 | | A |
| 1359 | | A |
| 1360 | | A |

TABLE 1-continued
| Preparative Example | Compound | Ki* Range |
|---|---|---|
| 1361 | 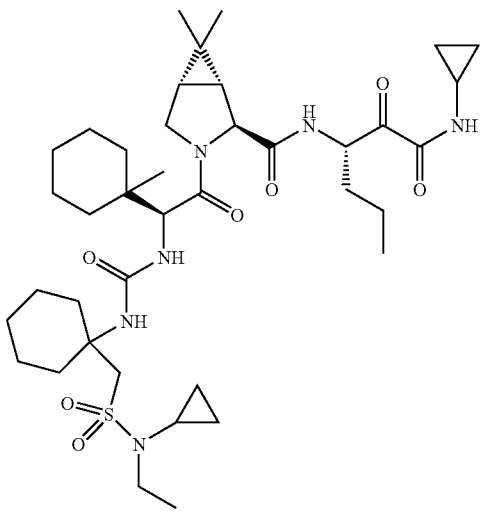 | A |
| 1362 | 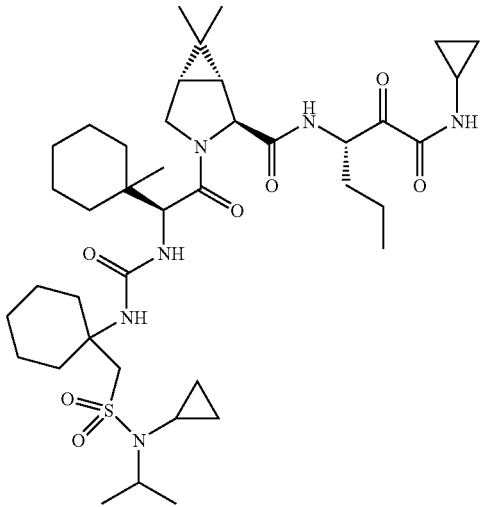 | A |
| 1363 | 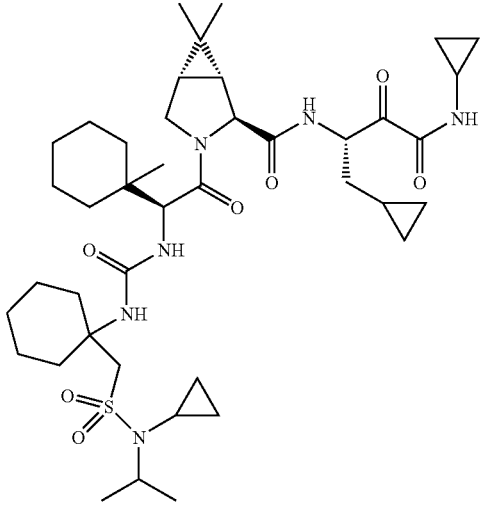 | A |

TABLE 1-continued

| Preparative Example | Compound | Ki* Range |
|---|---|---|
| 1364 | | A |
| 1365 | | A |
| 1366 | | A |

TABLE 1-continued

| Preparative Example | Compound | Ki* Range |
|---|---|---|
| 1367 | | A |
| 1368 | | A |
| 1369 | | A |

TABLE 1-continued

| Preparative Example | Compound | Ki* Range |
|---|---|---|
| 1370 | | A |
| 1371 | | A |
| 1372 | | A |

TABLE 1-continued
| Preparative Example | Compound | Ki* Range |
|---|---|---|
| 1373 | 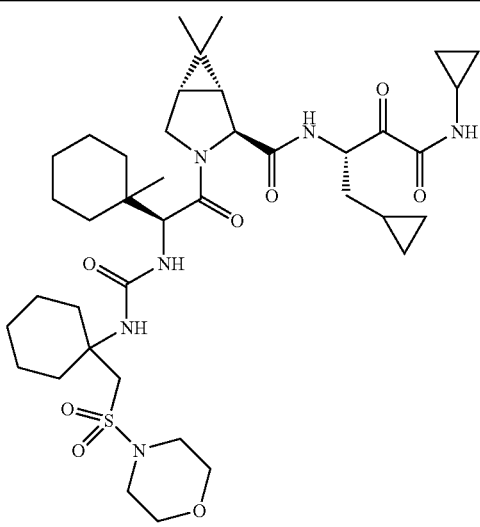 | A |
| 1374 | 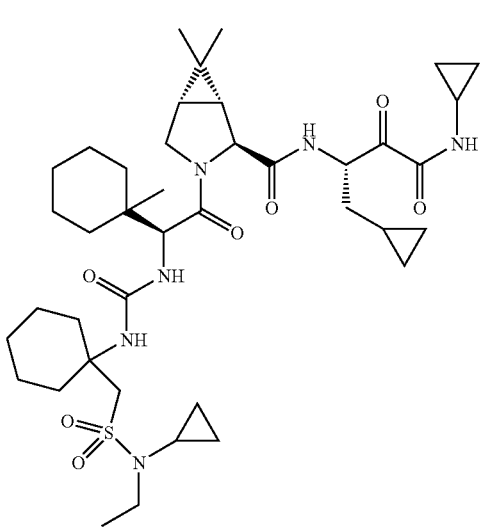 | A |
| 1375 | 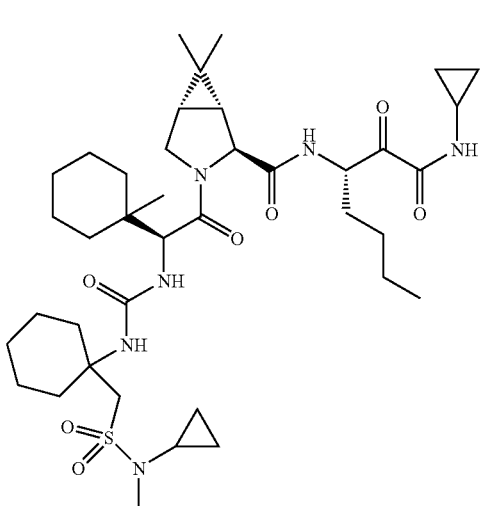 | A |

TABLE 1-continued

| Preparative Example | Compound | Ki* Range |
|---|---|---|
| 1376 | | A |
| 1377 | | A |
| 1378 | | A |

TABLE 1-continued

| Preparative Example | Compound | Ki* Range |
|---|---|---|
| 1379 | | A |
| 1380 | | A |
| 1381 | | A |

TABLE 1-continued

| Preparative Example | Compound | Ki* Range |
|---|---|---|
| 1382 | | A |
| 1383 | | A |
| 1384 | | A |

TABLE 1-continued

| Preparative Example | Compound | Ki* Range |
|---|---|---|
| 1385 | | A |
| 1386 | | A |
| 1387 | | A |

TABLE 1-continued
| Preparative Example | Compound | Ki* Range |
|---|---|---|
| 1388 | 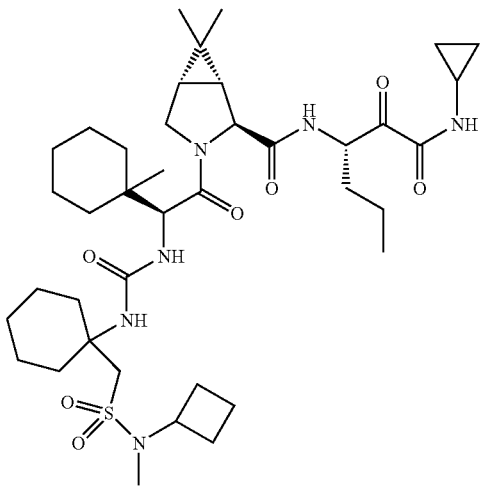 | A |
| 1389 | 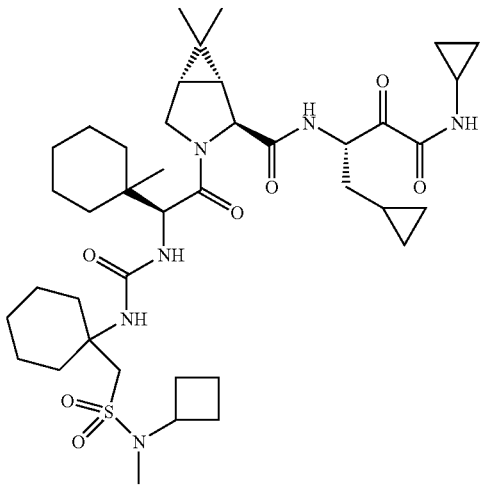 | A |
| 1390 | 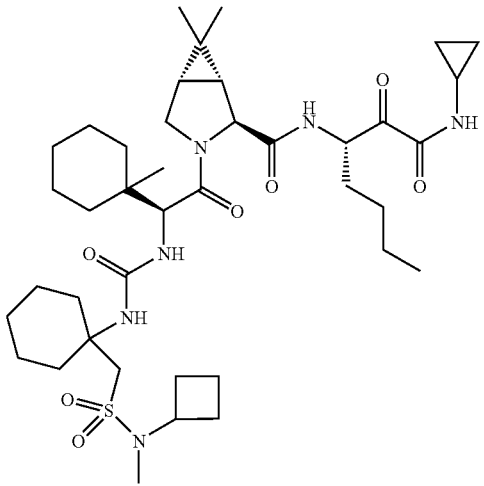 | A |

TABLE 1-continued

| Preparative Example | Compound | Ki* Range |
|---|---|---|
| 1391 | | A |
| 1392 | | A |
| 1393 | | A |

TABLE 1-continued

| Preparative Example | Compound | Ki* Range |
|---|---|---|
| 1394 | | A |
| 1395 | | A |
| 1396 | | A |

TABLE 1-continued

| Preparative Example | Compound | Ki* Range |
|---|---|---|
| 1397 | | A |
| 1398 | | A |
| 1399 | | A |

TABLE 1-continued

| Preparative Example | Compound | Ki* Range |
|---|---|---|
| 1400 | | A |
| 1401 | | A |
| 1402 | | A |

TABLE 1-continued

| Preparative Example | Compound | Ki* Range |
|---|---|---|
| 1403 | | A |
| 1404 | | A |
| 1405 | | A |

TABLE 1-continued

| Preparative Example | Compound | Ki* Range |
|---|---|---|
| 1406 | | A |
| 1407 | | A |
| 1408 | | A |

TABLE 1-continued

| Preparative Example | Compound | Ki* Range |
|---|---|---|
| 1409 | | A |
| 1410 | | A |
| 1411 | | A |

TABLE 1-continued

| Preparative Example | Compound | Ki* Range |
|---|---|---|
| 1412 | | A |
| 1413 | | A |
| 1414 | | A |

TABLE 1-continued

| Preparative Example | Compound | Ki* Range |
|---|---|---|
| 1415 | | A |
| 1416 | | A |
| 1417 | | A |

TABLE 1-continued
| Preparative Example | Compound | Ki* Range |
|---|---|---|
| 1418 | 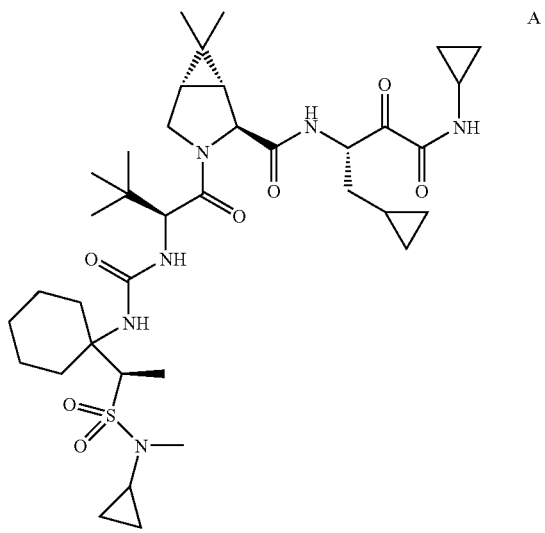 | A |
| 1419 | 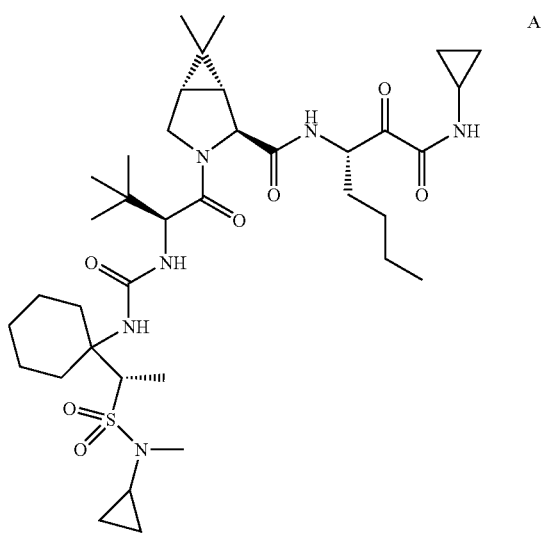 | A |

TABLE 1-continued
| Preparative Example | Compound | Ki* Range |
|---|---|---|
| 1420 | 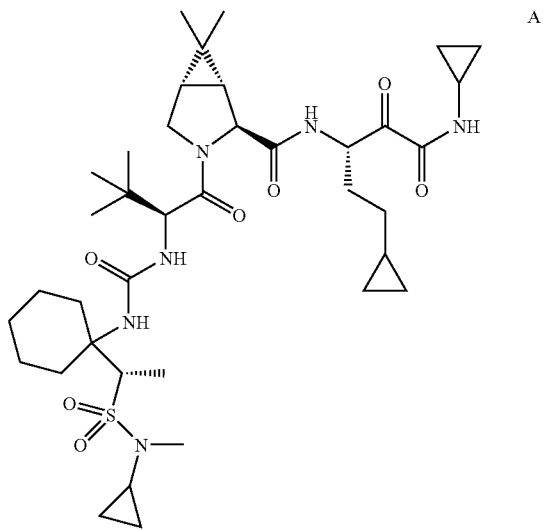 | A |
| 1421 | 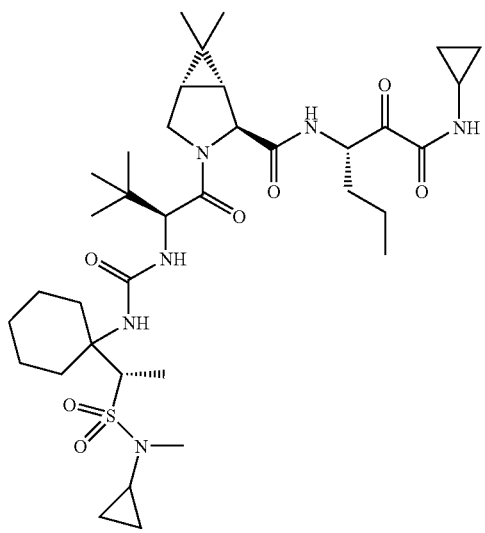 | A |

TABLE 1-continued

| Preparative Example | Compound | Ki* Range |
|---|---|---|
| 1422 | 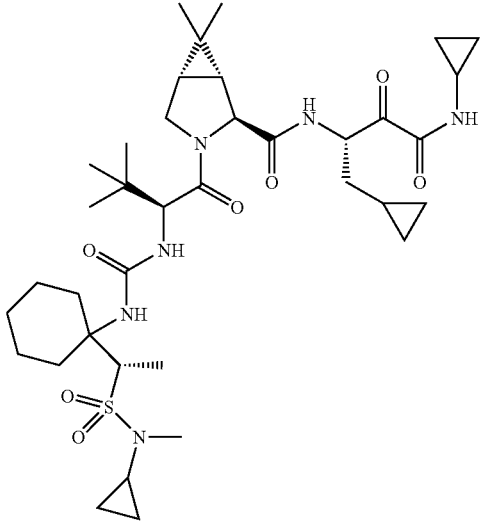 | A |

The present invention relates to novel HCV protease inhibitors. This utility can be manifested in their ability to inhibit the HCV NS2/NS4a serine protease. A general procedure for such demonstration is illustrated by the following in vitro assay.

Assay for HCV Protease Inhibitory Activity:

Spectrophotometric Assay: Spectrophotometric assay for the HCV serine protease can be performed on the inventive compounds by following the procedure described by R. Zhang et al, *Analytical Biochemistry*, 270 (1999) 268-275, the disclosure of which is incorporated herein by reference. The assay based on the proteolysis of chromogenic ester substrates is suitable for the continuous monitoring of HCV NS3 protease activity. The substrates are derived from the P side of the NS5A-NS5B junction sequence (Ac-DTEDVVX(Nva), where X=A or P) whose C-terminal carboxyl groups are esterified with one of four different chromophoric alcohols (3- or 4-nitrophenol, 7-hydroxy-4-methyl-coumarin, or 4-phenylazophenol). Illustrated below are the synthesis, characterization and application of these novel spectrophotometric ester substrates to high throughput screening and detailed kinetic evaluation of HCV NS3 protease inhibitors.

Materials and Methods:

Materials: Chemical reagents for assay related buffers are obtained from Sigma Chemical Company (St. Louis, Mo.). Reagents for peptide synthesis were from Aldrich Chemicals, Novabiochem (San Diego, Calif.), Applied Biosystems (Foster City, Calif.) and Perseptive Biosystems (Framingham, Mass.). Peptides are synthesized manually or on an automated ABI model 431A synthesizer (from Applied Biosystems). UV/VIS Spectrometer model LAMBDA 12 was from Perkin Elmer (Norwalk, Conn.) and 96-well UV plates were obtained from Corning (Corning, N.Y.). The prewarming block can be from USA Scientific (Ocala, Fla.) and the 96-well plate vortexer is from Labline Instruments (Melrose Park, Ill.). A Spectramax Plus microtiter plate reader with monochrometer is obtained from Molecular Devices (Sunnyvale, Calif.).

Enzyme Preparation: Recombinant heterodimeric HCV NS3/NS4A protease (strain 1a) is prepared by using the procedures published previously (D. L. Sali et al, *Biochemistry*, 37 (1998) 3392-3401). Protein concentrations are determined by the Biorad dye method using recombinant HCV protease standards previously quantified by amino acid analysis. Prior to assay initiation, the enzyme storage buffer (50 mM sodium phosphate pH 8.0, 300 mM NaCl, 10% glycerol, 0.05% lauryl maltoside and 10 mM DTT) is exchanged for the assay buffer (25 mM MOPS pH 6.5, 300 mM NaCl, 10% glycerol, 0.05% lauryl maltoside, 5 μM EDTA and 5 μM DTT) utilizing a Biorad Bio-Spin P-6 prepacked column.

Substrate Synthesis and Purification: The synthesis of the substrates is done as reported by R. Zhang et al, (ibid.) and is initiated by anchoring Fmoc-Nva-OH to 2-chlorotrityl chloride resin using a standard protocol (K. Barlos et al, *Int. J. Pept. Protein Res.*, 37 (1991), 513-520). The peptides are subsequently assembled, using Fmoc chemistry, either manually or on an automatic ABI model 431 peptide synthesizer. The N-acetylated and fully protected peptide fragments are cleaved from the resin either by 10% acetic acid (HOAc) and 10% trifluoroethanol (TFE) in dichloromethane (DCM) for 30 min, or by 2% trifluoroacetic acid (TFA) in DCM for 10 min. The combined filtrate and DCM wash is evaporated azeotropically (or repeatedly extracted by aqueous $Na_2CO_3$ solution) to remove the acid used in cleavage. The DCM phase is dried over $Na_2SO_4$ and evaporated.

The ester substrates are assembled using standard acid-alcohol coupling procedures (K. Holmber et al, *Acta Chem. Scand.*, B33 (1979) 410-412). Peptide fragments are dissolved in anhydrous pyridine (30-60 mg/ml) to which 10 molar equivalents of chromophore and a catalytic amount (0.1 eq.) of para-toluenesulfonic acid (pTSA) were added. Dicyclohexylcarbodiimide (DCC, 3 eq.) is added to initiate the coupling reactions. Product formation is monitored by HPLC and can be found to be complete following 12-72 hour reaction at room temperature. Pyridine solvent is evaporated under vacuum and further removed by azeotropic evaporation with toluene. The peptide ester is deprotected with 95% TFA in DCM for two hours and extracted three times with anhydrous ethyl ether to remove excess chromophore. The deprotected substrate is purified by reversed phase HPLC on a C3 or C8 column with a 30% to 60% acetonitrile gradient (using six column volumes). The overall yield following HPLC purification can be approximately 20-30%. The molecular mass can be confirmed by electrospray ionization mass spectroscopy. The substrates are stored in dry powder form under desiccation.

Spectra of Substrates and Products: Spectra of substrates and the corresponding chromophore products are obtained in the pH 6.5 assay buffer, Extinction coefficients are determined at the optimal off-peak wavelength in 1-cm cuvettes (340 nm for 3-Np and HMC, 370 nm for PAP and 400 nm for 4-Np) using multiple dilutions. The optimal off-peak wavelength is defined as that wavelength yielding the maximum fractional difference in absorbance between substrate and product (product OD−substrate OD)/substrate OD).

Protease Assay: HCV protease assays are performed at 30° C. using a 200 µl reaction mix in a 96-well microtiter plate. Assay buffer conditions (25 mM MOPS pH 6.5, 300 mM NaCl, 10% glycerol, 0.05% lauryl maltoside, 5 µM EDTA and 5 µM DTT) are optimized for the NS3/NS4A heterodimer (D. L. Sali et al, ibid.)). Typically, 150 µl mixtures of buffer, substrate and inhibitor are placed in wells (final concentration of DMSO≦4% v/v) and allowed to preincubate at 30° C. for approximately 3 minutes. Fifty µls of prewarmed protease (12 nM, 30° C.) in assay buffer, is then used to initiate the reaction (final volume 200 µl). The plates are monitored over the length of the assay (60 minutes) for change in absorbance at the appropriate wavelength (340 nm for 3-Np and HMC, 370 nm for PAP, and 400 nm for 4-Np) using a Spectromax Plus microtiter plate reader equipped with a monochrometer (acceptable results can be obtained with plate readers that utilize cutoff filters). Proteolytic cleavage of the ester linkage between the Nva and the chromophore is monitored at the appropriate wavelength against a no enzyme blank as a control for non-enzymatic hydrolysis. The evaluation of substrate kinetic parameters is performed over a 30-fold substrate concentration range (~6-200 µM). Initial velocities are determined using linear regression and kinetic constants are obtained by fitting the data to the Michaelis-Menten equation using non-linear regression analysis (Mac Curve Fit 1.1, K. Raner). Turnover numbers ($k_{cat}$) are calculated assuming the enzyme is fully active.

Evaluation of Inhibitors and Inactivators: The inhibition constants ($K_i$) for the competitive inhibitors Ac-D-(D-Gla)-L-I-(Cha)-C—OH (27), Ac-DTEDVVA(Nva)-OH and Ac-DT-EDVVP(Nva)-OH are determined experimentally at fixed concentrations of enzyme and substrate by plotting $v_o/v_i$ vs. inhibitor concentration ($[I]_o$) according to the rearranged Michaelis-Menten equation for competitive inhibition kinetics: $v_o/v_i = 1 + [I]_o/(K_i(1+[S]_o/K_m))$, where $v_O$ in the uninhibited initial velocity, $v_i$ is the initial velocity in the presence of inhibitor at any given inhibitor concentration ($[I]_o$) and $[S]_o$ is the substrate concentration used. The resulting data are fitted using linear regression and the resulting slope, $1/(K_i(1+[S]_o/K_m))$, is used to calculate the $K_i$ value. The following Table 2 lists the Ki* values (in micromolar) for some of the inventive compounds.

TABLE 2

| Preparative Example | Ki* (µM) |
|---|---|
| 1200 | 0.012 |
| 1261 | 0.011 |
| 1252 | 0.005 |
| 1258 | 0.008 |
| 1262 | 0.006 |
| 1263 | 0.008 |
| 1397 | 0.002 |
| 1410 | 0.0012 |

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A compound exhibiting HCV protease inhibitory activity, or an enantiomer, stereoisomer, rotamer, tautomer, or racemate of said compound, or a pharmaceutically acceptable salt or solvate or ester of said compound or of said enantiomer, stereoisomer, rotamer, tautomer, or racemate, said compound being selected from the group consisting of the compounds of structures listed below:

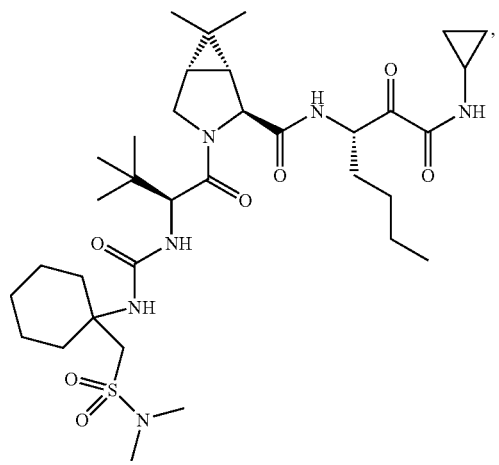

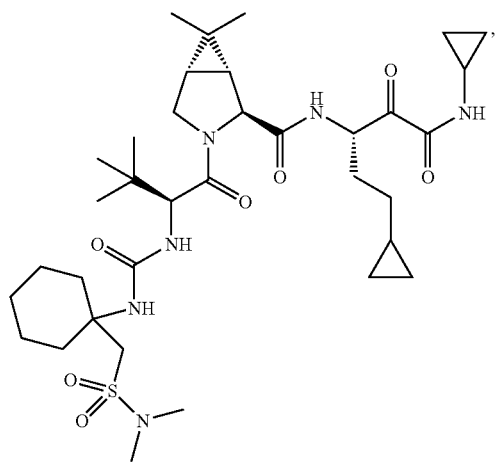

251 252
-continued -continued
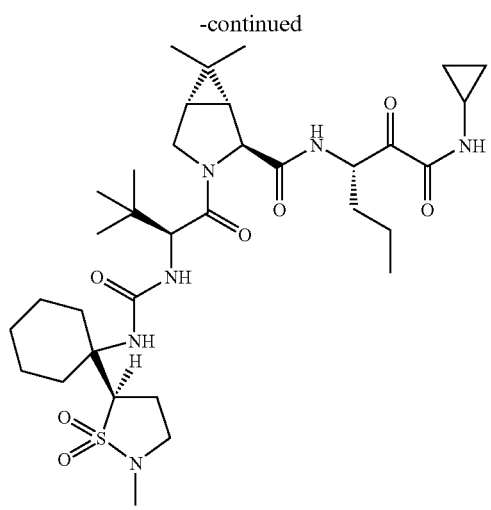
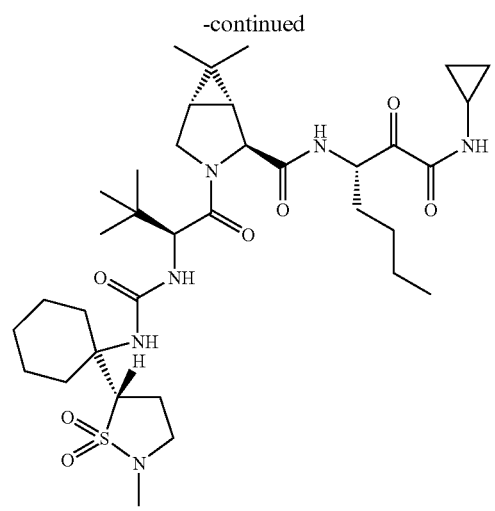
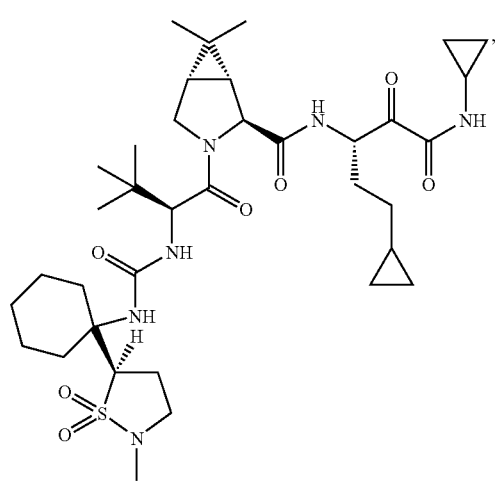
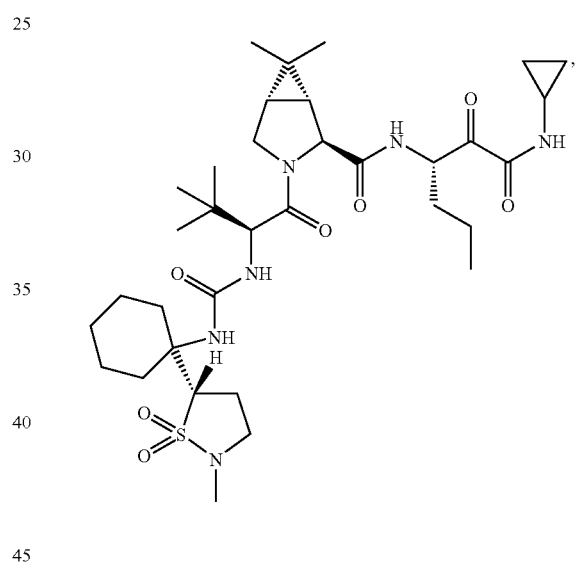
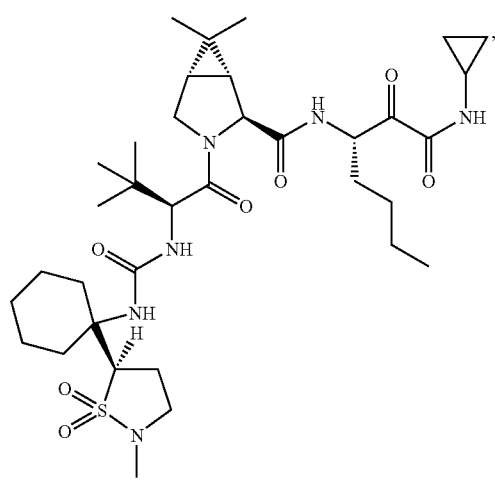
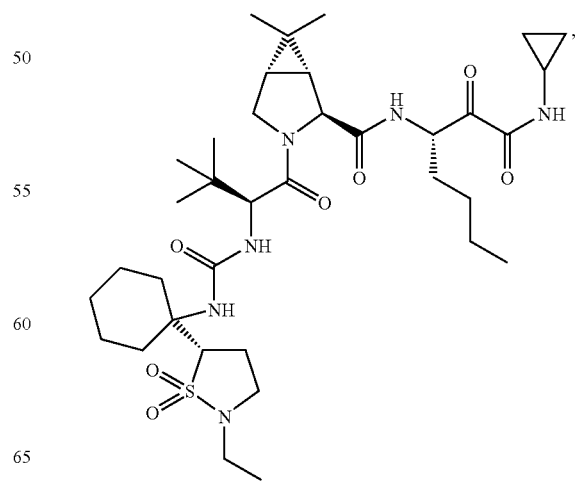

-continued
253
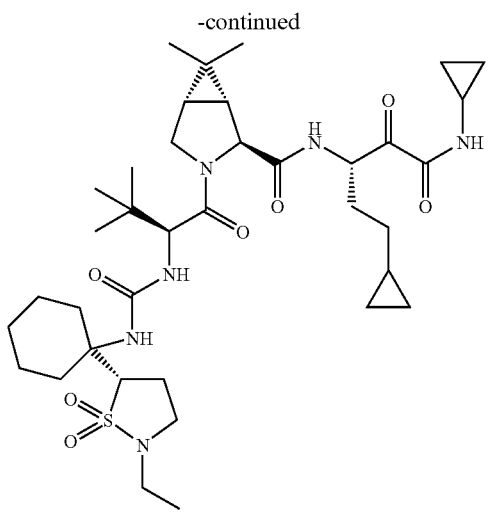
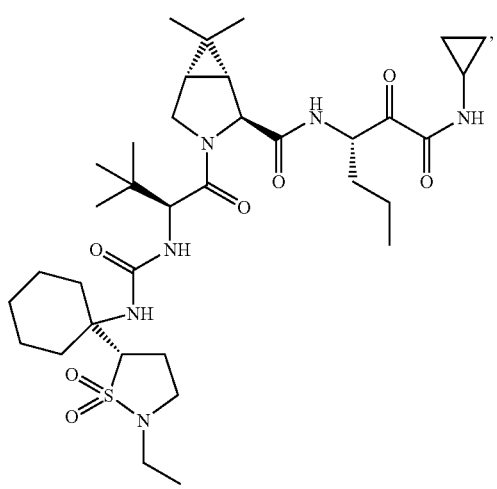
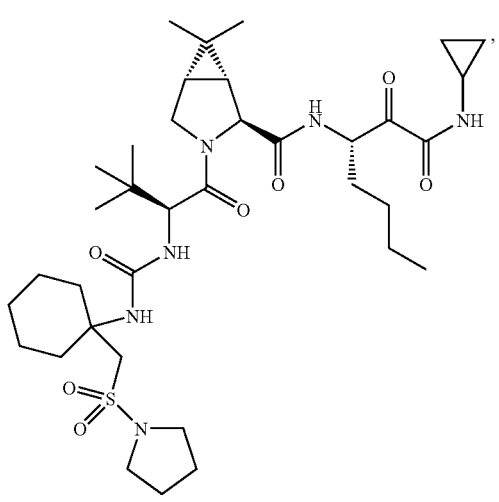
254
-continued
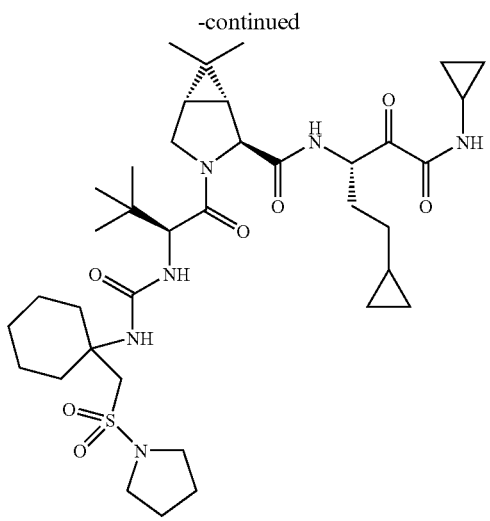
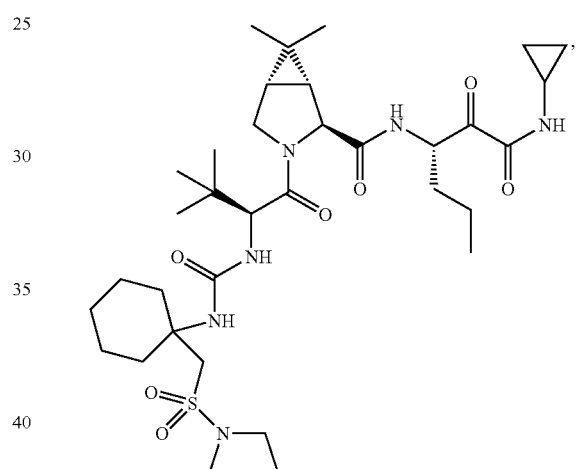
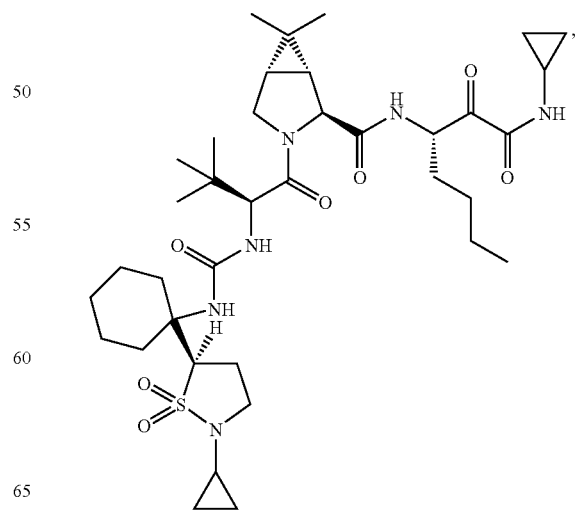

255
-continued
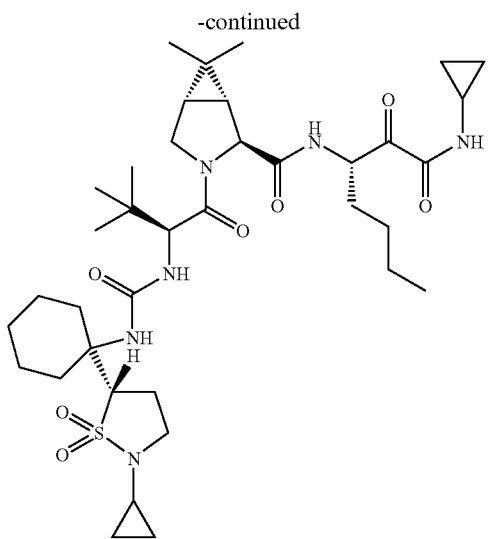
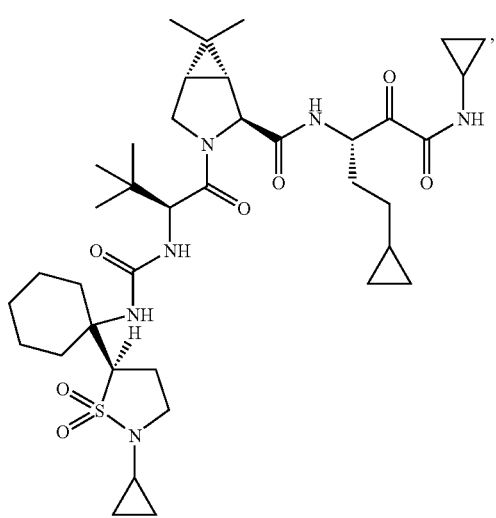
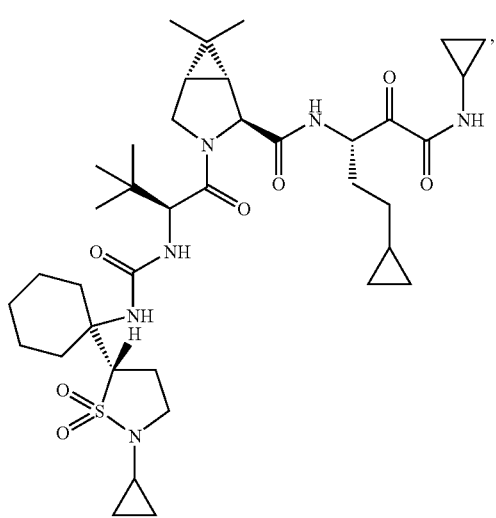
256
-continued
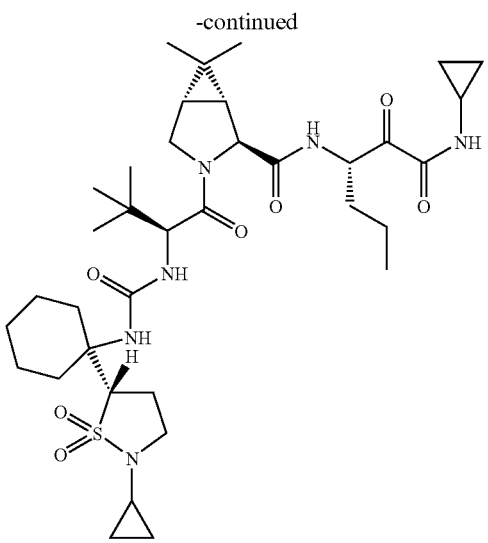
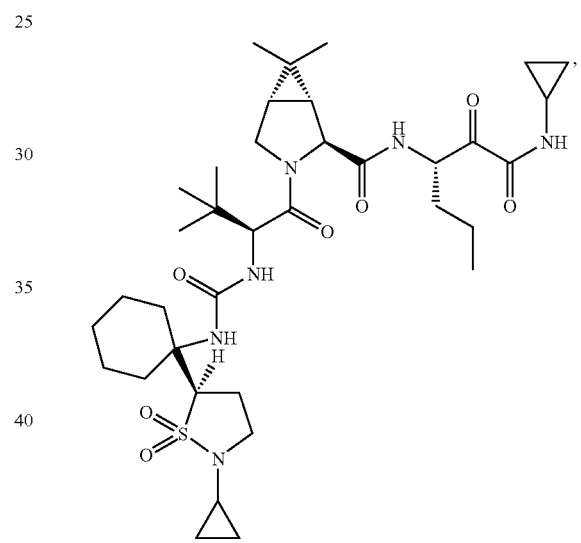
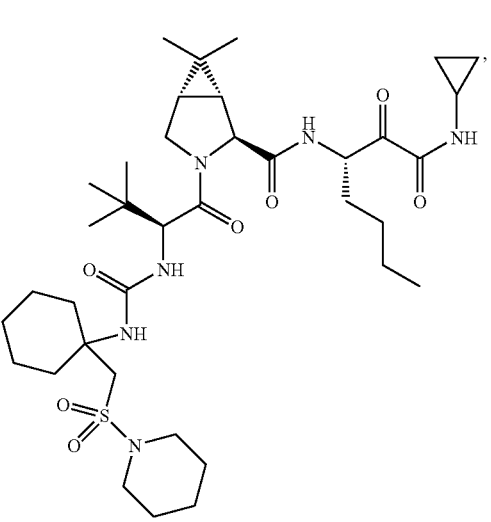

257
-continued
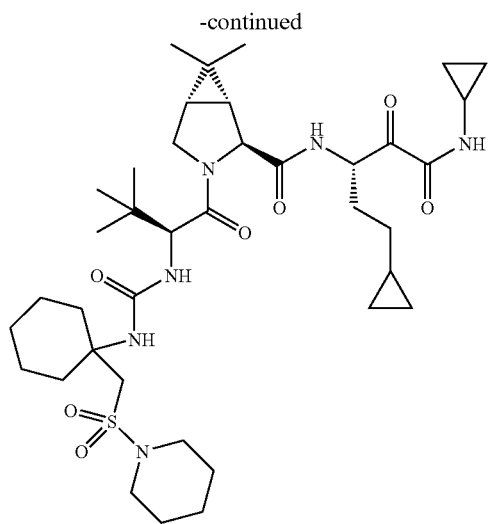
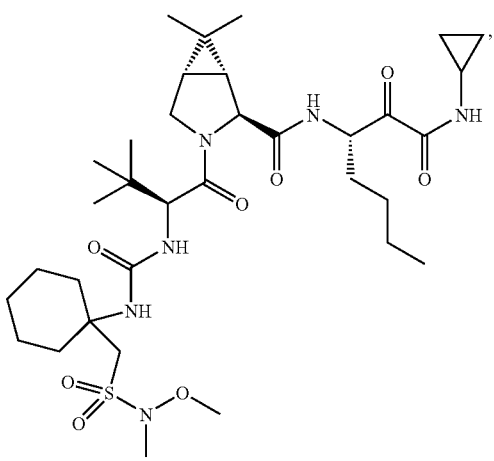
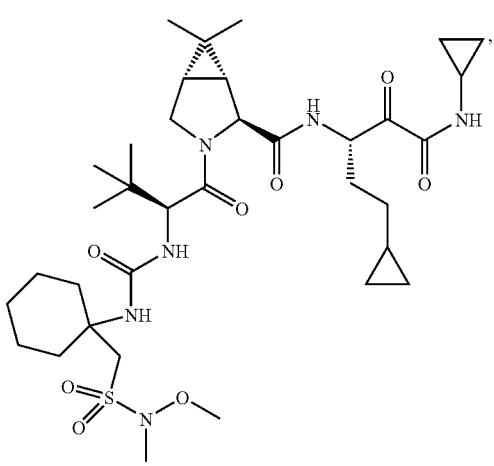
258
-continued
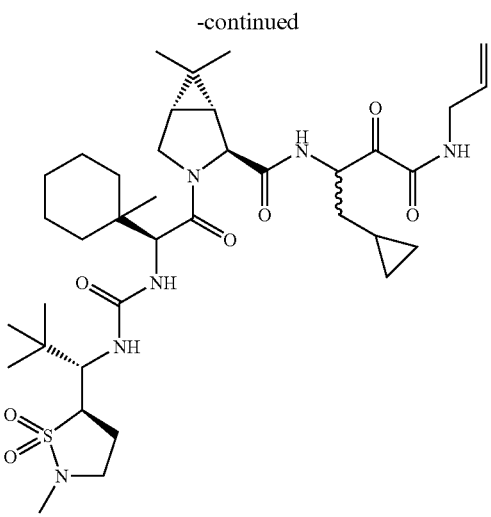
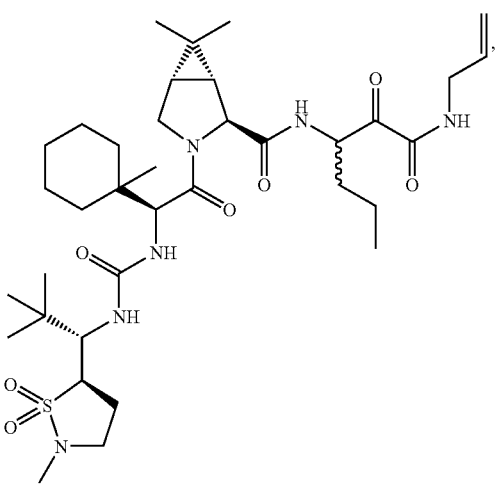
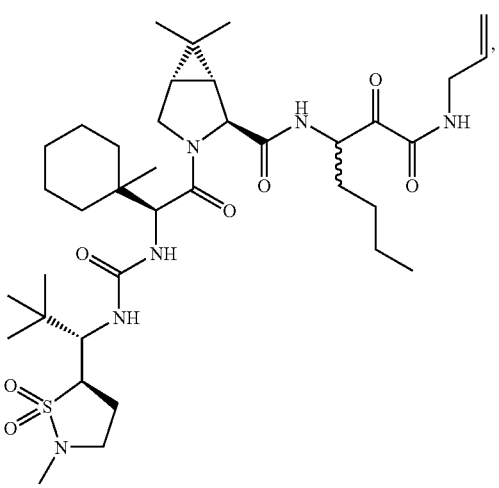

259
-continued
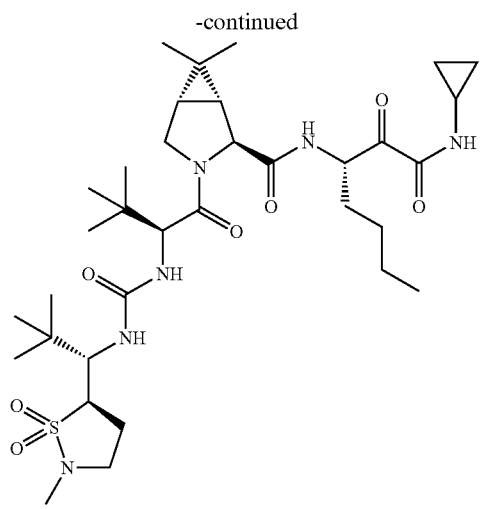
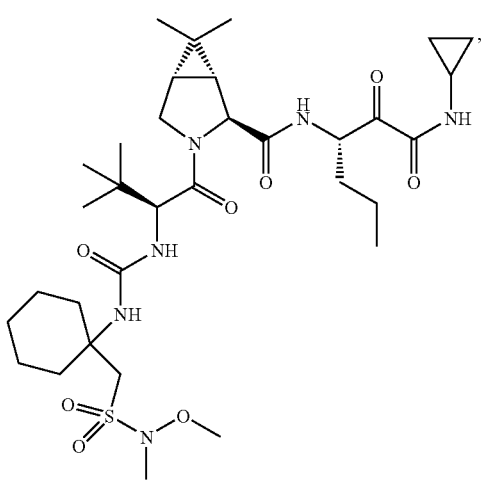
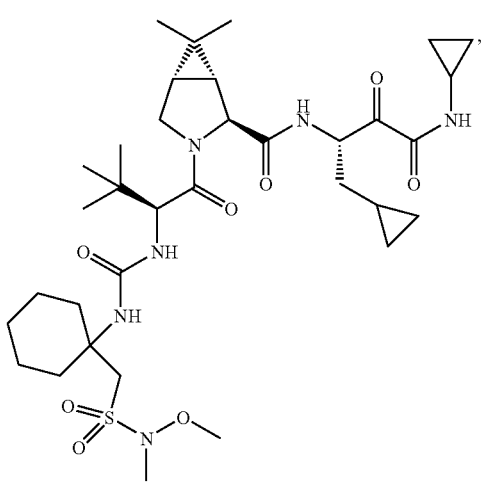
260
-continued
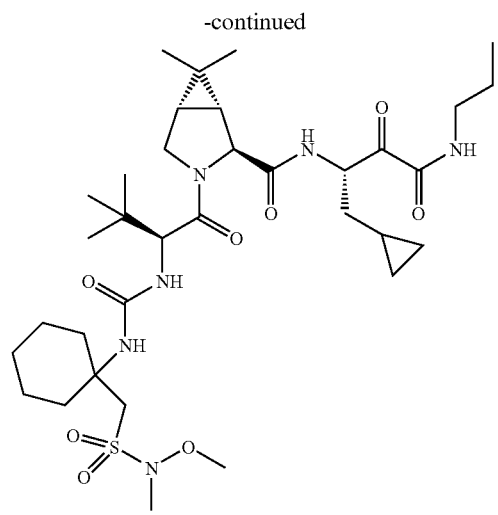
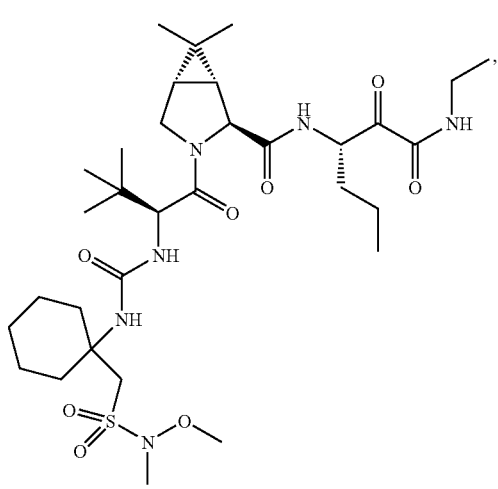
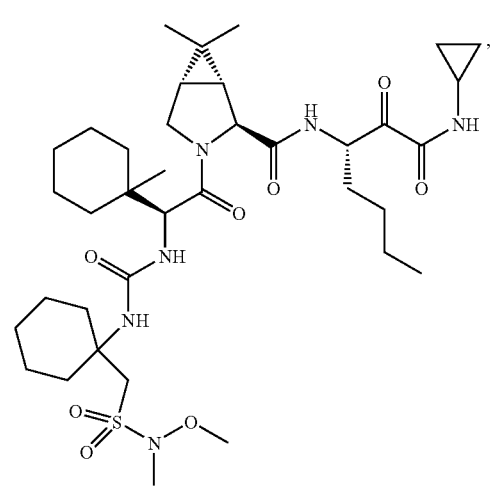

261 -continued
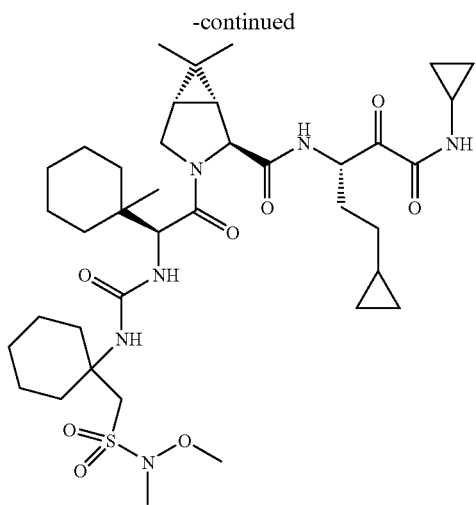
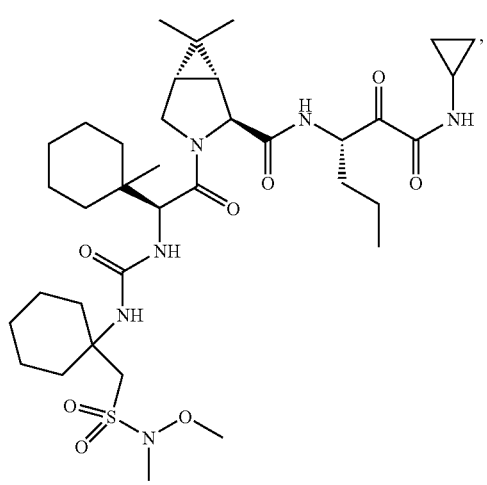
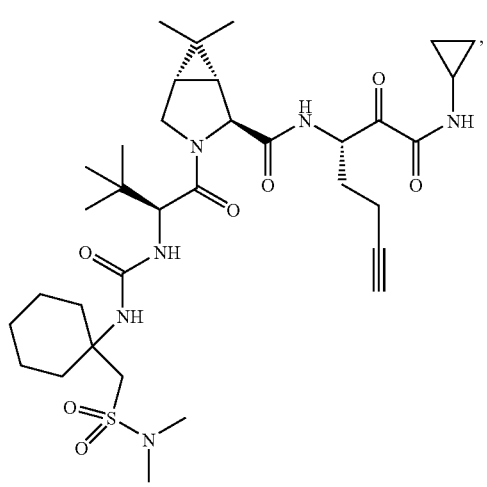
262 -continued
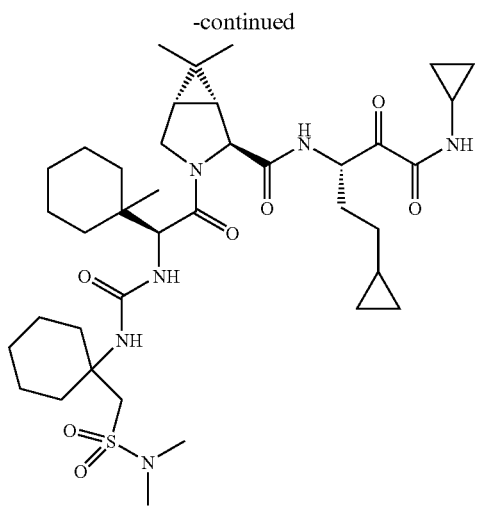
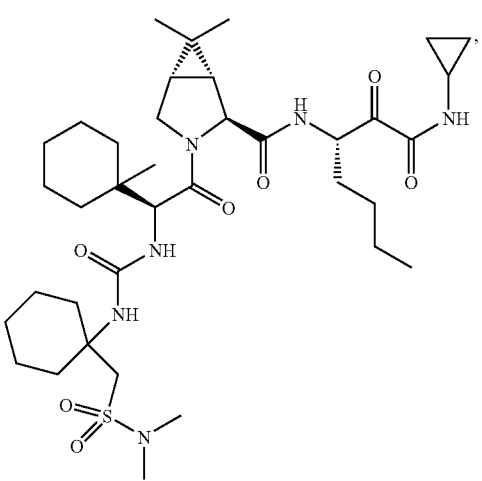
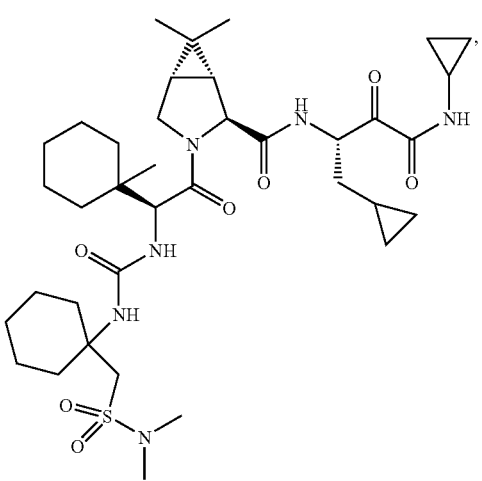

263
-continued
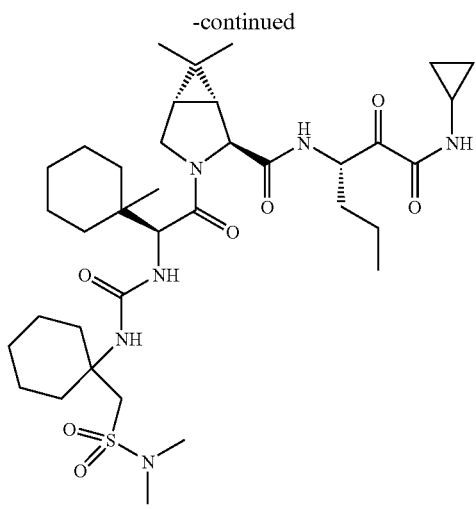
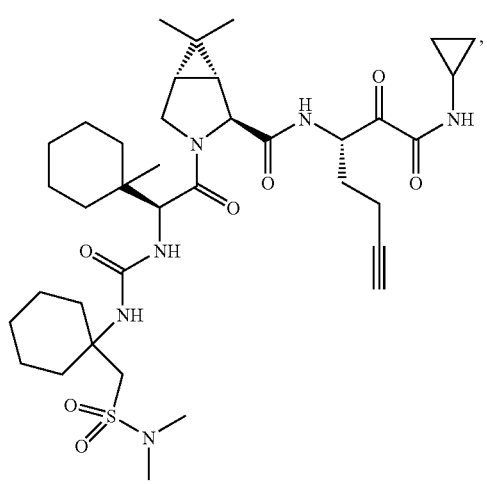
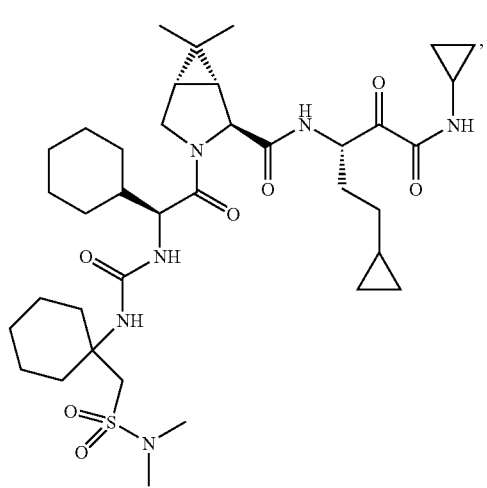
264
-continued
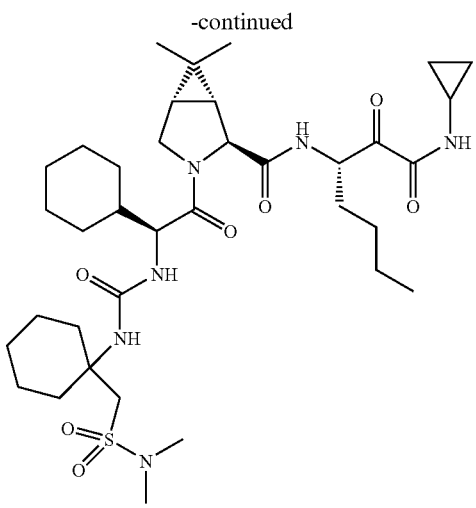
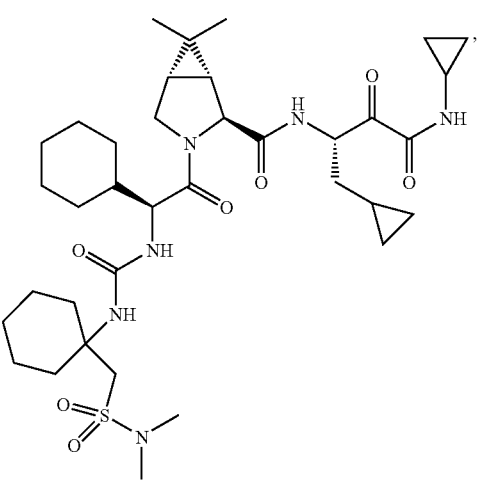
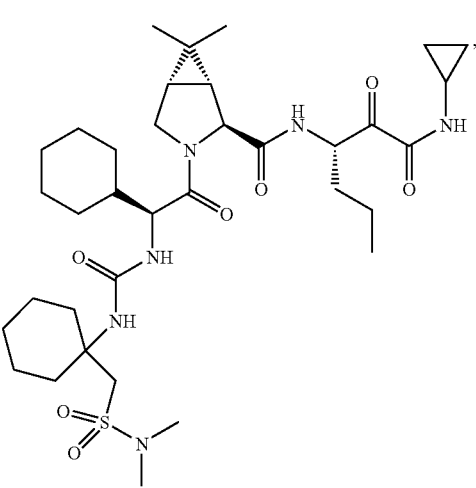

265
-continued
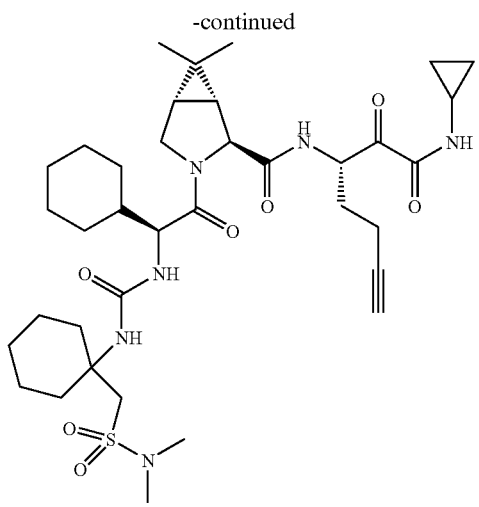
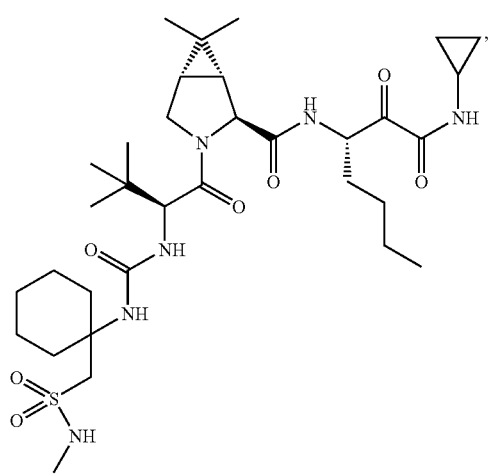
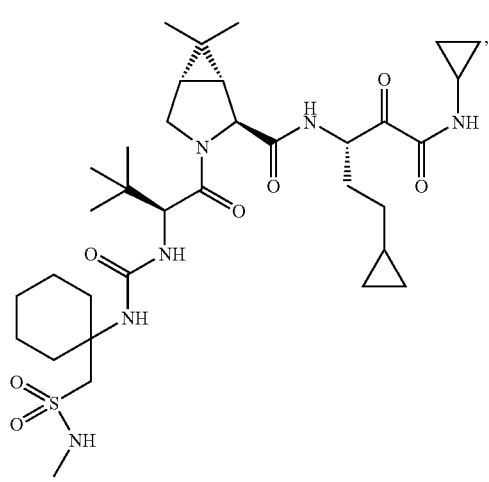
266
-continued
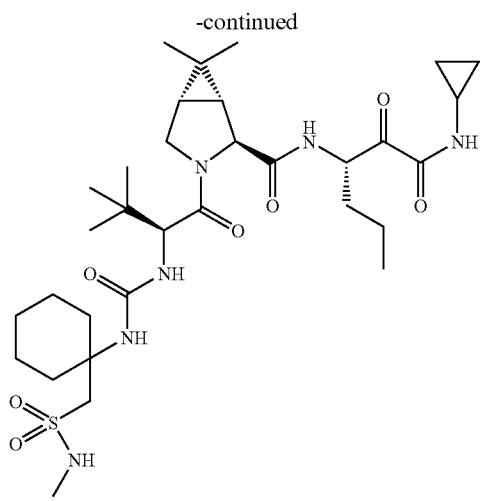
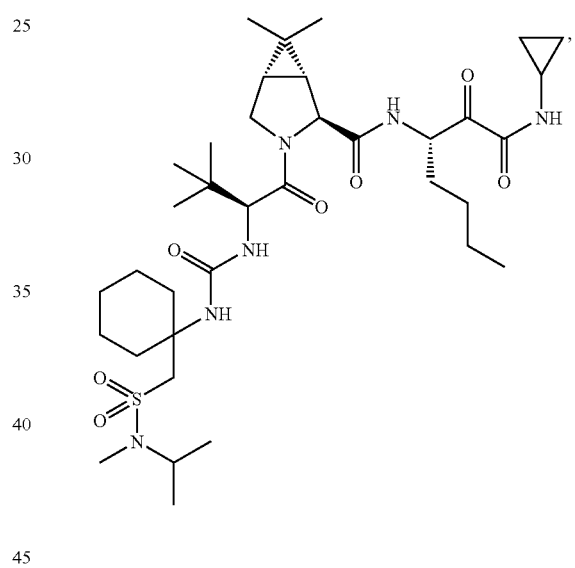
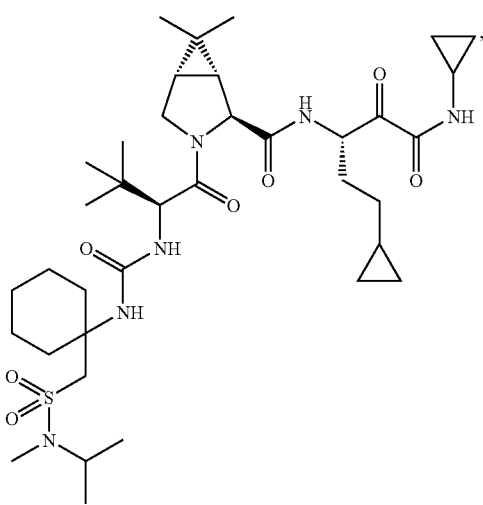

267
-continued
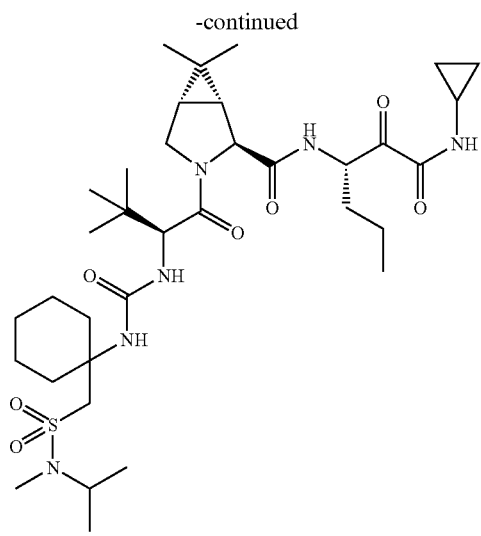
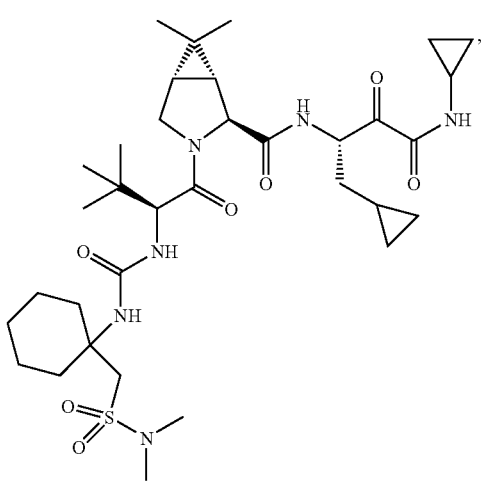
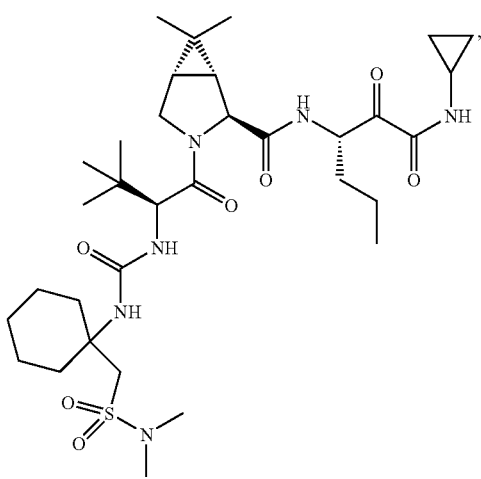
268
-continued
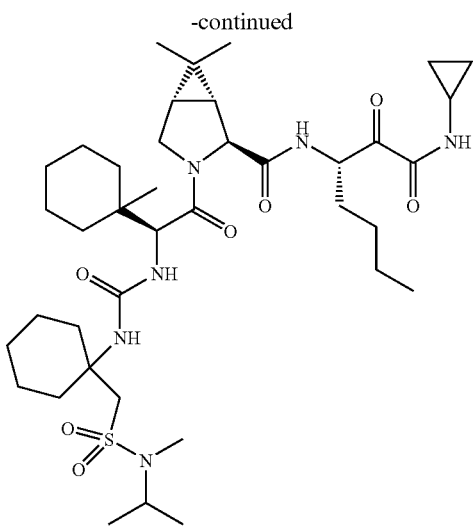
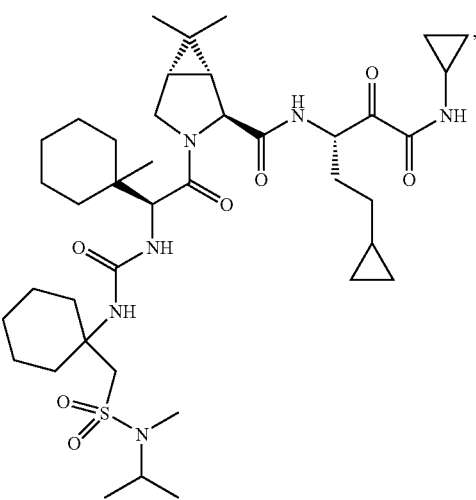
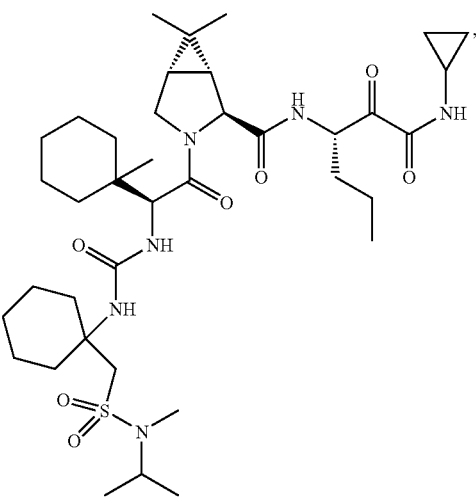

269
-continued
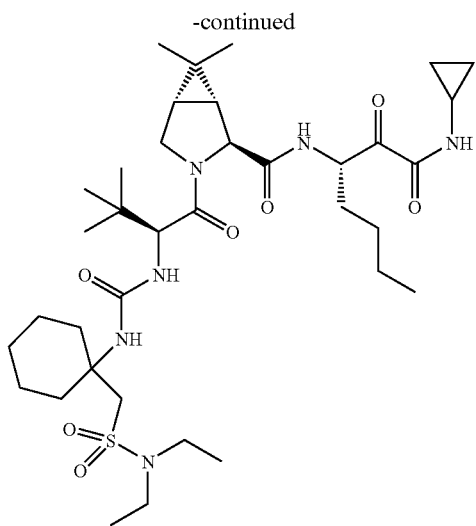
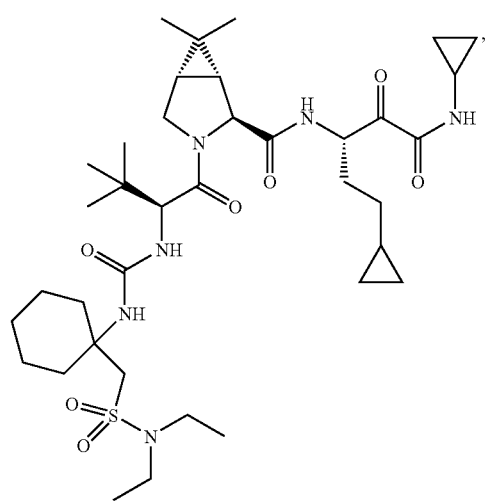
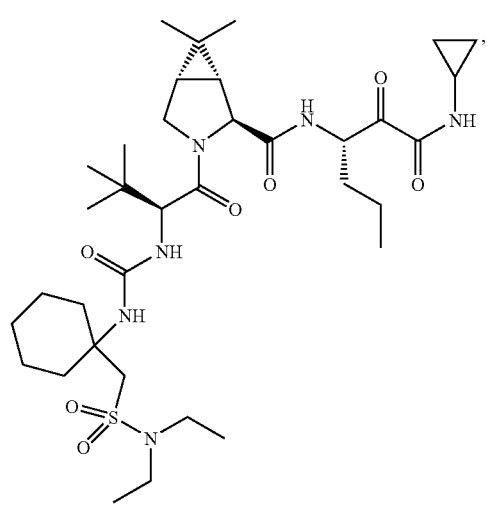
270
-continued
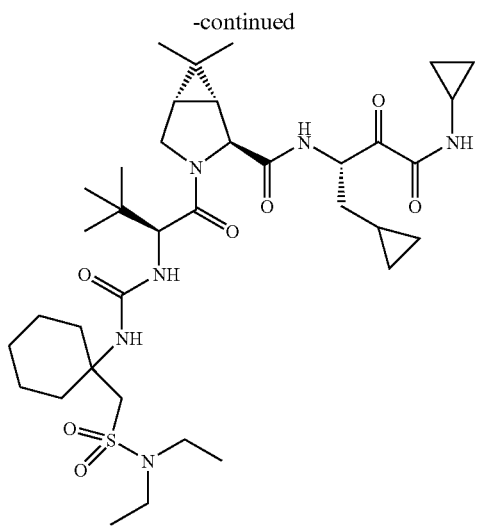
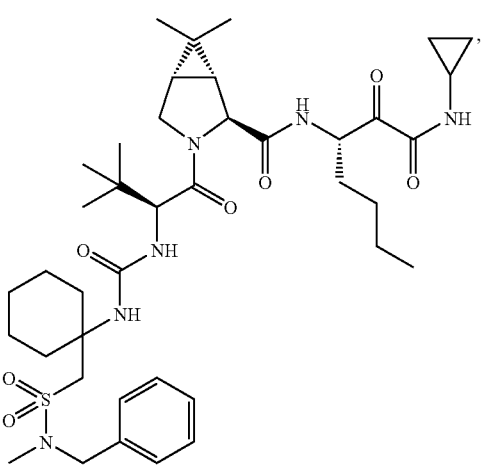
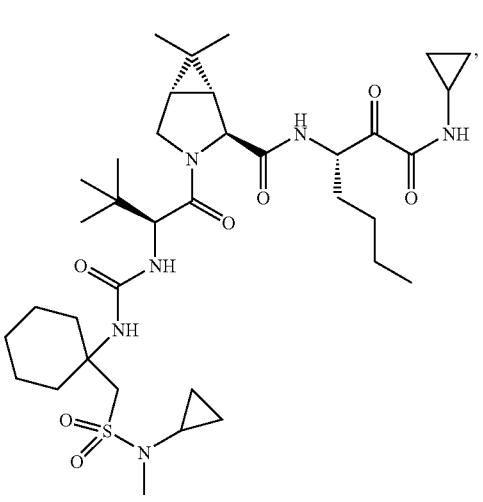

271
-continued
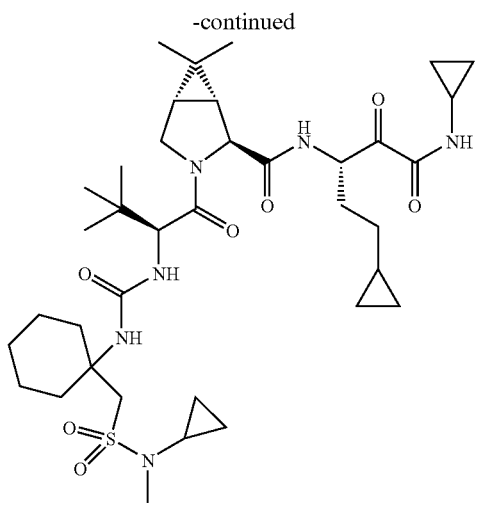
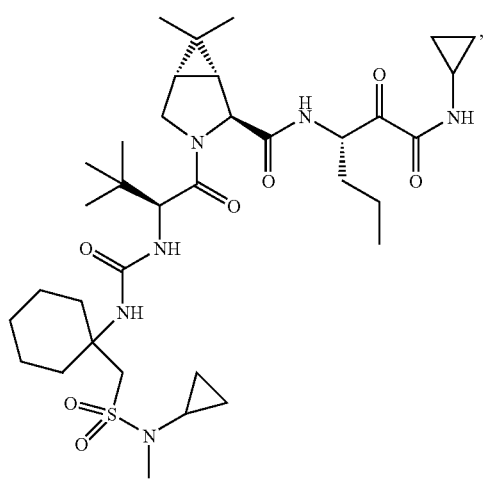
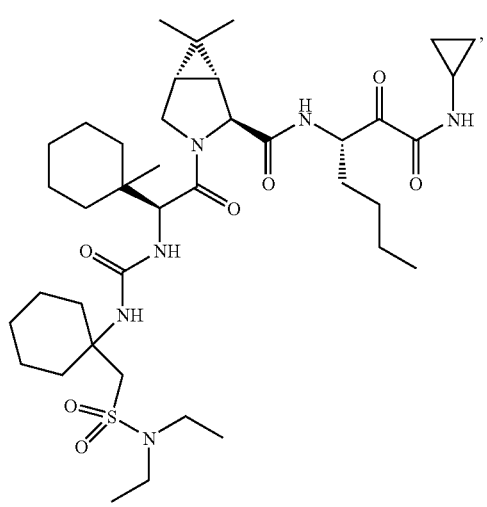
272
-continued
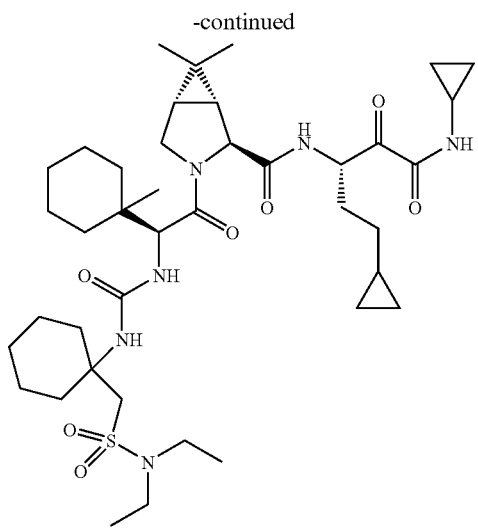
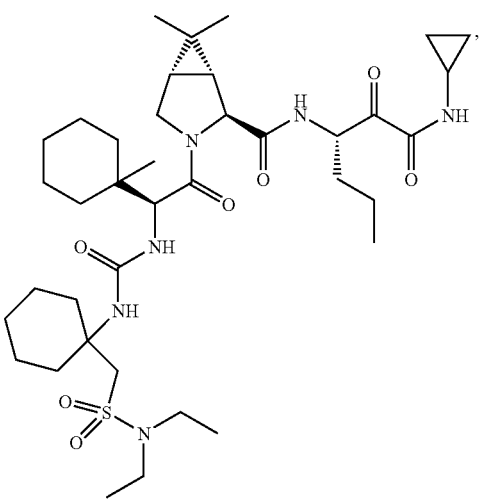
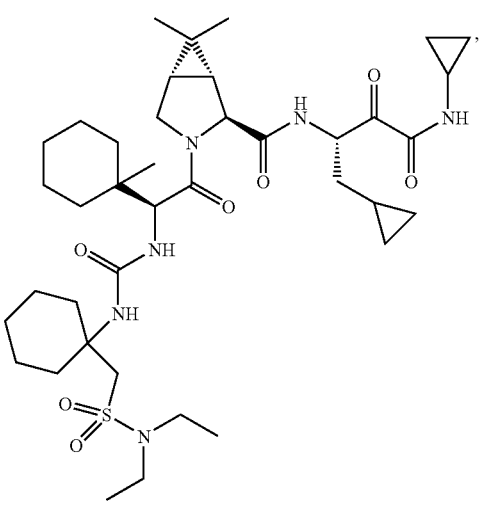

273
-continued
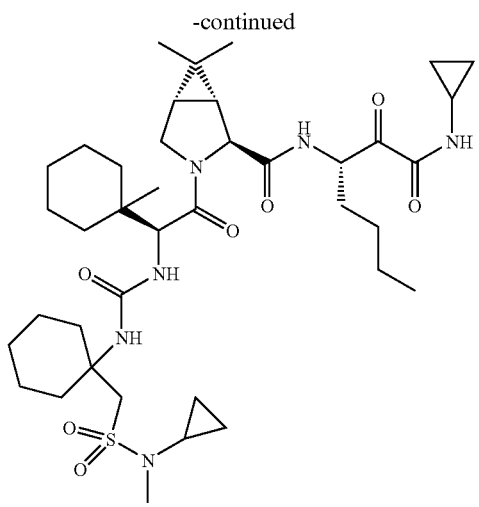
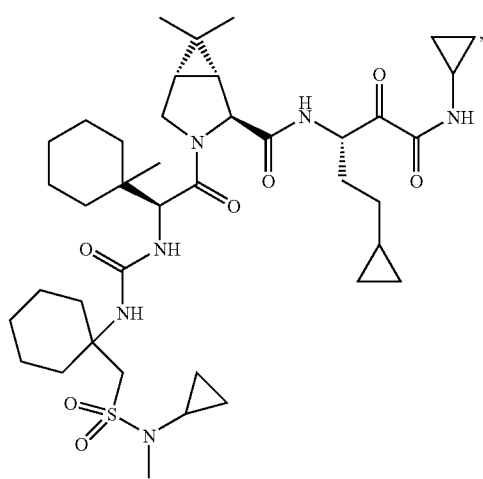
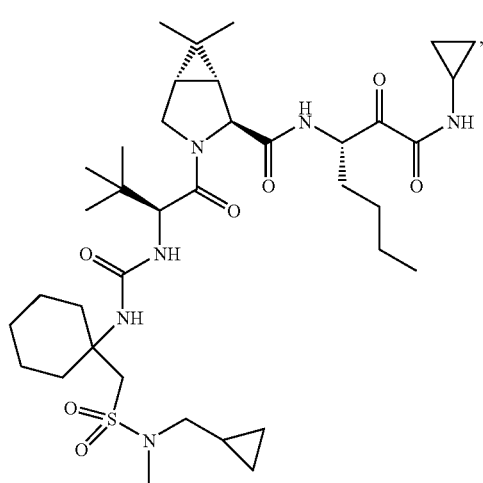
274
-continued
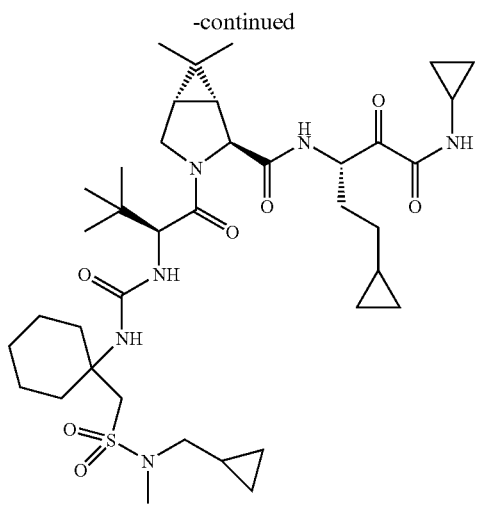
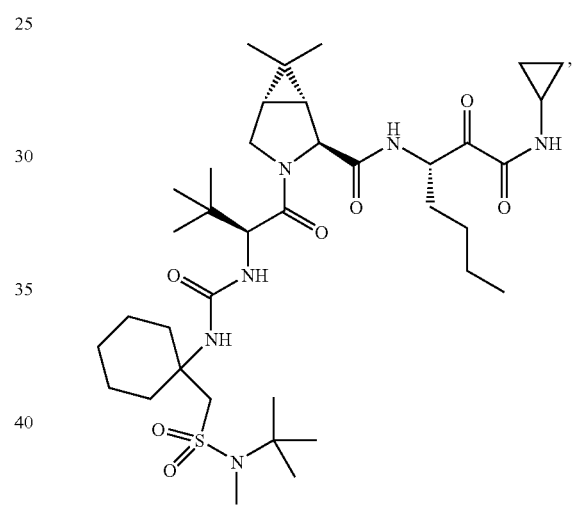
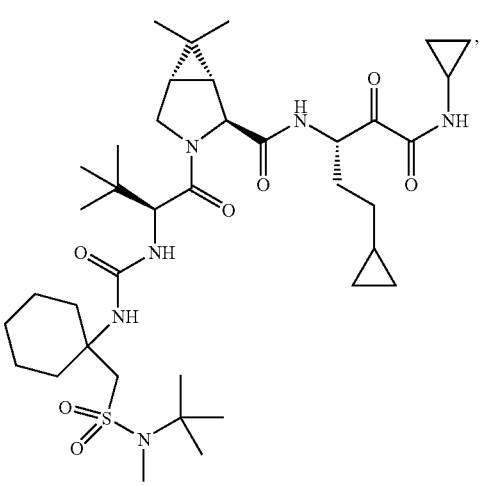

275
-continued
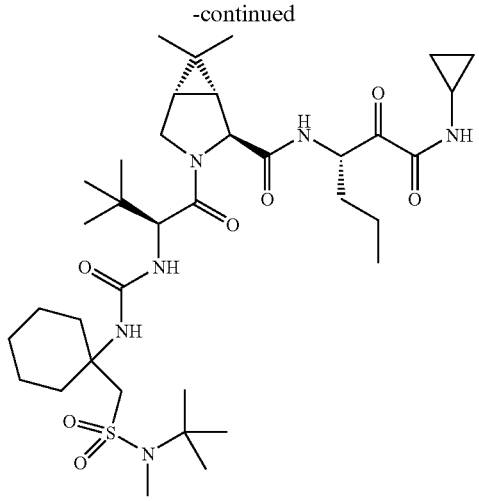
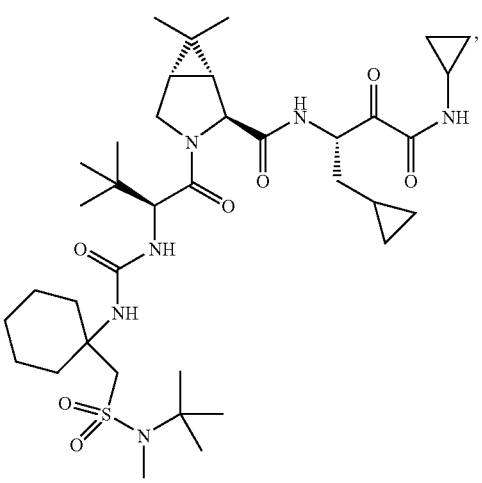
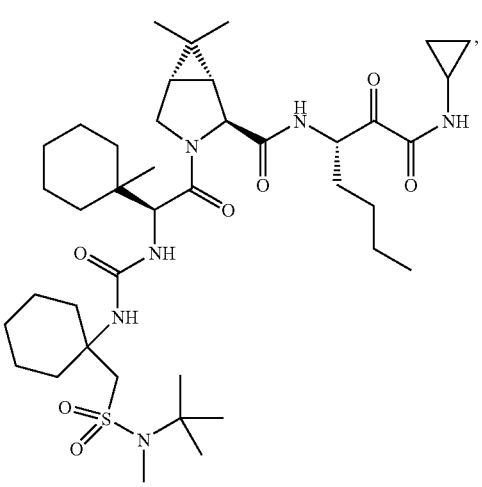
276
-continued
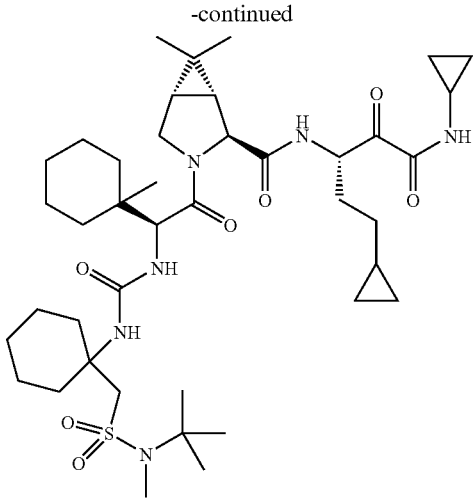
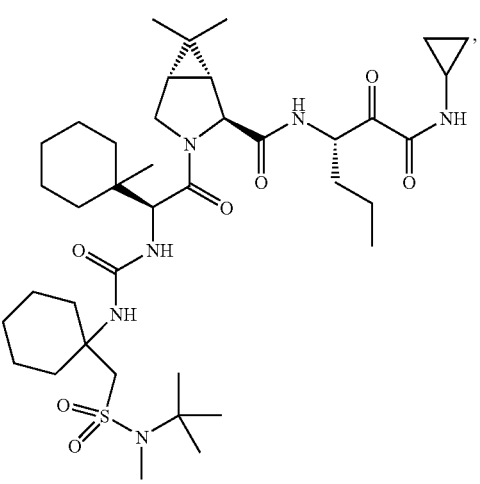
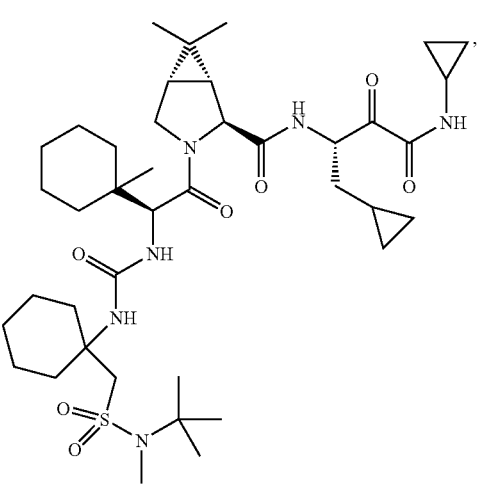

277
-continued
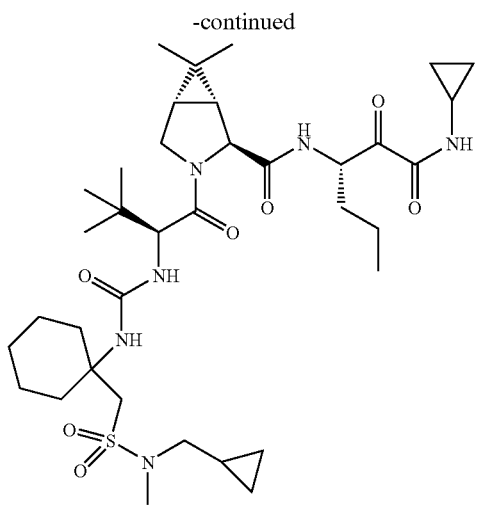
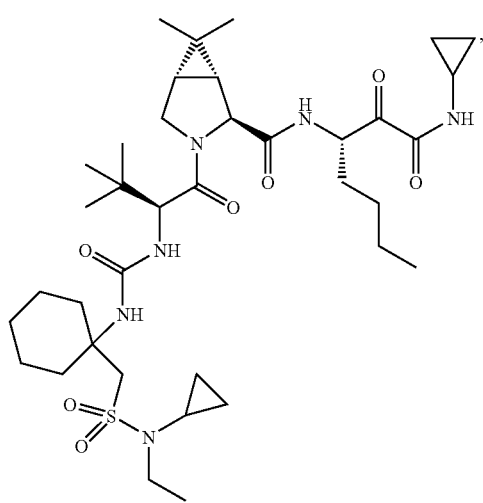
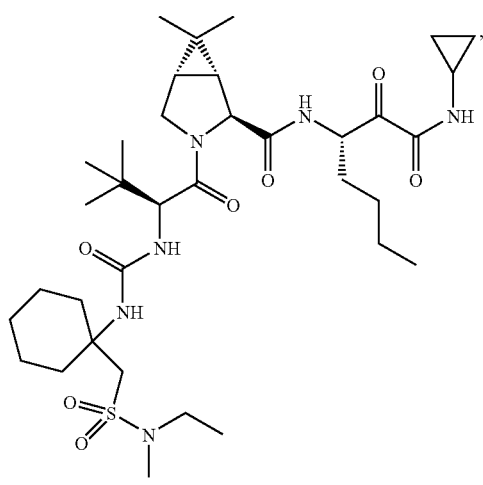
278
-continued
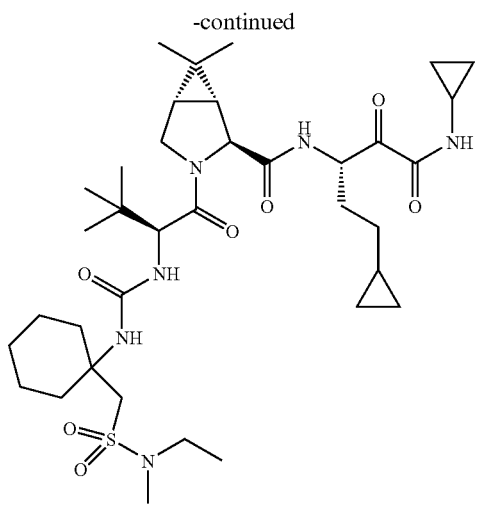
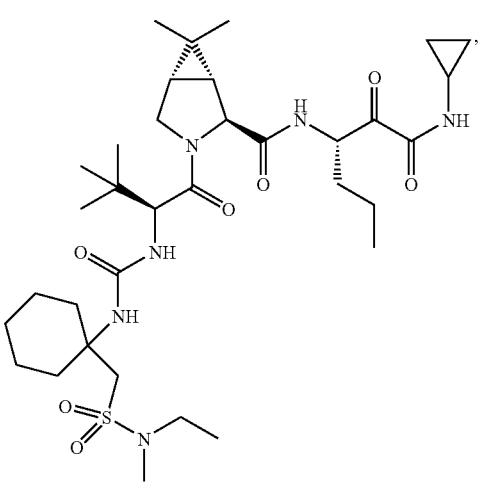
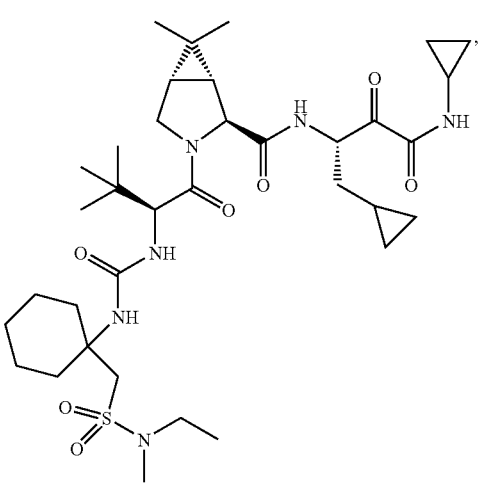

279
-continued
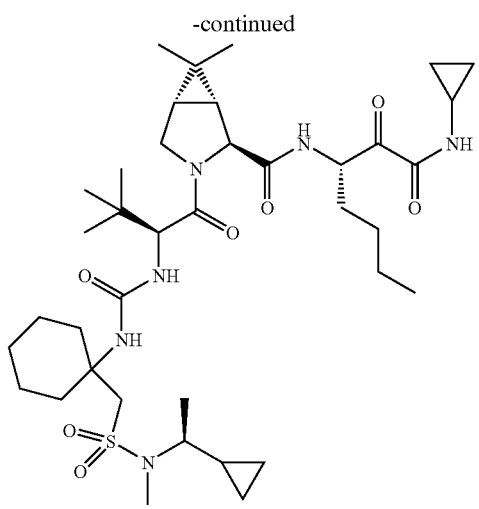
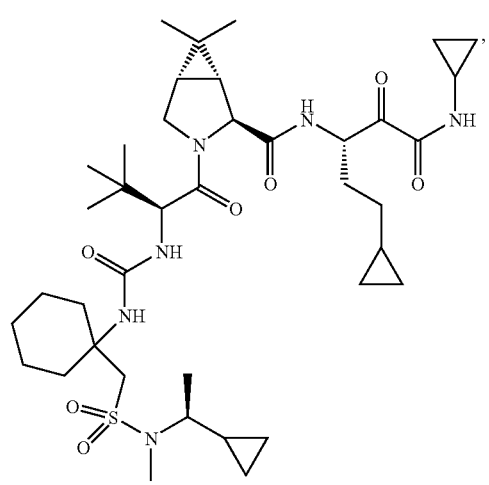
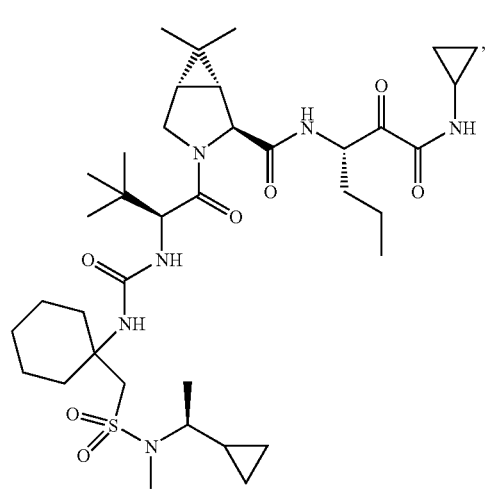
280
-continued
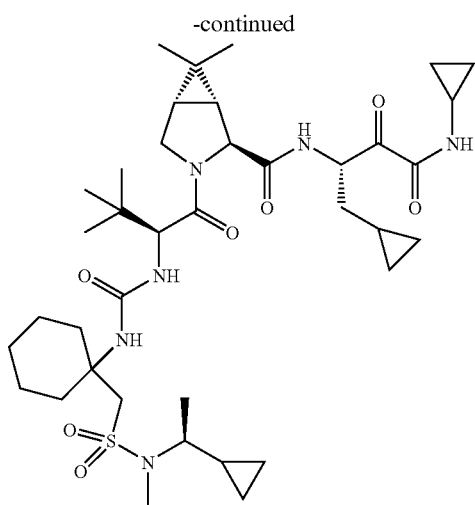
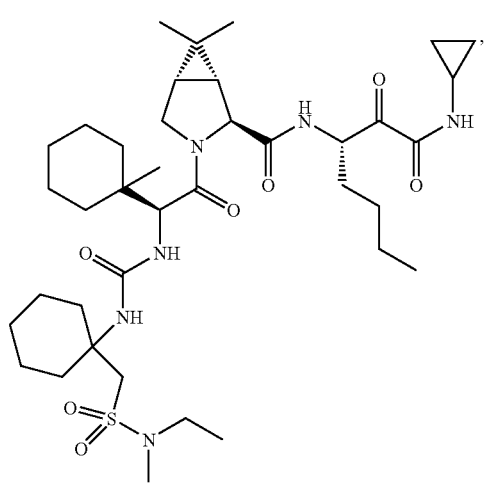
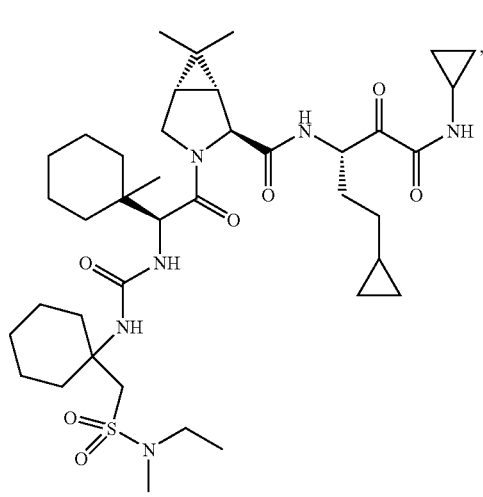

-continued
281
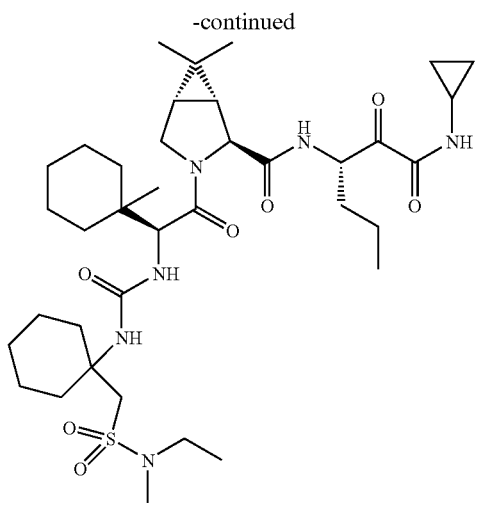
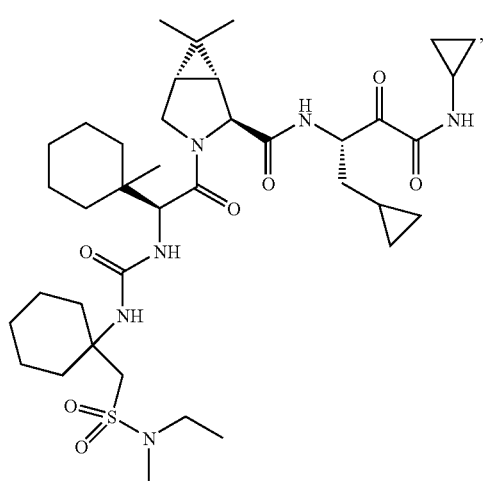
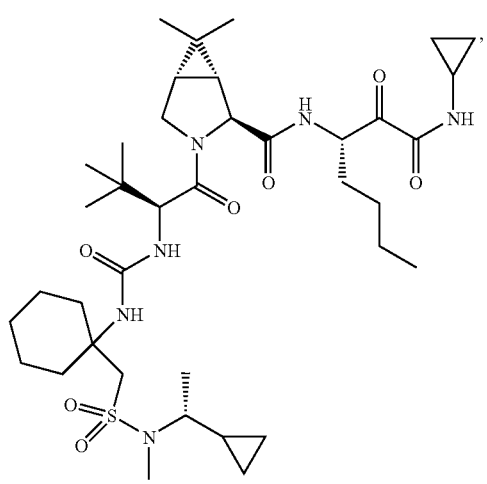
282
-continued
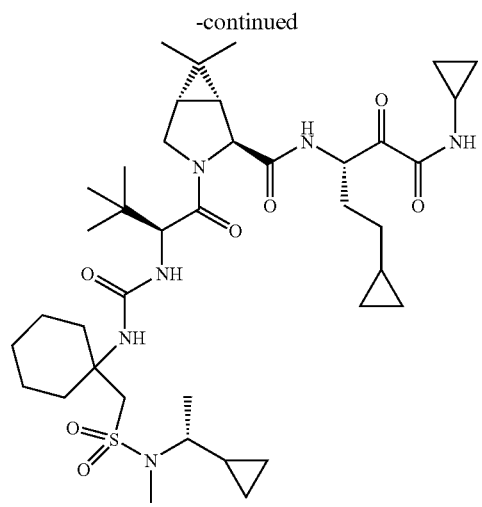
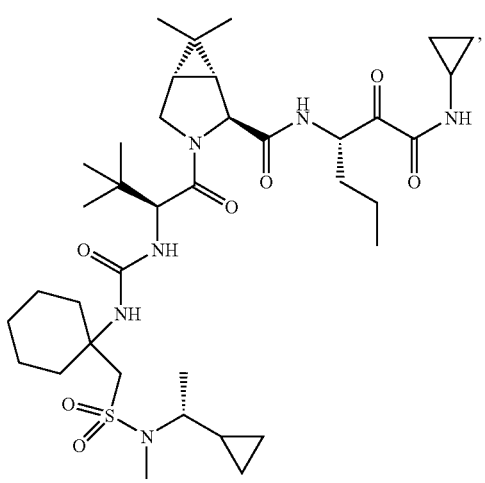
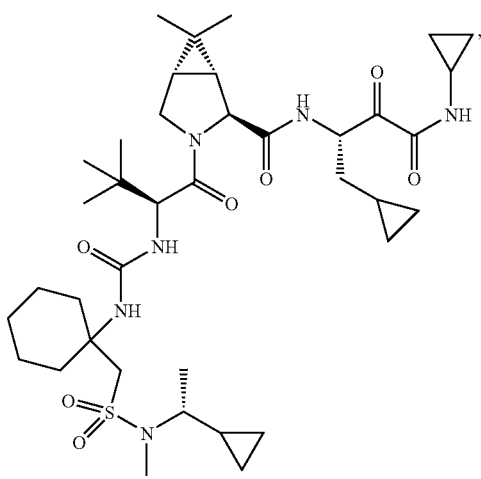

283
-continued
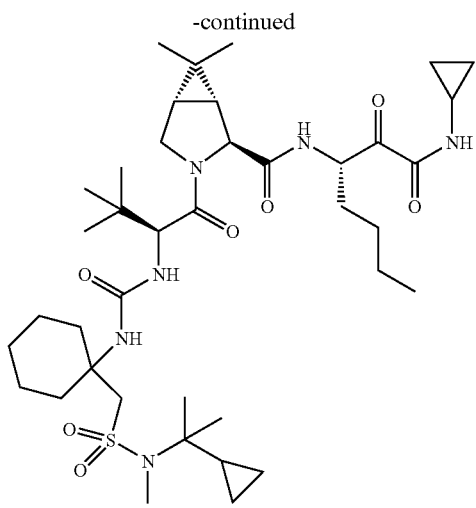
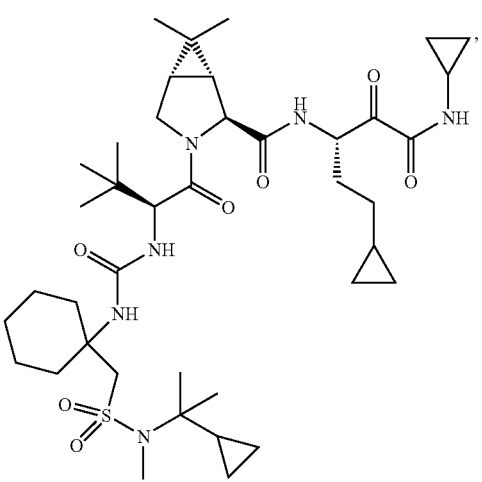
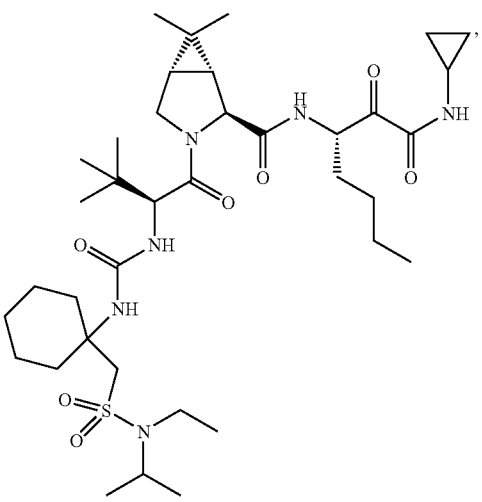
284
-continued
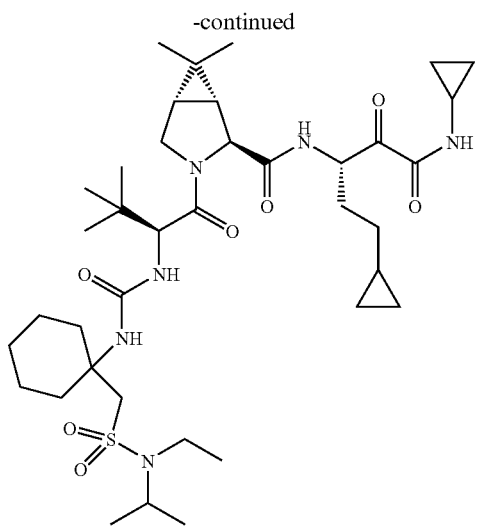
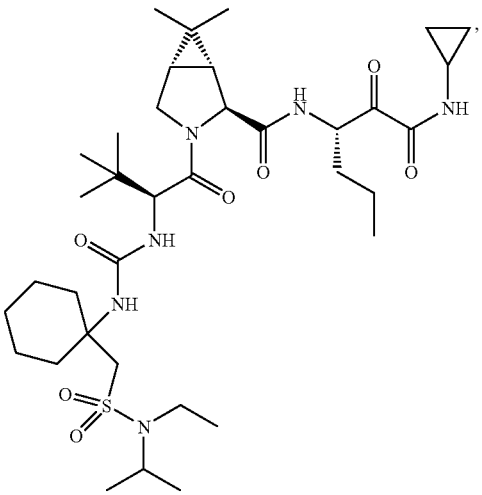
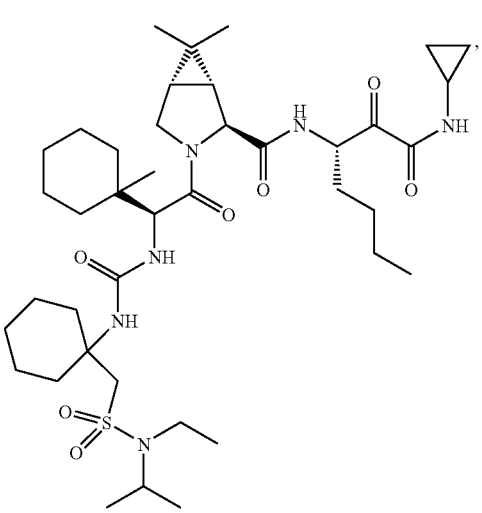

285
-continued
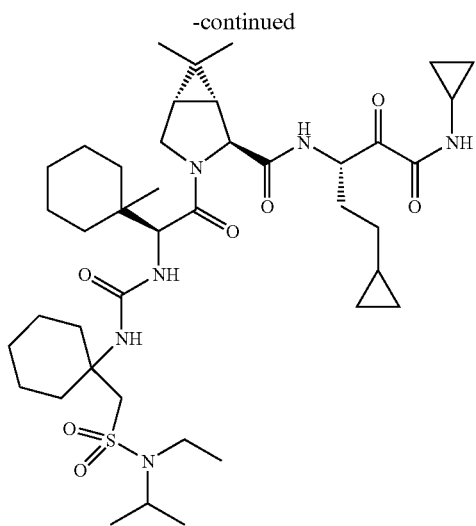
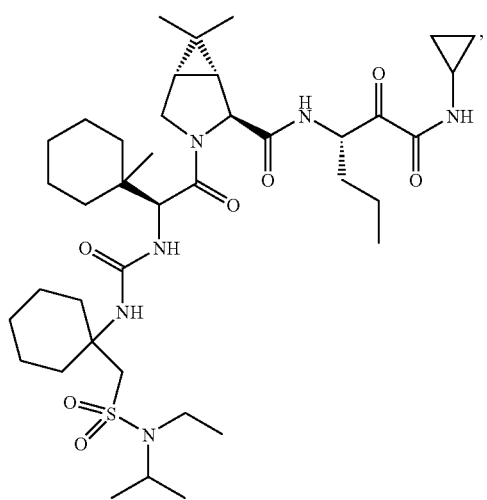
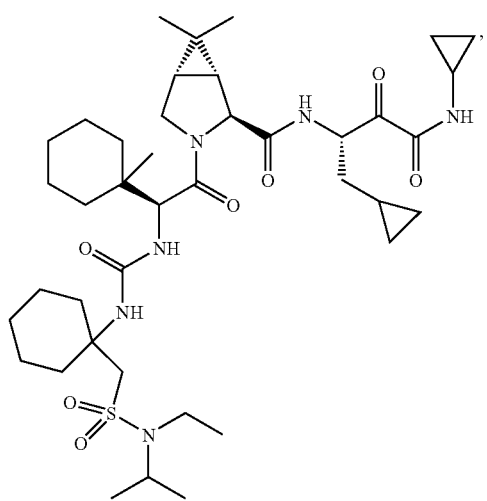
286
-continued
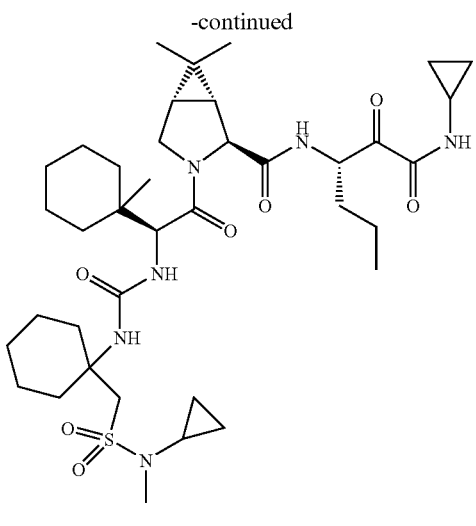
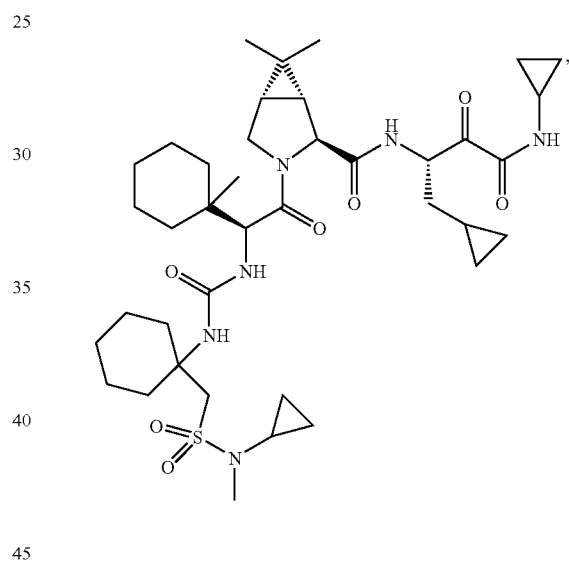
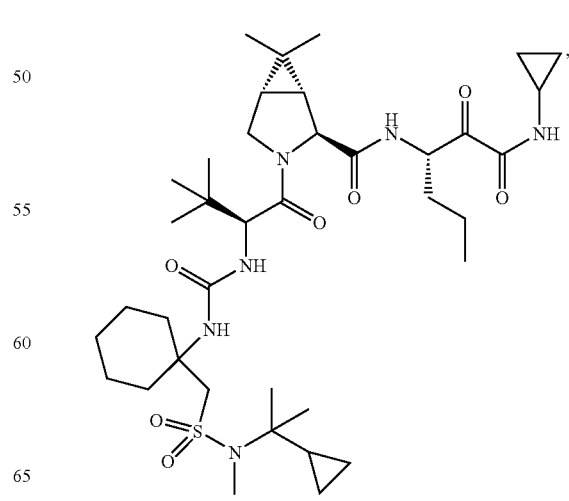

287
-continued
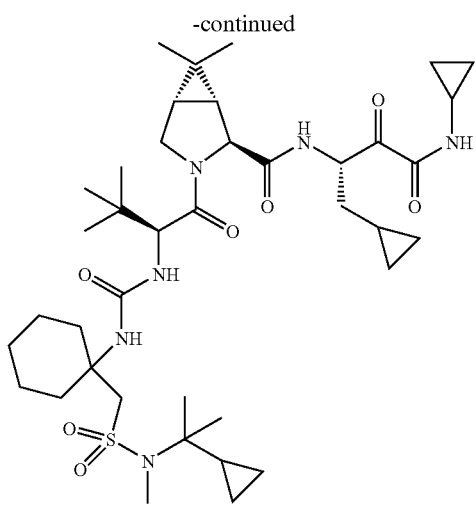
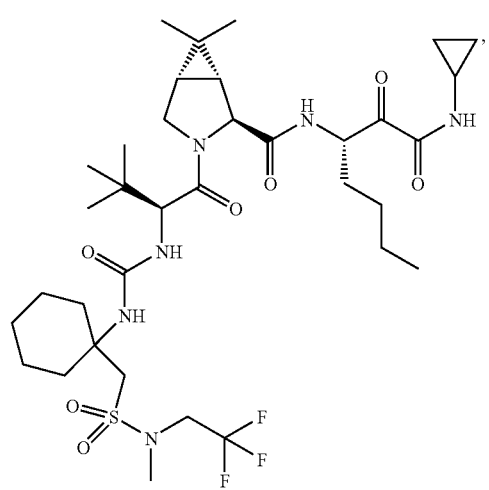
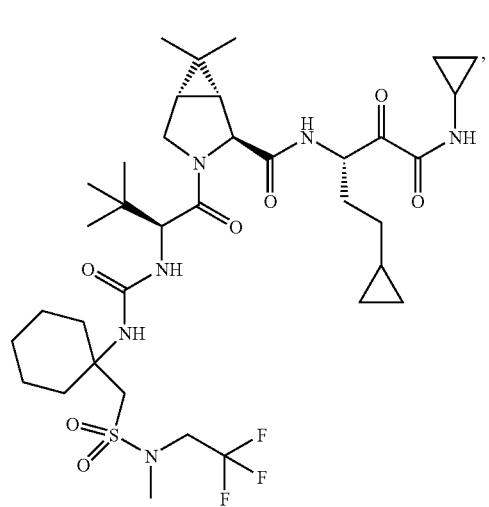
288
-continued
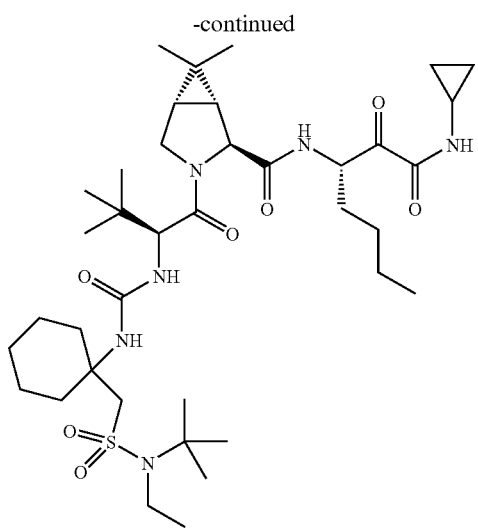
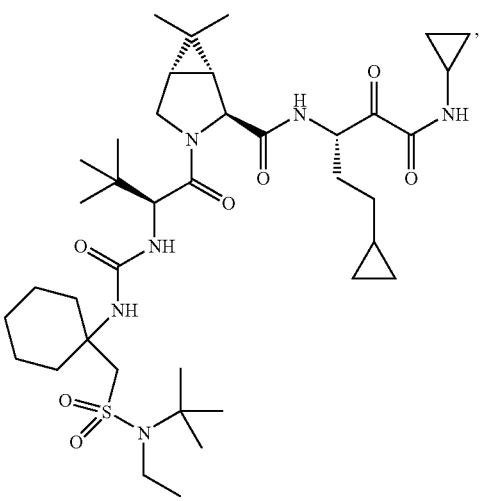
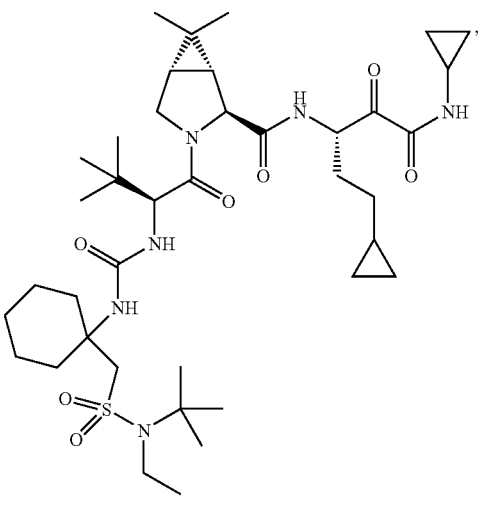

289
-continued
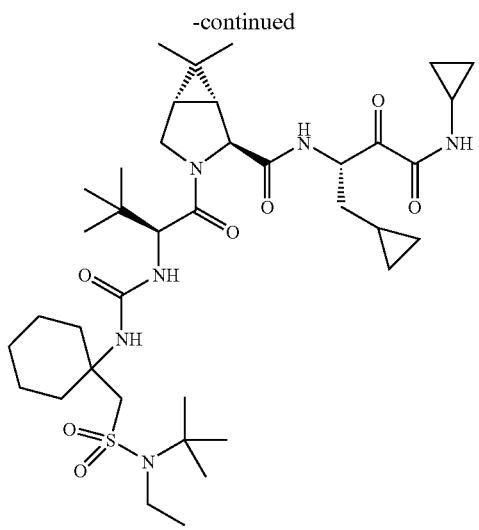
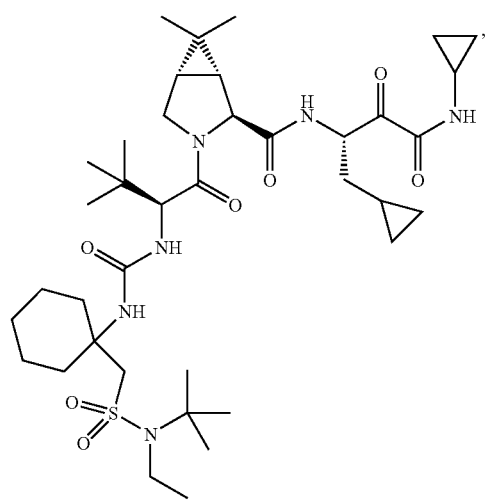
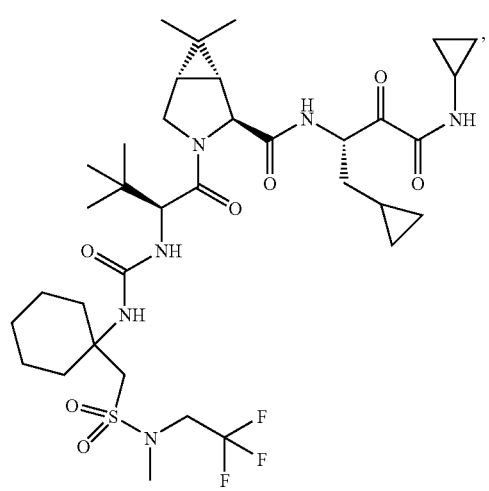
290
-continued
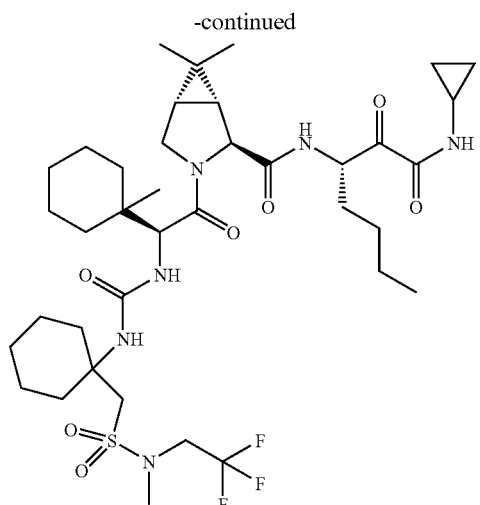
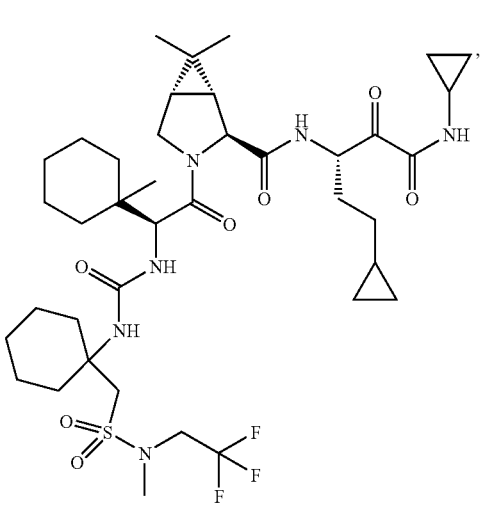
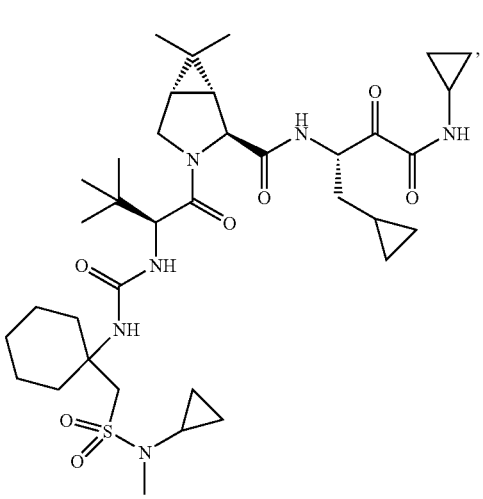

-continued
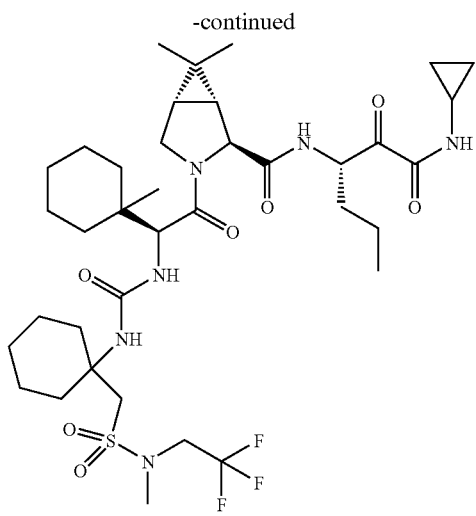
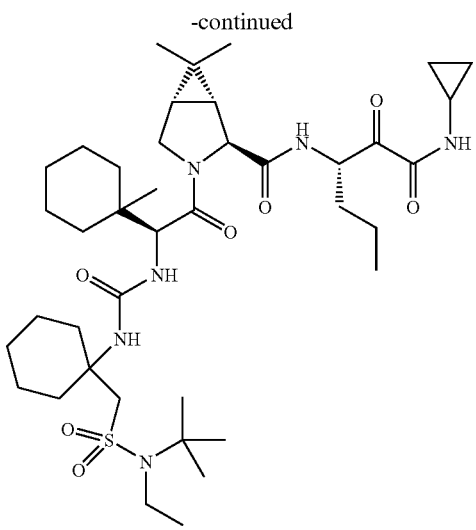
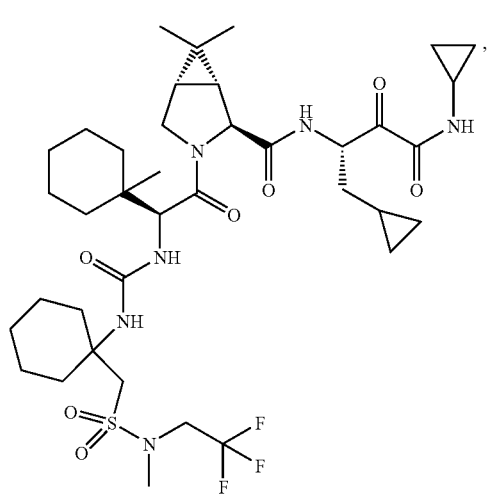
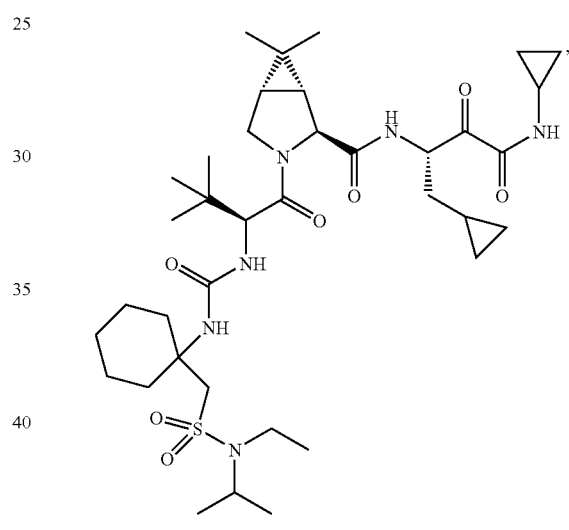
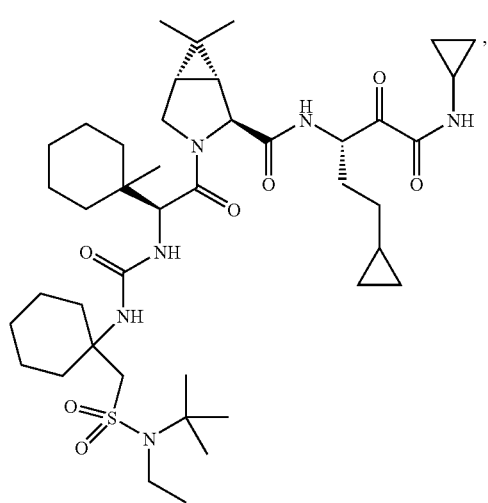
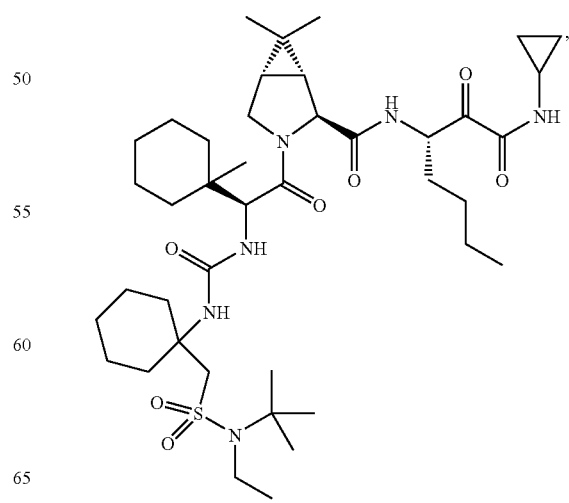

293
-continued
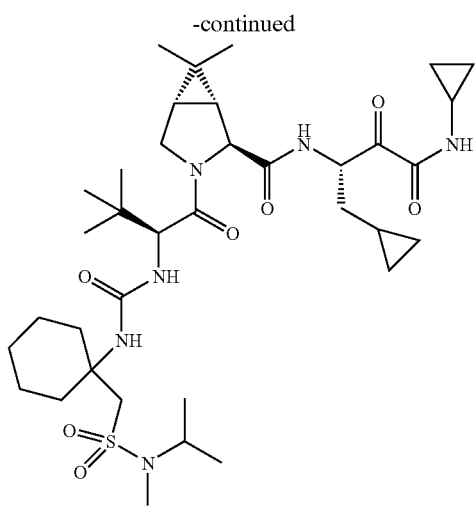
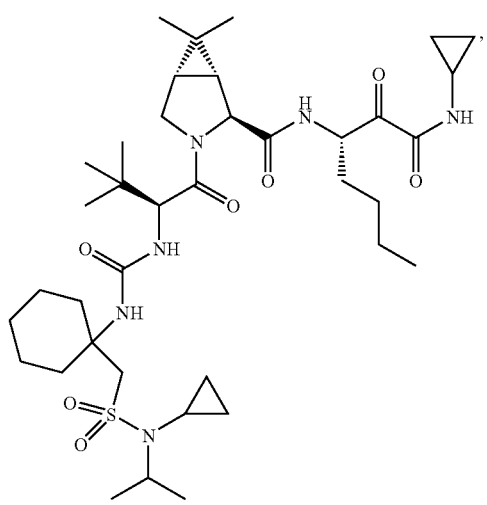
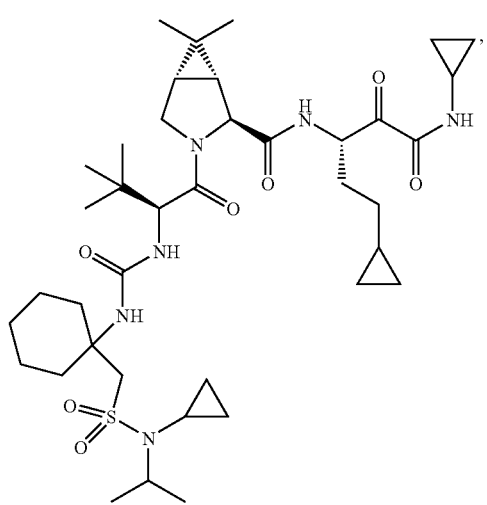
294
-continued
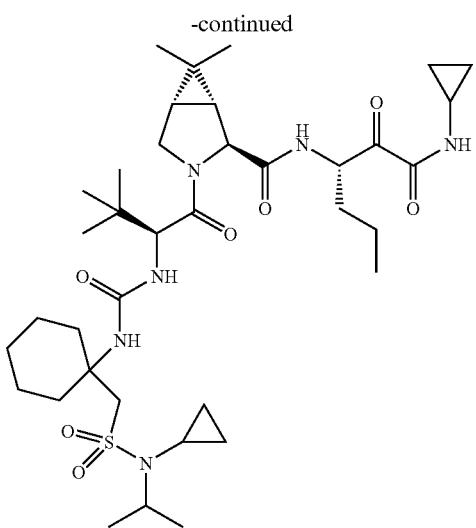
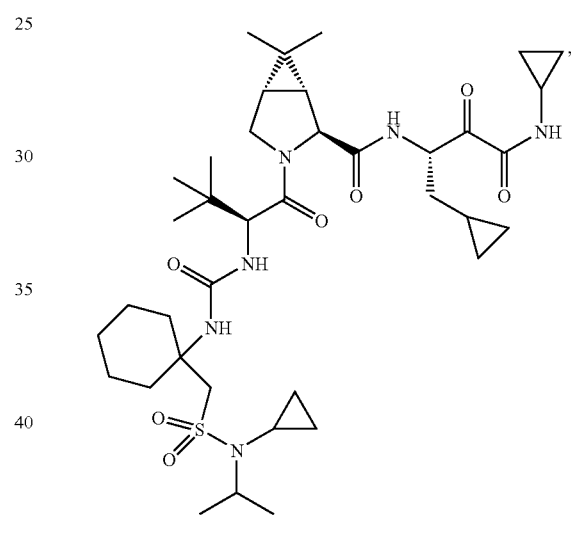
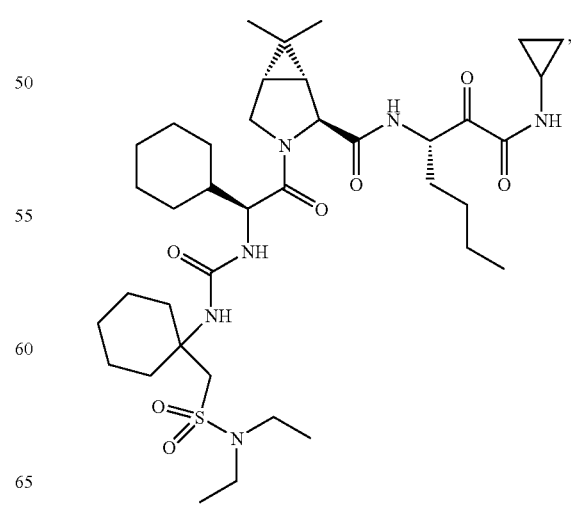

295
-continued
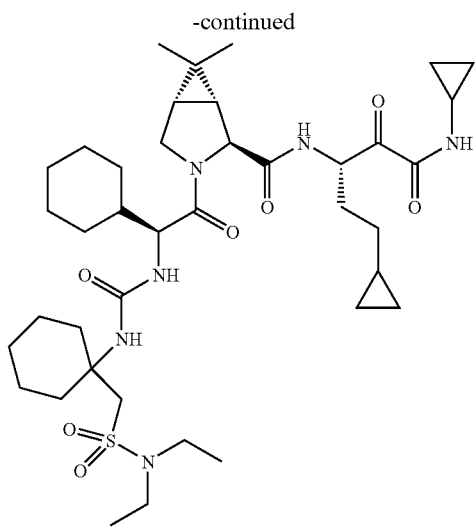
296
-continued
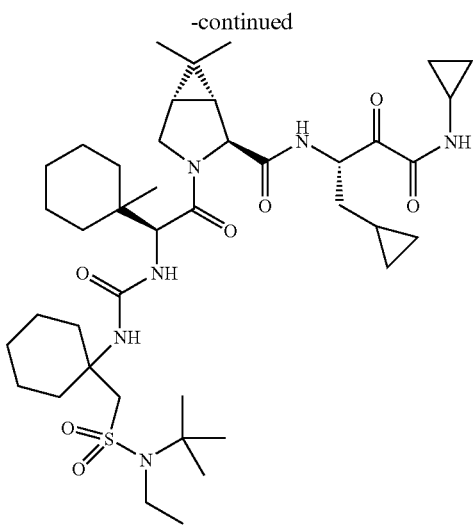
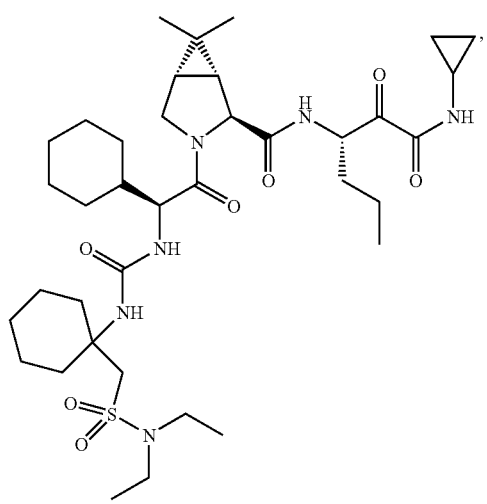
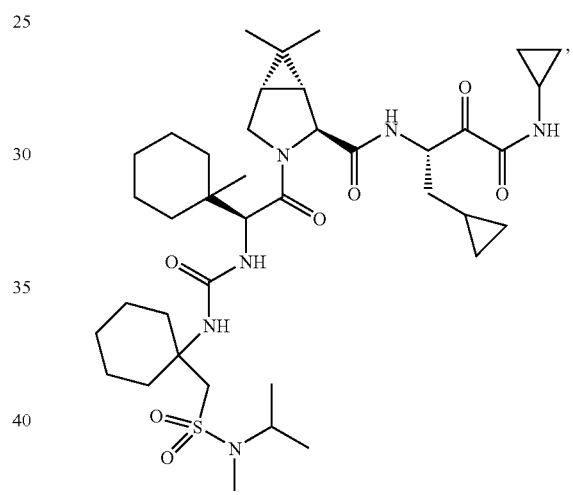
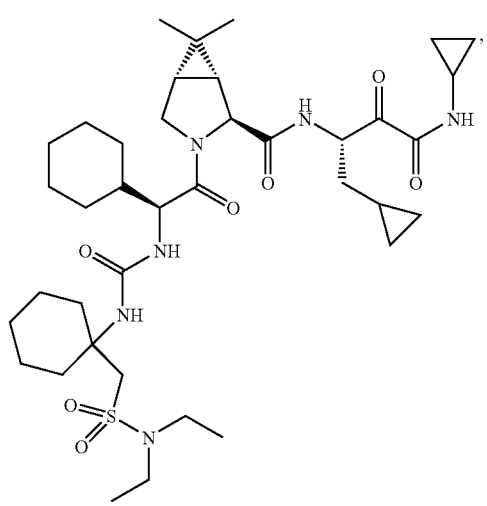
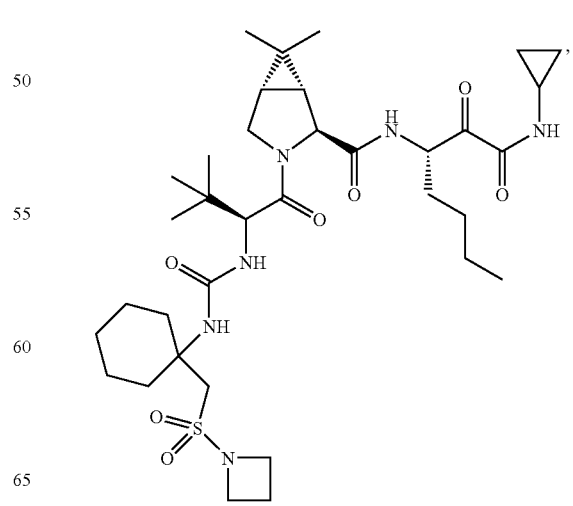

297
-continued
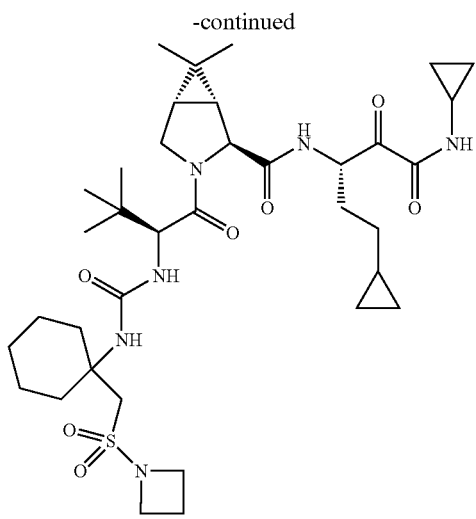
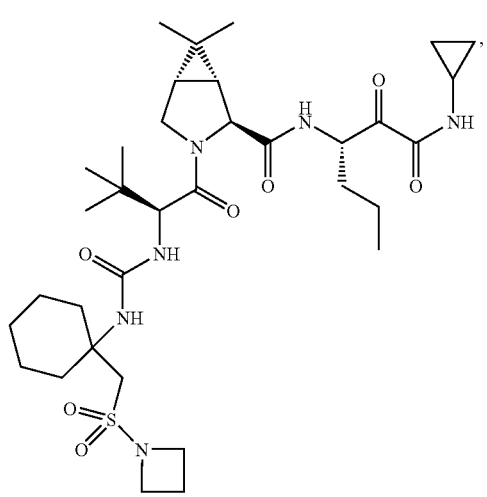
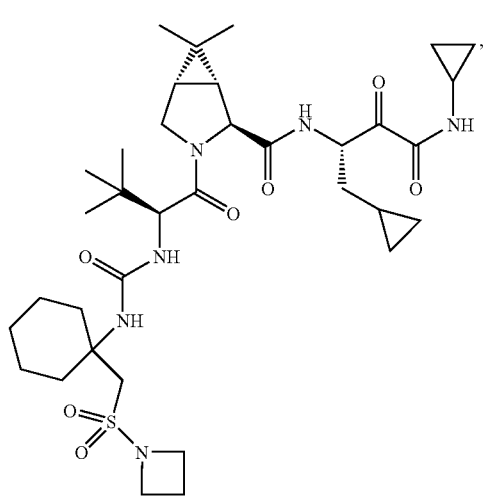
298
-continued
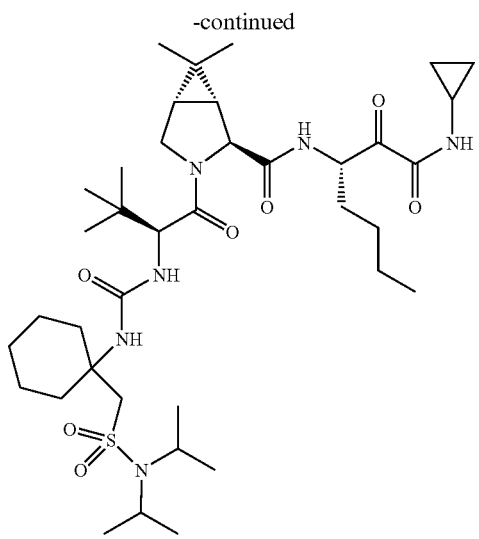
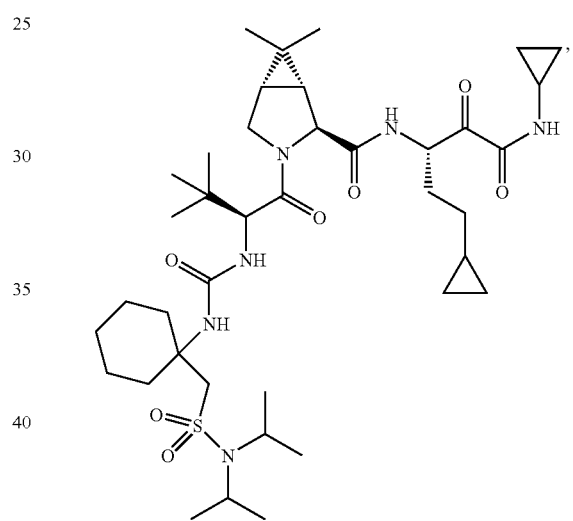
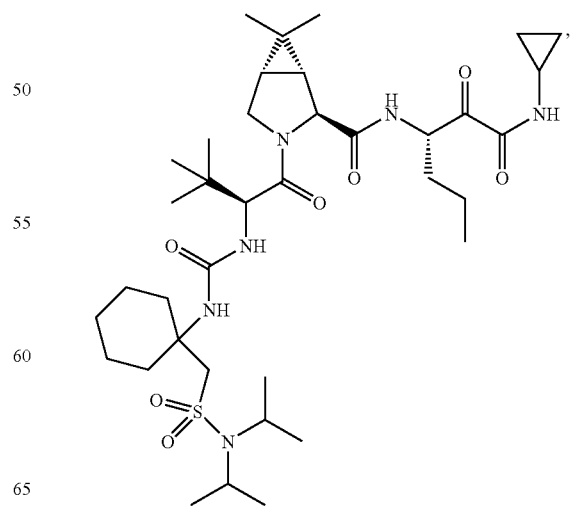

299
-continued
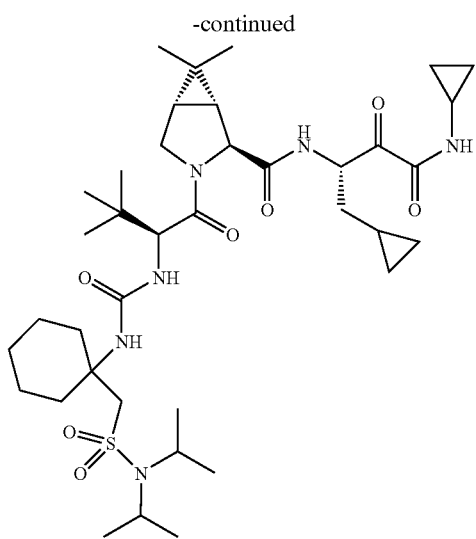
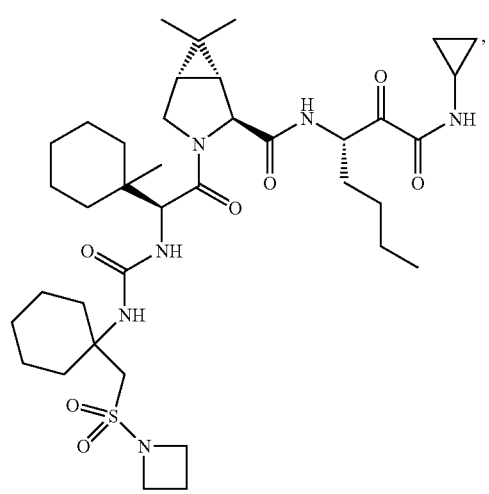
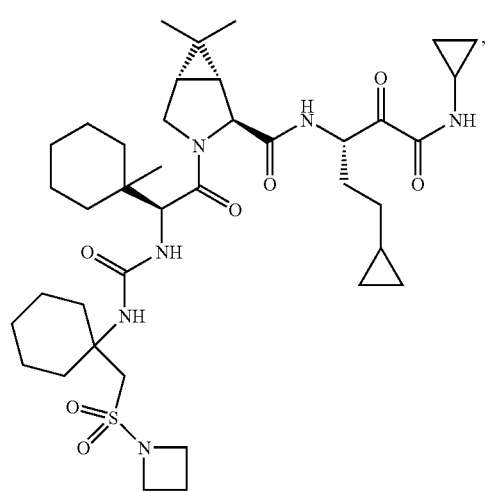
300
-continued
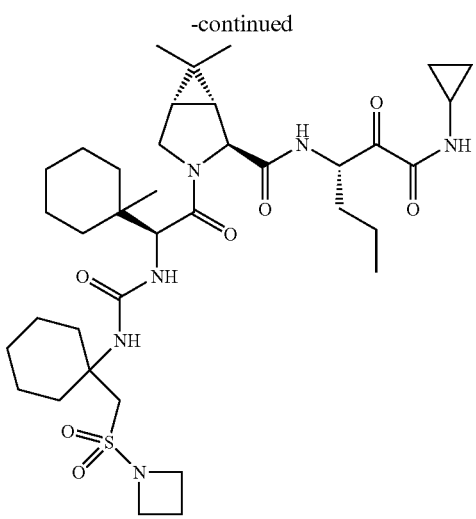
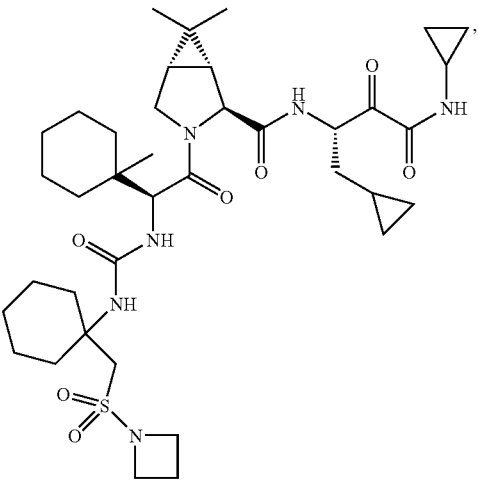
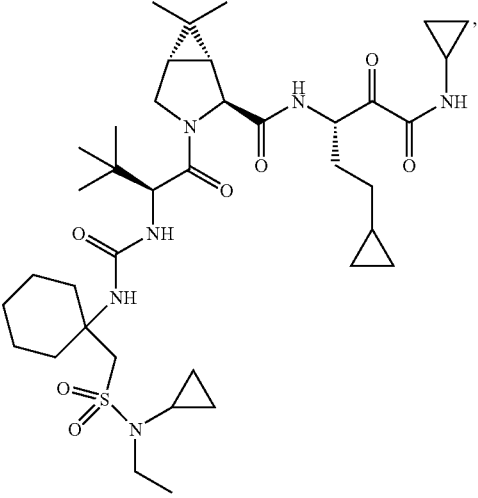

301
-continued
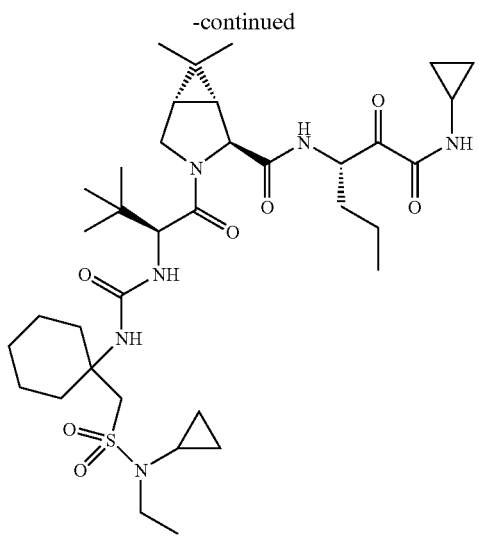
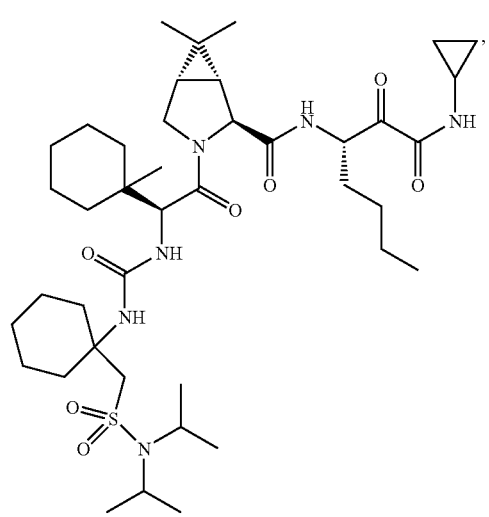
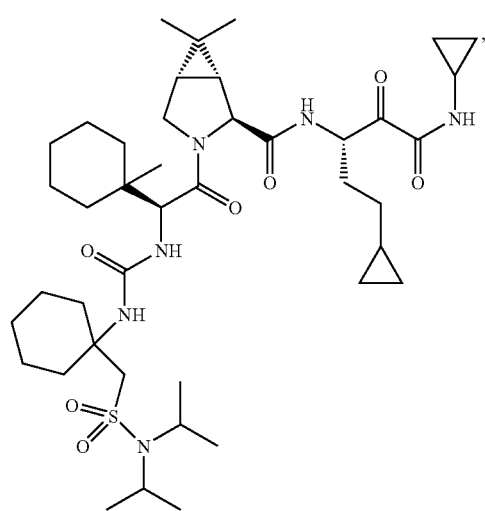
302
-continued
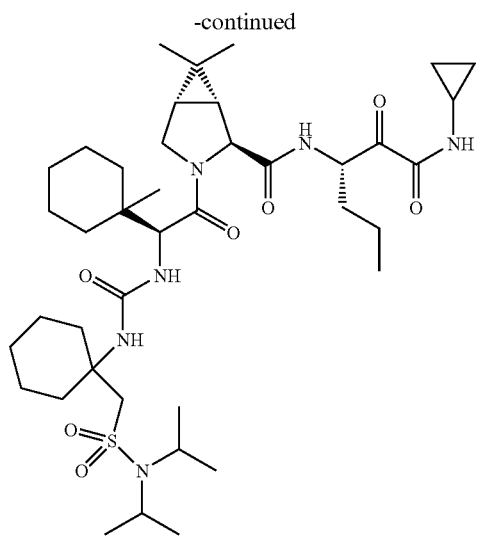
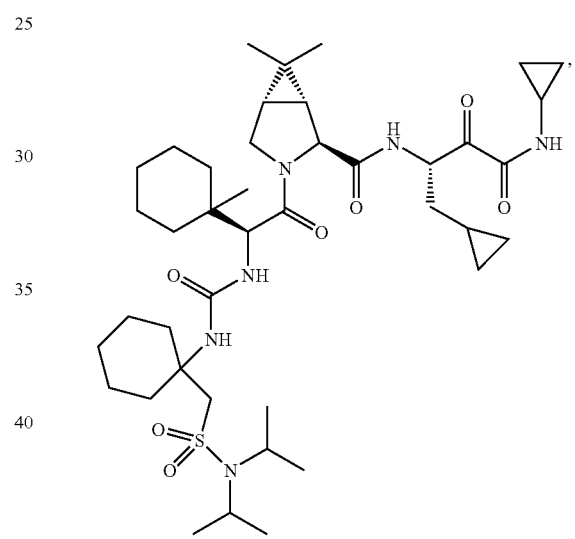
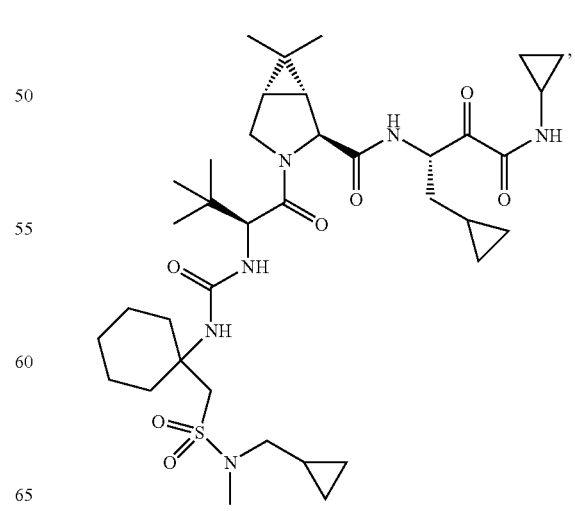

303
-continued
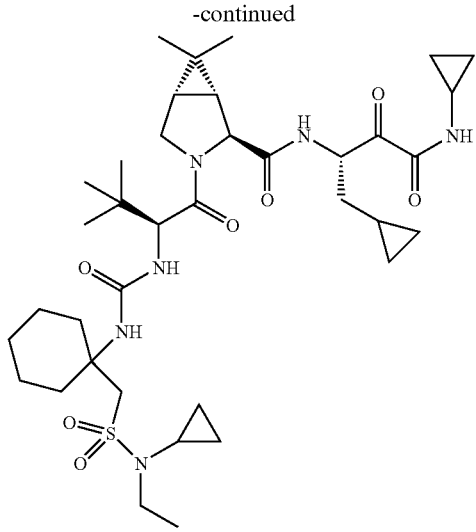
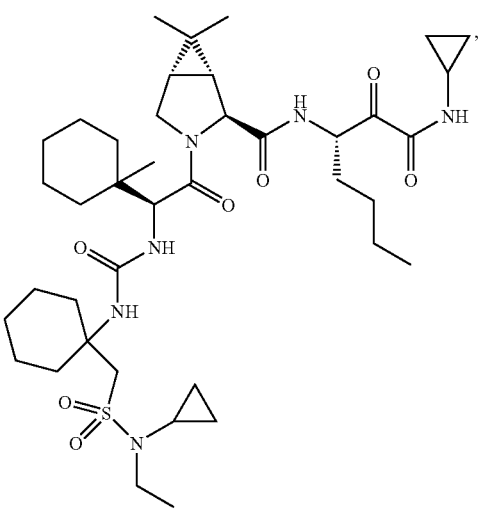
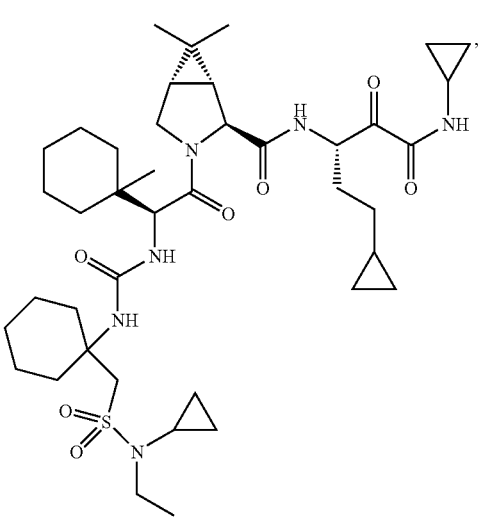
304
-continued
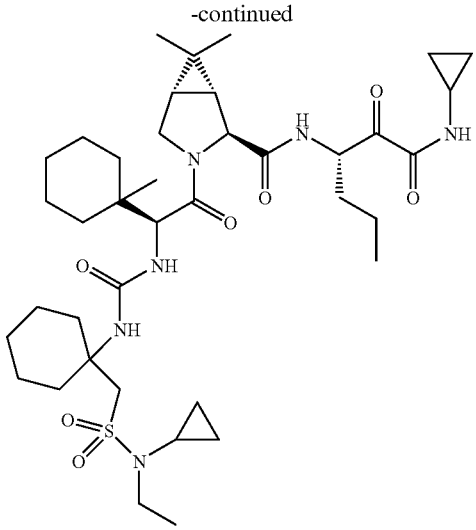
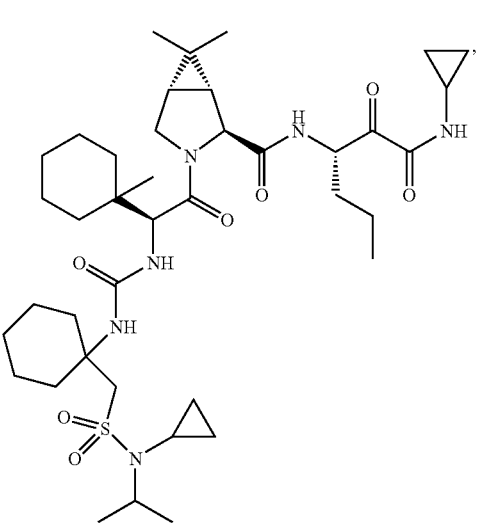
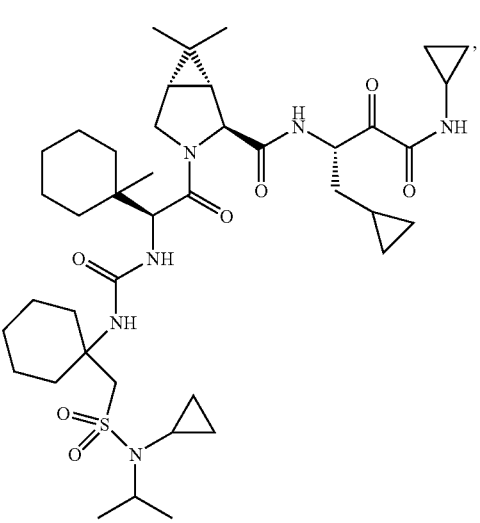

305
-continued
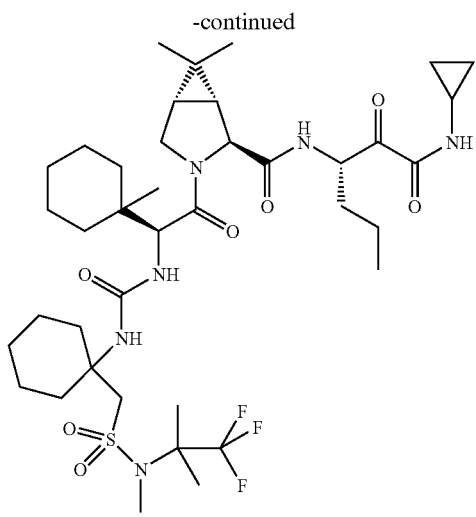
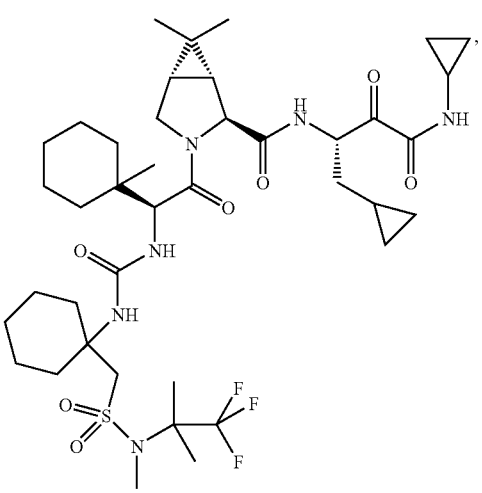
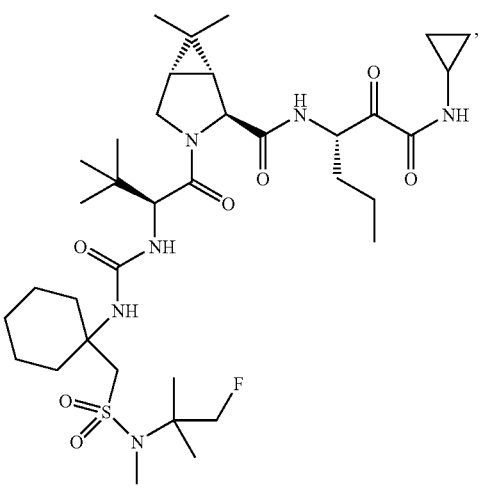
306
-continued
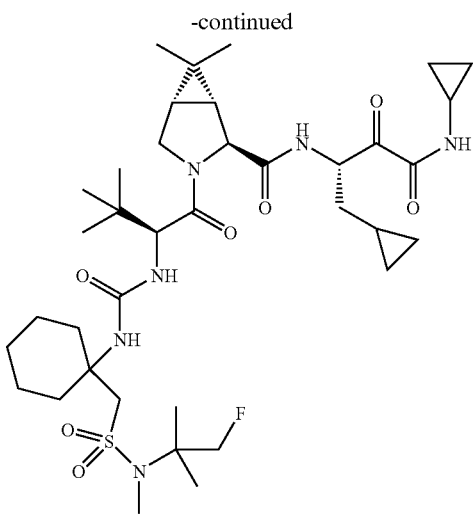
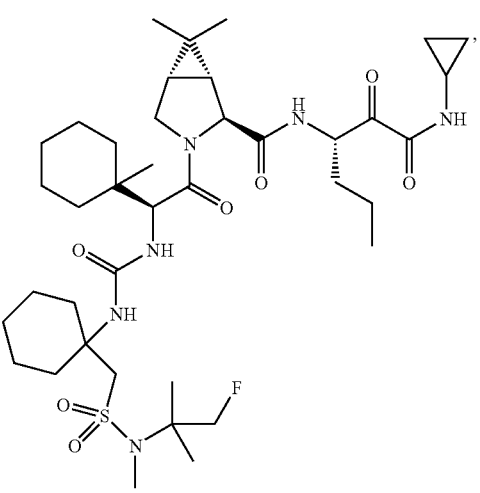
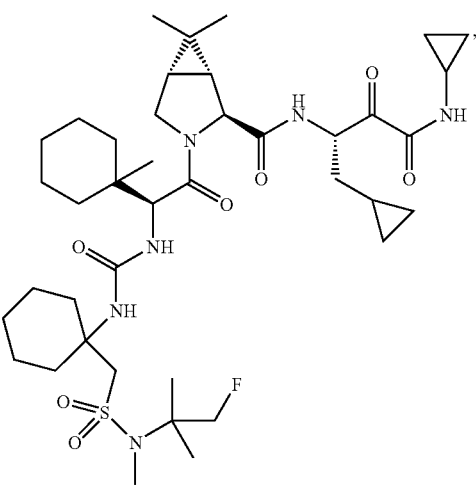

307  308
-continued  -continued
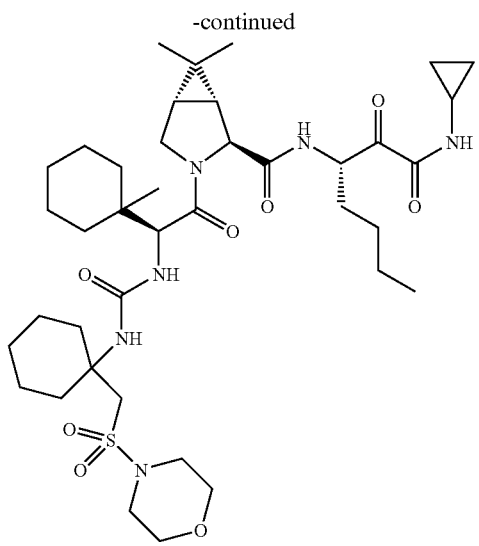
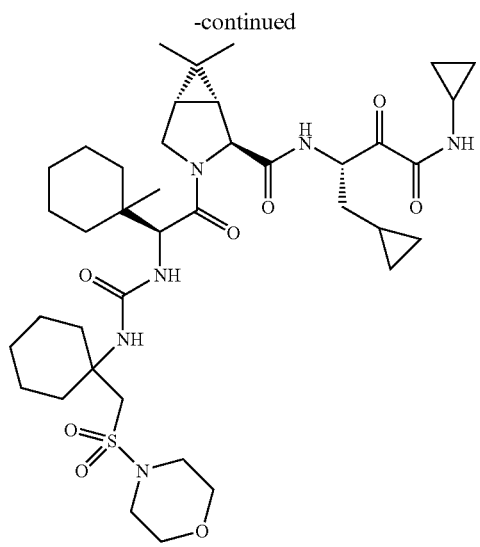
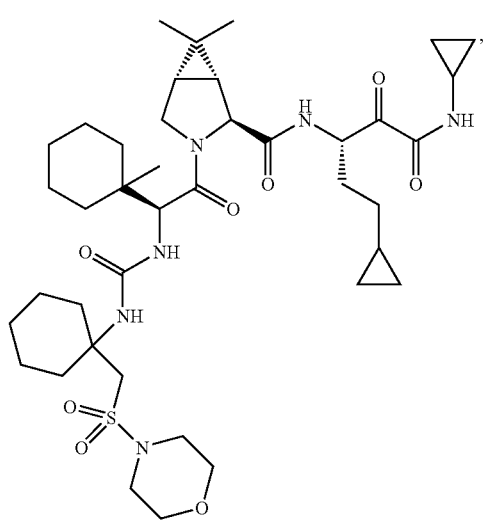
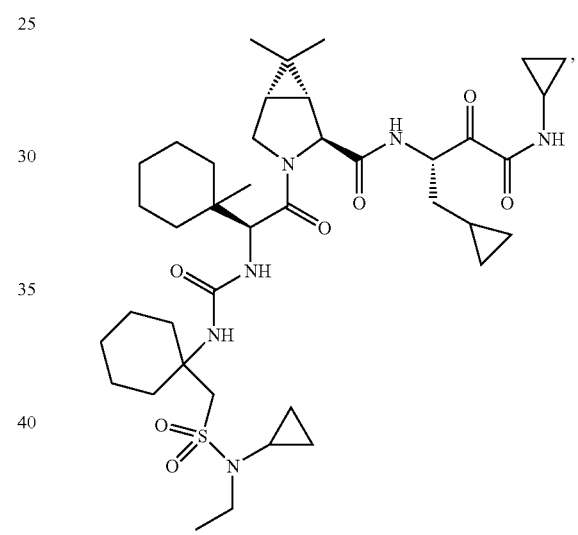
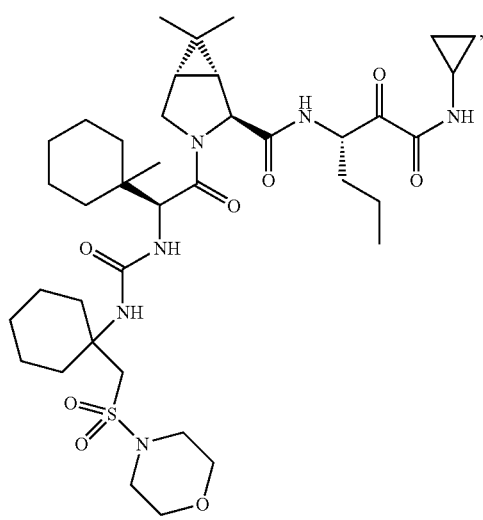
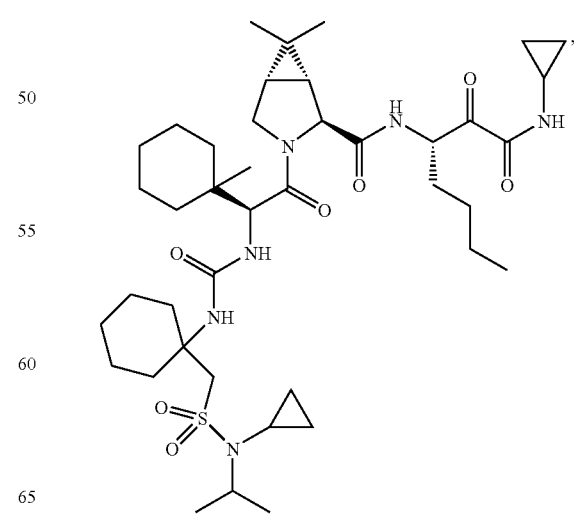

309
-continued
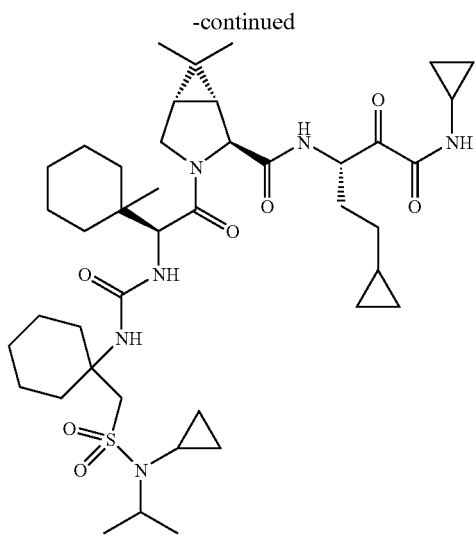
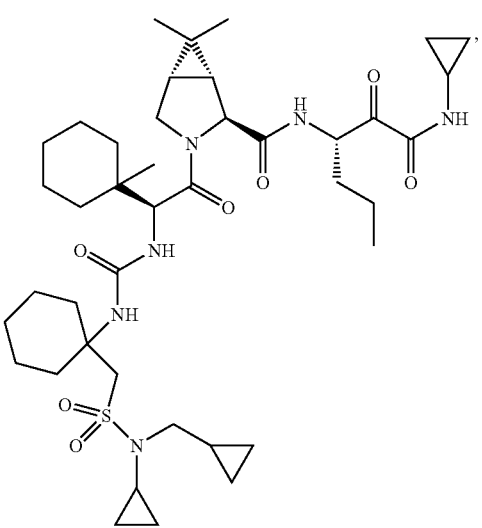
310
-continued
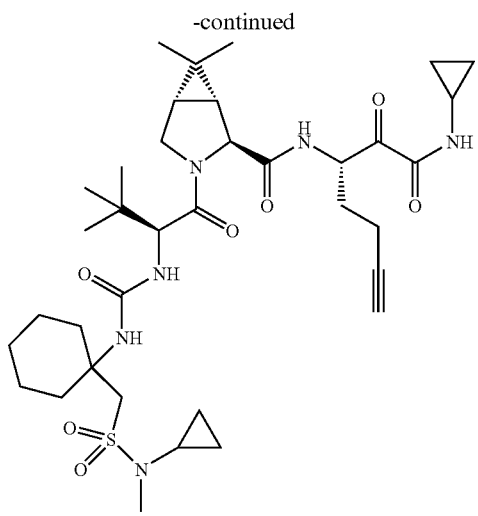
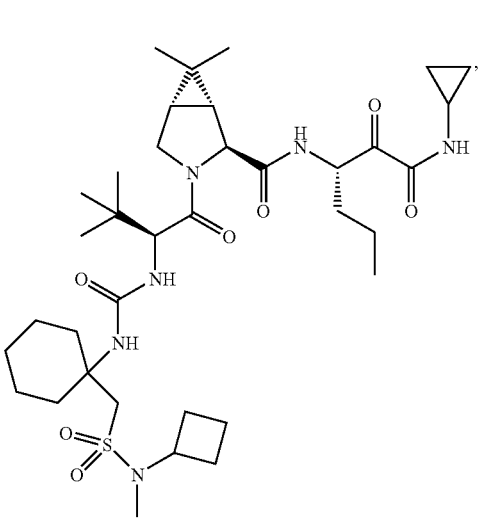

311
-continued
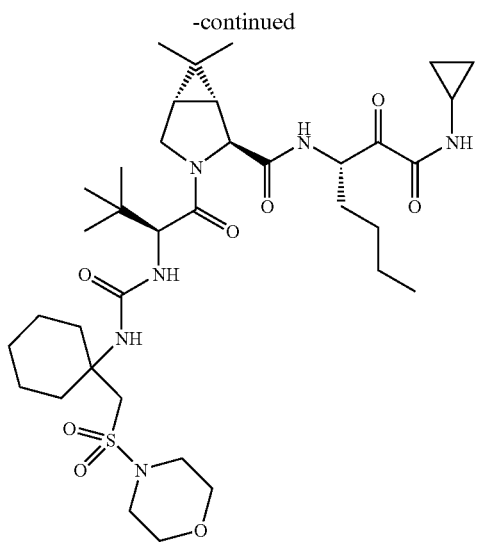
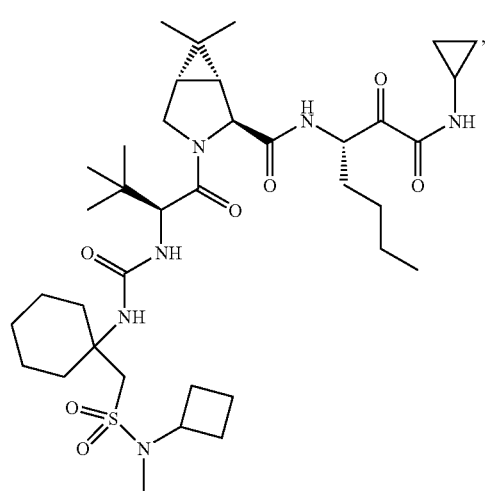
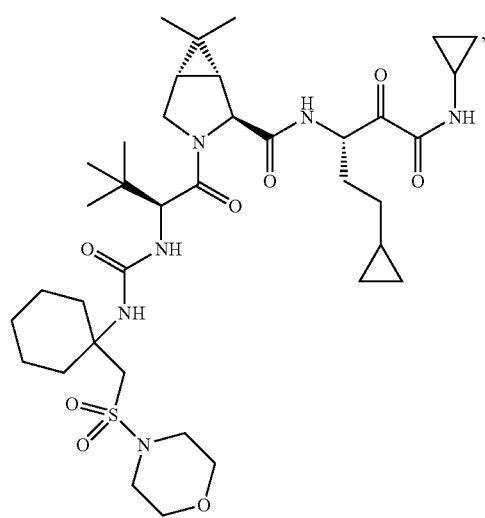
312
-continued
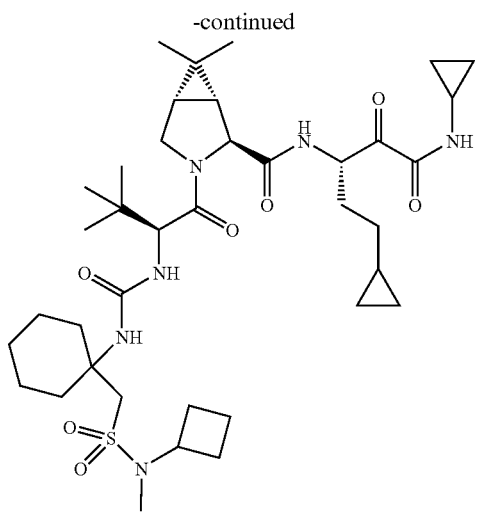
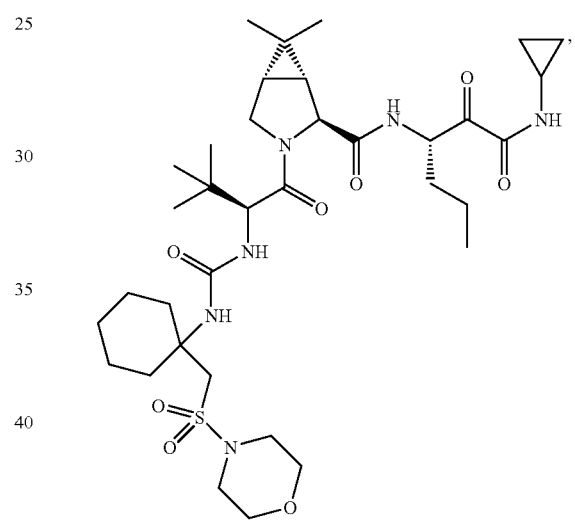
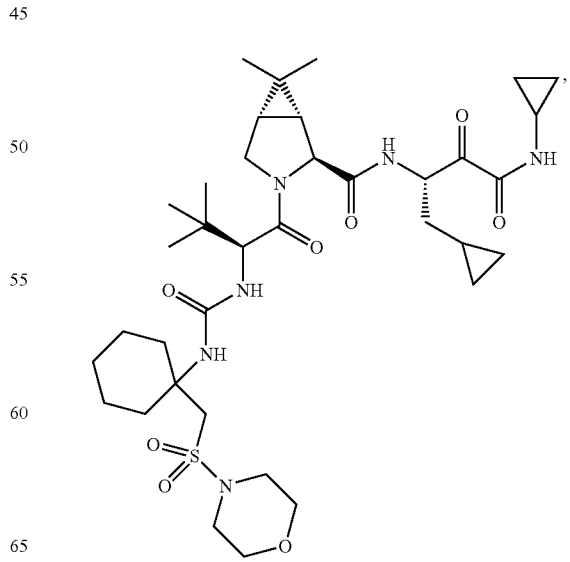

-continued
313
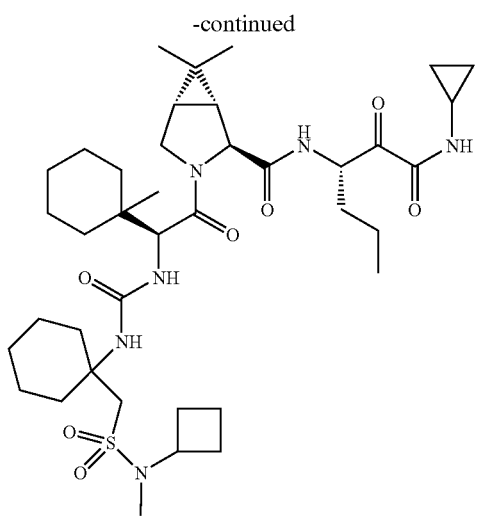
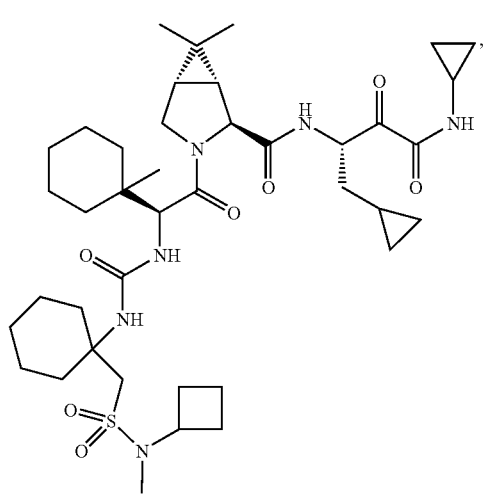
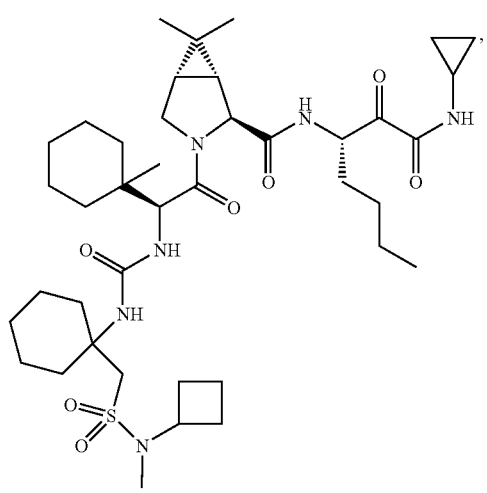
314
-continued
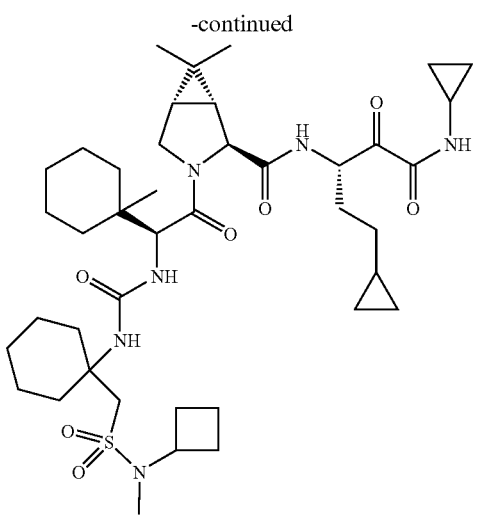
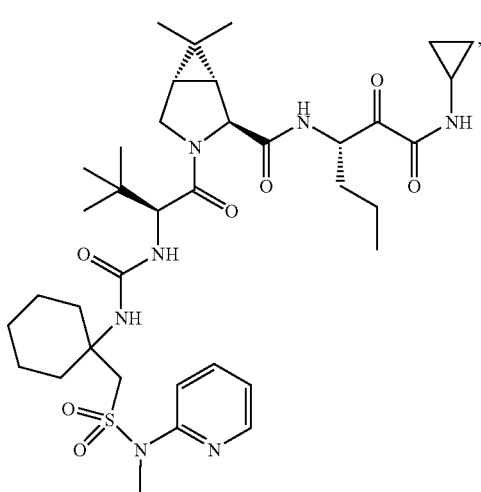
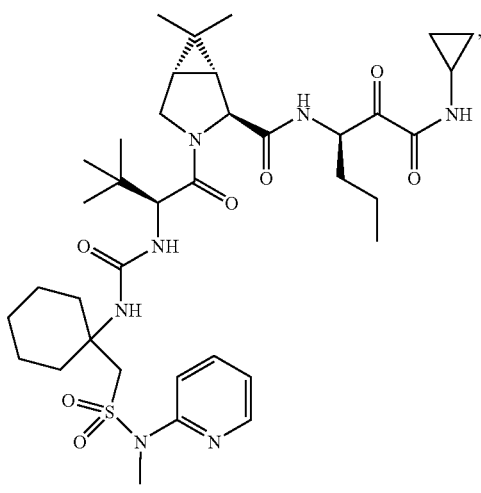

315
-continued
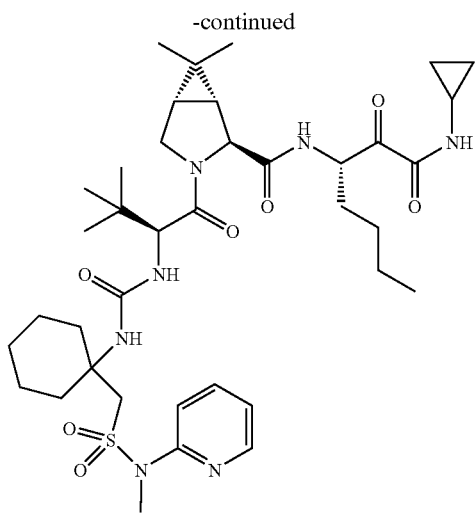
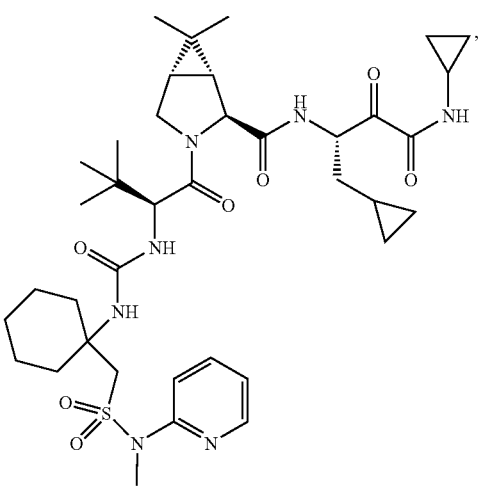
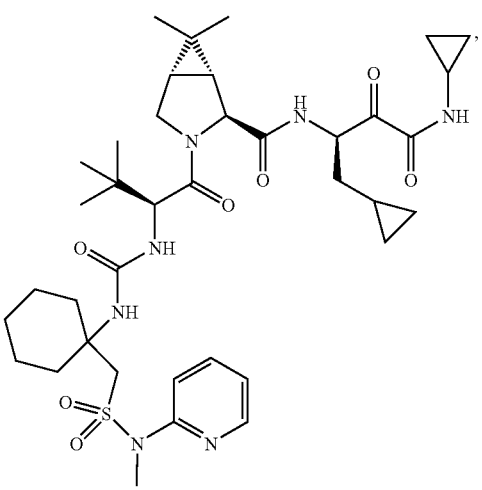
316
-continued
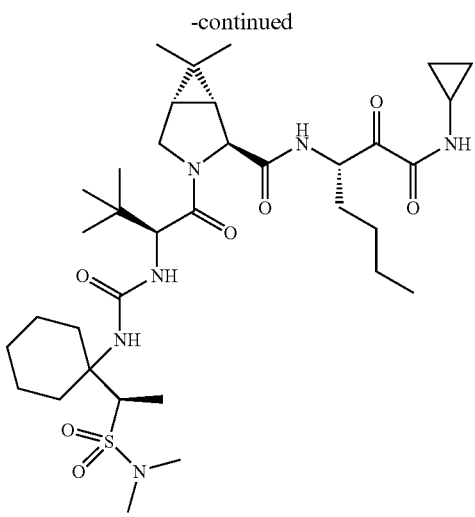
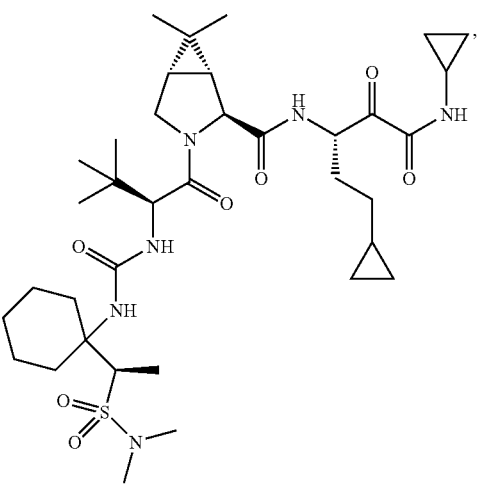
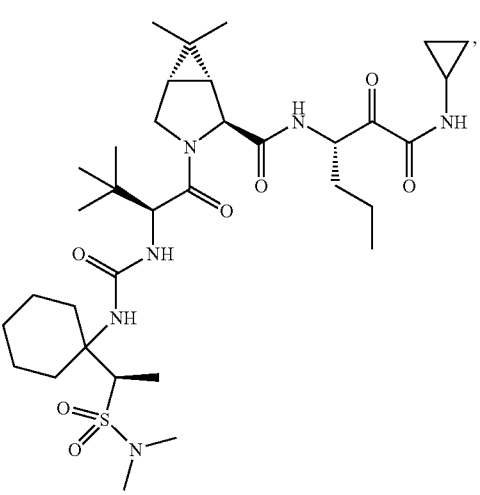

317
-continued
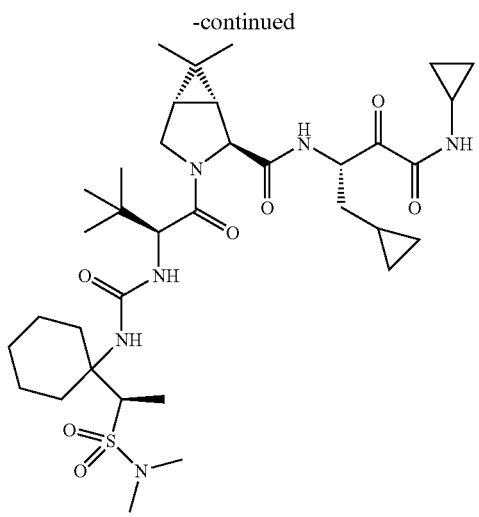
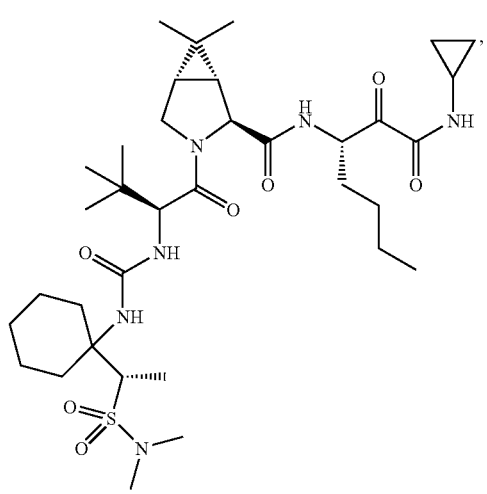
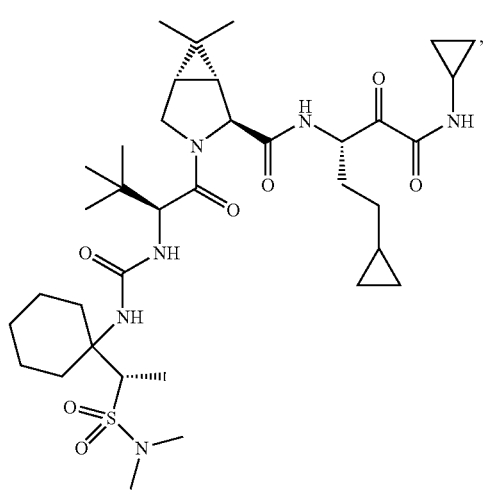
318
-continued
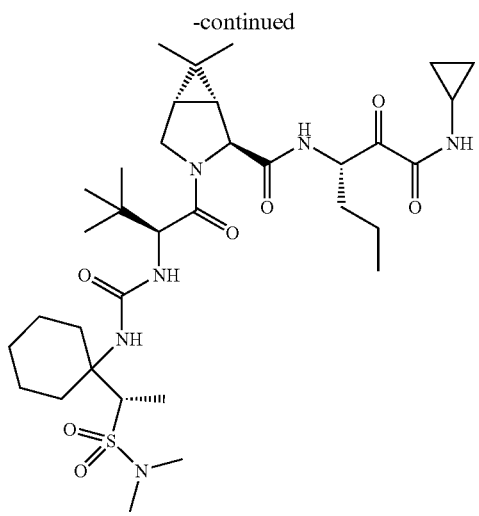
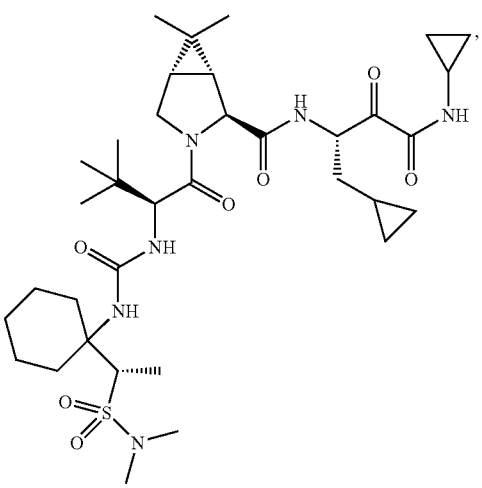
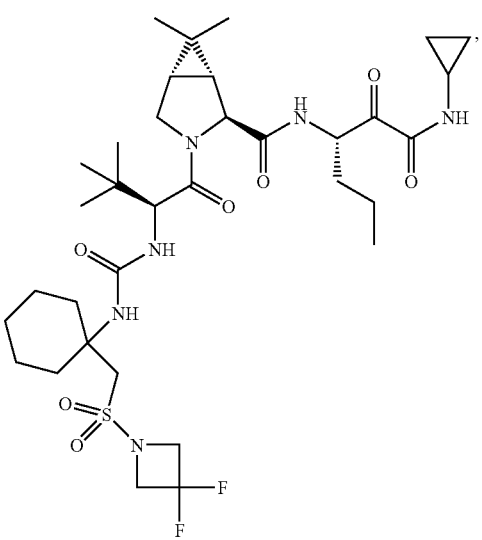

319
-continued
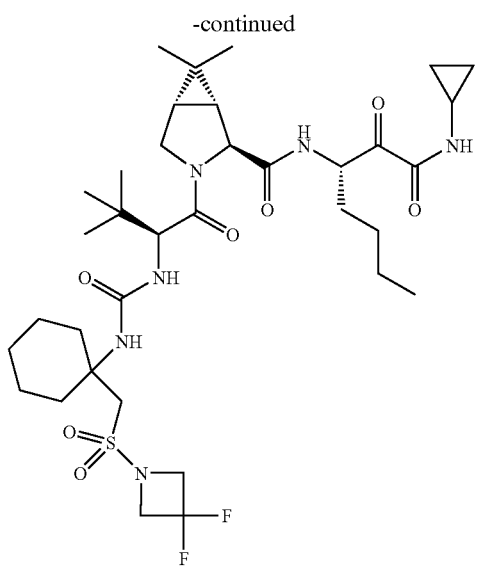
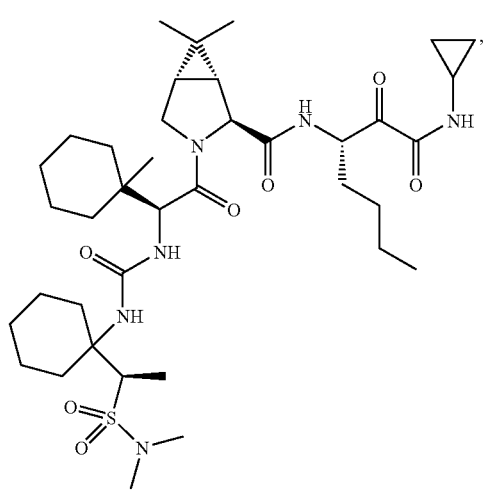
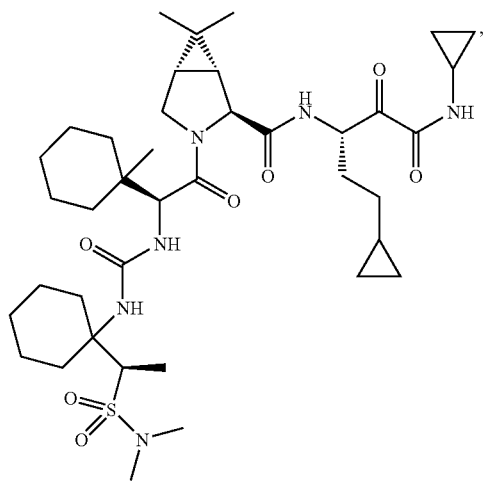
320
-continued
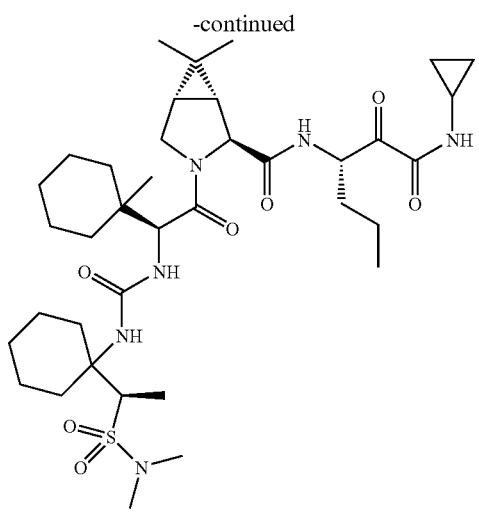
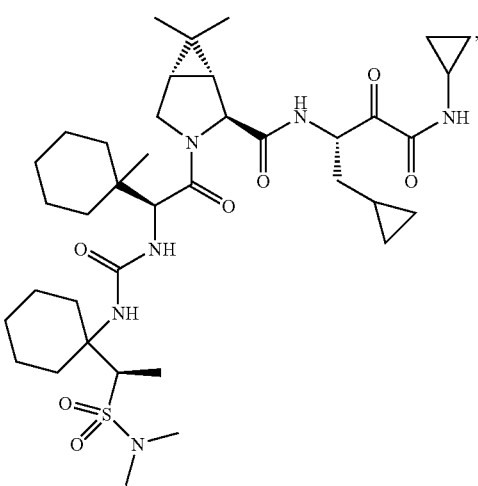
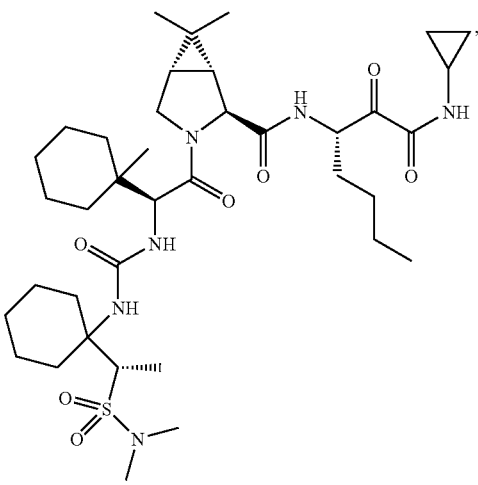

321
-continued
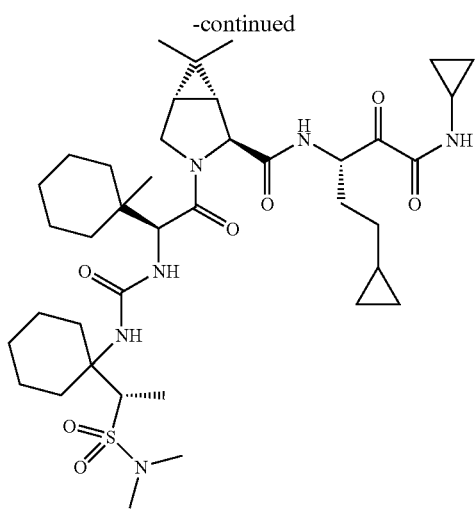
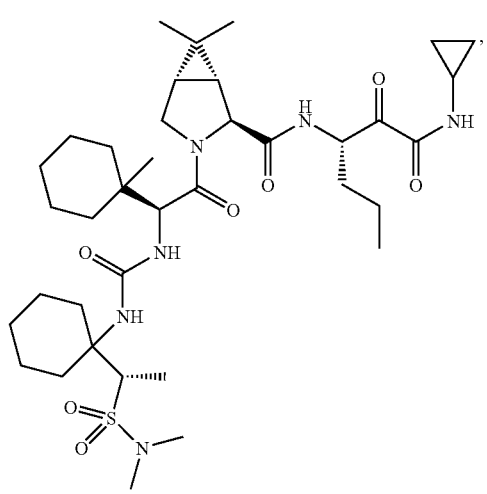
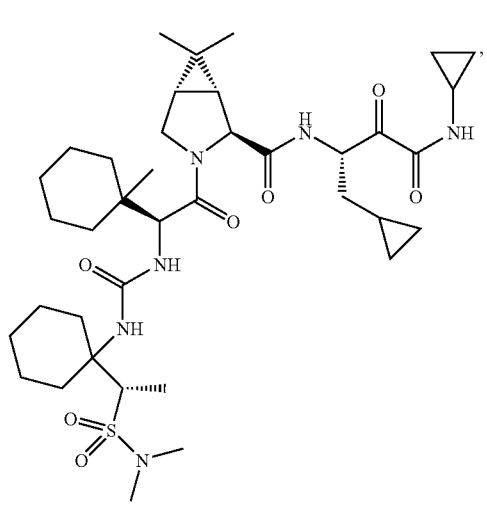
322
-continued
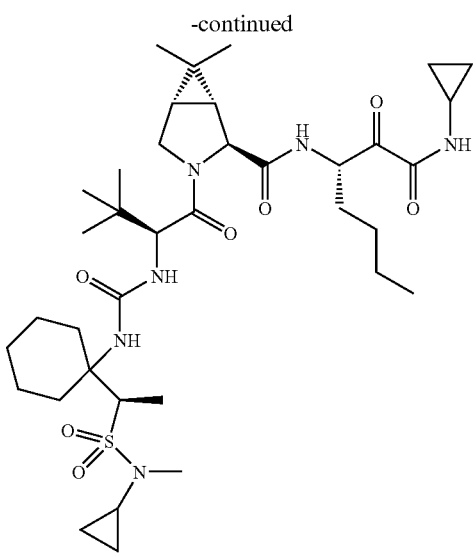
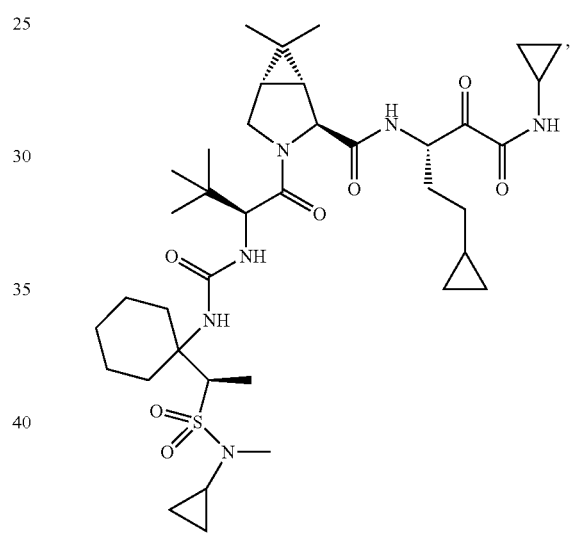
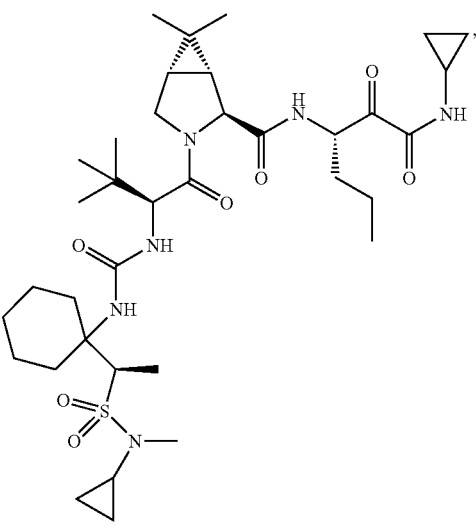

-continued

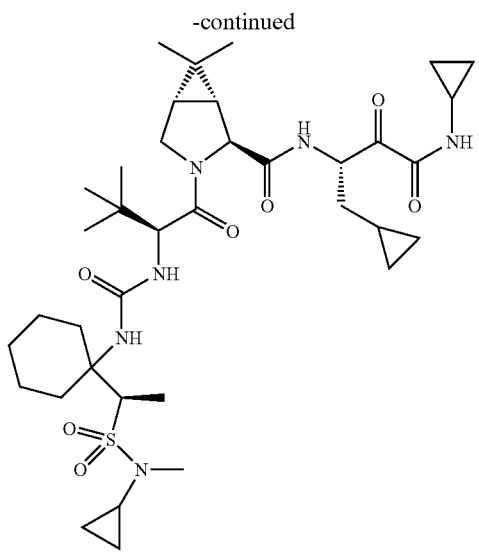

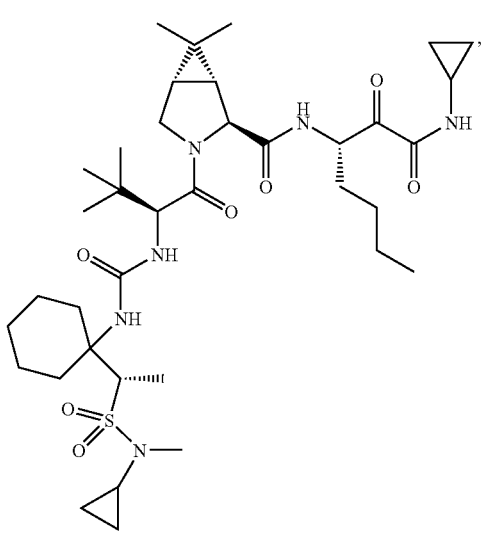

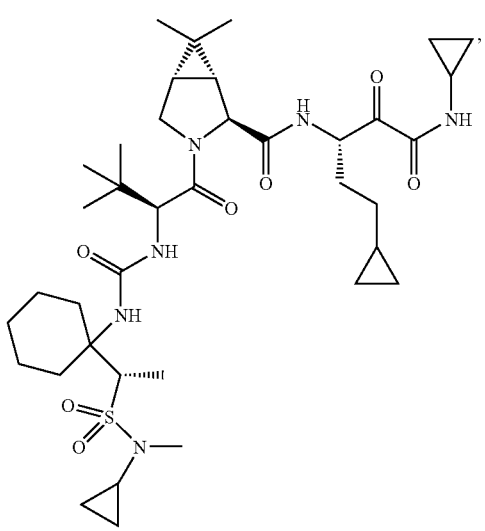

-continued

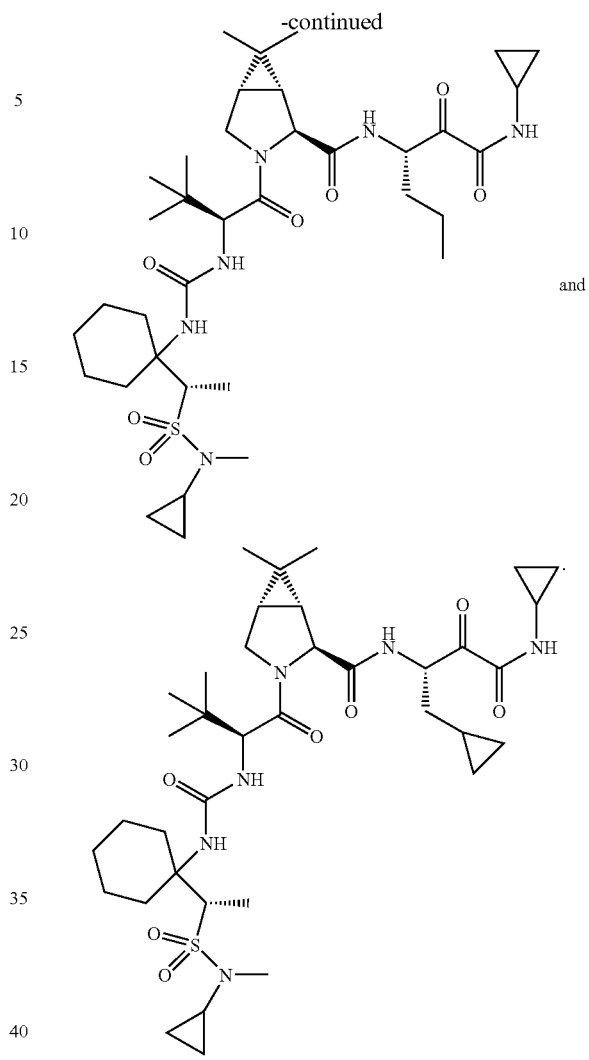

and

2. A pharmaceutical composition comprising as an active ingredient therapeutically effective amounts of at least one compound of claim 1.

3. The pharmaceutical composition of claim 2 for use in treating disorders associated with hepatitis C virus ("HCV").

4. The pharmaceutical composition of claim 2 additionally comprising at least one pharmaceutically acceptable carrier.

5. The pharmaceutical composition of claim 4, additionally containing at least one antiviral agent.

6. The pharmaceutical composition of claim 5, still additionally containing at least one interferon.

7. The pharmaceutical composition of claim 6, wherein said at least one antiviral agent is ribavirin and said at least one interferon is α-interferon or pegylated interferon.

8. A method of treating disorders associated with the HCV, said method comprising administering to a patient in need of such treatment a pharmaceutical composition which comprises therapeutically effective amounts of at least one compound of claim 1.

9. The method of claim 8, wherein said administration is oral or subcutaneous.

10. A compound exhibiting HCV protease inhibitory activity, or an enantiomer, stereoisomer, rotamer, tautomer, or racemate of said compound, or a pharmaceutically acceptable salt or solvate or ester of said compound or of said enantiomer, stereoisomer, rotamer, tautomer, or racemate, said compound having the structure:

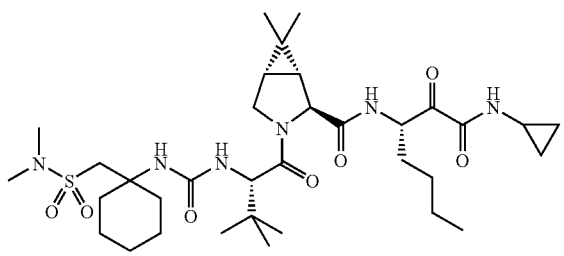

11. A compound exhibiting HCV protease inhibitory activity, or an enantiomer, stereoisomer, rotamer, tautomer, or racemate of said compound, or a pharmaceutically acceptable salt or solvate or ester of said compound or of said enantiomer, stereoisomer, rotamer, tautomer, or racemate, said compound having the structure:

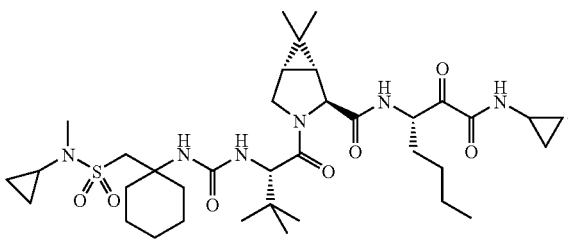

12. A compound exhibiting HCV protease inhibitory activity, or an enantiomer, stereoisomer, rotamer, tautomer, or racemate of said compound, or a pharmaceutically acceptable salt or solvate or ester of said compound or of said enantiomer, stereoisomer, rotamer, tautomer, or racemate, said compound having the structure:

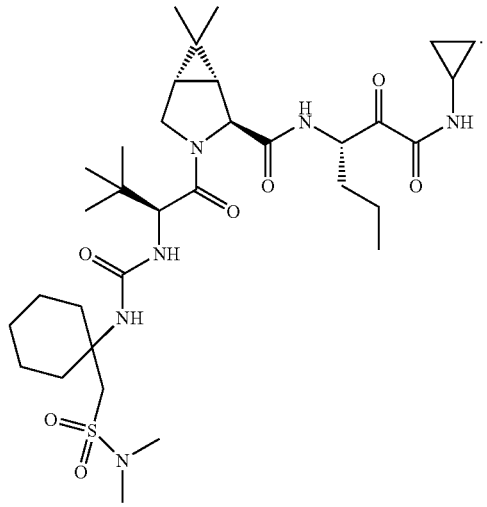

13. A compound exhibiting HCV protease inhibitory activity, or an enantiomer, stereoisomer, rotamer, tautomer, or racemate of said compound, or a pharmaceutically acceptable salt or solvate or ester of said compound or of said enantiomer, stereoisomer, rotamer, tautomer, or racemate, said compound having the structure:

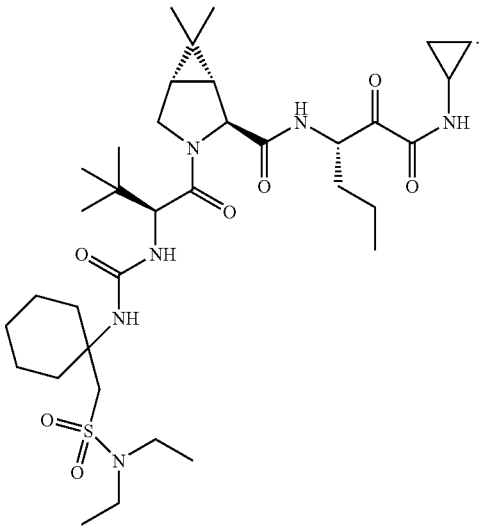

14. A compound exhibiting HCV protease inhibitory activity, or an enantiomer, stereoisomer, rotamer, tautomer, or racemate of said compound, or a pharmaceutically acceptable salt or solvate or ester of said compound or of said enantiomer, stereoisomer, rotamer, tautomer, or racemate, said compound having

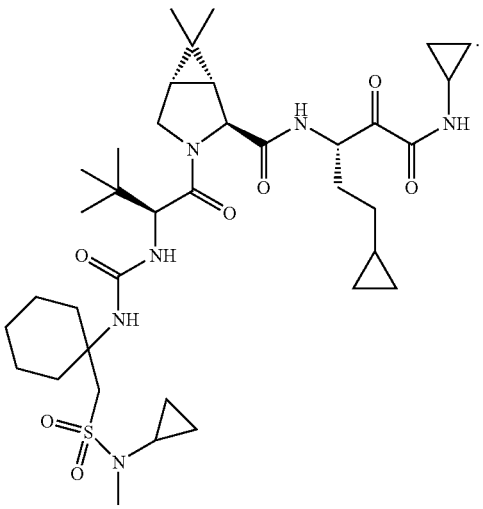

15. A compound exhibiting HCV protease inhibitory activity, or an enantiomer, stereoisomer, rotamer, tautomer, or racemate of said compound, or a pharmaceutically acceptable salt or solvate or ester of said compound or of said enantiomer, stereoisomer, rotamer, tautomer, or racemate, said compound having the structure:

16. A compound exhibiting HCV protease inhibitory activity, or an enantiomer, stereoisomer, rotamer, tautomer, or racemate of said compound, or a pharmaceutically acceptable salt or solvate or ester of said compound or of said enantiomer, stereoisomer, rotamer, tautomer, or racemate, said compound having the structure:

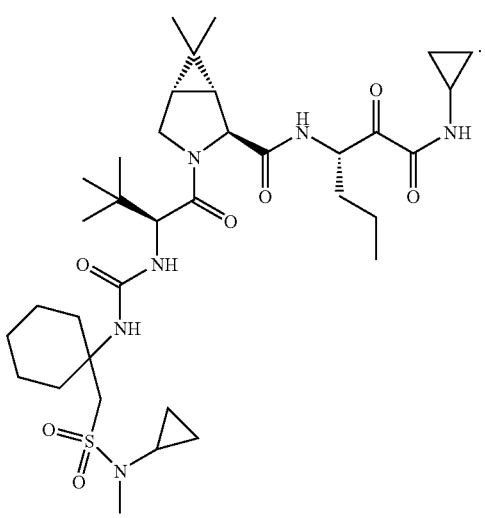

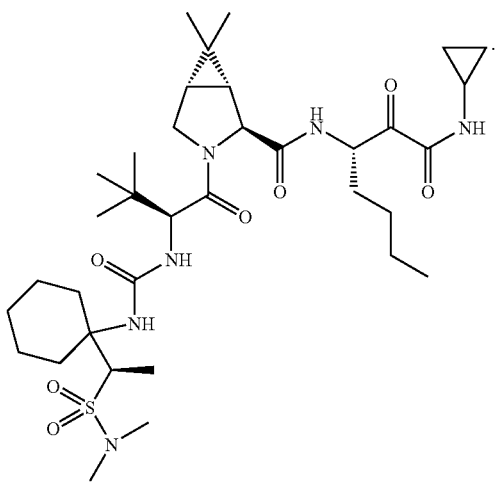

17. A compound exhibiting HCV protease inhibitory activity, or an enantiomer, stereoisomer, rotamer, tautomer, or racemate of said compound, or a pharmaceutically acceptable salt or solvate or ester of said compound or of said enantiomer, stereoisomer, rotamer, tautomer, or racemate, said compound having the structure:

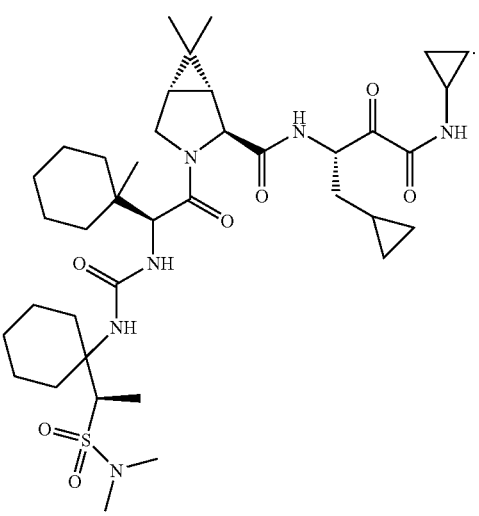

18. A compound of claim 1 in purified form.

* * * * *